US010450378B2

(12) United States Patent
Winters et al.

(10) Patent No.: US 10,450,378 B2
(45) Date of Patent: Oct. 22, 2019

(54) CYTOTOXIC AND ANTI-MITOTIC COMPOUNDS, AND METHODS OF USING THE SAME

(71) Applicant: ZYMEWORKS INC., Vancouver (CA)

(72) Inventors: Geoffrey C. Winters, Vancouver (CA); James R. Rich, Vancouver (CA); Graham Albert Edwin Garnett, West Vancouver (CA); Alexander Laurence Mandel, Vancouver (CA); Tom Han Hsiao Hsieh, Vancouver (CA); Elyse Marie Josee Bourque, Etang-du-Nord (CA); Stuart Daniel Barnscher, Vancouver (CA)

(73) Assignee: ZYMEWORKS INC., Vancouver (CA)

( * ) Notice: Subject to any disclaimer, the term of this patent is extended or adjusted under 35 U.S.C. 154(b) by 0 days.

(21) Appl. No.: 15/512,030

(22) PCT Filed: Sep. 17, 2015

(86) PCT No.: PCT/CA2015/050910
§ 371 (c)(1),
(2) Date: Mar. 16, 2017

(87) PCT Pub. No.: WO2016/041082
PCT Pub. Date: Mar. 24, 2016

(65) Prior Publication Data
US 2017/0247408 A1     Aug. 31, 2017

Related U.S. Application Data

(60) Provisional application No. 62/051,883, filed on Sep. 17, 2014.

(51) Int. Cl.
*C07K 16/30* (2006.01)
*C07K 16/32* (2006.01)
*C07K 5/02* (2006.01)
*A61K 38/00* (2006.01)
*A61K 38/06* (2006.01)
*A61K 47/54* (2017.01)
*C07K 16/28* (2006.01)
*A61K 47/68* (2017.01)

(52) U.S. Cl.
CPC .......... *C07K 16/2887* (2013.01); *A61K 38/06* (2013.01); *A61K 47/54* (2017.08); *A61K 47/6813* (2017.08); *A61K 47/6851* (2017.08); *A61K 47/6855* (2017.08); *A61K 47/6867* (2017.08); *C07K 5/0205* (2013.01); *C07K 16/2878* (2013.01); *C07K 16/30* (2013.01); *C07K 16/32* (2013.01); *A61K 38/00* (2013.01); *C07K 2317/24* (2013.01); *C07K 2317/73* (2013.01)

(58) Field of Classification Search
CPC .......... C07K 16/30; C07K 16/32; C07K 5/02; A61K 38/00; A61K 38/06; A61K 47/54
See application file for complete search history.

(56) References Cited

U.S. PATENT DOCUMENTS

| | | |
|---|---|---|
| 5,349,066 A | 9/1994 | Kaneko et al. |
| 5,502,032 A | 3/1996 | Haupt et al. |
| 5,635,483 A | 6/1997 | Pettit et al. |
| 5,663,149 A | 9/1997 | Pettit et al. |
| 5,780,588 A | 7/1998 | Pettit et al. |
| 6,124,431 A | 9/2000 | Sakakibara et al. |
| 6,153,590 A | 11/2000 | Anderson et al. |
| 6,323,315 B1 | 11/2001 | Pettit et al. |
| 6,569,834 B1 | 5/2003 | Pettit et al. |
| 6,870,028 B1 | 3/2005 | Anderson et al. |
| 6,884,869 B2 | 4/2005 | Pettit et al. |
| 7,064,211 B2 | 6/2006 | Kowalczyk et al. |
| 7,078,562 B2 | 7/2006 | Furukawa et al. |
| 7,078,572 B2 | 7/2006 | Kendall |
| 7,192,972 B2 | 3/2007 | Kowalczyk et al. |
| 7,211,696 B2 | 5/2007 | Werbovetz et al. |
| 7,390,910 B2 | 6/2008 | Zask et al. |
| 7,410,951 B2 | 8/2008 | Anderson et al. |
| 7,528,152 B2 | 5/2009 | Kowalczyk et al. |
| 7,553,969 B1 | 6/2009 | Matsuoka et al. |
| 7,579,323 B1 | 8/2009 | Anderson et al. |
| 7,585,976 B2 | 9/2009 | Campagna et al. |
| 7,626,023 B2 | 12/2009 | Zask et al. |

(Continued)

FOREIGN PATENT DOCUMENTS

| | | |
|---|---|---|
| CN | 101039701 A | 9/2007 |
| EP | 2620433 A1 | 7/2013 |

(Continued)

OTHER PUBLICATIONS

Cancer-Prevention, 2018, http://www.cancerresearchuk.org/about-cancer/causes-of-cancer/can-cancer-be-prevented.*
Winters et al., caplus abstract, 2015, caplus an 2015:1087672.*
Winters et al 2, caplus abstract, 2015, caplus an 2015:1087672.*
Rich et al., caplus abstract, 2015, caplus an 2015:1087487.*
Rich et al. 2, caplus abstract, 2015, caplus an 2015:1087487.*
Alexander-Bryant et al., "Bioengineering Strategies for Designing Targeted Cancer Therapies," Adv Cancer Res, vol. 118, pp. 1-59 (2013).
Bongo et al., "Efficient approach for profiling photoaffinity labeled peptides with a cleavable biotinyl photoprobe," Bioorganic & Medicinal Chemistry Letters, vol. 20, pp. 1834-1836 (2010).

(Continued)

*Primary Examiner* — Sun Jae Yoo
(74) *Attorney, Agent, or Firm* — Squire Patton Boggs (US) LLP

(57) ABSTRACT

Compounds having cytotoxic and/or anti-mitotic activity are disclosed. Methods associated with preparation and use of such compounds, as well as pharmaceutical compositions comprising such compounds, are also disclosed. Also disclosed are compositions having the structure: (T)-(L)-(D), wherein (T) is a targeting moiety, (L) is an optional linker, and (D) is a compound having cytotoxic and/or anti-mitotic activity.

61 Claims, 11 Drawing Sheets

(56) References Cited

U.S. PATENT DOCUMENTS

| | | | |
|---|---|---|---|
| 7,659,241 B2 | 2/2010 | Senter et al. | |
| 7,772,397 B2 | 8/2010 | Anderson et al. | |
| 7,851,437 B2 | 12/2010 | Senter et al. | |
| 8,097,648 B2 | 1/2012 | Littlefield et al. | |
| 8,129,407 B2 | 3/2012 | Kowalczyk et al. | |
| 8,394,922 B2 | 3/2013 | Cheng et al. | |
| 8,609,105 B2 | 12/2013 | Senter et al. | |
| 8,633,224 B2 | 1/2014 | Kowalczyk et al. | |
| 8,992,932 B2 | 3/2015 | Lerchen et al. | |
| 9,522,876 B2 | 12/2016 | Winters et al. | |
| 9,801,951 B2 * | 10/2017 | Miao | A61K 47/6889 |
| 9,879,086 B2 | 1/2018 | Winters et al. | |
| 2004/0121965 A1 | 6/2004 | Greenberger et al. | |
| 2005/0171014 A1 | 8/2005 | Tarasova et al. | |
| 2006/0106082 A1 | 5/2006 | Del Soldato et al. | |
| 2007/0026478 A1 | 2/2007 | Greenberger et al. | |
| 2008/0300192 A1 | 2/2008 | Doronina et al. | |
| 2008/0108820 A1 | 5/2008 | Campagna et al. | |
| 2008/0305044 A1 | 12/2008 | McDonagh et al. | |
| 2009/0155289 A1 | 6/2009 | Roberts et al. | |
| 2009/0264487 A1 | 10/2009 | Anderson et al. | |
| 2011/0020343 A1 | 1/2011 | Senter et al. | |
| 2011/0027274 A1 | 2/2011 | Cheng et al. | |
| 2011/0293704 A1 | 12/2011 | Holst et al. | |
| 2012/0041196 A1 | 2/2012 | Raffaella et al. | |
| 2013/0095123 A1 | 4/2013 | Lerchen et al. | |
| 2013/0129753 A1 | 5/2013 | Doroski et al. | |
| 2013/0190248 A1 | 7/2013 | Mendelsohn et al. | |
| 2013/0231320 A1 | 9/2013 | Kawaminami et al. | |
| 2015/0105540 A1 | 4/2015 | Miao et al. | |
| 2015/0141646 A1 | 5/2015 | Miao et al. | |
| 2015/0250896 A1 | 9/2015 | Zhao | |
| 2015/0284416 A1 | 10/2015 | Zhao | |
| 2016/0311853 A1 | 10/2016 | Geirstanger et al. | |
| 2017/0029490 A1 * | 2/2017 | Winters | C07K 16/18 |
| 2017/0246310 A1 * | 8/2017 | Rich | C07K 14/445 |

FOREIGN PATENT DOCUMENTS

| | | |
|---|---|---|
| WO | WO 1996/14856 A1 | 5/1996 |
| WO | WO 1996/33211 A1 | 10/1996 |
| WO | WO 1999/32509 A2 | 7/1999 |
| WO | WO 2001/18032 A2 | 3/2001 |
| WO | WO 2003/072754 A2 | 9/2003 |
| WO | WO 2003/082268 A2 | 10/2003 |
| WO | WO 2004/010957 A2 | 2/2004 |
| WO | WO 2004/026293 A2 | 4/2004 |
| WO | WO 2004/026814 A2 | 4/2004 |
| WO | WO 2005/026169 A1 | 3/2005 |
| WO | WO 2005/030794 A2 | 4/2005 |
| WO | WO 2005/039492 A2 | 5/2005 |
| WO | WO 2006/027711 A2 | 3/2006 |
| WO | WO 2006/132670 A2 | 12/2006 |
| WO | WO 2007/008603 A1 | 1/2007 |
| WO | WO 2007/008848 A2 | 1/2007 |
| WO | WO 2009/047264 A2 | 4/2009 |
| WO | WO 2009/059309 A2 | 5/2009 |
| WO | WO 2009/095447 A1 | 8/2009 |
| WO | WO 2009/117531 A1 | 9/2009 |
| WO | WO 2010/115981 A1 | 10/2010 |
| WO | WO 2011/154359 A1 | 12/2011 |
| WO | WO 2012/113847 A1 | 8/2012 |
| WO | WO 2012/123957 A1 | 9/2012 |
| WO | WO 2012/135440 A1 | 10/2012 |
| WO | WO 2013/068874 A1 | 5/2013 |
| WO | WO 2013/173391 A1 | 11/2013 |
| WO | WO 2013/173392 A1 | 11/2013 |
| WO | WO 2013/173393 A1 | 11/2013 |
| WO | WO 2013/185117 A1 | 12/2013 |
| WO | WO 2013/192360 A1 | 12/2013 |
| WO | WO 2014/004376 A2 | 1/2014 |
| WO | WO 2014/080251 A1 | 5/2014 |
| WO | WO 2014/100762 A1 | 6/2014 |
| WO | WO 2014/144871 A1 | 9/2014 |
| WO | WO 2015/095301 A2 | 6/2015 |
| WO | WO 2015/095952 A1 | 7/2015 |
| WO | WO 2015/095953 A1 | 7/2015 |
| WO | WO 2016/123412 A1 | 8/2016 |

OTHER PUBLICATIONS

Cancer-prevention, http://www.mcancer.org/cancer-prevention, downloaded Nov. 10, 2017.

Cheng-Bin Yim et al., "Spacer Effects on in vivo Properties of DOTA-Conjugated Dimeric [Tyr3]Octreotate Peptides Synthesized by a "Cul-Click" and "Sulfo-Click" Ligation Method," Chembiochem, vol. 12, No. 5, pp. 750-760 (2011).

Govindaraju et al., "Supporting Information Surface Immobilization of Biomolecules by Click Sulfonamide Reaction," Supplemental Material (ESI) for Chemical Communications, The Royal Society of Chemistry (2008) Downloaded from: (http://www.rsc.org/suppdata/cc/b8/b80674c/b806764c.pdf).

Matsuoka et al., "Preparation of peptides or analogs containing substituted phenethylamine moiety as motilin receptor antagonists," caplus an, PCT Int. Appl., p. 403, 2000:535162.

Sigmund, F. and Wesseley, F., "Untersuchungen über α-Amino-N-Carbonsäureanhydride. II.," Z. Physiol. Chem, vol. 157, pp. 91-105 (1926).

U.S. Appl. No. 14/213,504, entitled, "Cytotoxic and Anti-Mitotic Compounds, and Methods of Using the Same," filed Mar. 14, 2014, of Zymeworks Inc. (Issued as U.S. Pat. No. 9,522,876 on Dec. 20, 2016).

U.S. Appl. No. 14/776,654, entitled, "Cytotoxic and Anti-Mitotic Compounds, and Methods of Using the Same," filed Sep. 14, 2015, of Zymeworks Inc. (Published as 2016-0038606 on Feb. 11, 2016).

U.S. Appl. No. 14/857,733, entitled, "Cytotoxic and Anti-Mitotic Compounds, and Methods of Using the Same," filed Sep. 17, 2015, of Zymeworks Inc. (Published as 2016-0075735 on Mar. 17, 2016).

U.S. Appl. No. 15/108,247, entitled, "Sulfonamide-Containing Linkage Systems for Drug Conjugates," filed Jun. 24, 2016, of Zymeworks Inc. (Published as 2017-0029490 on Feb. 2, 2017).

U.S. Appl. No. 15/108,258, entitled, "VAR2CSA—Drug Conjugates," filed Jun. 24, 2016, of Zymeworks Inc.

Alley et al., "Contribution of Linker Stability to the Activities of Anticancer Immunoconjugates," Bioconjugate Chem., vol. 19, pp. 759-765 (2008).

Badescu et al, "Bridging Disulfides for Stable and Defined Antibody Drug Conjugates," Bioconjugate Chem., vol. 25 (6), pp. 1124-1136 (2014).

Bai et al., "Interactions of the Sponge-Derived Antimitotic Tripeptide Hemiasterlin with Tubulin: Comparison with Dolastatin 10 and Cyrpotphycin 1," Biochemistry, vol. 38, pp. 14302-14310 (1999).

Baldwin, A. D. and Kiick, K. L., "Tunable Degradation of Maleimide-Thiol Adducts in Reducing Environments," Bioconjugate Chem., Vo. 22, pp. 1946-1953 (2011).

Beaulieu, P.L. et al., "Allosteric N-acetamide-indole-6-carboxylic acid thumb pocket 1 inhibitors of hepatitis C virus NS5B polymerase—Acylsulfonamides and acylsulfamides as carboxylic acid replacements," Can J. Chem., vol. 91, pp. 66-81 (2013).

Burke et al., "Design, Synthesis and Biological Evaluation of Antibody-Drug Conjugates Comprised of Potent Camptothecin Analogues," Bioconjugate Chem., vol. 20, pp. 1242-1250 (2009).

Burke et al., "Novel immunoconjugates comprised of streptonigrin and 17-amino-geldanamycin attached via dipeptide-p-aminobenzylamine linker system," Biorg. Med. Chem. Lett., vol. 19, pp. 2650-2653 (2009).

Chakraborty et al., "Nucleation of β-Hairpin Structures with Cis Amide Bonds in E-Vinylogous Proline-Containing Peptides," J. Org. Chem., vol. 68, pp. 6459-6462 (2003).

Chan et al., "Mitosis-targeted anti-cancer therapies: where they stand," Cell Death and Disease, vol. 3, pp. 1-11 (2012).

Chen, J. et al., "The Bcl-2/Bcl-XL/Bcl-w Inhibitor, Navitoclax, Enhances the Activity of Chemotherapeutic Agents In Vitro and In Vivo," Mol Cancer Ther, 10(12), pp. 2340-2349, (2011).

Choi, K.Y., "Protease-Activated Drug Development," Theranostics, 2(2), pp. 156-178, (2012).

(56) References Cited

OTHER PUBLICATIONS

Coleman et al., "Cytotoxic Peptides from the Marine Sponge *Cymbastella* sp.," Tetrahedron vol. 51, No. 39, pp. 10653-10662 (1995).
Doronina et al., "Development of potent monoclonal antibody auristatin conjugates for cancer therapy," Nature Biotechnology, vol. 21, No. 7, pp. 778-784 (2003).
Doronina et al., "Enhanced Activity of Monomethylauristatin F through Monoclonal Antibody Delivery: Effects of Linker Technology on Efficacy and Toxicity," Bioconjugate Chem., vol. 17, pp. 114-124 (2006).
Doronina et al., "Novel Peptide Linkers for Highly Potent Antibody—Auristatin Conjugate," Bioconjugate Chem., vol. 19, pp. 1960-1963 (2008).
Dubowchik et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity," Bioconjugate Chem., vol. 13, pp. 855-869 (2002).
"Expert Scientific Group on Phase One Clinical Trails Final Report" Nov. 30, 2006, pp. C1, C35-C38.
Fennell et al., "Effects of the antimitotic natural product dolastatin 10, and related peptides, on the human malarial parasite *Plasmodium falciparum*," Antimicrob. Chemother., vol. 51, pp. 833-841 (2003).
Francisco et al., "cAC10-vcMMAE, and anti-CD30-monomethyl auristatin E conjugate with potent and selective antitumor activity," Blood, vol. 102, No. 4, pp. 1458-1465 (2003).
Gajula et al., "A Synthetic Dolastatin 10 Analgoue Supresses Mictrotubule Dynamics, Inhibits Cell Proliferation, and Induces Apoptotic Cell Death," J. Med. Chem, vol. 56, pp. 2235-2245 (2013).
Grison, C. et al., "Stereoselective synthesis of vinylogous peptides," Tetrahedron, 57, pp. 4903-4923 (2001).
Grison et al., "Structural Investigation of "cis" and "trans" Vinylogous Peptides: cis-Vinylog Turn in Folded cis-Vinylogous Peptides, an Excelletn Mimic of the Natural β-Turn," J. Org. Chem. vol. 70, pp. 10753-10764 (2005).
Gura, T.,"Cancer Models: Systems for Identifiying New Drugs Are Often Faulty," Science 7, vol. 278, No. 5340, pp. 1041-1042 (2007).
Haba, K., "Single-Triggered Trimeric Prodrugs," Angew. Chem. Int. Ed., vol. 44, pp. 716-720 (2005).
Hadaschik, B.A. et al., "Intravesical Chemotherapy of High-Grade Bladder Cancer with HTI-286, A Synthetic Analogue of the Marine Sponge Product Hemiasterlin," Clin Cancer Res., vol. 14, pp. 1510-1518 (2008).
Huang, S. et al., "Synthesis and evaluation of N-acyl sulfonamides as potential prodrugs of cyclin-dependent kinase inhibitor JNJ-7706621," Bioorganic & Medicinal Chemistry Letters, vol. 16, pp. 3639-3641 (2006).
Ishikawa et al, "Preparation of endothelin antagonistic peptide derivatives," caplus an Eur. Pat. Appl., p. 121, 1992:256053.
Jeffrey et al., "Design, Synthesis, and in Vitro Evaluation of Dipeptide-Based Antibody Minor Groove Binder Conjugates," J. Med. Chem., vol. 48, pp. 1344-1358 (2005).
Jeffrey et al., "Dipeptide-based highly potent doxorubicin antibody conjugates," Biorg. Med. Chem. Lett. vol. 16, pp. 358-362 (2006).
Jeffrey et al., "Expanded Utility of the β-Glucuronide Linker: ADCs That Deliver Phenolic Cytotoxic Agents," ACS Med. Chem. lett., vol. 1, pp. 277-280 (2010).
Jiang, Y. et al., "Discovery of Danoprevir (ITMN-191/R7227), a Highly Selective and Potent Inhibitor of Hepatitis C Virus (HCV) NS3/4A Protease," J. Med. Chem., vol. 57, pp. 1753-1769 (2014).
Johansson, A. et al., "Acyl Sulfonamides as Potent Protease Inhibitors of the Hepatitis C Virus Full-Length NS3 (Protease-Helicase/NTPase): A Comparative Study of Different C-Terminals," Bioorganic & Medicinal Chemistry, 11, pp. 2551-2568 (2003).
Kamb, A., "What's wrong with our cancer models?," Nature Reviews Drug Discovery 4, vol. 4, pp. 161-165 (2005).

Koniev, O. et al, "Selective Irreversible Chemical Tagging of Cysteine with 3-Arylpropiolonitriles," Bioconjugate Chem., vol. 25 (2), pp. 202-206 (2014).
Kuznetsov et al., "Tubulin-based antimitotic mechanism of E7974, a novel analogue of the marine sponge natural product hemiasterlin," Mol Cancer Ther, 8(10), pp. 2852-2860 (2009).
Leaf, C., "Why Are We Losing the War on Cancer (and How to Win it)," Health Administrator vol. XVII, No. 1, pp. 172-183 (2005).
Lesma, et al., "Hemiasterlin Analogues Incorporating an Aromatic, and Heterocyclic Type C-terminus: Design, Synthesis and Biological Evaluation," Mol Divers.,18(2), pp. 357-373 (2004).
Loganzo et al., "HTI-286 , a Synthetic Analogue of the Tripeptide Hemiasterlin, is a Potent Antimicrotubule Agent that Circumvents P-Glycoprotein-mediated Resistance in Vitro and in Vivo," Cancer Res, 63, pp. 1838-1845 (2003).
Luo et al., "Principle of Cancer Therapy: Oncogen and Non-oncogene Addiction," Cell vol. 136, pp. 823-837 (2009).
Mader, M.M. et al., "Acyl sulfonamide anti-proliferatives. Part 2: Activity of heterocyclic sulfonamide derivatives," Bioorganic & Medicinal Chemistry Letters, 15, pp. 617-620 (2005).
Marzo et al., "Antimitotic drugs in cancer chemotherapy: Promises and pitfalls," Biochemical Pharmacology, Vo. 86, pp. 703-710 (2013).
Merkx et al., "Resin-bound sulfonyl-azides: Efficient loading and activation strategy for the preparation of the N-acyl sulfonamide linker," J. Org. Chem., vol. 72, pp. 4574-4577 (2007).
Melnyk, O. et al, "Phenylthiocarbamate or N-Carbothiophenyl Group Chemistry in Peptide Synthesis and Bioconjugation," Bioconjugate Chem., vol. 25, pp. 629-639 (2014).
Mitra, A. and Sept D., "Localization of the Antimitotic Peptide and Depsipeptide Binding Site on B-tubulin," Biochemistry, 43, pp. 13955-13962 (2004).
Miyazawa, T. et al, "Effect of copper(II) chloride on suppression of racemization in peptide synthesis by the carbodiimide method," Int. J. Peptide Protein Res., vol. 39, pp. 237-244 (1992).
Neidle, S., "Failure Modes in Clinical Development," Cancer Drug Design and Discovery, ed. (Elsevier/Academic Press) pp. 427-431 (2008).
Niu et al., "Absolute configurations of tubulin inhibitors taltobulin (HTI-286) and HTI-042 characterized by X-ray diffraction analysis and NMR studies," Bioorganic & Medicinal Chmistry Letters, 20, pp. 1535-1538 (2010).
Otani et al., "TZT-1027, an antimicrotubule agent, attacks tumor vasculature and induces tumor cell death," Jpn. J. Cancer Res., vol. 91, pp. 837-844 (2000).
Papisov et al., "Semisynthetic Hydrophilic Polyals," Biomacromolecules,vol. 6, pp. 2659-2670 (2005).
Pettit et al., "Antineoplastic agents 337. Synthesis of dolastatin 10 structural modifications," Anti-Cancer Drug Des., vol. 10, pp. 529-544 (1995).
Pettit et al., "Specific activities of dolastatin 10 and peptide derivatives against *Cryptococcus neoformans*," Antimicrob. Agents Chemother., vol. 42, pp. 2961-2965 (1998).
Pettit et al., "Antineoplastic agents 365. Dolastatin 10 SAR probes," Anti-Cancer Drug Des., vol. 13, pp. 243-277 (1998).
Pettit et al., "Antineoplastic agents. 592. Highly effective cancer cell growth inhibitory structural modifications of dolastatin 10," J. Nat. Prod., vol. 74, pp. 962-968 (2011).
Ratain et al., "Phase I and pharmacological study of HTI-286, a novel antimicrotubule agent: correlation of neutropenia with time above a threshold serum concentration," Proc. Am. Soc. Clin. Oncol., vol. 22, p. 129 (2003).
Ravi M. et al., "Structure-Based Identification of the Binding Site for the Hemiasterlin Analogue HTI-286 on Tubulin," Biochemistry, 44, pp. 15871-15879 (2005).
Rocha-Lima et al., "A Phase 1 Trial of E7974 Administrated on Day 1 of a 21 Day Cycle in Patients with Advanced Solid Tumors," Cancer, pp. 4262-4270, Sep. 1, 2012.
Scola, P.M. et al., "The Discovery of Asunaprevir (BMS-650032), An Orally Efficacious NS3 Protease Inhibitor for the Treatment of Hepatitis C Virus Infection," J. Med. Chem., 57, pp. 1730-1752 (2014).

(56) References Cited

OTHER PUBLICATIONS

Schumacher, F.F. et al, "In Situ Maleimide Bridging of Disulfides and a New Approach to Protein Pegylation," Bioconjugate Chem., vol. 22, pp. 132-136 (2011).
Shabat et al., "In vivo activity in a catalytic antibody-prodrug system: Antibody catalyzed etoposide prodrug activation for selective chemotherapy," PNAS, vol. 98, No. 13, pp. 7528-7533 (2001).
Shannon et al., "Investigating the Proteome Reactivity and Selectivity of Aryl Halides," J. Am. Chem. Soc., vol. 136, pp. 3330-3333 (2014).
Shnyder et al., "Auristatin PYE, a novel synthetic derivative of dolastatin 10, is highly effective in human colon tumour models," Int. J. Oncol., vol. 31, pp. 353-360 (2007).
Steiner, M. et al., "Spacer length shapes drug release and therapeutic efficacy of traceless disulfide-linked ADCs targeting the tumor neovasculature," Chem. Sci., vol. 4, pp. 297-302 (2013).
Sutherland, M.S.K., et al., "Lysosomal Trafficking and Cysteine Protease Metabolism Confer Target-specific Cytotoxicity by Peptide-linked Anti-CD30-Auristatin Conjugates," Journal of Biological Chemistry, Vo. 281, No. 15, pp. 10540-10547 (2006).
Talpir et al., "Hemiasterlin and Geodiamolide TA; Two New Cytotoxic Peptides from the Marine Sponge Hemiasterella Minor (Kirkpatrick)," Tetrahedron Letters, vol. 35, No. 25, pp. 4453-4456 (1994).
Temming et al., "Improved Efficacy of αvβ3-Targeted Albumin Conjugates by Conjugation of a Novel Auristatin Derivative," Molecular Pharmaceutics, vol. 4, No. 5, pp. 686-694 (2007).
Thomssen et al., "Prognostic value of the cysteine proteases cathepsins B and cathepsin L in human breast cancer," Clinical Cancer Research, vol. 1, pp. 741-746 (1995).
Toki et al., "Protease-Mediated Fragmentation of p-Aminobenzyl Ethers: A New Strategy for the Activation of Anticancer Prodrugs," J. Org. Chem., vol. 67, pp. 1866-1872 (2002).
Toure, B.C. et al., "The Role of the Acidity of N-Heteroaryl Sulfonamides as Inhibitors of Bcl-2 Family Protein-Protein Interactions," ACS Med. Chem. Lett., vol. 4, pp. 186-190 (2013).
Uehling, D.E. et al., "Synthesis and Evaluation of Potent and Selective β3 Adrenergic Receptor Agonists Containing Acylsulfonamide, Sulfonylsulfonamide, and Sulfonylurea Carboxylic Acid Isosteres," J. Med. Chem., vol. 45, pp. 567-583 (2002).
Vedejs, et al., "A Total Synthesis of (-)-Hemiasterlin Using N-Bts Methodology," J. Org. Chem., vol. 66, pp. 7355-7364 (2001).
Walker et al., "Monoclonal antibody mediated intracellular targeting of tallysomycin S10b," Bioorganic & Medicinal Chemistry Letters, vol. 14, pp. 4323-4327 (2004).
Werboretz et al., "Selective Antimicrotubule Activity of N1-Phenyl-3- 5-dinitro-4,N-4-di-n-propylsulfanilamide (GB-II-5) against Kinetoplastid Parasites," Mol. Pharmacol., vol. 64, pp. 1325-1333 (2003).
Woyke et al., "In vitro activities and postantifungal effects of the potent dolastatin 10 derivative Auristatin PHE," Antimicrob. Agents Chemother., vol. 45, pp. 3580-3584 (2001).
Yamashita et al., "Synthesis and Activity of Novel Analogs of Hemiasterlin as Inhibitors of Tubulin Polymerization: Modification of the A Segment," Bioorganic and Medicinal Chemistry Letters, vol. 14, pp. 5317-5322 (2004).
Yan, S. et al., "Thiazolone-acylsulfonamides as novel HCV NS5B polymerase allosteric inhibitors: convergence of structure-based drug design and X-ray crystallographic study," Bioorganic & Medicinal Chemistry Letters, vol. 17, pp. 1991-1995 (2007).
Yurkovestkiy et al., "Synthesis of a Macromolecular Camptothecin Conjugate with Dual Phase Drug Release," Mol Pharm., vol. 1:5, pp. 375-382 (2004).
Zask et al., "D-piece Modifications of the Hemiasterlin Analog HTI-286 Produce Potent Tubulin Inhibitors," Bioorganic & Medicinal Chemistry Letters, vol. 14, pp. 4353-4358 (2004).
Zask et al., "Synthesis and Biological Activity of Analogues of the Antimicrotubule Agent N,β,β-Trimethyl-l-phenylalanyl-N1-[(1S,2E)-3-carboxy-1-isopropylbut-2-enyl]-N1,3-dimethyl-l-valinamide (HTI-286)," J. Med. Chem., vol. 47, pp. 4774-4786 (2004).
Rich, J.R., et al., Caplus AN 2015:1087487.
Winters, G., et al., Caplus AN 2015:1087672.
U.S. Appl. No. 15/108,258 Restriction Requirement dated Oct. 5, 2017.
Neiman et al., "Synthesis and Antimitotic/Cytotoxic Activity of Hemiasterlin Analogues," J. Nat. Prod. vol. 66, pp. 183-199 (2003).
Restriction Requirement dated Aug. 30, 2016 in U.S. Appl. No. 14/857,733.
Non-final Office Action dated Nov. 14, 2016 in U.S. Appl. No. 14/857,733.
Non-final Office Action dated Jun. 6, 2017 in U.S. Appl. No. 14/857,733.
Notice of Allowance dated Sep. 14, 2017 in U.S. Appl. No. 14/857,733.
Restriction Requirement dated Jun. 4, 2018 in U.S. Appl. No. 15/108,247.
Restriction Requirement dated May 16, 2018 in U.S. Appl. No. 15/872,642.
Non-final Office Action dated Sep. 13, 2018 in U.S. Appl. No. 15/872,642.
U.S. Appl. No. 15/872,642 (U.S. Publication No. 2018-0208667A1), entitled, "Cytotoxic and Anti-Mitotic Compounds, and Methods of Using the Same" filed Jan. 16, 2018, of Zymeworks Inc.

* cited by examiner

CYTOTOXIC AND ANTI-MITOTIC COMPOUNDS, AND METHODS OF USING THE SAME

BACKGROUND

Field

The invention relates to biologically active compounds, compositions comprising the same, and methods of using such biologically active compounds and compositions for the treatment of cancer and other diseases.

Description of the Related Art

Promising new cancer therapeutics include the dolastatins and synthetic dolastatin analogs such as auristatins (U.S. Pat. Nos. 5,635,483, 5,780,588, 6,323,315, and 6,884,869; Shnyder et al. (2007) Int. J. Oncol. 31:353-360; Otani, M. et al. Jpn. J. Cancer Res. 2000, 91, 837-844; PCT Intl. Publ. Nos. WO 01/18032 A3, WO 2005/039492, WO2006/132670, and WO 2009/095447; Fennell, B. J. et al. J. Antimicrob. Chemther. 2003, 51, 833-841). Dolastatins and auristatins have been shown to interfere with microtubule dynamics, thus disrupt cell division (Woyke et al. (2001) Antimicrob. Agents Chemother. 45(12):3580-3584) and have anticancer (U.S. Pat. No. 5,663,149) and antifungal activity (Pettit et al. (1998) Antimicrob. Agents Chemother. 42:2961-2965). Unfortunately, despite early enthusiasm, dolastatin 10 showed poor results as a single agent in phase II clinical trials (Shnyder (2007), supra). Certain compounds in the auristatins family have shown greater promise as clinical candidates with improved efficacy and pharmacological characteristics over the dolastatins (Pettit et al. (1995) Anti-Cancer Drug Des. 10:529-544; Pettit et al. (1998) Anti-Cancer Drug Des. 13:243-277; Shnyder (2007), supra). Various synthetic analogs of this structural type have been described (U.S. Pat. Nos. 6,569,834; 6,124,431; and Pettit et al. (2011) J. Nat. Prod. 74:962-968).

The auristatins have several properties which make them attractive for pharmaceutical development. First, these compounds are extremely potent. Second, their preparation is straight-forward because of the peptidic scaffold. Third, they possess good pharmacokinetic and metabolic profiles compared to peptides in general, or to other cancer drug classes in particular. Finally, the peptidic structure of the auristatins is similar to that of an antibody, so when these compounds are used as part of an antibody-drug conjugate (ADC), they are less likely to cause precipitation or formation of high molecular weight aggregates (Doronina et al. (2003) Nat. Biotechnology 21(7):778-784).

Potent cytotoxic and anti-mitotic compositions are highly desired for the treatment of a number of devastating disorders, including cancer. While a wide variety of auristatin analogs have been generated, many, exhibit reduced potency that limits utility in methods of medical treatment. For the foregoing reasons, while progress has been made in this field, there is a need for additional potent anti-mitotic and cytotoxic compounds having preferred characteristics that render them suitable for the treatment of a variety of disorders, including cancer. The present disclosure fulfills these needs and provides further related advantages.

BRIEF SUMMARY

In brief, the present disclosure is directed to biologically active compounds, compositions comprising the same, and methods of using such compounds and compositions. Provided are compounds of Formula I:

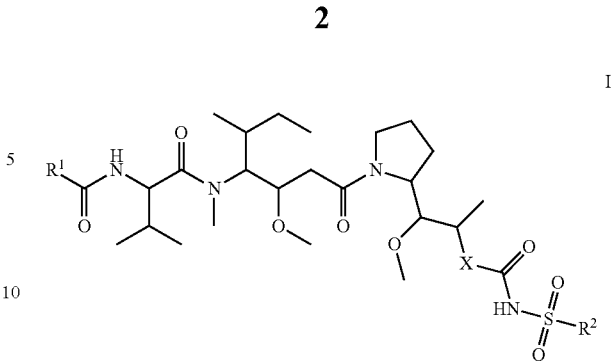

and pharmaceutically acceptable salts thereof, wherein:

$R^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloalkyl, heterocyclyl, heterocyclyl-$C_1$-$C_6$ alkyl, hydroxyl, and thio; or $R^1$ is $R^a R^b NCH(R^c)$—;

$R^a$ is selected from: H and $C_1$-$C_6$ alkyl;

$R^b$ is $C_1$-$C_6$ alkyl; and $R^c$ is $R^d$—$C(CH_3)_2$—; and $R^d$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio; or $R^b$ and $R^c$ taken together with the atoms to which they are each bonded form a heterocyclyldiyl;

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl; and X is —C(O)NHCH(CH$_2$R$^3$)—, or X is absent; and $R^3$ is selected from: aryl, heteroaryl, and $C_3$-$C_7$ cycloalkyl, each optionally substituted with one substituent selected from amino and hydroxyl.

In one embodiment, the invention provides a method of making a compound described herein or pharmaceutically acceptable salt thereof.

In another embodiment, a pharmaceutical composition is provided comprising a compound described herein or a pharmaceutically acceptable salt thereof, and a pharmaceutically acceptable carrier, diluent or excipient.

In another embodiment, a method of using a compound described herein or a pharmaceutically acceptable salt thereof, in therapy is provided. In particular, the present disclosure provides a method of treating cancer in a mammal comprising administering to a mammal in need thereof an effective amount of a compound described herein or a pharmaceutically acceptable salt thereof, or a pharmaceutical composition comprising a compound described herein or a pharmaceutically acceptable salt thereof, and a pharmaceutically acceptable carrier diluent or excipient.

In another embodiment, the present disclosure provides a method of inhibiting tumor growth in a mammal comprising administering to a mammal in need thereof an effective amount of a compound described herein or a pharmaceutically acceptable salt thereof, or a pharmaceutical composition comprising a compound described herein or a pharmaceutically acceptable salt thereof, and a pharmaceutically acceptable carrier, diluent or excipient.

In another embodiment, the present disclosure provides a method of killing cancer cells in vitro using a compound described herein or a pharmaceutically acceptable salt thereof. In another embodiment, the present disclosure provides a method of killing cancer cells in vivo in a mammal, comprising administering to a mammal in need thereof an effective amount of a compound described herein or a pharmaceutically acceptable salt thereof, or a pharmaceutical composition comprising a compound described herein or a pharmaceutically acceptable salt thereof, and a pharmaceutically acceptable carrier, diluent or excipient.

In another embodiment, the present disclosure provides a method of increasing the survival time of a mammal having cancer, comprising administering to such mammal an effective amount of a compound described herein or a pharmaceutically acceptable salt thereof, or a pharmaceutical composition comprising a compound described herein or a pharmaceutically acceptable salt thereof, and a pharmaceutically acceptable carrier, diluent or excipient.

In another embodiment, the present disclosure provides a use of a compound described herein, or a pharmaceutically acceptable salt thereof, in the manufacture of a medicament for treating cancer in a mammal.

In another embodiment, the present disclosure provides a use of a compound described herein, or a pharmaceutically acceptable salt thereof, in the manufacture of a medicament for inhibiting tumor growth in a mammal.

In another embodiment, the present disclosure provides a use of a compound described herein, or a pharmaceutically acceptable salt thereof, in the manufacture of a medicament for increasing survival of a mammal having cancer.

In another embodiment, the present disclosure provides a compound or a pharmaceutical composition described herein, for use in a method of treatment of the human or animal body by therapy.

In another embodiment, the present disclosure provides a compound or a pharmaceutical composition described herein, for use in treating cancer in a mammal.

In another embodiment, the present disclosure provides a compound or a pharmaceutical composition described herein, for use in inhibiting tumor growth in a mammal.

In another embodiment, the present disclosure provides a compound or a pharmaceutical composition described herein, for use in increasing survival of a mammal having cancer.

In one embodiment, compositions comprising a biologically active compound as described herein or a pharmaceutically acceptable salt thereof, linked directly or indirectly to a targeting moiety are provided.

In one embodiment, the invention provides compositions of Formula II:

$$(T)-(L)-(D) \quad \text{II}$$

wherein (T) is a targeting moiety, (L) is an optional linker, and (D) is a compound of Formula I, Ia, Ib, Ic, Id, Ie, If, Ig, Ih, Ii, Ij, or Ik, or a pharmaceutically acceptable salt thereof. (D) is covalently attached to (L), if (L) is present, or (T), if (L) is not present.

In one embodiment, the targeting moiety is an antibody. Accordingly, in one embodiment, antibody-drug conjugates (ADCs) comprising a compound described herein, or a pharmaceutically acceptable salt or prodrug thereof, are provided.

In one embodiment, the invention provides a method of making a composition of Formula II.

In another embodiment, a pharmaceutical composition is provided comprising a composition of Formula II, or a pharmaceutically acceptable salt thereof, and a pharmaceutically acceptable carrier, diluent or excipient.

In another embodiment, a method of using a composition of Formula II in therapy is provided. In particular, the present disclosure provides a method of treating cancer in a mammal comprising administering to a mammal in need thereof an effective amount of a composition of Formula II or a pharmaceutical composition comprising a composition of Formula II and a pharmaceutically acceptable carrier diluent or excipient.

In another embodiment, the present disclosure provides a method of inhibiting tumor growth in a mammal comprising administering to a mammal in need thereof an effective amount of a composition of Formula II or a pharmaceutical composition comprising a composition of Formula II and a pharmaceutically acceptable carrier, diluent or excipient.

In another embodiment, the present disclosure provides a method of killing cancer cells in vitro using a composition of Formula II. In another embodiment, the present disclosure provides a method of killing cancer cells in vivo in a mammal, comprising administering to a mammal in need thereof an effective amount of a composition of Formula II or a pharmaceutical composition comprising a composition of Formula II and a pharmaceutically acceptable carrier, diluent or excipient.

In another embodiment, the present disclosure provides a method of increasing the survival time of a mammal having cancer, comprising administering to a mammal in need thereof an effective amount of a composition of Formula II or a pharmaceutical composition comprising a composition of Formula II and a pharmaceutically acceptable carrier, diluent or excipient.

In another embodiment, the present disclosure provides a use of a composition of Formula II, or a pharmaceutically acceptable salt thereof, in the manufacture of a medicament for treating cancer in a mammal.

In another embodiment, the present disclosure provides a use of a composition of Formula II, in the manufacture of a medicament for inhibiting tumor growth in a mammal.

In another embodiment, the present disclosure provides a use of a composition of Formula II, in the manufacture of a medicament for increasing survival of a mammal having cancer.

In another embodiment, the present disclosure provides a composition of Formula II or a pharmaceutical composition comprising a composition of Formula II, for use in a method of treatment of the human or animal body by therapy.

In another embodiment, the present disclosure provides a composition of Formula II or a pharmaceutical composition comprising a composition of Formula II, for use in treating cancer in a mammal.

In another embodiment, the present disclosure provides a composition of Formula II or a pharmaceutical composition comprising a composition of Formula II, for use in inhibiting tumor growth in a mammal.

In another embodiment, the present disclosure provides a composition of Formula II or a pharmaceutical composition comprising a composition of Formula II, for use in increasing survival of a mammal having cancer.

These and other aspects of the disclosure will be apparent upon reference to the following detailed description.

DETAILED DESCRIPTION

Figure 1:
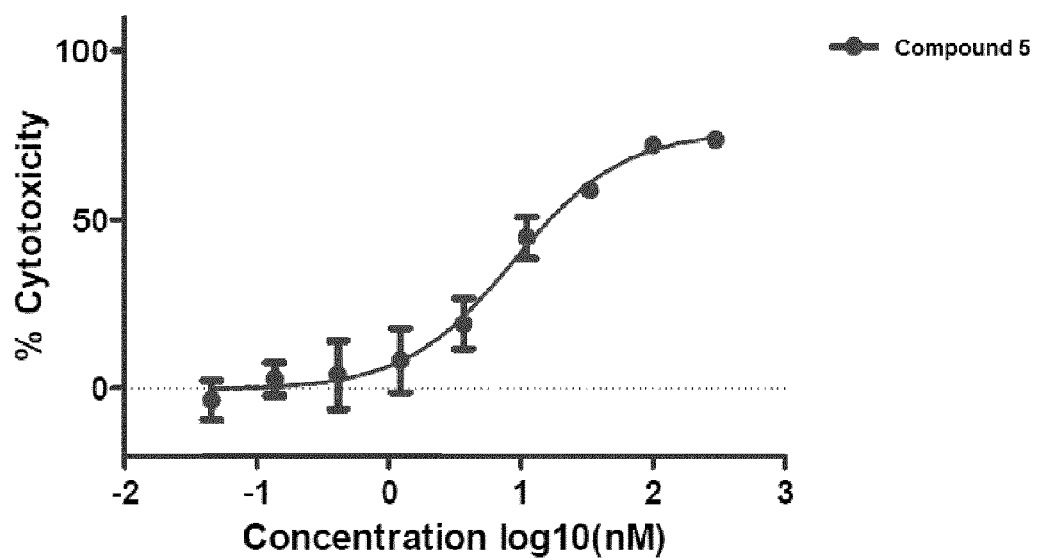
FIG. 1 shows the cytotoxicity of Compound 5 on the Her2-Positive HCC1954 cell line.

In the following description, certain specific details are set forth in order to provide a thorough understanding of various embodiments of the disclosure. However, one skilled in the art will understand that the disclosure may be practiced without these details.

Definitions

Unless stated otherwise, the following terms and phrases as used herein are intended to have the following meanings. When trade names are used herein, applicants intend to independently include the trade name product formulation, the generic drug, and the active pharmaceutical ingredient(s) of the trade name product.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Chemical Groups

All combinations of the embodiments pertaining to the chemical groups represented by the variables (e.g., $R^a$, $R^b$, $R^c$, $R^d$, $R^e$, $R^f$, $R^g$, $R^h$, $R^i$, $R^j$, $R^k$, $R^m$, $R^1$, $R^2$, $R^{2a}$, $R^3$, $R^4$, $R^5$, $R^6$, $R^7$, $R^8$, $R^9$, $R^4$, $R^{10}$, $R^{11}$, $R^{12}$, $R^{13}$, $R^{14}$, $R^{15}$, $R^{16}$, X, Y, and Z contained within the generic chemical formulae described herein (e.g., I, Ia, Ib, Ic, Id, Ie, If, Ig, Ih, Ii, Ij, Ik, Im, In, II, III, IV, V, VI, VII, and VIII) are specifically embraced by the present invention just as if each and every combination was individually explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein. In addition, in the event that a list of substituents is listed for any particular $R^a$, $R^b$, $R^c$, $R^d$, $R^e$, $R^f$, $R^g$, $R^h$, $R^i$, $R^j$, $R^k$, $R^m$, $R^1$, $R^2$, $R^{2a}$, $R^3$, $R^4$, $R^5$, $R^6$, $R^7$, $R^8$, $R^9$, $R^4$, $R^{10}$, $R^{11}$, $R^{12}$, $R^{13}$, $R1^4$, $R^{15}$, $R^{16}$, X, Y, or Z in a particular embodiment and/or claim, it is understood that each individual substituent may be deleted from the particular embodiment and/or claim and that the remaining list of substituents will be considered to be within the scope of the present disclosure.

The term "acyloxy", as used herein, includes —OC(O)-alkyl, wherein alkyl is as defined herein. Examples of acyloxy include, but are not limited to: formyloxy, acetoxy, propionyloxy, isobutyryloxy, pivaloyloxy, and the like.

The term "acylthio", as used herein, refers to —SC(O)-alkyl, wherein alkyl is as defined herein. Examples of acylthio include, but are not limited to: formylthio, acetylthio, propionylthio, isobutyrylthio, pivaloylthio, and the like.

The term "alkoxy", as used herein, refers to —O-alkyl, wherein alkyl is as defined herein. Examples of alkyl include, but are not limited to: methoxy, ethoxy, n-propoxy, isopropoxy, n-butoxy, sec-butoxy, isobutoxy, t-butoxy, pentyloxy, isopentyloxy, t-pentyloxy, neo-pentyloxy, 1-methylbutoxy, 2-methylbutoxy, n-hexyloxy, and the like.

The term "alkoxycarbonyl", as used herein, refers to —C(O)O-alkyl. Examples of alkoxycarbonyl include, but are not limited to: methoxycarbonyl, ethoxycarbonyl, n-propoxycarbonyl, isopropoxycarbonyl, n-butoxycarbonyl, sec-butoxycarbonyl, isobutoxycarbonyl, t-butoxycarbonyl, pentyloxycarbonyl, isopentyloxycarbonyl, t-pentyloxycarbonyl, neo-pentyloxycarbonyl, 1-methylbutoxycarbonyl, 2-methylbutoxycarbonyl, n-hexyloxycarbonyl, and the like.

The term "alkenyldiyl", as used herein, refers to a straight or branched unsaturated hydrocarbon a divalent radical containing the specified number of carbon atoms, and one or more carbon-carbon double bonds, e.g., $C_2$-$C_6$ alkenyldiyl, $C_2$-$C_4$ alkenyldiyl, or $C_2$ alkenyldiyl. Examples of alkenyldiyl include, but are not limited to: ethenyldiyl, n-propenyldiyl, isopropenyldiyl, n-butenyldiyl, sec-butenyldiyl, isobutenyldiyl, t-butenyldiyl, pentenyldiyl, isopentenyldiyl, t-pentenyldiyl, neo-pentenyldiyl, 1-methylbutenyldiyl, 2-methylbutenyldiyl, n-hexenyldiyl, and the like.

The term "alkyl", as used herein, refers to a straight or branched saturated hydrocarbon radical containing the specified number of carbon atoms, e.g., $C_1$-$C_6$ alkyl, $C_1$-$C_4$ alkyl, or $C_2$ alkyl. Examples of alkyl include, but are not limited to: methyl, ethyl, n-propyl, isopropyl, n-butyl, sec-butyl, isobutyl, t-butyl, pentyl, isopentyl, t-pentyl, neo-pentyl, 1-methylbutyl, 2-methylbutyl, n-hexyl, and the like.

The term "alkyldiyl", as used herein, refers to a straight or branched saturated hydrocarbon a divalent radical containing the specified number of carbon atoms, e.g., $C_1$-$C_6$ alkyldiyl, $C_1$-$C_4$ alkyldiyl, or $C_2$ alkyldiyl. Examples of alkyldiyl include, but are not limited to: methyldiyl, ethyldiyl, n-propyldiyl, isopropyldiyl, n-butyldiyl, sec-butyldiyl, isobutyldiyl, t-butyldiyl, pentyldiyl, isopentyldiyl, t-pentyldiyl, neo-pentyldiyl, 1-methylbutyldiyl, 2-methylbutyldiyl, n-hexyldiyl, and the like.

The term "alkylamino", as used herein, refers to —NH-alkyl, wherein alkyl is as defined herein. Examples of alkylamino include, but are not limited to: methylamino, ethylamino, n-propylamino, isopropylamino, n-butylamino, sec-butylamino, isobutylamino, t-butylamino, pentylamino, isopentylamino, t-pentylamino, neo-pentylamino, 1-methylbutylamino, 2-methylbutylamino, n-hexylamino, and the like.

The term "alkylthio", as used herein, refers to —S-alkyl, wherein alkyl is as defined herein. Examples of alkylthio include, but are not limited to: methylthio, ethylthio, n-propylthio, isopropylthio, n-butylthio, sec-butylthio, isobutylthio, t-butylthio, pentylthio, isopentylthio, t-pentylthio, neo-pentylthio, 1-methylbutylthio, 2-methylbutylthio, n-hexylthio, and the like.

The term "amino", as used herein, refers to —$NH_2$.

The term "amino-cycloalkyl", as used herein, refers to a cycloalkyl group, substituted with one amino substituent, as those terms are defined herein. Examples of amino-cycloalkyl include, but are not limited to: aminocyclopropyl, aminocyclobutyl, aminocyclopentyl, aminocyclohexyl, and the like.

The term "amino-alkyl", as used herein, refers to an alkyl group, substituted with one amino substituent, as those terms are defined herein. Examples of amino-alkyl include, but are not limited to: aminomethyl, aminoethyl, amino-n-propyl, amino-isopropyl, amino-n-butyl, amino-sec-butyl, amino-isobutyl, amino-t-butyl, amino-pentyl, amino-isopentyl, amino-t-pentyl, amino-neo-pentyl, amino-1-methylbutyl, amino-2-methylbutyl, amino-n-hexyl, and the like.

The term "amino-aryl", as used herein, refers to an aryl group, substituted with one amino substituent, as those terms are defined herein. Examples of amino-aryl include, but are not limited to: amino-phenyl, amino-naphthalenyl, and the like.

The term "amino-heterocyclyl", as used herein, refers to an heterocyclyl group, substituted with one amino substituent, as those terms are defined herein. Examples of amino-heterocyclyl include, but are not limited to: amino-pyrrolidinyl, amino-piperidinyl, and the like.

The term "aryl", as used herein, refers to a radical derived from a 6- to 12-membered mono- or bicyclic hydrocarbon ring system wherein at least one ring aromatic. Examples of aryl include, but are not limited to: phenyl, naphthalenyl, 1,2,3,4-tetrahydro-naphthalenyl, 5,6,7,8-tetrahydro-naphthalenyl, indanyl, and the like.

The term "aryl-alkyl", as used herein, refers to an alkyl group, substituted with one aryl substituent, as those terms are defined herein. Examples of aryl-alkyl include, but are not limited to: benzyl, phenethyl, phenylpropyl, naphthalenylmethyl, and the like.

The term "aryldiyl", as used herein, refers to a divalent radical derived from a 6- to 12-membered mono- or bicyclic hydrocarbon ring system wherein at least one ring aromatic. Examples of aryldiyl include, phenyldiyl, naphthalenyldiyl, 1,2,3,4-tetrahydro-naphthalenyldiyl, 5,6,7,8-tetrahydro-naphthalenyldiyl, indanyldiyl, and the like.

The term "carboxamide", as used herein, refers to —C(O)$NH_2$.

The term "carboxyl", as used herein, refers to —C(O)OH.

The term "cyano", as used herein, refers to —CN.

The term "cycloalkyl", as used herein, refers to a cyclic saturated hydrocarbon radical containing the specified number of carbon atoms, e.g., $C_3$-$C_7$ alkyl, or $C_4$-$C_7$ alkyldiyl. Examples of cycloalkyl include, but are not limited to: cyclopropyl, cyclobutyl, cyclopentyl, cyclohexyl, and the like.

The term "cycloalkyl-alkyl", as used herein, refers to an alkyl group, substituted with one cycloalkyl substituent, as those terms are defined herein. Examples of cycloalkyl-alkyl include, but are not limited to: cyclopropylmethyl, cyclobutylmethyl, cyclopentylmethyl, cyclohexylmethyl, cyclopropylethyl, cyclobutylethyl, cyclopentylethyl, cyclohexylethyl, and the like.

The term "cycloalkyldiyl", as used herein, refers to a divalent cyclic saturated hydrocarbon radical containing the specified number of carbon atoms, e.g., $C_3$-$C_7$ cycloalkyldiyl, or $C_4$-$C_7$ alkyldiyl. Examples of cycloalkyldiyl include, but are not limited to: cyclopropyldiyl, cyclobutyldiyl, cyclopentyldiyl, cyclohexyldiyl, and the like.

The term "guanidino", as used herein, refers to —NH—C(=NH)—$NH_2$.

The term "halo", as used herein, refers to —F, —Cl, —Br, and —I.

The term "haloacyl", as used herein, refers to —C(O)-haloalkyl, wherein haloalkyl is as defined herein. Examples of haloacyl include, but are not limited to: difluoroacetyl, trifluoroacetyl, 3,3,3-trifluoropropanoyl, pentafluoropropanoyl, and the like.

The term "haloalkoxy", as used herein, refers to —O-haloalkyl, wherein haloalkyl is as defined herein. Examples of haloalkoxy include, but are not limited to: difluoromethoxy, trifluoromethoxy, 2,2,2-trifluoroethoxy, pentafluoroethoxy, and the like.

The term "haloalkyl", as used herein, refers to and alkyl group as defined herein substituted with from one or more halogens. A fully substituted haloalkyl can be represented by the formula $C_nL_{2n+1}$ wherein L is a halogen. When more than one halogen is present then they may be the same or different and selected from the group consisting of F, Cl, Br, and I. Examples of haloalkyl groups include, but are not limited to: fluoromethyl, difluoromethyl, trifluoromethyl, chlorodifluoromethyl, 2,2,2-trifluoroethyl, pentafluoroethyl, and the like.

The term "heteroaryl", as used herein, refers to a radical derived from a 6- to 12-membered mono- or bicyclic ring system wherein at least one ring atom is a heteroatom and at least one ring is aromatic. Examples of a heteroatom include, but are not limited to: O, S, N, and the like. Examples of heteroaryl include, but are not limited to: pyridyl, benzofuranyl, pyrazinyl, pyridazinyl, pyrimidinyl, triazinyl, quinolinyl, benzoxazolyl, benzothiazolyl, 1H-benzimidazolyl, isoquinolinyl, quinazolinyl, quinoxalinyl, pyrrolyl, indolyl, 1H-benzoimidazol-2-yl, benzo[1,3]dioxol-5-yl, 3,4-dihydro-2H-benzo[1,4]oxazin-7-yl, 2,3-dihydro-benzofurn-7-yl, 2,3-dihydro-indol-1-yl, and the like.

The term "heteroaryl-alkyl", as used herein, refers to an alkyl group, substituted with one heteroaryl substituent, as those terms are defined herein. Examples of heteroaryl-alkyl include, but are not limited to: pyridylmethyl, benzofuranylmethyl, pyrazinylmethyl, pyridazinylmethyl, pyrimidinylmethyl, triazinylmethyl, quinolinylmethyl, benzoxazolylmethyl, benzothiazolylmethyl, 1H-benzimidazolylmethyl, isoquinolinylmethyl, quinazolinylmethyl, quinoxalinylmethyl, pyrrolylmethyl, indolylmethyl, 1H-benzoimidazol-2-ylmethyl, benzo[1,3]dioxol-5-ylmethyl, 3,4-dihydro-2H-benzo[1,4]oxazin-7-ylmethyl, 2,3-dihydro-benzofurn-7-ylmethyl, 2,3-dihydro-indol-1-ylmethyl, and the like.

The term "heteroaryldiyl", as used herein, refers to a divalent radical derived from a 6- to 12-membered mono- or bicyclic ring system wherein at least one ring atom is a heteroatom and at least one ring is aromatic. Examples of a heteroatom include, but are not limited to: O, S, N, and the like. Examples of heteroaryldiyl include, but are not limited to: thiazolyldiyl, 2,4-thiazolyldiyl, triazolyldiyl, 1,2,3-triazolyl-1,4-diyl, pyridyldiyl, benzofuranyldiyl, pyrazinyldiyl, pyridazinyldiyl, pyrimidinyldiyl, triazinyldiyl, quinolinyldiyl, benzoxazolyldiyl, benzothiazolyldiyl, 1H-benzimidazolyldiyl, isoquinolinyldiyl, quinazolinyldiyl, quinoxalinyldiyl, pyrrolyldiyl, indolyldiyl, 1H-benzoimidazol-2-yldiyl, benzo[1,3]dioxol-5-yldiyl, 3,4-dihydro-2H-benzo[1,4]oxazin-7-yldiyl, 2,3-dihydro-benzofurn-7-yldiyl, 2,3-dihydro-indol-1-yldiyl, and the like. Examples of include, but are not limited to: and the like.

The term "heterocyclyl", as used herein, refers to a radical derived from a 3- to 12-membered mono- or bicyclic non-aromatic ring system wherein at least one ring atom is a heteroatom. Examples of a heteroatom include, but are not limited to: O, S, N, and the like. A heterocyclyl substituent can be attached via any of its available ring atoms, for example, a ring carbon, or a ring nitrogen. In some embodiments, the heterocyclyl group is a 3-, 4-, 5-, 6- or 7-membered containing ring. Examples of a heterocyclyl group include, but are not limited to: aziridin-1-yl, aziridin-2-yl, azetidin-1-yl, azetidin-2-yl, azetidin-3-yl, piperidin-1-yl, piperidin-2-yl, piperidin-3-yl, piperidin-4-yl, morpholin-2-yl, morpholin-3-yl, morpholin-4-yl, piperazin-1-yl, piperazin-2-yl, piperazin-3-yl, piperazin-4-yl, pyrrolidin-1-yl, pyrrolidin-2-yl, pyrrolidin-3-yl, [1,3]-dioxolan-2-yl, thiomorpholin-4-yl, [1,4]oxazepan-4-yl, 1,1-dioxo-1$\lambda^6$-thiomorpholin-4-yl, azepan-1-yl, azepan-2-yl, azepan-3-yl, azepan-4-yl, octahydro-quinolin-1-yl, octahydro-isoquinolin-2-yl, and the like.

The term "heterocyclyl-alkyl", as used herein, refers to an alkyl group, substituted with one heterocyclyl substituent, as those terms are defined herein. Examples of heterocyclyl-alkyl include, but are not limited to: azetidin-3-ylmethyl, piperidin-1-ylmethyl, piperidin-2-ylmethyl, piperidin-3-ylmethyl, piperidin-4-ylmethyl, morpholin-2-ylmethyl, morpholin-3-ylmethyl, morpholin-4-ylmethyl, piperazin-1-ylmethyl, piperazin-2-ylmethyl, piperazin-3-ylmethyl, piperazin-4-ylmethyl, pyrrolidin-1-ylmethyl, pyrrolidin-2-ylmethyl, pyrrolidin-3-ylmethyl, [1,3]-dioxolan-2-ylmethyl, thiomorpholin-4-ylmethyl, [1,4]oxazepan-4-ylmethyl, 1,1-dioxo-1$\lambda^6$-thiomorpholin-4-ylmethyl, azepan-1-ylmethyl, azepan-2-ylmethyl, azepan-3-ylmethyl, azepan-4-ylmethyl, octahydro-quinolin-1-ylmethyl, octahydro-isoquinolin-2-yl, and the like.

The term "heterocyclyldiyl", as used herein, refers to a divalent radical derived from a 3- to 12-membered mono- or bicyclic non-aromatic ring system wherein at least one ring atom is a heteroatom. Examples of a heteroatom include, but are not limited to: O, S, N, and the like. A heterocyclyldiyl substituent can be attached via any two of its available ring atoms, for example, ring carbons, or ring nitrogens. In some embodiments, the heterocyclyldiyl is a 3-, 4-, 5-, 6- or 7-membered containing ring. Examples of a heterocyclyldiyl group include, but are not limited to: aziridin-1-yldiyl, aziridin-2-yldiyl, azetidin-1-yldiyl, azetidin-2-yldiyl, azetidin-3-yldiyl, piperidin-1-yldiyl, piperidin-2-yldiyl, piperidin-3-yldiyl, piperidin-4-yldiyl, morpholin-2-yldiyl, morpholin-3-yldiyl, morpholin-4-yldiyl, piperazin-1-yldiyl, piperazin-2-yldiyl, piperazin-3-yldiyl, piperazin-4-yldiyl, pyrrolidin-1-yldiyl, pyrrolidin-2-yldiyl, pyrrolidin-3-yldiyl, [1,3]-dioxolan-2-yldiyl, thiomorpholin-4-yldiyl, [1,4]oxazepan-4-yldiyl, 1,1-dioxo-1$\lambda^6$-thiomorpholin-4-yldiyl, azepan-1-yldiyl, azepan-2-yldiyl, azepan-3-yldiyl, azepan-4-yldiyl, octahydro-quinolin-1-yldiyl, octahydro-isoquinolin-2-yldiyl, and the like.

The term "hydroxyl", as used herein, refers to —OH.

The term "hydroxy-alkyl", as used herein, refers to an alkyl group, substituted with one hydroxy substituent, as those terms are defined herein. Examples of hydroxy-alkyl include, but are not limited to: hydroxymethyl, hydroxyethyl, hydroxy-n-propyl, hydroxy-isopropyl, hydroxy-n-butyl, hydroxy-sec-butyl, hydroxy-isobutyl, hydroxy-t-butyl, hydroxy-pentyl, hydroxy-isopentyl, hydroxy-t-pentyl, hydroxy-neo-pentyl, hydroxy-1-methylbutyl, hydroxy-2-methylbutyl, hydroxy-n-hexyl, and the like.

The term "nitro", as used herein, refers to —NO$_2$.

The term "oxo", as used herein, refers to =O.

The term "thio", as used herein, refers to —SH.

The term "thio-alkyl", as used herein, refers to —S-alkyl, wherein alkyl is as defined herein. Examples of include, but are not limited to: methylthio, ethylthio, n-propylthio, isopropylthio, n-butylthio, sec-butylthio, isobutylthio, t-butylthio, pentylthio, isopentylthio, t-pentylthio, neo-pentylthio, 1-methylbutylthio, 2-methylbutylthio, n-hexylthio, and the like.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene (methyldiyl) group can be substituted by 1 or 2 substituents, a phenyl group can be substituted by 1, 2, 3, 4, or 5 substituents, a naphthyl group can be substituted by 1, 2, 3, 4, 5, 6, or 7 substituents, and the like. Likewise, "substituted with one or more substituents" refers to the substitution of a group with one substituent up to the total number of substituents physically allowed by the group. Further, when a group is substituted with more than one group they can be identical or they can be different.

Compounds described herein can also include tautomeric forms, such as keto-enol tautomers, and the like. Tautomeric forms can be in equilibrium or sterically locked into one form by appropriate substitution. It is understood that the various tautomeric forms are within the scope of the compounds of the present invention.

It is understood and appreciated that compounds of Formula I and formulae related thereto may have one or more chiral centers and therefore can exist as enantiomers and/or diastereoisomers. The invention is understood to extend to and embrace all such enantiomers, diastereoisomers and mixtures thereof, including but not limited to racemates. It is understood that compounds of Formula I and formulae used throughout this disclosure are intended to represent all individual enantiomers and mixtures thereof, unless stated or shown otherwise.

The term "protecting group," as used herein, refers to a labile chemical moiety which is known in the art to protect reactive groups including without limitation, hydroxyl and amino groups, against undesired reactions during synthetic procedures. Hydroxyl and amino groups which protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Groups can be selectively incorporated into compounds of the present disclosure as precursors. For example, an amino group can be placed into a compound described herein as an azido group that can be chemically converted to the amino group at a desired point in the synthesis. Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1 72. Examples of "hydroxyl protecting groups" include, but are not limited to, t-butyl, t-butoxymethyl, methoxymethyl, tetrahydropyranyl, 1-ethoxyethyl, 1-(2-chloroethoxy) ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TBDPS), triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Examples of "amino protecting groups" include, but are not limited to, carbamate-protecting groups, such as 2-trimethylsilylethoxycarbonyl (Teoc), 1-methyl-1-(4-biphenylyfiethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide-protecting groups, such as 2-nitrobenzenesulfonyl; and imine and cyclic imide protecting groups, such as phthalimido and dithiasuccinoyl.

"Prodrug", as used herein, refers to a compound that may be converted under physiological conditions or by solvolysis to a biologically active compound described herein. Thus, the term "prodrug" refers to a metabolic precursor of a compound described herein that is pharmaceutically acceptable. A prodrug may be inactive when administered to a subject in need thereof, but is converted in vivo to an active compound described herein. In one embodiment, a prodrug is rapidly transformed in vivo to yield the parent compound described herein, for example, by hydrolysis in blood. In one embodiment, a prodrug may be stable in plasma or blood. In one embodiment, a prodrug may be targeted form of a compound described herein. The prodrug compound often offers advantages of solubility, tissue compatibility or delayed release in a mammalian organism (see, Bundgard, H., Design of Prodrugs (1985), pp. 7 9, 21 24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" includes any covalently bonded carriers, which release the active compound described herein in vivo when such prodrug is administered to a mammalian subject. Conjugates, including ADCs, as disclosed herein, are such prodrugs of the compounds described herein. Prodrugs of a compound described herein may be prepared by modifying functional groups present in a compound described herein in such a way that the modifications are cleaved, either in routine manipulation or in vivo, to the parent compound described herein. Prodrugs include compounds described herein wherein a hydroxy, amino or mercapto group is bonded to any group that, when the prodrug of the compound described herein is administered to a mammalian subject, cleaves to form a free hydroxy, free amino or free mercapto group, respectively. Examples of prodrugs include, but are not limited to, acetate, formate and benzoate derivatives of alcohol functional groups, and amide derivatives of amine functional groups in the compounds described herein, and the like.

The present disclosure also encompasses all compounds described herein being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds are useful to help determine or measure the effectiveness of the compounds, by characterizing, for example, the site or mode of action, or binding affinity to pharmacologically important site of action. Certain isotopically-labelled compounds described herein, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds described herein can generally be prepared by conventional techniques known to those skilled in the art or by processes analogous to those described in the Preparations and Examples as set out below using an appropriate isotopically-labeled reagent in place of the non-labeled reagent previously employed.

The present disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the present disclosure includes compounds produced by a process comprising administering a compound of this disclosure to a mammal for a period of time sufficient to yield a metabolic product thereof. Such products are typically identified by administering a radiolabelled compound described herein in a detectable dose to an animal, such as rat, mouse, guinea pig, monkey, or to human, allowing sufficient time for metabolism to occur, and isolating its conversion products from the urine, blood or other biological samples.

"Stable compound" and "stable structure", as used herein, refer to a compound that is sufficiently robust to survive isolation to a useful degree of purity from a reaction mixture, and formulation into an efficacious therapeutic agent.

Other Definitions

The term "antibody" herein is used in the broadest sense and specifically covers intact monoclonal antibodies, polyclonal antibodies, multispecific antibodies (e.g., bispecific antibodies) formed from at least two intact antibodies, and antibody fragments, so long as they exhibit the desired biological activity. The term "antibody" refers to a full-length immunoglobulin molecule or a functionally active portion of a full-length immunoglobulin molecule, i.e., a molecule that contains an antigen binding site that immunospecifically binds an antigen of a target of interest or part thereof.

The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect the immunoglobulin is of human, murine, or rabbit origin. In another aspect, the antibodies are polyclonal, monoclonal, multi-specific (e.g., bispecific), human, humanized or chimeric antibodies, linear antibodies, single chain antibodies, diabodies, maxibodies, minibodies, Fv, Fab fragments, F(ab') fragments, F(ab')2 fragments, fragments produced by a Fab expression library, anti-idiotypic (anti-Id) antibodies, CDRs, and epitope-binding fragments of any of the above which immunospecifically bind to a target antigen.

The term "monoclonal antibody", as used herein, refers to an antibody obtained from a population of substantially homogeneous antibodies, i.e., the individual antibodies comprising the population are identical except for possible naturally-occurring mutations that may be present in minor amounts. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(S) is identical with or homologous to corresponding sequences in antibodies derived from another species or belonging to another antibody class or subclass, as well as fragments of such antibodies (see, e.g., U.S. Pat. No. 4,816,567; and Morrison et al., 1984, Proc. Natl. Acad. Sci. USA 81:6851-6855). Monoclonal antibodies also include humanized antibodies may contain a completely human constant region and a CDRs from a nonhuman source.

An "intact" antibody is one which comprises an antigen-binding variable region as well as a light chain constant domain (CL) and heavy chain constant domains, $C_{H1}$, $C_{H2}$ and $C_{H3}$. The constant domains may be native sequence constant domains (e.g., human native sequence constant domains) or amino acid sequence variant thereof.

An intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. In some embodiments, the antibody lacks effector function.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; maxibodies; minibodies; and multispecific antibodies formed from antibody fragment(S).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" an antigen of interest is one capable of binding that antigen with sufficient affinity such that the antibody is useful in targeting a cell expressing the antigen.

A "native sequence" polypeptide is one which has the same amino acid sequence as a polypeptide derived from nature. Such native sequence polypeptides can be isolated from nature or can be produced by recombinant or synthetic means. Thus, a native sequence polypeptide can have the amino acid sequence of naturally-occurring human polypeptide, murine polypeptide, or polypeptide from any other mammalian species.

The term "intracellular metabolite" refers to a compound resulting from a metabolic process or reaction inside a cell on a composition described herein (e.g., an antibody drug conjugate (ADC)). The metabolic process or reaction may be an enzymatic process such as proteolytic cleavage of a peptide linker of the subject composition, or hydrolysis of a functional group such as a hydrazone, ester, or amide within the subject composition. In the context of conjugates, including ADCs, intracellular metabolites include, but are not limited to, antibodies and free drug which have been separated intracellularly, i.e., after entry, diffusion, uptake or transport into a cell (e.g., by enzymatic cleavage of an ADC by an intracellular enzyme).

In the context of conjugates, including ADCs, the terms "intracellularly cleaved" and "intracellular cleavage" refer to metabolic processes or reactions inside a cell on a composition described herein whereby the covalent attachment, e.g., the linker (L), between the drug moiety (D) and the targeting moiety (T) (e.g., an antibody) is broken, resulting in the free drug dissociated from (T) inside the cell. In one embodiment, the cleaved moieties of the subject compositions are thus intracellular metabolites (e.g., T, T-L fragment, D-L fragment, and D). Accordingly, in one embodiment, the invention provides compositions that are cleavage products of a composition of Formula II, which cleavage products include compositions comprising compounds of Formula I.

The term "extracellular cleavage" refers a metabolic process or reaction outside a cell on a composition described herein whereby the covalent attachment, e.g., the linker (L), between the drug moiety (D) and the targeting moiety (T) (e.g., an antibody) is broken, resulting in the free drug dissociated from (T) outside the cell. In one embodiment, the cleaved moieties of the subject compositions are thus initially extracellular metabolites (e.g., T, T-L fragment, D-L fragment, and D), which may move intracellularly by diffusion and cell permeability or transport. Accordingly, in one embodiment, the invention provides compositions that are cleavage products of a composition of Formula II, which cleavage products include compositions comprising compounds of Formula I.

"Mammal" includes humans and both domestic animals such as laboratory animals and household pets (e.g., cats, dogs, swine, cattle, sheep, goats, horses, rabbits), and non-domestic animals such as wildlife, and the like.

"Optional" or "optionally" means that the subsequently described event of circumstances may or may not occur, and that the description includes instances where said event or circumstance occurs and instances in which it does not. For example, "optionally substituted aryl" means that the aryl substituent may or may not be substituted and that the description includes both substituted aryl substituents and aryl substituents having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration (or other similar regulatory agency of another jurisdiction) as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid, and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins, and the like. Particularly preferred organic bases are isopropylamine, diethylamine, ethanolamine, trimethylamine, dicyclohexylamine, choline and caffeine.

Often crystallizations produce a solvate of the compound described herein. As used herein, the term "solvate" refers to an aggregate that comprises one or more molecules of a compound described herein with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate, and the like, as well as the corresponding solvated forms. The compound described herein may be true solvates, while in other cases, the compound described herein may merely retain adventitious water or be a mixture of water plus some adventitious solvent.

A "pharmaceutical composition" refers to a formulation of a compound described herein and a medium generally accepted in the art for the delivery of the biologically active compound to mammals, e.g., humans. Such a medium includes all pharmaceutically acceptable carriers, diluents or excipients therefor.

Non-limiting examples of disorders to be treated herein include benign and malignant tumors; leukemia and lymphoid malignancies, in particular breast, ovarian, stomach, endometrial, salivary gland, lung, kidney, colon, thyroid, pancreatic, prostate or bladder cancer; neuronal, glial, astrocytal, hypothalamic and other glandular, macrophagal, epithelial, stromal and blastocoelic disorders, autoimmune disease, inflammatory disease, fibrosis, and infectious disease. Given the characteristics, and particularly the potency of the subject compositions, it will be apparent to the artisan of reasonable skill that the compounds described herein may be indicated for use to treat any disease where exertion of a cytotoxic or cytotoxic effect on a target cell is desirable.

In one embodiment, compositions described herein are used to treat autoimmune disease. Antibodies immunospecific for an antigen of a cell that is responsible for producing autoimmune antibodies can be obtained from any organization (e.g., a university scientist or a company such as Genentech) or produced by any method known to one of skill in the art such as, e.g., chemical synthesis or recombinant expression techniques. In another embodiment, useful ligand antibodies that are immunospecific for the treatment of autoimmune diseases include, but are not limited to: Anti-Nuclear Antibody; Anti ds DNA; Anti ss DNA, Anti Cardiolipin Antibody IgM, IgG; Anti Phospholipid Antibody IgM, IgG; Anti SM Antibody; Anti Mitochondrial Antibody; Thyroid Antibody; Microsomal Antibody; Thyroglobulin Antibody; Anti SCL-70; Anti-Jo; Anti-U1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody. In certain preferred embodiments, antibodies useful in the present methods, can bind to both a receptor or a receptor complex expressed on an activated lymphocyte.

The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA-4, PD-1, and ICOS.

Non-limiting examples of suitable TNF receptor superfamily members are CD27, CD40, CD95/Fas, CD134/OX40, CD137/4-1BB, TNF-R1, TNFR-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C-type, S-type, and I-type lectin.

In one embodiment, the ligand is an antibody that binds to an activated lymphocyte that is associated with an autoimmune disease.

Immunological diseases that are characterized by inappropriate activation of immune cells and that can be treated or prevented by the methods described herein can be classified, for example, by the type(s) of hypersensitivity reaction(s) that underlie the disorder. These reactions are typically classified into four types: anaphylactic reactions, cytotoxic (cytolytic) reactions, immune complex reactions, or cell-mediated immunity (CMI) reactions (also referred to as delayed-type hypersensitivity (DTH) reactions). (See, e.g., Fundamental Immunology (William E. Paul ed., Raven Press, N.Y., 3rd ed. 1993)).

Specific examples of such immunological diseases include the following: rheumatoid arthritis, autoimmune demyelinative diseases (e.g., multiple sclerosis, allergic encephalomyelitis), endocrine ophthalmopathy, uveoretinitis, systemic lupus erythematosus, myasthenia gravis, Grave's disease, glomerulonephritis, autoimmune hepatological disorder, inflammatory bowel disease (e.g., Crohn's disease), anaphylaxis, allergic reaction, Sjogren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyl), and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, antiphospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstroms's macroglobulemia, Evan's syndrome, and autoimmune gonadal failure. Accordingly, the methods described herein encompass treatment of disorders of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjorgren's syndrome, Hashimoto's thyroiditis, Grave's disease, primary biliary cirrhosis, Wegener's granulomatosis, tuberculosis, or acute graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes.

In certain embodiments, the immunological disorder is T cell-mediated, which may include activated T cells. ADC's or ADC derivatives can be administered to deplete such activated T cells.

In one embodiment, compositions described herein may be used to treat fibrosis. Fibrosis can occur in many tissues within the body, typically as a result of inflammation or damage, examples include but are not limited to; Lungs, Pulmonary fibrosis, Idiopathic pulmonary fibrosis, Cystic fibrosis; Liver, Cirrhosis; Heart, Endomyocardial fibrosis, Old myocardial infarction, Atrial Fibrosis; Others, Mediastinal fibrosis (soft tissue of the mediastinum), Myelofibrosis (bone marrow), Retroperitoneal fibrosis (soft tissue of the retroperitoneum), Progressive massive fibrosis (lungs); a complication of coal workers' pneumoconiosis, Nephrogenic systemic fibrosis (skin), Crohn's Disease (intestine), Keloid (skin), Scleroderma/systemic sclerosis (skin, lungs), Arthrofibrosis (knee, shoulder, other joints), Peyronie's disease (penis), Dupuytren's contracture (hands, fingers) and some forms of adhesive capsulitis (shoulder).

With respect to infectious disease, compositions described herein may be used directly on certain infectious agents or pathogens, or may be used to exert a cytostatic or cytotoxic effect on a host cell that harbors or otherwise provides for the infectious agent or pathogen.

"Effective amount" or "therapeutically effective amount" refers to that amount of a compound described herein which, when administered to a mammal, preferably a human, is sufficient to effect treatment, as defined below, of the particular indication (e.g., cancer or tumor cells in the mammal, preferably a human). The amount of a compound described herein which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes: preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition.

A therapeutically effective amount of compound in respect of cancer treatment may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; increase survival time; and/or relieve to some extent one or more of the symptoms associated with the cancer. To the extent the drug may prevent growth and/or kill existing cancer cells, it may be cytostatic and/or cytotoxic. Compounds of the present invention are preferably cytotoxic. For cancer therapy, efficacy can, for example, be measured by assessing the time to disease progression (TTP) and/or determining the response rate (RR).

An "effective amount" in respect of a particular result to be achieved is an amount sufficient to achieve the desired result. For example, an "effective amount" of drug when referred to in respect of the killing of cancer cells, refers to an amount of drug sufficient to produce the killing effect.

Solid tumors contemplated for treatment using the presently disclosed compounds include but are not limited to: sarcoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer (e.g., gastrointestinal cancer), oral cancer, nasal cancer, throat cancer, squamous cell carcinoma (e.g., of the lung), basal cell carcinoma, adenocarcinoma (e.g., of the lung), sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, non-small cell lung cancer, epithelial carcinoma, glioma, glioblastoma, multiforme astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma. Blood-borne cancers contemplated for treatment using the presently disclosed compounds include but are not limited to: acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia "CML", chronic lymphocytic leukemia "CLL", hairy cell leukemia, and multiple myeloma. Acute and chronic leukemias contemplated for treatment using the presently disclosed compounds include but are not limited to: lymphoblastic, myelogenous, lymphocytic, and myelocytic leukemias. Lymphomas contemplated for treatment using the presently disclosed compounds include but are not limited to: Hodgkin's disease, non-Hodgkin's lymphoma, multiple myeloma, Waldenstrom's macroglobulinemia, heavy chain disease, and polycythemia vera. Other cancers contemplated for treatment using the presently disclosed compounds include but are not limited to: peritoneal cancer, hepatocellular cancer, hepatoma, salivary cancer, vulval cancer, thyroid, penile cancer, anal cancer, head and neck cancer, renal cell carcinoma, acute anaplastic large cell carcinoma, and cutaneous anaplastic large cell carcinoma.

Cancers, including, but not limited to, a tumor, metastasis, or other disease or disorder characterized by uncontrolled or undesired cell growth, can be treated or prevented by administration of the presently disclosed compounds.

In other embodiments, methods for treating or preventing cancer are provided, including administering to a patient in need thereof an effective amount of a compound disclosed herein in combination with an additional method of treatment. In one embodiment, the additional method of treatment includes treatment with a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The compound described herein may be administered before, after, or at the same time as the chemotherapeutic agent.

In one embodiment, the additional method of treatment is radiation therapy. The compound described herein may be administered before, after, or at the same time as the radiation.

Compounds described herein may also be administered to a patient that has undergone or will undergo surgery as treatment for the cancer.

In a specific embodiment, the compound described herein is administered concurrently with the chemotherapeutic agent or with radiation therapy. In another specific embodiment, the chemotherapeutic agent or radiation therapy is administered prior or subsequent to administration of compound described herein, in one aspect at least an hour, five hours, 12 hours, a day, a week, a month, in further aspects several months (e.g., up to three months), prior or subsequent to administration of a compound described herein.

A chemotherapeutic agent can be administered over a series of sessions. Any one or a combination of the chemotherapeutic agents listed herein or otherwise known in the art can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, methods of treatment of cancer with a compound described herein are provided as an alternative to chemotherapy or radiation therapy where the chemotherapy or the radiation therapy has proven or can prove too toxic, e.g., results in unacceptable or unbearable side effects, for the subject being treated. Additionally, methods of treatment of cancer with a compound described herein are provided as an alternative to surgery where the surgery has proven or can prove unacceptable or unbearable for the subject being treated.

The compounds described herein can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the animal's remaining bone-marrow cell population is then eradicated via the administration of a high dose of a compound described herein with or without accompanying high dose radiation therapy, and the stem cell graft is infused back into the animal. Supportive care is then provided while bone marrow function is restored and the animal recovers.

Methods for treating cancer further include administering to a patient in need thereof an effective amount of a compound described herein and another therapeutic agent that is an anti-cancer agent. Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, actinomycin D, dactinomycin, plicamycin, mitoxantrone, asparaginase, vinblastine, vincristine, vindesine, vinorelbine, paclitaxel, and docetaxel.

Other examples of chemotherapeutic agents include alkylating agents such as thiotepa and CYTOXAN® cyclosphosphamide; alkyl sulfonates such as busulfan, treosulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; triazines such as decarbazine; nitrosureas such as carmustine, chlorozotocin, fotemustine, lomustine, nimustine, and ranimnustine; epipodophyllins, such as etoposide, teniposide, topotecan, 9-aminocamptothecin, camptothecin orcrisnatol; bisphosphonates, such as clodronate; antibiotics such as the enediyne antibiotics (e.g., calicheamicin, especially calicheamicin gamma1I and calicheamicin omega1I (see, e.g., Agnew, Chem. Intl. Ed. Engl., 33:183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins (e.g., A2 and B2), cactinomycin, carabicin, caminomycin, carzinophilin, chromomycinis, dactinomycin, detorubicin, 6-diazo-5-oxo-L-norleucine, ADRIAMYCIN® doxorubicin (including morpholinodoxorubicin, cyanomorpholino-doxorubicin, 2-pyrrolinodoxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; photodynamic therapies, such as vertoporfin (BPD-MA), phthalocyanine, photosensitizer Pc4, and demethoxy-hypocrellin A (2BA-2-DMHA); folic acid analogues such as denopterin, pteropterin, and trimetrexate; dpurine analogs such as fludarabine, 6-mercaptopurine, thiamiprine, and thioguanine; pyrimidine analogs such as ancitabine, azacitidine, 6-azauridine, carmofur, cytarabine, cytosine arabinoside, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate and trimetrexate; anti-metabolites such as 5-fluorouracil (5-FU) and its prodrugs such as UFT, S-1 and capecitabine, floxuridine, doxifluridine and ratitrexed; and thymidylate synthase inhibitors and glycinamide ribonucleotide formyltransferase inhibitors such as raltitrexed (TOMUDEX®, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophorfree, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); velcade; revlimid; thalidomide; IMiD3; lovastatin; verapamil; thapsigargin; 1-methyl-4-phenylpyridinium; cell cycle inhibitors such as staurosporine; novantrone; edatrexate; daunomycin; mtoxantrone; aminopterin; xeloda; ibandronate; topoisomerase inhibitor RFS 2000; difluoromethylornithine (DMFO); vitamin D3 analogs, such as EB 1089, CB 1093 and KH 1060; retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, megastrol, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, bicalutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

Novel Compounds

Provided are compounds of Formula I:

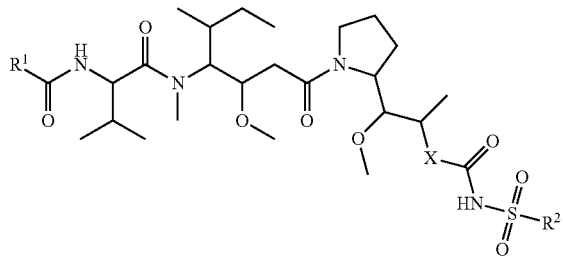

I and pharmaceutically acceptable salts thereof, wherein:
$R^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloacyl, $C_1$-$C_6$ haloalkyl, heterocyclyl, heterocyclyl-$C_1$-$C_6$ alkyl, hydroxyl, and thio; or
$R^1$ is $R^aR^bNCH(R^c)$—;
$R^a$ is selected from: H and $C_1$-$C_6$ alkyl;
$R^b$ is $C_1$-$C_6$ alkyl; and
$R^c$ is $R^d$—$C(CH_3)_2$—; and
$R^d$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio; or
$R^b$ and $R^c$ taken together with the atoms to which they are each bonded form a heterocyclyldiyl;
$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl; and
X is —C(O)NHCH($CH_2R^3$)—, or X is absent; and
$R^3$ is selected from: aryl, heteroaryl, and $C_3$-$C_7$ cycloalkyl, each optionally substituted with one substituent selected from amino and hydroxyl.

In some embodiments, when $R^1$ is 2-methyl-1-(methylamino)propyl, and X is —C(O)NHCH($CH_2$Ph)-, $R^2$ is other than ethyl, isopropyl, n-butyl, and phenyl.

Also provided are compounds of Formula I:

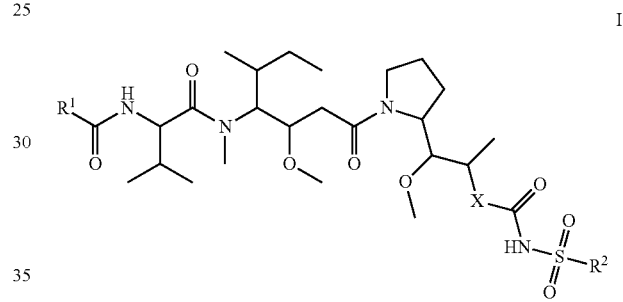

I and pharmaceutically acceptable salts thereof, wherein:
$R^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloacyl, $C_1$-$C_6$ haloalkyl, heterocyclyl, heterocyclyl-$C_1$-$C_6$ alkyl, hydroxyl, and thio; or
$R^1$ is $R^aR^bNCH(R^c)$—;
$R^a$ is selected from: H and $C_1$-$C_6$ alkyl;
$R^b$ is $C_1$-$C_6$ alkyl; and
$R^c$ is $R^d$—$C(CH_3)_2$—; and
$R^d$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio; or
$R^b$ and $R^c$ taken together with the atoms to which they are each bonded form a heterocyclyldiyl;
$R^2$ is selected from: $C_1$-$C_6$ alkyl, aryl, aryl-$C_1$-$C_6$ alkyl, $C_3$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino- $C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl; and X is —C(O)NHCH(CH$_2$R$^3$)—, or X is absent; and R$^3$ is selected from: aryl, heteroaryl, and $C_3$-$C_7$ cycloalkyl, each optionally substituted with one substituent selected from amino and hydroxyl.

In some embodiments, when R$^1$ is 2-methyl-1-(methylamino)propyl, and X is —C(O)NHCH(CH$_2$Ph)-, R$^2$ is other than methyl, ethyl, isopropyl, n-butyl, cyclopropyl, and phenyl.

Also provided are compounds of Formula I:

and pharmaceutically acceptable salts thereof, wherein:

R$^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloacyl, $C_1$-$C_6$ haloalkyl, heterocyclyl, heterocyclyl-$C_1$-$C_6$ alkyl, hydroxyl, and thio; or R$^1$ is R$^a$R$^b$NCH(R$^c$)—;

R$^a$ is selected from: H and $C_1$-$C_6$ alkyl;

R$^b$ is $C_1$-$C_6$ alkyl; and

R$^c$ is R$^d$—C(CH$_3$)$_2$—; and

R$^d$ is selected from: H, aryl, $C_3$-$C_7$ cycloalkyl, and heteroaryl, each of which is optionally substituted with one or more substituents selected from: $C_1$-$C_4$ acylamino, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio; or R$^b$ and R$^c$ taken together with the atoms to which they are each bonded form a heterocyclyldiyl;

R$^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl; and X is absent.

The Variable R$^1$

In some embodiments, R$^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloalkyl, heterocyclyl, heterocyclyl-$C_1$-$C_6$ alkyl, hydroxyl, and thio.

In some embodiments, R$^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from $C_1$-$C_6$ alkyl and halo.

In some embodiments, R$^1$ is selected from: 1-(dimethylamino)-2-methylpropyl, 2-methyl-1-(methylamino)propyl, 1-aminocyclopentyl, 1-aminocyclopropyl, 4-aminophenyl, 2-aminopropan-2-yl, 1-aminocyclohexyl, 3-aminooxetan-3-yl, 2-(methylamino)propan-2-yl, 1-amino-2-methylpropan-2-yl, 2-methylpyrrolidin-2-yl, 2-amino-3-methylbutan-2-yl, 2-aminobutan-2-yl, 2-methyl-1-(methylamino)propan-2-yl, 1-methylpiperidin-2-yl, 3-fluoropyrrolidin-3-yl, 1,2-dimethylpyrrolidin-2-yl, and 2-(dimethylamino)propan-2-yl).

In some embodiments, R$^1$ is selected from: 1-(dimethylamino)-2-methylpropyl, 2-methyl-1-(methylamino)propyl, 1-aminocyclopentyl, 1-aminocyclopropyl, 4-aminophenyl, 2-aminopropan-2-yl, 1-aminocyclohexyl, 3-aminooxetan-3-yl, 2-(methylamino)propan-2-yl, 1-amino-2-methylpropan-2-yl, 2-methylpyrrolidin-2-yl, 2-amino-3-methylbutan-2-yl, 2-aminobutan-2-yl, 2-methyl-1-(methylamino)propan-2-yl, 1-methylpiperidin-2-yl, 3-fluoropyrrolidin-3-yl, 1,2-dimethylpyrrolidin-2-yl, 2-(dimethylamino)propan-2-yl), 2-methyl-1-(methylamino)-2-phenylpropyl, 1-isopropylpiperidin-2-yl, 2-azabicyclo[2.2.1]heptan-3-yl, and 2-methyl-2-azabicyclo[2.2.1]heptan-3-yl.

In some embodiments, R$^1$ is 1-(dimethylamino)-2-methylpropyl.

In some embodiments, R$^1$ is 2-methyl-1-(methylamino)propyl.

In some embodiments, R$^1$ is 1-aminocyclopentyl.

In some embodiments, R$^1$ is 1-aminocyclopropyl.

In some embodiments, R$^1$ is 4-aminophenyl.

In some embodiments, R$^1$ is 2-aminopropan-2-yl.

In some embodiments, R$^1$ is 1-aminocyclohexyl.

In some embodiments, R$^1$ is 3-aminooxetan-3-yl.

In some embodiments, R$^1$ is 2-(methylamino)propan-2-yl.

In some embodiments, R$^1$ is 1-amino-2-methylpropan-2-yl.

In some embodiments, R$^1$ is 2-methylpyrrolidin-2-yl.

In some embodiments, R$^1$ is 2-amino-3-methylbutan-2-yl.

In some embodiments, R$^1$ is 2-aminobutan-2-yl.

In some embodiments, R$^1$ is 2-methyl-1-(methylamino)propan-2-yl.

In some embodiments, R$^1$ is 1-methylpiperidin-2-yl.

In some embodiments, R$^1$ is 3-fluoropyrrolidin-3-yl.

In some embodiments, R$^1$ is 2-methyl-1-(methylamino)propyl.

In some embodiments, R$^1$ is (R)-1-(dimethylamino)-2-methylpropyl.

In some embodiments, R$^1$ is (R)-2-methyl-1-(methylamino)propyl.

In some embodiments, R$^1$ is R$^a$R$^b$NCH(R$^c$)—.

In some embodiments, R$^1$ is 2-methyl-1-(methylamino)-2-phenylpropyl.

In some embodiments, R$^1$ is 1-isopropylpiperidin-2-yl.

In some embodiments, R$^1$ is 2-azabicyclo[2.2.1]heptan-3-yl.

In some embodiments, R$^1$ is 2-methyl-2-azabicyclo[2.2.1]heptan-3-yl.

The Variable R$^a$

In some embodiments, R$^a$ is selected from: H and $C_1$-$C_6$ alkyl;

In some embodiments, $R^b$ is selected from: H, methyl, and isopropyl.

In some embodiments, $R^c$ is H.

In some embodiments, $R^d$ is methyl.

In some embodiments, $R^e$ is isopropyl.

The Variable $R^b$

In some embodiments, $R^b$ is $C_1$-$C_6$ alkyl.

In some embodiments, $R^b$ is methyl.

The Variable $R^c$

In some embodiments, $R^c$ is $R^d$—$C(CH_3)_2$—.

The Variable $R^d$

In some embodiments, $R^d$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio.

In some embodiments, $R^d$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from p-tolyl, hydroxyl, and thio.

In some embodiments, $R^d$ is selected from: H, aryl, $C_3$-$C_7$ cycloalkyl, and heteroaryl, each of which is optionally substituted with one or more substituents selected from: (2-hydroxyethyl)amino, (2-mercaptoethyl)amino, 2-(acetylthio)ethoxy, 2-aminoethoxy, 2-hydroxyethoxy, 2-mercaptoethoxy, 3-methoxy, 4-methylstyryl, amino, aminomethyl, chloro, fluoro, hydroxyl, hydroxymethyl, methyl, thio, trifluoromethyl.

In some embodiments, $R^d$ is selected from: H, cyclohexyl, 1H-indol-3-yl, phenyl, and thien-2-yl each of which is optionally substituted with one or more substituents selected from: (2-hydroxyethyl)amino, (2-mercaptoethyl)amino, 2-(acetylthio)ethoxy, 2-aminoethoxy, 2-hydroxyethoxy, 2-mercaptoethoxy, 3-methoxy, 4-methylstyryl, amino, aminomethyl, chloro, fluoro, hydroxyl, hydroxymethyl, methyl, thio, and trifluoromethyl.

In some embodiments, $R^d$ is selected from: H, 1H-indol-3-yl, 1-methyl-1H-indol-3-yl, 2-methoxyphenyl, 3-((2-hydroxyethyl)amino)phenyl, 3-((2-mercaptoethyl)amino)phenyl, 3-(2-(acetylthio)ethoxy)phenyl, 3-(2-hydroxyethoxy)phenyl, 3-(2-mercaptoethoxy)phenyl, 3-(4-methylstyryl)phenyl, 3-(aminomethyl)phenyl, 3-(hydroxymethyl)phenyl, 3-hydroxyphenyl, 3,5-difluorophenyl, 3,5-dimethylphenyl, 3-aminophenyl, 3-chlorophenyl, 3-mercaptophenyl, 3-methoxyphenyl, 3-trifluoromethylphenyl, 4-((2-hydroxyethyl)amino)phenyl, 4-((2-mercaptoethyl)amino)phenyl, 4-(2-(acetylthio)ethoxy)phenyl, 4-(2-aminoethoxy)phenyl, 4-(2-hydroxyethoxy)phenyl, 4-(2-mercaptoethoxy)phenyl, 4-(aminomethyl)phenyl, 4-(hydroxymethyl)phenyl, 4-aminophenyl, 4-hydroxyphenyl, 4-mercaptophenyl, 4-methoxyphenyl, cyclohexyl, thien-2-yl, m-tolyl, and phenyl.

In some embodiments, $R^d$ is selected from: H, 1H-indol-3-yl, 1-methyl-1H-indol-3-yl, 2-methoxyphenyl, 3-((2-hydroxyethyl)amino)phenyl, 3-((2-mercaptoethyl)amino)phenyl, 3-(2-hydroxyethoxy)phenyl, 3-(2-mercaptoethoxy) phenyl, 3,5-difluorophenyl, 3,5-dimethylphenyl, 3-chlorophenyl, 3-mercaptophenyl, 3-methoxyphenyl, 3-trifluoromethylphenyl, 4-((2-hydroxyethyl)amino)phenyl, 4-((2-mercaptoethyl)amino)phenyl, 4-4-(2-hydroxyethoxy)phenyl, 4-(2-mercaptoethoxy)phenyl, 4-mercaptophenyl, 4-methoxyphenyl, cyclohexyl, thien-2-yl, m-tolyl, and phenyl.

In some embodiments, $R^d$ is phenyl.

In some embodiments, $R^d$ is 1H-indol-3-yl.

In some embodiments, $R^d$ is 1-methyl-1H-indol-3-yl.

In some embodiments, $R^d$ is 2-methoxyphenyl.

In some embodiments, $R^d$ is 3-((2-hydroxyethyl)amino) phenyl.

In some embodiments, $R^d$ is 3-((2-mercaptoethyl)amino) phenyl.

In some embodiments, $R^d$ is 3-(2-hydroxyethoxy)phenyl.

In some embodiments, $R^d$ is 3-(2-mercaptoethoxy)phenyl.

In some embodiments, $R^d$ is 3,5-difluorophenyl.

In some embodiments, $R^d$ is 3,5-dimethylphenyl.

In some embodiments, $R^d$ is 3-chlorophenyl.

In some embodiments, $R^d$ is 3-mercaptophenyl.

In some embodiments, $R^d$ is 3-methoxyphenyl.

In some embodiments, $R^d$ is 3-trifluoromethylphenyl.

In some embodiments, $R^d$ is 4-((2-hydroxyethyl)amino) phenyl.

In some embodiments, $R^d$ is 4-((2-mercaptoethyl)amino) phenyl.

In some embodiments, $R^d$ is 4-4-(2-hydroxyethoxy)phenyl.

In some embodiments, $R^d$ is 4-(2-mercaptoethoxy)phenyl.

In some embodiments, $R^d$ is 4-mercaptophenyl.

In some embodiments, $R^d$ is 4-methoxyphenyl.

In some embodiments, $R^d$ is cyclohexyl.

In some embodiments, $R^d$ is thien-2-yl.

In some embodiments, $R^d$ is m-tolyl.

The Variable $R^2$

In some embodiments, $R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl.

In some embodiments, $R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: 1-aminocyclopropyl, 4-aminophenyl, amino, aminomethyl, bromo, tert-butyl, carboxamide, carboxyl, chloro, cyano, ethyl, fluoro, hydroxy, isopropyl, methoxy, methyl, nitro, phenyl, thio, thiomethyl, trifluoromethoxy, and trifluoromethyl.

In some embodiments, $R^2$ is selected from: 5,6,7,8-tetrahydronaphthalen-1-yl, benzyl, cyclohexyl, ethyl, hexan-2-yl, methyl, naphthalen-2-yl, piperidin-1-yl, phenyl, propyl, pyridin-3-yl, and thien-2-yl, each optionally substituted with one or more substituents selected from: 1-aminocyclopropyl, 4-aminophenyl, amino, aminomethyl, bromo, tert-butyl, carboxamide, carboxyl, chloro, cyano, ethyl, fluoro, hydroxy, isopropyl, methoxy, methyl, nitro, phenyl, thio, thiomethyl, trifluoromethoxy, and trifluoromethyl.

In some embodiments, $R^2$ is selected from: 5,6,7,8-tetrahydronaphthalen-1-yl, benzyl, cyclohexyl, ethyl, hexan-2-yl, naphthalen-2-yl, piperidin-1-yl, phenyl, propyl, pyridin- 3-yl, and thien-2-yl, each optionally substituted with one or more substituents selected from: 1-aminocyclopropyl, 4-aminophenyl, amino, aminomethyl, bromo, tert-butyl, carboxamide, carboxyl, chloro, cyano, ethyl, fluoro, hydroxy, isopropyl, methoxy, methyl, nitro, phenyl, thio, thiomethyl, trifluoromethoxy, and trifluoromethyl.

In some embodiments, $R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl.

In some embodiments, $R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, 4-amino-3-(trifluoromethyl)phenyl, and 4-(methoxycarbonyl)phenyl.

In some embodiments, wherein $R^2$ is selected from: aryl and aryl-$C_1$-$C_6$ alkyl, each optionally substituted with one or more substituents selected from: amino and amino-$C_1$-$C_6$ alkyl.

In some embodiments, $R^2$ is selected from: 4-aminobenzyl, 4-(aminomethyl)benzyl, 4-(aminomethyl)phenyl, 4-aminophenyl, and benzyl.

In some embodiments, $R^2$ is 4-aminobenzyl.
In some embodiments, $R^2$ is 4-(aminomethyl)benzyl.
In some embodiments, $R^2$ is 4-(aminomethyl)phenyl.
In some embodiments, $R^2$ is 4-aminophenyl.
In some embodiments, $R^2$ is benzyl.
In some embodiments, $R^2$ is 3-mercaptopropyl.
In some embodiments, $R^2$ is 2-mercaptoethyl.
In some embodiments, $R^2$ is 4-(mercaptomethyl)phenyl.
In some embodiments, $R^2$ is p-tolyl.
In some embodiments, $R^2$ is 2,4,6-trimethylphenyl.
In some embodiments, $R^2$ is 4-(trifluoromethoxy)phenyl.
In some embodiments, $R^2$ is 2,4,6-triisopropylphenyl.
In some embodiments, $R^2$ is 4-tert-butylphenyl.
In some embodiments, $R^2$ is 4-chlorophenyl.
In some embodiments, $R^2$ is 3-cyanophenyl.
In some embodiments, $R^2$ is 2-nitrophenyl.
In some embodiments, $R^2$ is 4-methoxy-2-nitrophenyl.
In some embodiments, $R^2$ is 4-aminocarbonyl-2-nitrophenyl.
In some embodiments, $R^2$ is 4-methoxyphenyl.
In some embodiments, $R^2$ is phenyl.
In some embodiments, $R^2$ is 2-fluorobenzyl.
In some embodiments, $R^2$ is piperidin-1-yl.
In some embodiments, $R^2$ is o-tolyl.
In some embodiments, $R^2$ is 4-bromophenyl.
In some embodiments, $R^2$ is naphthalen-2-yl.
In some embodiments, $R^2$ is 4-methoxycarbonyphenyl.
In some embodiments, $R^2$ is -(trifluoromethyl)benzyl.
In some embodiments, $R^2$ is hexan-2-yl.
In some embodiments, $R^2$ is 2-methoxyethyl.
In some embodiments, $R^2$ is cyclopentylmethyl.
In some embodiments, $R^2$ is cyclohexyl.
In some embodiments, $R^2$ is pyridin-3-ylmethyl.
In some embodiments, $R^2$ is 4-carboxyphenyl.
In some embodiments, $R^2$ is 3-aminophenyl.
In some embodiments, $R^2$ is pyridin-3-yl.
In some embodiments, $R^2$ is thien-2-yl.
In some embodiments, $R^2$ is 4-hydroxyphenyl.
In some embodiments, $R^2$ is 4-(1-aminocyclopropyl)benzyl.
In some embodiments, $R^2$ is 4-(1-aminocyclopropyl)phenyl.
In some embodiments, $R^2$ is 2-methylbenzyl.
In some embodiments, $R^2$ is 4-nitrobenzyl.
In some embodiments, $R^2$ is 4-chlorobenzyl.
In some embodiments, $R^2$ is phenethyl.
In some embodiments, $R^2$ is 4-bromobenzyl.
In some embodiments, $R^2$ is 4-cyanobenzyl.
In some embodiments, $R^2$ is 3-nitrobenzyl.
In some embodiments, $R^2$ is 4-tert-butylbenzyl.
In some embodiments, $R^2$ is 2-nitrobenzyl.
In some embodiments, $R^2$ is -nitrophenethyl.
In some embodiments, $R^2$ is 2-chloro-3-methoxycarbonylphenyl.
In some embodiments, $R^2$ is 2-aminophenyl.
In some embodiments, $R^2$ is [1,1'-biphenyl]-4-yl.
In some embodiments, $R^2$ is 4'-amino-[1,1'-biphenyl]-4-yl.
In some embodiments, $R^2$ is 4-fluorobenzyl.
In some embodiments, $R^2$ is 3-(trifluoromethyl)benzyl.
In some embodiments, $R^2$ is 3-(trifluoromethoxy)benzyl.
In some embodiments, $R^2$ is 3,4-dichlorobenzyl.
In some embodiments, $R^2$ is 2-cyanobenzyl.
In some embodiments, $R^2$ is 3-chlorobenzyl.
In some embodiments, $R^2$ is 4-amino-2-ethylphenyl.
In some embodiments, $R^2$ is 4-amino-3-(trifluoromethoxy)phenyl.
In some embodiments, $R^2$ is 4-amino-2,3-dimethylphenyl.

In some embodiments, R² is 4-amino-5,6,7,8-tetrahydronaphthalen-1-yl.

In some embodiments, R² is 4-amino-3-methylphenyl.

In some embodiments, R² is 4-amino-3-fluorophenyl.

In some embodiments, R² is 4-amino-3-ethylphenyl.

In some embodiments, R² is 4-amino-3-(trifluoromethyl)phenyl.

In some embodiments, R² is 4-(methoxycarbonyl)phenyl.

The Variable R³

In some embodiments, R³ is selected from: aryl, heteroaryl, and C₃-C₇ cycloalkyl, each optionally substituted with one substituent selected from amino and hydroxyl.

In some embodiments, R³ is selected from: 1H-indol-3-yl, 4-aminophenyl, 4-hydroxyphenyl, 5-hydroxypyridin-2-yl, cyclohexyl, and phenyl.

In some embodiments, R³ is 1H-indol-3-yl.

In some embodiments, R³ is 4-aminophenyl.

In some embodiments, R³ is 4-hydroxyphenyl.

In some embodiments, R³ is 5-hydroxypyridin-2-yl.

In some embodiments, R³ is cyclohexyl.

In some embodiments, R³ is phenyl.

The Variable R⁴

In some embodiments, R⁴ is selected from: H and C₁-C₆ alkyl.

In some embodiments, R⁴ is H.

In some embodiments, R⁴ is C₁-C₆ alkyl.

In some embodiments, R⁴ is methyl.

The Variable R⁵

In some embodiments, R⁵ is selected from: H and C₁-C₆ alkyl.

In some embodiments, R⁵ is H.

In some embodiments, R⁵ is C₁-C₆ alkyl.

In some embodiments, R⁵ is methyl.

The Variable X

In some embodiments, X is —C(O)NHCH(CH₂R³)—, or X is absent.

In some embodiments, X is —C(O)NHCH(CH₂R³)—

In some embodiments, X is absent.

Certain Combinations

In some embodiments, R^b is C₁-C₆ alkyl; and R^c is R^d—C(CH₃)₂—.

In some embodiments, R^b and R^c taken together with the atoms to which they are each bonded form a heterocyclyldiyl.

In some embodiments, R^b and R^c taken together with the atoms to which they are each bonded form a heterocyclyldiyl selected from: pyrrolidinyldiyl, piperidinyldiyl, and azepanyldiyl.

In some embodiments, R^b and R^c taken together with the atoms to which they are each bonded form pyrrolidinyldiyl.

In some embodiments, R^b and R^c taken together with the atoms to which they are each bonded form piperidinyldiyl.

In some embodiments, R^b and R^c taken together with the atoms to which they are each bonded form azepanyldiyl.

In some embodiments, R⁴ and R⁵ are each independently selected from: H and C₁-C₆ alkyl.

In some embodiments, R⁴ and R⁵ are each independently selected from: H and methyl.

In some embodiments, R⁴ and R⁵ are each methyl.

In some embodiments, R⁴ is H and R⁵ is methyl.

Also provided are compounds of Formula Ia:

Ia and pharmaceutically acceptable salts thereof, wherein:

R² is selected from: C₂-C₆ alkyl, aryl, aryl-C₁-C₆ alkyl, C₄-C₇ cycloalkyl, C₃-C₇ cycloalkyl-C₁-C₆ alkyl, heteroaryl, heteroaryl-C₁-C₆ alkyl, and heterocyclyl, each optionally substituted with one or more substituents selected from: C₁-C₆ alkoxy, C₁-C₆ alkoxycarbonyl, C₁-C₆ alkyl, C₁-C₆ alkylamino, amino, amino-C₁-C₆ alkyl, amino-aryl, amino-C₃-C₇ cycloalkyl, aryl, carboxamide, carboxyl, cyano, C₁-C₆ haloalkyl, C₁-C₆ haloalkoxy, halo, hydroxyl, nitro, thio, and thio-C₁-C₆ alkyl; and R⁴ and R⁵ are each independently selected from: H and C₁-C₆ alkyl.

Also provided are compounds of Formula Ia:

Ia and pharmaceutically acceptable salts thereof, wherein:

R² is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl; and $R^4$ and $R^5$ are each independently selected from: H and methyl.

Also provided are compounds of Formula Ib:

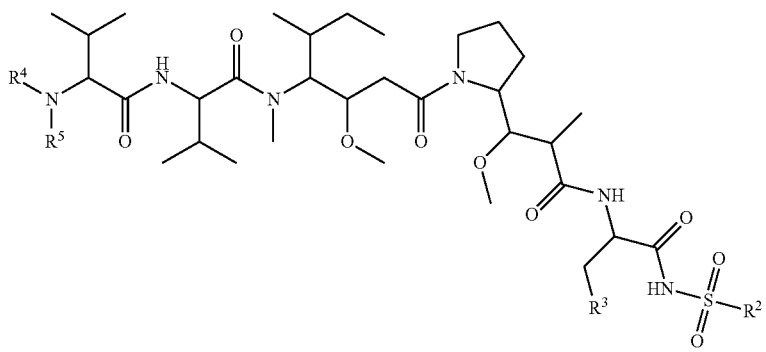

Ib and pharmaceutically acceptable salts thereof, wherein:

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl;

$R^3$ is selected from: aryl, heteroaryl, and $C_3$-$C_7$ cycloalkyl, each optionally substituted with one substituent selected from amino and hydroxyl; and $R^4$ and $R^5$ are each independently selected from: H and $C_1$-$C_6$ alkyl.

Also provided are compounds of Formula Ib:

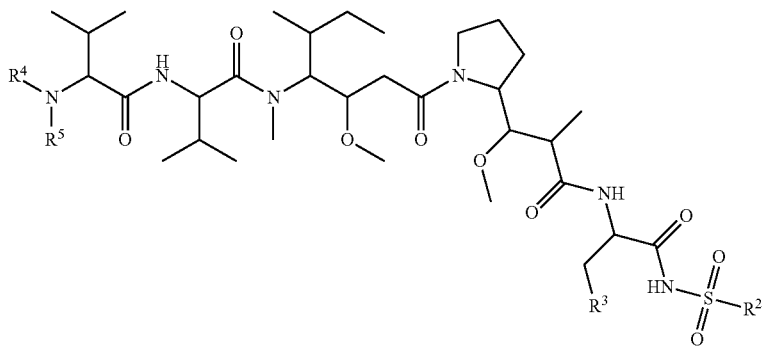

Ib and pharmaceutically acceptable salts thereof, wherein:

$R^2$ is selected from: 4-aminobenzyl, 4-(aminomethyl) benzyl, 4-(aminomethyl)phenyl, 4-aminophenyl, benzyl, 3-mercaptopropyl, 2-mercaptoethyl, 4-(mercaptomethyl) phenyl, p-tolyl, 2,4,6-trimethylphenyl, 4-(trifluoromethoxy) phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl;

$R^3$ is selected from: 1H-indol-3-yl, 4-aminophenyl, 4-hydroxyphenyl, 5-hydroxypyridin-2-yl, cyclohexyl, and phenyl; and $R^4$ and $R^5$ are each independently selected from: H and methyl.

Also provided are compounds of Formula Ic:

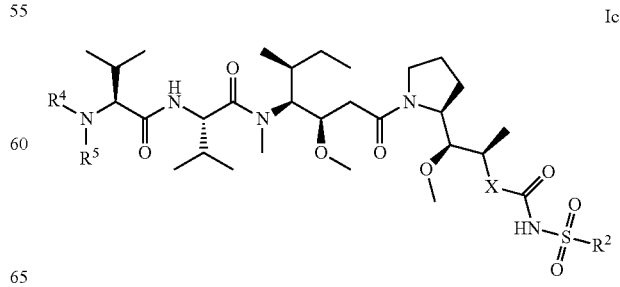

Ic and pharmaceutically acceptable salts thereof, wherein:

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl; and X is —C(O)NHCH(CH$_2$R$^3$)—, or X is absent; and $R^3$ is selected from: aryl, heteroaryl, and $C_3$-$C_7$ cycloalkyl, each optionally substituted with one substituent selected from amino and hydroxyl; and $R^4$ and $R^5$ are each independently selected from: H and $C_1$-$C_6$ alkyl.

Also provided are compounds of Formula Ic:

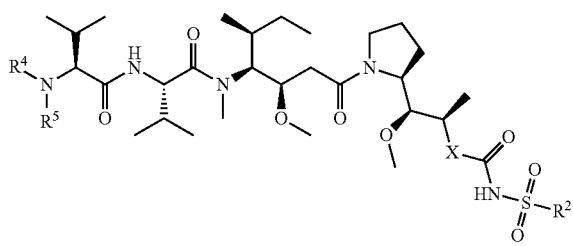

Ic or a pharmaceutically acceptable salt thereof,
wherein:

$R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl; and X is —C(O)NHCH(CH$_2$R$^3$)—, or X is absent; and $R^3$ is selected from: 1H-indol-3-yl, 4-aminophenyl, 4-hydroxyphenyl, 5-hydroxypyridin-2-yl, cyclohexyl, and phenyl; and $R^4$ and $R^5$ are each independently selected from: H and methyl.

Also provided are compounds of Formula Id:

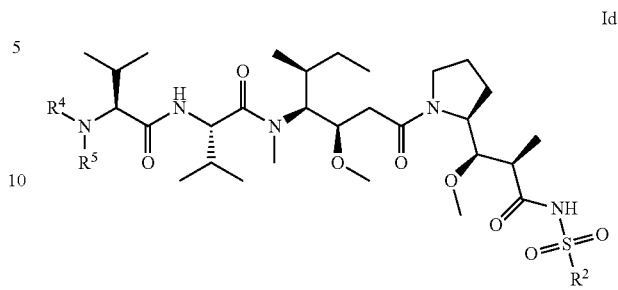

Id and pharmaceutically acceptable salts thereof, wherein:

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl; and $R^4$ and $R^5$ are each independently selected from: H and $C_1$-$C_6$ alkyl.

Also provided are compounds of Formula Id:

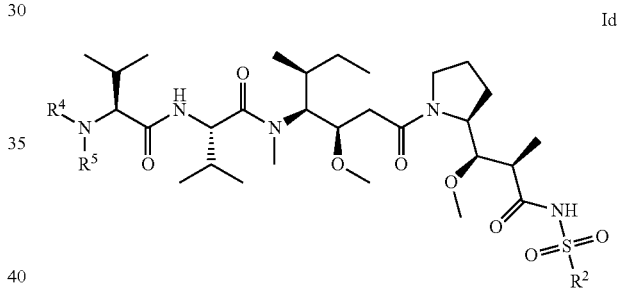

Id and pharmaceutically acceptable salts thereof, wherein:

$R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl; and $R^4$ and $R^5$ are each independently selected from: H and methyl.

Also provided are compounds of Formula Ie:

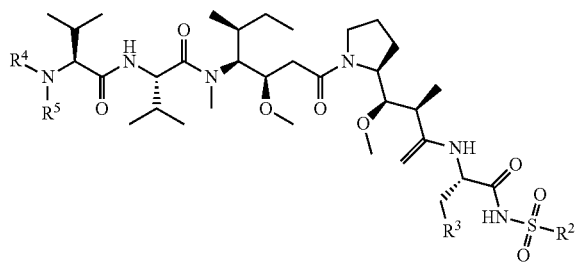

Ie and pharmaceutically acceptable salts thereof, wherein:

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl; and $R^3$ is selected from: aryl, heteroaryl, and $C_3$-$C_7$ cycloalkyl, each optionally substituted with one substituent selected from amino and hydroxyl; and $R^4$ and $R^5$ are each independently selected from: H and $C_1$-$C_6$ alkyl.

Also provided are compounds of Formula Ie:

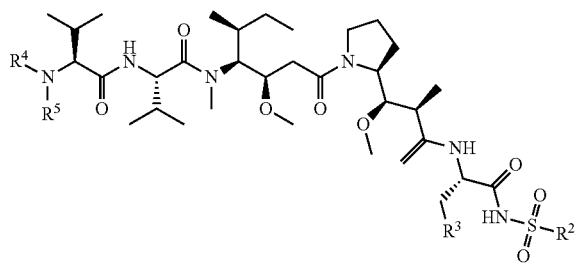

Ie and pharmaceutically acceptable salts thereof, wherein:

$R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl; and $R^3$ is selected from: 1H-indol-3-yl, 4-aminophenyl, 4-hydroxyphenyl, 5-hydroxypyridin-2-yl, cyclohexyl, and phenyl; and $R^4$ and $R^5$ are each independently selected from: H and methyl.

Also provided are compounds of Formula If:

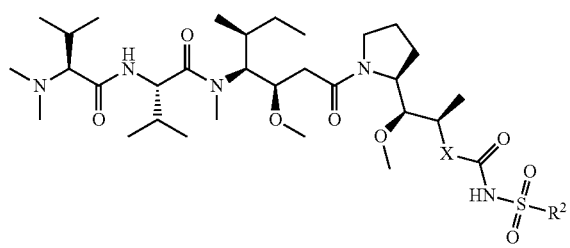

If and pharmaceutically acceptable salts thereof, wherein:

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl; and X is —C(O)NHCH($CH_2R^3$)—, or X is absent; and $R^3$ is selected from: aryl, heteroaryl, and $C_3$-$C_7$ cycloalkyl, each optionally substituted with one substituent selected from amino and hydroxyl.

Also provided are compounds of Formula If:

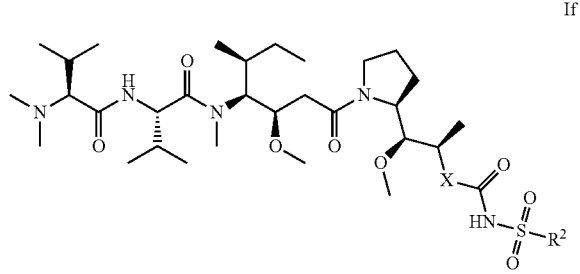

If and pharmaceutically acceptable salts thereof, wherein:

R² is selected from: 4-aminobenzyl, 4-(aminomethyl)benzyl, 4-(aminomethyl)phenyl, 4-aminophenyl; and X is —C(O)NHCH(CH₂R³)—, or X is absent; and R³ is selected from: 1H-indol-3-yl, 4-aminophenyl, 4-hydroxyphenyl, 5-hydroxypyridin-2-yl, cyclohexyl, and phenyl.

Also provided are compounds of Formula Ig:

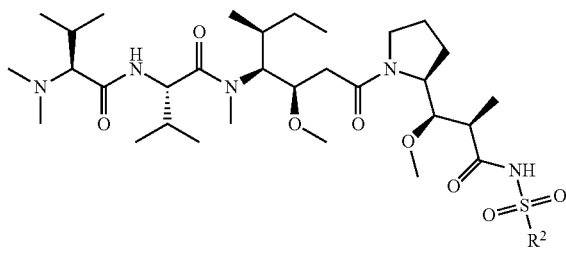

Ig and pharmaceutically acceptable salts thereof, wherein:

R² is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl.

Also provided are compounds of Formula Ig:

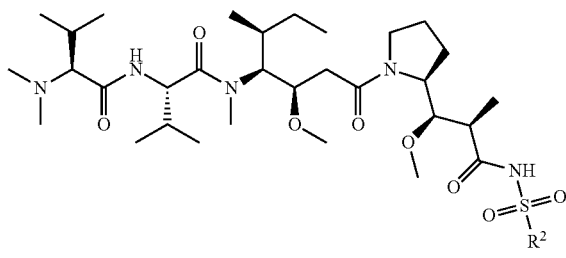

Ig and pharmaceutically acceptable salts thereof, wherein:

R² is selected from: 4-aminobenzyl, 4-(aminomethyl)benzyl, 4-(aminomethyl)phenyl, 4-aminophenyl.

Also provided are compounds of Formula Ih:

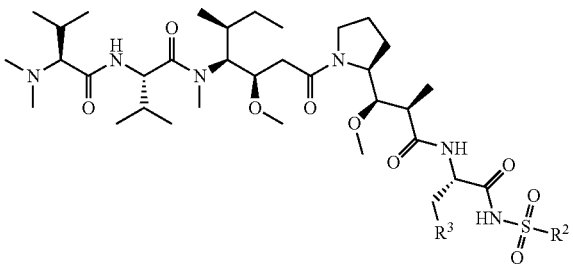

Ih and pharmaceutically acceptable salts thereof, wherein:

R² is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl; and R³ is selected from: aryl, heteroaryl, and $C_3$-$C_7$ cycloalkyl, each optionally substituted with one substituent selected from amino and hydroxyl.

Also provided are compounds of Formula Ih:

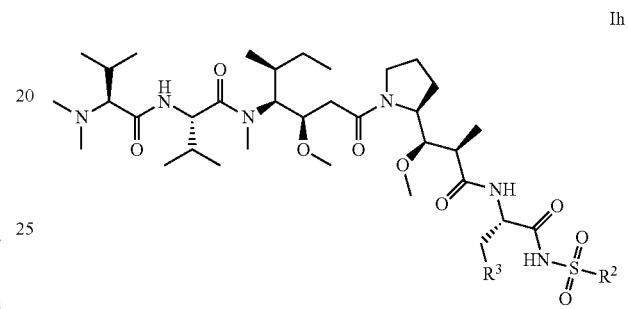

Ih and pharmaceutically acceptable salts thereof, wherein:

R² is selected from: 4-aminobenzyl, 4-(aminomethyl)benzyl, 4-(aminomethyl)phenyl, 4-aminophenyl; and R³ is selected from: 1H-indol-3-yl, 4-aminophenyl, 4-hydroxyphenyl, 5-hydroxypyridin-2-yl, cyclohexyl, and phenyl.

Also provided are compounds of Formula Ii:

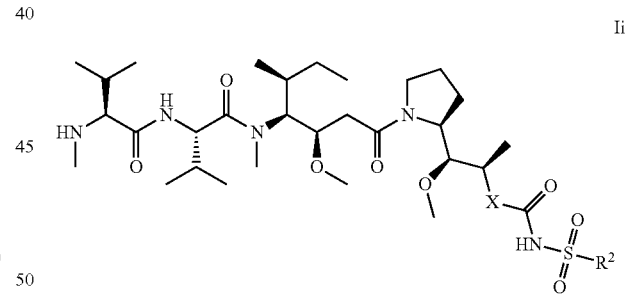

Ii and pharmaceutically acceptable salts thereof, wherein:

R² is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl;

X is —C(O)NHCH(CH₂R³)—, or X is absent; and

R³ is selected from: aryl, heteroaryl, and $C_3$-$C_7$ cycloalkyl, each optionally substituted with one substituent selected from amino and hydroxyl.

Also provided are compounds of Formula Ii:

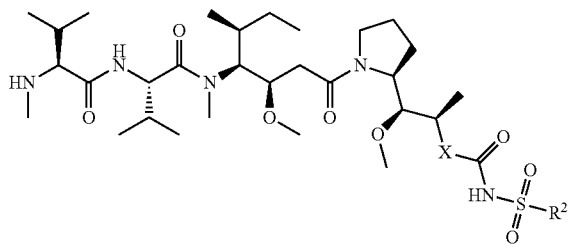

and pharmaceutically acceptable salts thereof, wherein:

R² is selected from: 4-aminobenzyl, 4-(aminomethyl) benzyl, 4-(aminomethyl)phenyl, 4-aminophenyl, benzyl, 3-mercaptopropyl, 2-mercaptoethyl, 4-(mercaptomethyl) phenyl, p-tolyl, 2,4,6-trimethylphenyl, 4-(trifluoromethoxy) phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl;

X is —C(O)NHCH(CH₂R³)—, or X is absent; and

R³ is selected from: 1H-indol-3-yl, 4-aminophenyl, 4-hydroxyphenyl, 5-hydroxypyridin-2-yl, cyclohexyl, and phenyl.

Also provided are compounds of Formula Ij:

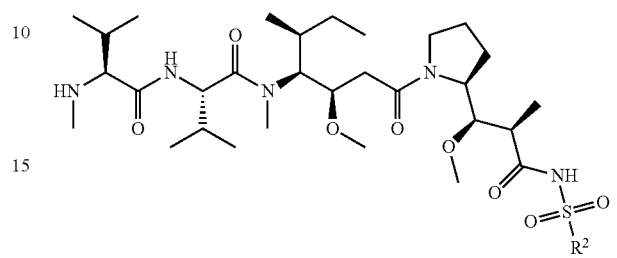

or a pharmaceutically acceptable salt thereof, wherein:

R² is selected from: 4-aminobenzyl, 4-(aminomethyl) benzyl, 4-(aminomethyl)phenyl, 4-aminophenyl, benzyl, 3-mercaptopropyl, 2-mercaptoethyl, 4-(mercaptomethyl) phenyl, p-tolyl, 2,4,6-trimethylphenyl, 4-(trifluoromethoxy) phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl.

Also provided are compounds of Formula Ik:

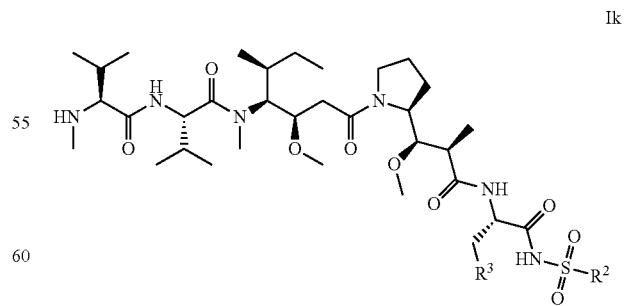

and pharmaceutically acceptable salts thereof, wherein:

R² is selected from: C₂-C₆ alkyl, aryl, aryl-C₁-C₆ alkyl, C₄-C₇ cycloalkyl, C₃-C₇ cycloalkyl-C₁-C₆ alkyl, heteroaryl, heteroaryl-C₁-C₆ alkyl, and heterocyclyl, each optionally Also provided are compounds of Formula Ij:

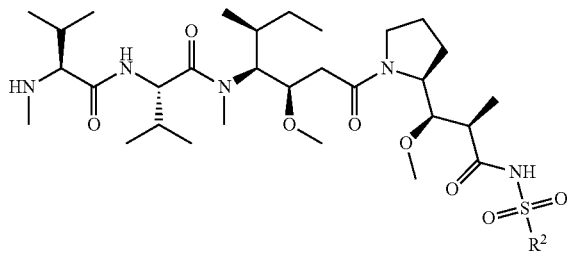

and pharmaceutically acceptable salts thereof, wherein:

R² is selected from: C₂-C₆ alkyl, aryl, aryl-C₁-C₆ alkyl, C₄-C₇ cycloalkyl, C₃-C₇ cycloalkyl-C₁-C₆ alkyl, heteroaryl, heteroaryl-C₁-C₆ alkyl, and heterocyclyl, each optionally substituted with one or more substituents selected from: C₁-C₆ alkoxy, C₁-C₆ alkoxycarbonyl, C₁-C₆ alkyl, C₁-C₆ alkylamino, amino, amino-C₁-C₆ alkyl, amino-aryl, amino-C₃-C₇ cycloalkyl, aryl, carboxamide, carboxyl, cyano, C₁-C₆ haloalkyl, C₁-C₆ haloalkoxy, halo, hydroxyl, nitro, thio, and thio-C₁-C₆ alkyl.

substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl; and $R^3$ is selected from: aryl, heteroaryl, and $C_3$-$C_7$ cycloalkyl, each optionally substituted with one substituent selected from amino and hydroxyl.

Also provided are compounds of Formula Ik:

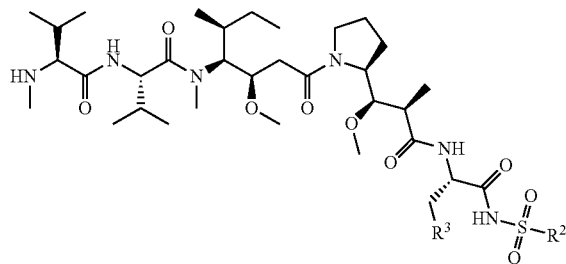

Ik and pharmaceutically acceptable salts thereof, wherein:

$R^2$ is selected from: 4-aminobenzyl, 4-(aminomethyl) benzyl, 4-(aminomethyl)phenyl, 4-aminophenyl, benzyl, 3-mercaptopropyl, 2-mercaptoethyl, 4-(mercaptomethyl) phenyl, p-tolyl, 2,4,6-trimethylphenyl, 4-(trifluoromethoxy) phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl; and $R^3$ is selected from: 1H-indol-3-yl, 4-aminophenyl, 4-hydroxyphenyl, 5-hydroxypyridin-2-yl, cyclohexyl, and phenyl.

Also provided are compounds of Formula Im:

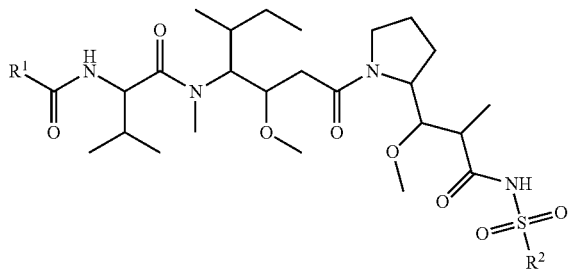

Im and pharmaceutically acceptable salts thereof, wherein:

$R^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloacyl, $C_1$-$C_6$ haloalkyl, heterocyclyl, heterocyclyl-$C_1$-$C_6$ alkyl, hydroxyl, and thio; or $R^1$ is $R^a R^b NCH(R^c)$—;

$R^a$ is selected from: H and $C_1$-$C_6$ alkyl;

$R^b$ is $C_1$-$C_6$ alkyl; and $R^c$ is $R^d$—$C(CH_3)_2$—; and $R^d$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio; or $R^b$ and $R^c$ taken together with the atoms to which they are each bonded form a heterocyclyldiyl;

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl.

Also provided are compounds of Formula Im:

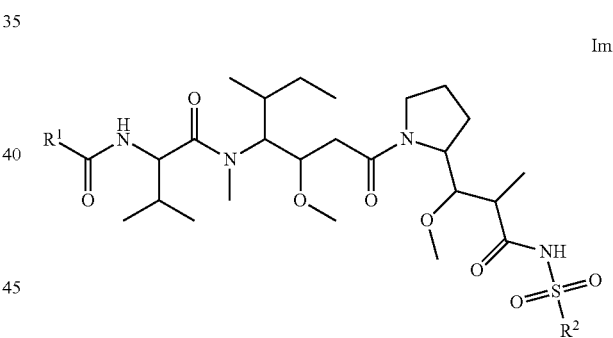

Im and pharmaceutically acceptable salts thereof, wherein:

$R^1$ is selected from: 1-(dimethylamino)-2-methylpropyl, 2-methyl-1-(methylamino)propyl, 1-aminocyclopentyl, 1-aminocyclopropyl, 4-aminophenyl, 2-aminopropan-2-yl, 1-aminocyclohexyl, 3-aminooxetan-3-yl, 2-(methylamino) propan-2-yl, 1-amino-2-methylpropan-2-yl, 2-methylpyrrolidin-2-yl, 2-amino-3-methylbutan-2-yl, 2-aminobutan-2-yl, 2-methyl-1-(methylamino)propan-2-yl, 1-methylpiperidin-2-yl, 3-fluoropyrrolidin-3-yl, 1,2-dimethylpyrrolidin-2-yl, and 2-(dimethylamino)propan-2-yl); and $R^2$ is selected from: 4-aminobenzyl, 4-(aminomethyl) benzyl, 4-(aminomethyl)phenyl, 4-aminophenyl, benzyl, 3-mercaptopropyl, 2-mercaptoethyl, 4-(mercaptomethyl) phenyl, p-tolyl, 2,4,6-trimethylphenyl, 4-(trifluoromethoxy) phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl.

Also provided are compounds of Formula Im:

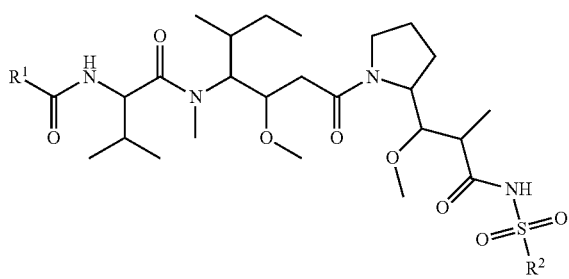

Im and pharmaceutically acceptable salts thereof, wherein:

$R^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloacyl, $C_1$-$C_6$ haloalkyl, heterocyclyl, heterocyclyl-$C_1$-$C_6$ alkyl, hydroxyl, and thio; or $R^1$ is $R^aR^bNCH(R^c)$—;

$R^a$ is selected from: H and $C_1$-$C_6$ alkyl;

$R^b$ is $C_1$-$C_6$ alkyl; and $R^c$ is $R^d$—$C(CH_3)_2$—; and $R^d$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio; or $R^b$ and $R^c$ taken together with the atoms to which they are each bonded form a heterocyclyldiyl;

$R^2$ is selected from: $C_1$-$C_6$ alkyl, aryl, aryl-$C_1$-$C_6$ alkyl, $C_3$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl.

Also provided are compounds of Formula Im:

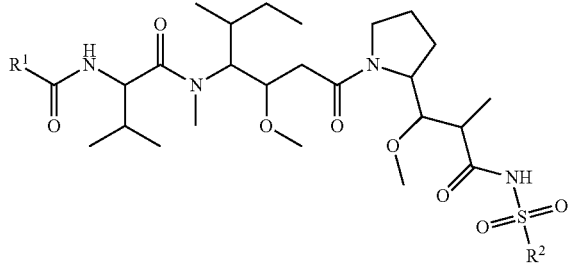

Im and pharmaceutically acceptable salts thereof, wherein:

$R^1$ is selected from: 1-(dimethylamino)-2-methylpropyl, 2-methyl-1-(methylamino)propyl, 1-aminocyclopentyl, 1-aminocyclopropyl, 4-aminophenyl, 2-aminopropan-2-yl, 1-aminocyclohexyl, 3-aminooxetan-3-yl, 2-(methylamino)propan-2-yl, 1-amino-2-methylpropan-2-yl, 2-methylpyrrolidin-2-yl, 2-amino-3-methylbutan-2-yl, 2-aminobutan-2-yl, 2-methyl-1-(methylamino)propan-2-yl, 1-methylpiperidin-2-yl, 3-fluoropyrrolidin-3-yl, 1,2-dimethylpyrrolidin-2-yl, 2-(dimethylamino)propan-2-methyl-1-(methylamino)-2-phenylpropyl, 1-isopropylpiperidin-2-yl, 2-azabicyclo[2.2.1]heptan-3-yl, and 2-methyl-2-azabicyclo[2.2.1]heptan-3-yl; and $R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, 4-amino-3-(trifluoromethyl)phenyl, and 4-(methoxycarbonyl)phenyl.

Also provided are compounds of Formula In:

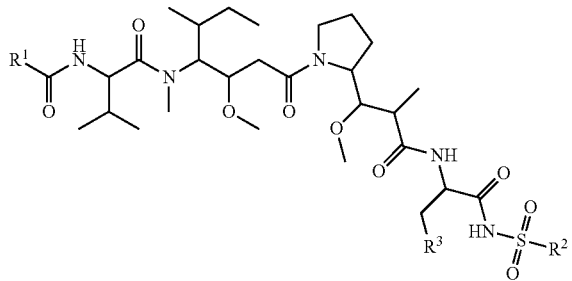

In and pharmaceutically acceptable salts thereof, wherein:

$R^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloacyl, $C_1$-$C_6$ haloalkyl, heterocyclyl, heterocyclyl-$C_1$-$C_6$ alkyl, hydroxyl, and thio; or $R^1$ is $R^a R^b NCH(R^c)$—;

$R^a$ is selected from: H and $C_1$-$C_6$ alkyl;

$R^b$ is $C_1$-$C_6$ alkyl; and $R^c$ is $R^d$—C(CH$_3$)$_2$—; and $R^d$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio; or $R^b$ and $R^c$ taken together with the atoms to which they are each bonded form a heterocyclyldiyl;

$R^2$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl; and $R^3$ is selected from: aryl, heteroaryl, and $C_3$-$C_7$ cycloalkyl, each optionally substituted with one substituent selected from amino and hydroxyl;

provided that when $R^1$ is 2-methyl-1-(methylamino)propyl, and $R^3$ is phenyl, $R^2$ is other than ethyl, isopropyl, n-butyl, and phenyl.

Also provided are compounds of Formula In:

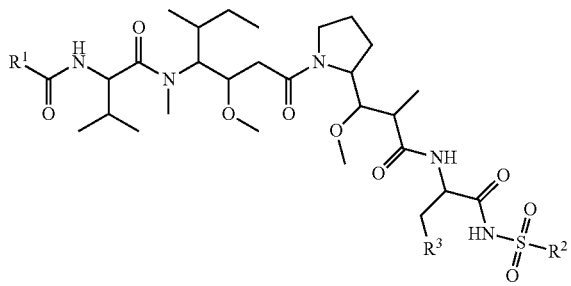

In and pharmaceutically acceptable salts thereof, wherein:

$R^1$ is selected from: 1-(dimethylamino)-2-methylpropyl, 2-methyl-1-(methylamino)propyl, 1-aminocyclopentyl, 1-aminocyclopropyl, 4-aminophenyl, 2-aminopropan-2-yl, 1-aminocyclohexyl, 3-aminooxetan-3-yl, 2-(methylamino)propan-2-yl, 1-amino-2-methylpropan-2-yl, 2-methylpyrrolidin-2-yl, 2-amino-3-methylbutan-2-yl, 2-aminobutan-2-yl, 2-methyl-1-(methylamino)propan-2-yl, 1-methylpiperidin-2-yl, 3-fluoropyrrolidin-3-yl, 1,2-dimethylpyrrolidin-2-yl, and 2-(dimethylamino)propan-2-yl); and $R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, and 4-amino-3-(trifluoromethyl)phenyl; and $R^3$ is selected from: 1H-indol-3-yl, 4-aminophenyl, 4-hydroxyphenyl, 5-hydroxypyridin-2-yl, cyclohexyl, and phenyl provided that when $R^1$ is 2-methyl-1-(methylamino)propyl, and $R^3$ is phenyl, $R^2$ is other than ethyl, isopropyl, n-butyl, and phenyl.

Also provided are compounds of Formula In:

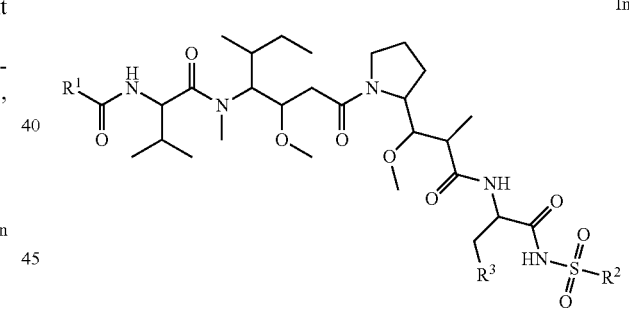

In and pharmaceutically acceptable salts thereof, wherein:

$R^1$ is selected from: 1-(dimethylamino)-2-methylpropyl, 2-methyl-1-(methylamino)propyl, 1-aminocyclopentyl, 1-aminocyclopropyl, 4-aminophenyl, 2-aminopropan-2-yl, 1-aminocyclohexyl, 3-aminooxetan-3-yl, 2-(methylamino)propan-2-yl, 1-amino-2-methylpropan-2-yl, 2-methylpyrrolidin-2-yl, 2-amino-3-methylbutan-2-yl, 2-aminobutan-2-yl, 2-methyl-1-(methylamino)propan-2-yl, 1-methylpiperidin-2-yl, 3-fluoropyrrolidin-3-yl, 1,2-dimethylpyrrolidin-2-yl, 2-(dimethylamino)propan-2-yl), 2-methyl-1-(methylamino)-2-phenylpropyl, 1-isopropylpiperidin-2-yl, 2-azabicyclo[2.2.1]heptan-3-yl, and 2-methyl-2-azabicyclo[2.2.1]heptan-3-yl; and $R^2$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2- nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, 4-amino-3-(trifluoromethyl)phenyl, and 4-(methoxycarbonyl)phenyl; and $R^3$ is selected from: 1H-indol-3-yl, 4-aminophenyl, 4-hydroxyphenyl, 5-hydroxypyridin-2-yl, cyclohexyl, and phenyl provided that when $R^1$ is 2-methyl-1-(methylamino)propyl, and $R^3$ is phenyl, $R^2$ is other than ethyl, isopropyl, n-butyl, and phenyl.

Also provided are compounds of Formula VI:

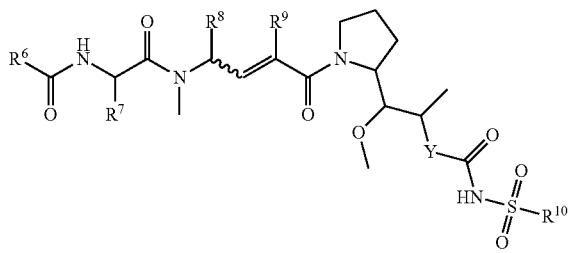

VI and pharmaceutically acceptable salts thereof, wherein:

$R^6$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloacyl, $C_1$-$C_6$ haloalkyl, heterocyclyl, heterocyclyl-$C_1$-$C_6$ alkyl, hydroxyl, and thio; or $R^6$ is $R^eR^fNCH(R^g)$—;

$R^e$ is selected from: H and $C_1$-$C_6$ alkyl;

$R^f$ is $C_1$-$C_6$ alkyl; and $R^g$ is $R^h$—$C(CH_3)_2$—; and $R^h$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio; or $R^e$ and $R^f$ taken together with the atoms to which they are each bonded form a heterocyclyldiyl;

$R^7$ is $C_2$-$C_4$ alkyl optionally substituted with $C_1$-$C_6$ alkylthio;

$R^8$ is $C_2$-$C_4$ alkyl optionally substituted with $C_1$-$C_6$ alkylthio;

$R^9$ is selected from: H and $C_1$-$C_3$ alkyl;

$R^{10}$ is selected from: $C_1$-$C_6$ alkyl, aryl, aryl-$C_1$-$C_6$ alkyl, $C_3$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl;

Y is —C(O)NHCH($CH_2R^{11}$)—, or Y is absent; and $R^{11}$ is selected from: aryl, heteroaryl, and $C_3$-$C_7$ cycloalkyl, each optionally substituted with one substituent selected from amino and hydroxyl.

Also provided are compounds of Formula VI:

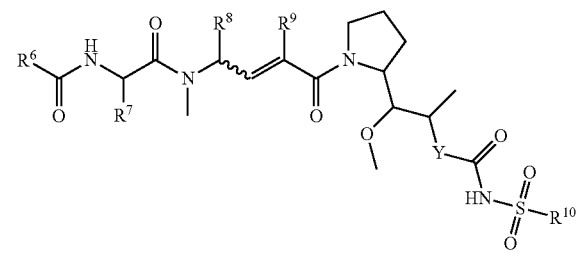

VI and pharmaceutically acceptable salts thereof, wherein:

$R^6$ is selected from: 1-(dimethylamino)-2-methylpropyl, 2-methyl-1-(methylamino)propyl, 1-aminocyclopentyl, 1-aminocyclopropyl, 4-aminophenyl, 2-aminopropan-2-yl, 1-aminocyclohexyl, 3-aminooxetan-3-yl, 2-(methylamino)propan-2-yl, 1-amino-2-methylpropan-2-yl, 2-methylpyrrolidin-2-yl, 2-amino-3-methylbutan-2-yl, 2-aminobutan-2-yl, 2-methyl-1-(methylamino)propan-2-yl, 1-methylpiperidin-2-yl, 3-fluoropyrrolidin-3-yl, 1,2-dimethylpyrrolidin-2-yl, 2-(dimethylamino)propan-2-yl), 2-methyl-1-(methylamino)-2-phenylpropyl, 1-isopropylpiperidin-2-yl, 2-azabicyclo[2.2.1]heptan-3-yl, and 2-methyl-2-azabicyclo[2.2.1]heptan-3-yl;

$R^7$ is selected from: isopropyl, isobutyl, sec-butyl, tert-butyl, and 2-(methylthio)ethyl;

$R^8$ is selected from: isopropyl, isobutyl, sec-butyl, and 2-(methylthio)ethyl;

$R^9$ is selected from: methyl, ethyl, and n-propyl;

$R^{10}$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin 1 yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl,3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, 4-amino-3-(trifluoromethyl)phenyl, and 4-(methoxycarbonyl)phenyl;

Y is —C(O)NHCH(CH$_2$R$^{11}$)—, or Y is absent; and

R$^{11}$ is selected from: 1H-indol-3-yl, 4-aminophenyl, 4-hydroxyphenyl, 5-hydroxypyridin-2-yl, cyclohexyl, and phenyl.

Also provided are compounds of Formula VII:

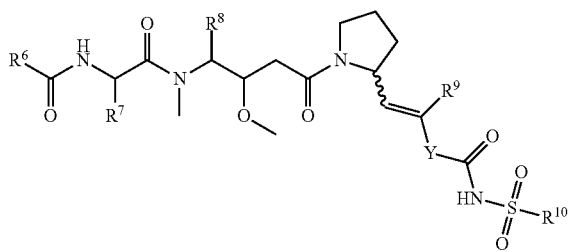

VII and pharmaceutically acceptable salts thereof, wherein:

R$^6$ is selected from: amino-C$_1$-C$_6$ alkyl, amino-aryl, amino-C$_3$-C$_7$ cycloalkyl, amino-heterocyclyl, and heterocyclyl, each optionally substituted with one or more substituents selected from aryl, aryl-C$_1$-C$_6$ alkyl, C$_1$-C$_6$ alkyl, C$_1$-C$_6$ alkylthio, carboxyl, carboxamide, C$_3$-C$_7$ cycloalkyl, C$_3$-C$_7$ cycloalkyl-C$_1$-C$_6$ alkyl, guanidino, halo, C$_1$-C$_6$ haloacyl, C$_1$-C$_6$ haloalkyl, heterocyclyl, heterocyclyl-C$_1$-C$_6$ alkyl, hydroxyl, and thio; or R$^6$ is R$^e$R$^f$NCH(R$^g$)—;

R$^e$ is selected from: H and C$_1$-C$_6$ alkyl;

R$^f$ is C$_1$-C$_6$ alkyl; and

R$^g$ is R$^h$—C(CH$_3$)$_2$—; and

R$^h$ is selected from: H, aryl, C$_3$-C$_7$ cycloalkyl, and heteroaryl, each of which is optionally substituted with one or more substituents selected from: C$_1$-C$_4$ acylthio, C$_2$-C$_4$ alkenyl, C$_1$-C$_4$ alkyl, C$_1$-C$_4$ alkylamino, C$_1$-C$_4$ alkyloxy, amino, amino-C$_1$-C$_4$ alkyl, halo, C$_1$-C$_4$ haloalkyl, hydroxyl, hydroxy-C$_1$-C$_4$ alkyl, and thio, wherein C$_2$-C$_4$ alkenyl, C$_1$-C$_4$ alkylamino and C$_1$-C$_4$ alkyloxy are further optionally substituted with one substituent selected from C$_1$-C$_4$ alkylaryl, hydroxyl, and thio; or R$^e$ and R$^f$ taken together with the atoms to which they are each bonded form a heterocyclyldiyl;

R$^7$ is C$_2$-C$_4$ alkyl optionally substituted with C$_1$-C$_6$ alkylthio;

R$^8$ is C$_2$-C$_4$ alkyl optionally substituted with C$_1$-C$_6$ alkylthio;

R$^9$ is selected from: H and C$_1$-C$_3$ alkyl;

R$^{10}$ is selected from: C$_1$-C$_6$ alkyl, aryl, aryl-C$_1$-C$_6$ alkyl, C$_3$-C$_7$ cycloalkyl, C$_3$-C$_7$ cycloalkyl-C$_1$-C$_6$ alkyl, heteroaryl, heteroaryl-C$_1$-C$_6$ alkyl, and heterocyclyl, each optionally substituted with one or more substituents selected from: C$_1$-C$_6$ alkoxy, C$_1$-C$_6$ alkoxycarbonyl, C$_1$-C$_6$ alkyl, C$_1$-C$_6$ alkylamino, amino, amino-C$_1$-C$_6$ alkyl, amino-aryl, amino-C$_3$-C$_7$ cycloalkyl, aryl, carboxamide, carboxyl, cyano, C$_1$-C$_6$ haloacyl, C$_1$-C$_6$ haloalkyl, C$_1$-C$_6$ haloalkoxy, halo, hydroxyl, nitro, thio, and thio-C$_1$-C$_6$ alkyl;

Y is —C(O)NHCH(CH$_2$R$^{11}$)—, or Y is absent; and

R$^{11}$ is selected from: aryl, heteroaryl, and C$_3$-C$_7$ cycloalkyl, each optionally substituted with one substituent selected from amino and hydroxyl.

Also provided are compounds of Formula VII:

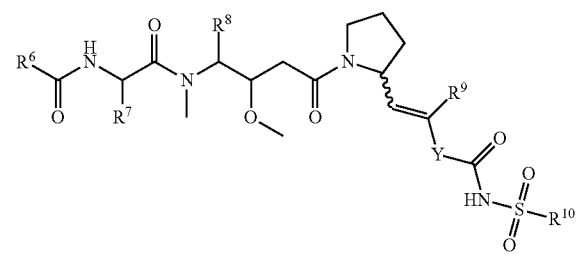

VII and pharmaceutically acceptable salts thereof, wherein:

R$^6$ is selected from: 1-(dimethylamino)-2-methylpropyl, 2-methyl-1-(methylamino)propyl, 1-aminocyclopentyl, 1-aminocyclopropyl, 4-aminophenyl, 2-aminopropan-2-yl, 1-aminocyclohexyl, 3-aminooxetan-3-yl, 2-(methylamino)propan-2-yl, 1-amino-2-methylpropan-2-yl, 2-methylpyrrolidin-2-yl, 2-amino-3-methylbutan-2-yl, 2-aminobutan-2-yl, 2-methyl-1-(methylamino)propan-2-yl, 1-methylpiperidin-2-yl, 3-fluoropyrrolidin-3-yl, 1,2-dimethylpyrrolidin-2-yl, 2-(dimethylamino)propan-2-yl), 2-methyl-1-(methylamino)-2-phenylpropyl, 1-isopropylpiperidin-2-yl, 2-azabicyclo[2.2.1]heptan-3-yl, and 2-methyl-2-azabicyclo[2.2.1]heptan-3-yl;

R$^7$ is selected from: isopropyl, isobutyl, sec-butyl, tert-butyl, and 2-(methylthio)ethyl;

R$^8$ is selected from: isopropyl, isobutyl, sec-butyl, and 2-(methylthio)ethyl;

R$^9$ is selected from: methyl, ethyl, and n-propyl;

R$^{10}$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, 4-amino-3-(trifluoromethyl)phenyl, and 4-(methoxycarbonyl)phenyl;

Y is —C(O)NHCH(CH$_2$R$^{11}$)—, or Y is absent; and

R$^{11}$ is selected from: 1H-indol-3-yl, 4-aminophenyl, 4-hydroxyphenyl, 5-hydroxypyridin-2-yl, cyclohexyl, and phenyl.

Also provided are compounds of Formula VIII:

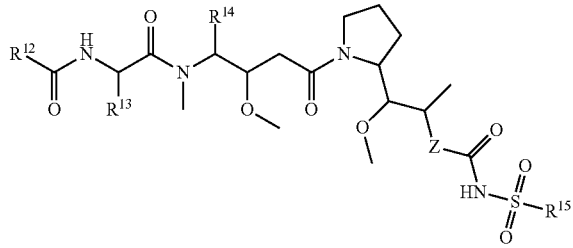

VIII and pharmaceutically acceptable salts thereof, wherein:

R$^{12}$ is selected from: amino-C$_1$-C$_6$ alkyl, amino-aryl, amino-C$_3$-C$_7$ cycloalkyl, amino-heterocyclyl, and heterocyclyl, each optionally substituted with one or more substituents selected from aryl, aryl-C$_1$-C$_6$ alkyl, C$_1$-C$_6$ alkyl, C$_1$-C$_6$ alkylthio, carboxyl, carboxamide, C$_3$-C$_7$ cycloalkyl, C$_3$-C$_7$ cycloalkyl-C$_1$-C$_6$ alkyl, guanidino, halo, C$_1$-C$_6$ haloacyl, C$_1$-C$_6$ haloalkyl, heterocyclyl, heterocyclyl-C$_1$-C$_6$ alkyl, hydroxyl, and thio; or R$^{12}$ is R$^i$R$^j$NCH(R$^k$)—;

R$^i$ is selected from: H and C$_1$-C$_6$ alkyl;

R$^j$ is C$_1$-C$_6$ alkyl; and

R$^k$ is R$^m$—C(CH$_3$)$_2$—; and

R$^m$ is selected from: H, aryl, C$_3$-C$_7$ cycloalkyl, and heteroaryl, each of which is optionally substituted with one or more substituents selected from: C$_1$-C$_4$ acylthio, C$_2$-C$_4$ alkenyl, C$_1$-C$_4$ alkyl, C$_1$-C$_4$ alkylamino, C$_1$-C$_4$ alkyloxy, amino, amino-C$_1$-C$_4$ alkyl, halo, C$_1$-C$_4$ haloalkyl, hydroxyl, hydroxy-C$_1$-C$_4$ alkyl, and thio, wherein C$_2$-C$_4$ alkenyl, C$_1$-C$_4$ alkylamino and C$_1$-C$_4$ alkyloxy are further optionally substituted with one substituent selected from C$_1$-C$_4$ alkylaryl, hydroxyl, and thio; or R$^i$ and R$^j$ taken together with the atoms to which they are each bonded form a heterocyclyldiyl;

R$^{13}$ is C$_2$-C$_4$ alkyl optionally substituted with C$_1$-C$_6$ alkylthio;

R$^{14}$ is C$_2$-C$_4$ alkyl optionally substituted with C$_1$-C$_6$ alkylthio;

R$^{15}$ is selected from: C$_2$-C$_6$ alkyl, aryl, aryl-C$_1$-C$_6$ alkyl, C$_4$-C$_7$ cycloalkyl, C$_3$-C$_7$ cycloalkyl-C$_1$-C$_6$ alkyl, heteroaryl, heteroaryl-C$_1$-C$_6$ alkyl, and heterocyclyl, each optionally substituted with one or more substituents selected from: C$_1$-C$_6$ alkoxy, C$_1$-C$_6$ alkoxycarbonyl, C$_1$-C$_6$ alkyl, C$_1$-C$_6$ alkylamino, amino, amino-C$_1$-C$_6$ alkyl, amino-aryl, amino-C$_3$-C$_7$ cycloalkyl, aryl, carboxamide, carboxyl, cyano, C$_1$-C$_6$ haloacyl, C$_1$-C$_6$ haloalkyl, C$_1$-C$_6$ haloalkoxy, halo, hydroxyl, nitro, thio, and thio-C$_1$-C$_6$ alkyl;

Z is —C(O)NHCH(CH$_2$R$^{16}$)—, or Z is absent; and

R$^{16}$ is selected from: aryl, heteroaryl, and C$_3$-C$_7$ cycloalkyl, each optionally substituted with one substituent selected from amino and hydroxyl;

provided that when R$^{12}$ is 2-methyl-1-(methylamino)propyl, R$^{13}$ is isopropyl, and R$^{14}$ is sec-butyl, and Z is —C(O)NHCH(CH$_2$Ph)-, R$^{15}$ is other than ethyl, isopropyl, n-butyl, and phenyl.

Also provided are compounds of Formula VIII:

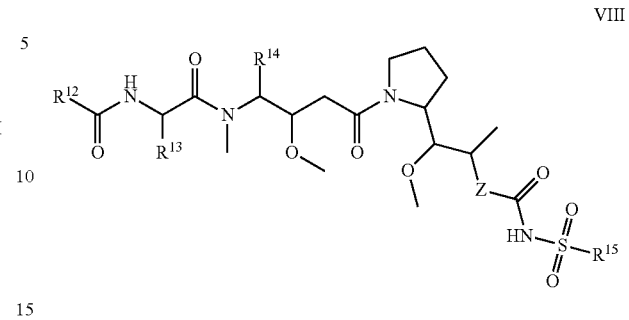

VIII and pharmaceutically acceptable salts thereof, wherein:

R$^{12}$ is selected from: 1-(dimethylamino)-2-methylpropyl, 2-methyl-1-(methylamino)propyl, 1-aminocyclopentyl, 1-aminocyclopropyl, 4-aminophenyl, 2-aminopropan-2-yl, 1-aminocyclohexyl, 3-aminooxetan-3-yl, 2-(methylamino)propan-2-yl, 1-amino-2-methylpropan-2-yl, 2-methylpyrrolidin-2-yl, 2-amino-3-methylbutan-2-yl, 2-aminobutan-2-yl, 2-methyl-1-(methylamino)propan-2-yl, 1-methylpiperidin-2-yl, 3-fluoropyrrolidin-3-yl, 1,2-dimethylpyrrolidin-2-yl, 2-(dimethylamino)propan-2-yl), 2-methyl-1-(methylamino)-2-phenylpropyl, 1-isopropylpiperidin-2-yl, 2-azabicyclo[2.2.1]heptan-3-yl, and 2-methyl-2-azabicyclo[2.2.1]heptan-3-yl;

R$^{13}$ is selected from: isopropyl, isobutyl, sec-butyl, tert-butyl, and 2-(methylthio)ethyl;

R$^{14}$ is selected from: isopropyl, isobutyl, sec-butyl, and 2-(methylthio)ethyl;

R$^{15}$ is selected from: 4-aminobenzyl, 4-(aminomethyl)benzyl, 4-(aminomethyl)phenyl, 4-aminophenyl, benzyl, 3-mercaptopropyl, 2-mercaptoethyl, 4-(mercaptomethyl)phenyl, p-tolyl, 2,4,6-trimethylphenyl, 4-(trifluoromethoxy)phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonyphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, 4-amino-3-(trifluoromethyl)phenyl, and 4-(methoxycarbonyl)phenyl;

Z is —C(O)NHCH(CH$_2$R$^{16}$)—, or Z is absent; and

R$^{16}$ is selected from: 1H-indol-3-yl, 4-aminophenyl, 4-hydroxyphenyl, 5-hydroxypyridin-2-yl, cyclohexyl, and phenyl;

provided that when R$^{12}$ is 2-methyl-1-(methylamino)propyl, R$^{13}$ is isopropyl, and R$^{14}$ is sec-butyl, and Z is —C(O)NHCH(CH$_2$Ph)-, R$^{15}$ is other than ethyl, isopropyl, n-butyl, and phenyl.

Also provided are compounds of Formula VIIIa:

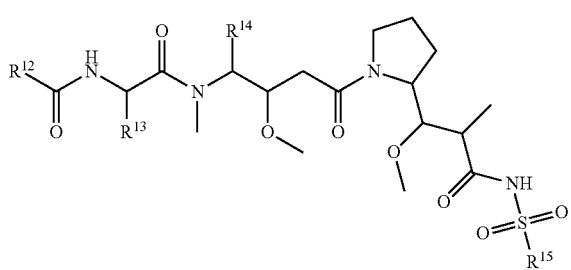

and pharmaceutically acceptable salts thereof, wherein:

$R^{12}$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloacyl, $C_1$-$C_6$ haloalkyl, heterocyclyl, heterocyclyl-$C_1$-$C_6$ alkyl, hydroxyl, and thio; or $R^{12}$ is $R^iR^jNCH(R^k)$—;

$R^i$ is selected from: H and $C_1$-$C_6$ alkyl;

$R^j$ is $C_1$-$C_6$ alkyl; and $R^k$ is $R^m$—$C(CH_3)_2$—; and $R^m$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio; or $R^i$ and $R^j$ taken together with the atoms to which they are each bonded form a heterocyclyldiyl;

$R^{13}$ is $C_2$-$C_4$ alkyl optionally substituted with $C_1$-$C_6$ alkylthio;

$R^{14}$ is $C_2$-$C_4$ alkyl optionally substituted with $C_1$-$C_6$ alkylthio; and $R^{15}$ is selected from: $C_1$-$C_6$ alkyl, aryl, aryl-$C_1$-$C_6$ alkyl, $C_3$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl.

Also provided are compounds of Formula VIIIa:

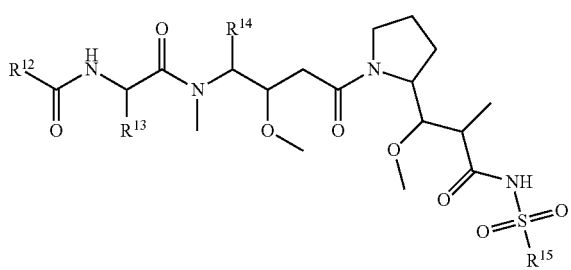

and pharmaceutically acceptable salts thereof, wherein:

$R^{12}$ is selected from: 1-(dimethylamino)-2-methylpropyl, 2-methyl-1-(methylamino)propyl, 1-aminocyclopentyl, 1-aminocyclopropyl, 4-aminophenyl, 2-aminopropan-2-yl, 1-aminocyclohexyl, 3-aminooxetan-3-yl, 2-(methylamino) propan-2-yl, 1-amino-2-methylpropan-2-yl, 2-methylpyrrolidin-2-yl, 2-amino-3-methylbutan-2-yl, 2-aminobutan-2-yl, 2-methyl-1-(methylamino)propan-2-yl, 1-methylpiperidin-2-yl, 3-fluoropyrrolidin-3-yl, 1,2-dimethylpyrrolidin-2-yl, 2-(dimethylamino)propan-2-yl), 2-methyl-1-(methylamino)-2-phenylpropyl, 1-isopropylpiperidin-2-yl, 2-azabicyclo[2.2.1]heptan-3-yl, and 2-methyl-2-azabicyclo[2.2.1]heptan-3-yl;

$R^{13}$ is selected from: isopropyl, isobutyl, sec-butyl, tert-butyl, and 2-(methylthio)ethyl;

$R^{14}$ is selected from: isopropyl, isobutyl, sec-butyl, and 2-(methylthio)ethyl; and $R^{15}$ is selected from: 4-aminobenzyl, 4-(aminomethyl) benzyl, 4-(aminomethyl)phenyl, 4-aminophenyl, benzyl, 3-mercaptopropyl, 2-mercaptoethyl, 4-(mercaptomethyl) phenyl, p-tolyl, 2,4,6-trimethylphenyl, 4-(trifluoromethoxy) phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, 4-amino-3-(trifluoromethyl)phenyl, and 4-(methoxycarbonyl)phenyl.

Also provided are compounds of Formula VIIIb:

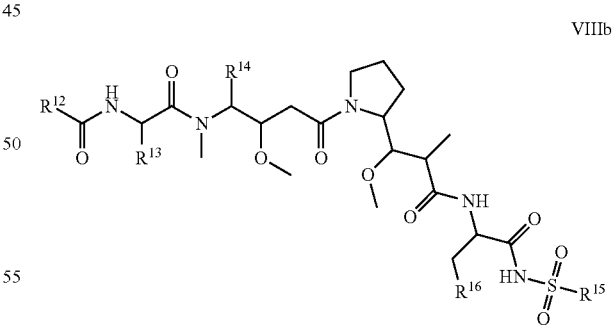

and pharmaceutically acceptable salts thereof, wherein:

$R^{12}$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloacyl, $C_1$-$C_6$ haloalkyl, heterocyclyl, heterocyclyl-$C_1$-$C_6$ alkyl, hydroxyl, and thio; or $R^{12}$ is $R^iR_jNCH(R^k)$—;

$R^i$ is selected from: H and $C_1$-$C_6$ alkyl;

$R^j$ is $C_1$-$C_6$ alkyl; and $R^k$ is $R^m$—$C(CH_3)_2$—; and $R^m$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio; or $R^i$ and $R^j$ taken together with the atoms to which they are each bonded form a heterocyclyldiyl;

$R^{13}$ is $C_2$-$C_4$ alkyl optionally substituted with $C_1$-$C_6$ alkylthio;

$R^{14}$ is $C_2$-$C_4$ alkyl optionally substituted with $C_1$-$C_6$ alkylthio;

$R^{15}$ is selected from: $C_2$-$C_6$ alkyl, aryl, aryl-$C_1$-$C_6$ alkyl, $C_4$-$C_7$ cycloalkyl, $C_3$-$C_7$ cycloalkyl-$C_1$-$C_6$ alkyl, heteroaryl, heteroaryl-$C_1$-$C_6$ alkyl, and heterocyclyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloacyl, $C_1$-$C_6$ haloalkyl, $C_1$-$C_6$ haloalkoxy, halo, hydroxyl, nitro, thio, and thio-$C_1$-$C_6$ alkyl; and $R^{16}$ is selected from: aryl, heteroaryl, and $C_3$-$C_7$ cycloalkyl, each optionally substituted with one substituent selected from amino and hydroxyl;

provided that when $R^{12}$ is 2-methyl-1-(methylamino)propyl, $R^{13}$ is isopropyl, and $R^{14}$ is sec-butyl, and $R^{16}$ is phenyl, $R^{15}$ is other than ethyl, isopropyl, n-butyl, and phenyl.

Also provided are compounds of Formula VIIIb:

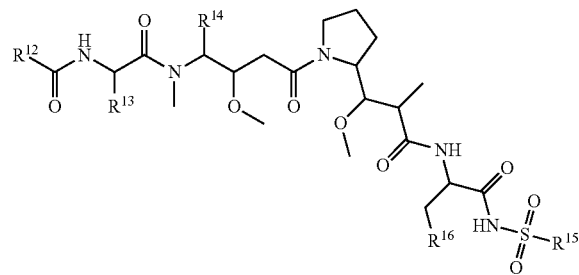

VIIIb and pharmaceutically acceptable salts thereof, wherein:

$R^{12}$ is selected from: 1-(dimethylamino)-2-methylpropyl, 2-methyl-1-(methylamino)propyl, 1-aminocyclopentyl, 1-aminocyclopropyl, 4-aminophenyl, 2-aminopropan-2-yl, 1-aminocyclohexyl, 3-aminooxetan-3-yl, 2-(methylamino)propan-2-yl, 1-amino-2-methylpropan-2-yl, 2-methylpyrrolidin-2-yl, 2-amino-3-methylbutan-2-yl, 2-aminobutan-2-yl, 2-methyl-1-(methylamino)propan-2-yl, 1-methylpiperidin-2-yl, 3-fluoropyrrolidin-3-yl, 1,2-dimethylpyrrolidin-2-yl, 2-(dimethylamino)propan-2-yl), 2-methyl-1-(methylamino)-2-phenylpropyl, 1-isopropylpiperidin-2-yl, 2-azabicyclo[2.2.1]heptan-3-yl, and 2-methyl-2-azabicyclo[2.2.1]heptan-3-yl;

$R^{13}$ is selected from: isopropyl, isobutyl, sec-butyl, tert-butyl, and 2-(methylthio)ethyl;

$R^{14}$ is selected from: isopropyl, isobutyl, sec-butyl, and 2-(methylthio)ethyl;

$R^{15}$ is selected from: 4-aminobenzyl, 4-(aminomethyl) benzyl, 4-(aminomethyl)phenyl, 4-aminophenyl, benzyl, 3-mercaptopropyl, 2-mercaptoethyl, 4-(mercaptomethyl) phenyl, p-tolyl, 2,4,6-trimethylphenyl, 4-(trifluoromethoxy) phenyl, 2,4,6-triisopropylphenyl, 4-tert-butylphenyl, 4-chlorophenyl, 3-cyanophenyl, 2-nitrophenyl, 4-methoxy-2-nitrophenyl, 4-aminocarbonyl-2-nitrophenyl, 4-methoxyphenyl, phenyl, 2-fluorobenzyl, piperidin-1-yl, o-tolyl, 4-bromophenyl, naphthalen-2-yl, 4-methoxycarbonylphenyl, 2-(trifluoromethyl)benzyl, hexan-2-yl, 2-methoxyethyl, cyclopentylmethyl, cyclohexyl, pyridin-3-ylmethyl, 4-carboxyphenyl, 3-aminophenyl, pyridin-3-yl, thien-2-yl, 4-hydroxyphenyl, 4-(1-aminocyclopropyl)benzyl, 4-(1-aminocyclopropyl)phenyl, 2-methylbenzyl, 4-nitrobenzyl, 4-chlorobenzyl, phenethyl, 4-bromobenzyl, 4-cyanobenzyl, 3-nitrobenzyl, 4-tert-butylbenzyl, 2-nitrobenzyl, 4-nitrophenethyl, 2-chloro-3-methoxycarbonylphenyl, 2-aminophenyl, [1,1'-biphenyl]-4-yl, 4'-amino-[1,1'-biphenyl]-4-yl, 4-fluorobenzyl, 3-(trifluoromethyl)benzyl, 3-(trifluoromethoxy)benzyl, 3,4-dichlorobenzyl, 2-cyanobenzyl, 3-chlorobenzyl, 4-amino-2-ethylphenyl, 4-amino-3-(trifluoromethoxy)phenyl, 4-amino-2,3-dimethylphenyl, 4-amino-5,6,7,8-tetrahydronaphthalen-1-yl, 4-amino-3-methylphenyl, 4-amino-3-fluorophenyl, 4-amino-3-ethylphenyl, 4-amino-3-(trifluoromethyl)phenyl, and 4-(methoxycarbonyl)phenyl; and $R^{16}$ is selected from: 1H-indol-3-yl, 4-aminophenyl, 4-hydroxyphenyl, 5-hydroxypyridin-2-yl, cyclohexyl, and phenyl;

provided that when $R^{12}$ is 2-methyl-1-(methylamino)propyl, $R^{13}$ is isopropyl, and $R^{14}$ is sec-butyl, and $R^{16}$ is phenyl, $R^{15}$ is other than ethyl, isopropyl, n-butyl, and phenyl.

Some embodiments of the present invention include every combination of one or more compounds selected from the following group shown in Table A.

Some embodiments of the present invention include every combination of one or more compounds selected from the following group shown in Table B.

Some embodiments of the present invention include every combination of one or more compounds selected from the following group shown in Table C.

TABLE A

| Chemical Structure | Chemical Name |
|---|---|
| 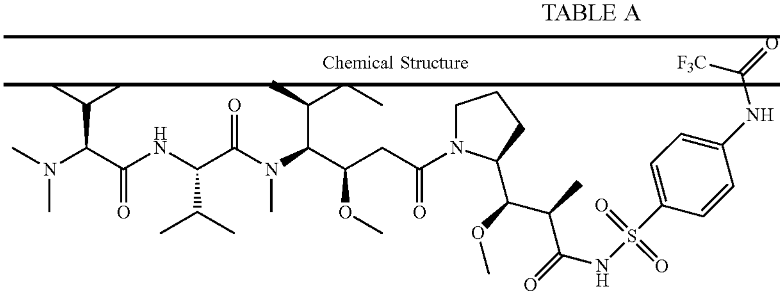 | (S)-2-((S)-2-(dimethylamino)-3-methylbutanamido)-N-((3R,4S,5S)-3-methoxy-1-((S)-2-((1R,2R)-1-methoxy-2-methyl-3-oxo-3-(4-(2,2,2-trifluoroacetamido)phenylsulfonamido) propyl)pyrrolidin-1-yl)-5-methl-1-oxoheptan-4-yl)-N,3-dimethylbutanamide (Compound 4) |

TABLE A-continued

| Chemical Structure | Chemical Name |
|---|---|
| 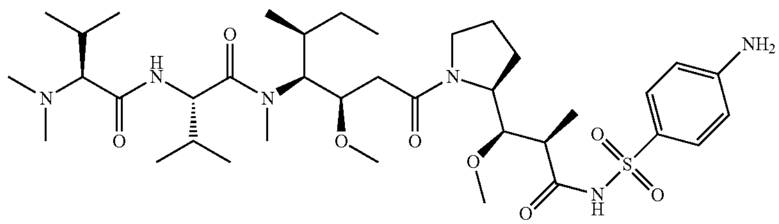 [SMILES: CC[C@H](C)[C@@H]([C@@H](CC(=O)N1CCC[C@H]1[C@H](OC)[C@@H](C)C(=O)NS(=O)(=O)c1ccc(N)cc1)OC)N(C)C(=O)[C@@H](NC(=O)[C@H](C(C)C)N(C)C)C(C)C] | (S)-N-((3R,4S,5S)-1-((S)-2-((1R,2R)-3-(4-aminophenylsulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 5) |
| | (S)-2-((S)-2-(dimethylamino)-3-methylbutanamido)-N-((3R,4S,5S)-3-methoxy-1-((S)-2-((1R,2R)-1-methoxy-2-methyl-3-oxo-3-((4-(2,2,2-trifluoroacetamido)phenyl)methylsulfonamido)propyl)pyrrolidin-1-yl)-5-methyl-1-oxoheptan-4-yl)-N,3-dimethylbutanamide (Compound 7) |
| 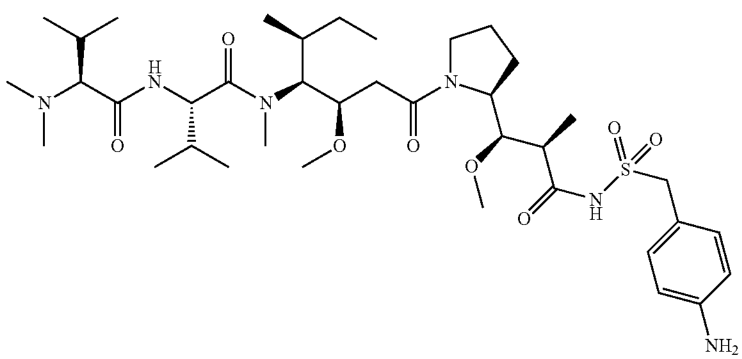 [SMILES: CC[C@H](C)[C@@H]([C@@H](CC(=O)N1CCC[C@H]1[C@H](OC)[C@@H](C)C(=O)NS(=O)(=O)Cc1ccc(N)cc1)OC)N(C)C(=O)[C@@H](NC(=O)[C@H](C(C)C)N(C)C)C(C)C] | (S)-N-((3R,4S,5S)-1-((S)-2-((1R,2R)-3-((4-aminophenyl)methylsulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 8) |
| 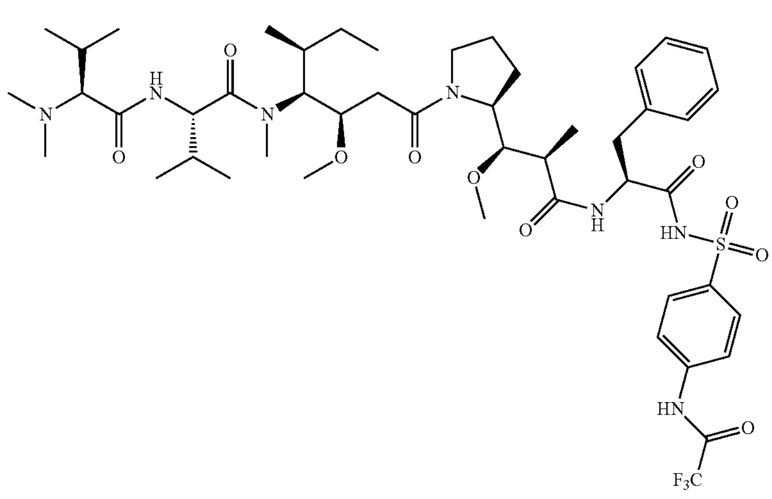 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(NC(=O)C(F)(F)F)cc1)OC)N(C)C(=O)[C@@H](NC(=O)[C@H](C(C)C)N(C)C)C(C)C] | (S)-2-((S)-2-(dimethylamino)-3-methylbutanamido)-N-((3R,4S,5S)-3-methoxy-1-((S)-2-((1R,2R)-1-methoxy-2-methyl-3-oxo-3-((S)-1-oxo-3-phenyl-1-(4-(2,2,2-trifluoroacetamido)phenylsulfonamido)propan-2-ylamino)propyl)pyrrolidin-1-yl)-5-methyl-1-oxoheptan-4-yl)-N,3-dimethylbutanamide (Compound 10) |

TABLE A-continued

| Chemical Structure | Chemical Name |
|---|---|
| 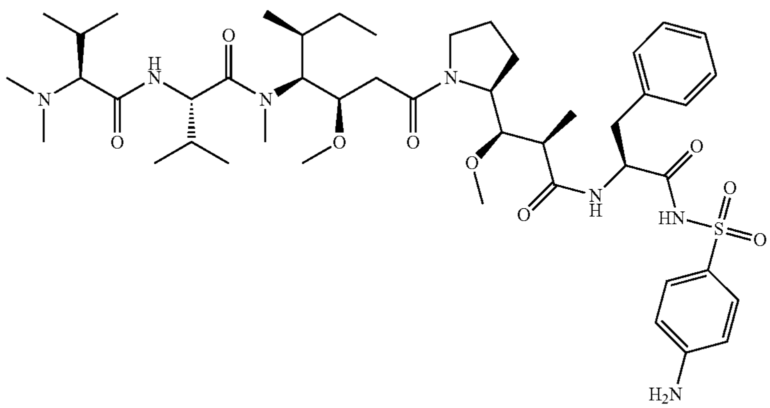 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(N)cc1)OC)N(C)C(=O)[C@@H](NC(=O)[C@H](C(C)C)N(C)C)C(C)C] | (S)-N-((3R,4S,5S)-1-((S)-2-((1R,2R)-3-((S)-1-(4-aminophenylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 11) |
| 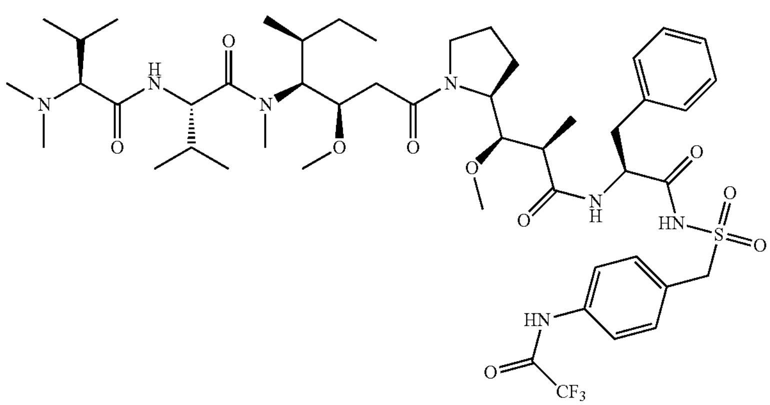 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)Cc1ccc(NC(=O)C(F)(F)F)cc1)OC)N(C)C(=O)[C@@H](NC(=O)[C@H](C(C)C)N(C)C)C(C)C] | (S)-2-((S)-2-(dimethylamino)-3-methylbutanamido)-N-((3R,4S,5S)-3-methoxy-1-((S)-2-((1R,2R)-1-methoxy-2-methyl-3-oxo-3-((S)-1-oxo-3-phenyl-1-(4-(2,2,2-trifluoroacetamido)phenylmethylsulfonamido)propan-2-ylamino)propyl)pyrrolidin-1-yl)-5-methyl-1-oxoheptan-4-yl)-N,3-dimethylbutanamide (Compound 13) |
| 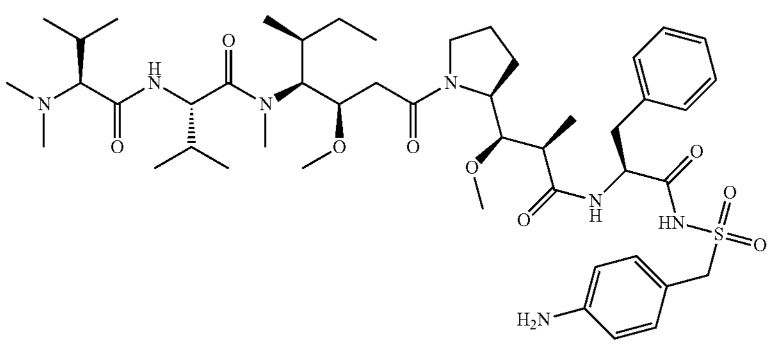 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)Cc1ccc(N)cc1)OC)N(C)C(=O)[C@@H](NC(=O)[C@H](C(C)C)N(C)C)C(C)C] | (S)-N-((3R,4S,5S)-1-((S)-2-((1R,2R)-3-((S)-1-(4-aminophenylmethylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 14) |

TABLE B

| Chemical Structure | Chemical Name |
|---|---|
| 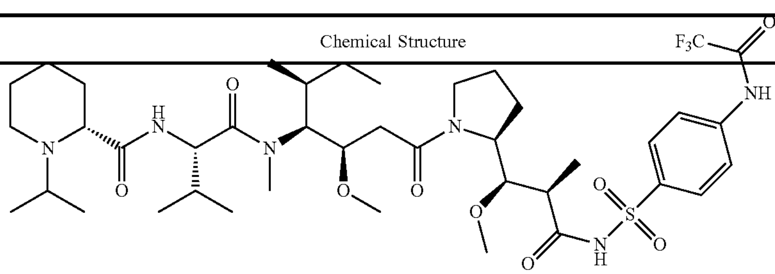 | (R)-1-isopropyl-N-((S)-1-(((3R,4S,5S)-3-methoxy-1-((S)-2-((1R,2R)-1-methoxy-2-methyl-3-oxo-3-((4-(2,2,2-trifluoroacetamido)phenyl)sulfonamido)propyl)pyrrolidin-1-yl)-5-methyl-1-oxoheptan-4-yl)(methyl)amino)-3-methyl-1-oxobutan-2-yl)piperidine-2-carboxamide (Compound 15) |

TABLE B-continued

| Chemical Structure | Chemical Name |
|---|---|
| | (R)-N-((S)-1-(((3R,4S,5S)-1-((S)-2-((1R,2R)-3-((4-aminophenyl)sulfonamido)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-1-isopropylpiperidine-2-carboxamide (Compound 16) |
| | (S)-2-(2-amino-2-methylpropanamido)-N-((3R,4S,5S)-1-((S)-2-((1R,2R)-3-((4-aminophenyl)sulfonamido)-1-methoxy-2-methyl-3-oxopropyl)pyrrolidin-1-yl)-3-methoxy-5-methyl-1-oxoheptan-4-yl)-N,3-dimethylbutanamide (Compound 17) |
| 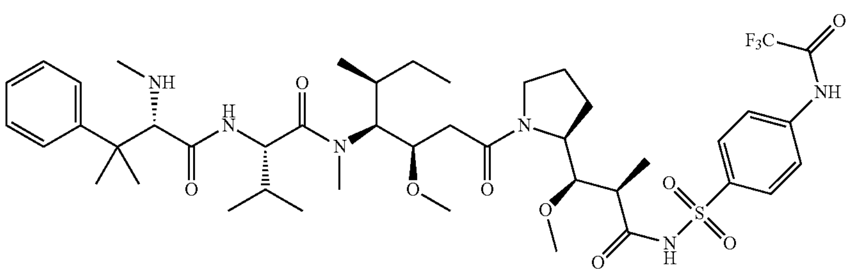 [SMILES: CC[C@H](C)[C@@H]([C@@H](CC(=O)N1CCC[C@H]1[C@H](OC)[C@@H](C)C(=O)NS(=O)(=O)c1ccc(NC(=O)C(F)(F)F)cc1)OC)N(C)C(=O)[C@@H](NC(=O)[C@@H](NC)C(C)(C)c1ccccc1)C(C)C] | tert-butyl (1-(((S)-1-(((3R,4S,5S)-3-methoxy-1-((S)-2-((1R,2R)-1-methoxy-2-methyl-3-oxo-3-((4-(2,2,2-trifluoroacetamido)phenyl)sulfonamido)propyl)pyrrolidin-1-yl)-5-methyl-1-oxoheptan-4-yl)(methyl)amino)-3-methyl-1-oxobutan-2-yl)amino)-2-methyl-1-oxopropan-2-yl)carbamate (Compound 18) |
| | (S)-N-((3R,4S,5S)-1-((S)-2-((1R,2R)-3-((4-aminophenyl)sulfonamido)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)-3-phenylbutanamido)butanamide (Compound 19) |
| 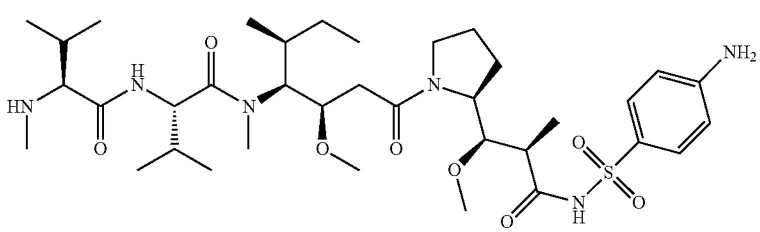 [SMILES: CC[C@H](C)[C@@H]([C@@H](CC(=O)N1CCC[C@H]1[C@H](OC)[C@@H](C)C(=O)NS(=O)(=O)c1ccc(N)cc1)OC)N(C)C(=O)[C@@H](NC(=O)[C@@H](NC)C(C)C)C(C)C] | (S)-N-((3R,4S,5S)-1-((S)-2-((1R,2R)-3-((4-aminophenyl)sulfonamido)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide (Compound 20) |
| 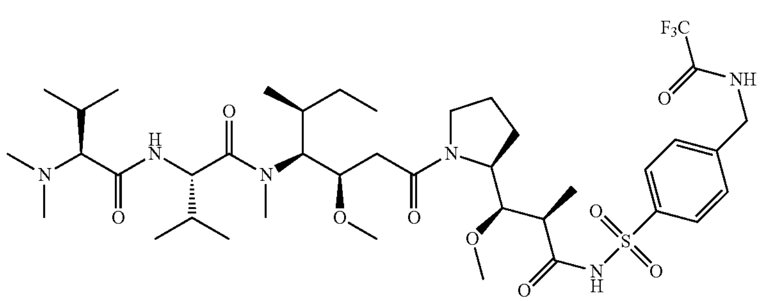 [SMILES: CC[C@H](C)[C@@H]([C@@H](CC(=O)N1CCC[C@H]1[C@H](OC)[C@@H](C)C(=O)NS(=O)(=O)c1ccc(CNC(=O)C(F)(F)F)cc1)OC)N(C)C(=O)[C@@H](NC(=O)[C@H](C(C)C)N(C)C)C(C)C] | (S)-2-((S)-2-(dimethylamino)-3-methylbutanamido)-N-((3R,4S,5S)-3-methoxy-1-((S)-2-((1R,2R)-1-methoxy-2-methyl-3-oxo-3-((4-((2,2,2-trifluoroacetamido)methyl)phenyl)sulfonamido)propyl)pyrrolidin-1-yl)-5-methyl-1-oxoheptan-4-yl)-N,3-dimethylbutanamide (Compound 21) |

| Chemical Structure | Chemical Name |
|---|---|
| 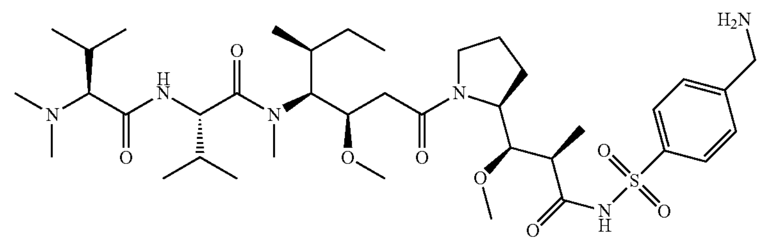 [SMILES: CC[C@H](C)[C@@H]([C@@H](CC(=O)N1CCC[C@H]1[C@H](OC)[C@@H](C)C(=O)NS(=O)(=O)c1ccc(CN)cc1)OC)N(C)C(=O)[C@@H](NC(=O)[C@H](C(C)C)N(C)C)C(C)C] | (S)-N-((3R,4S,5S)-1-((S)-2-((1R,2R)-3-((4-(aminomethyl)phenyl)sulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 22) |
| 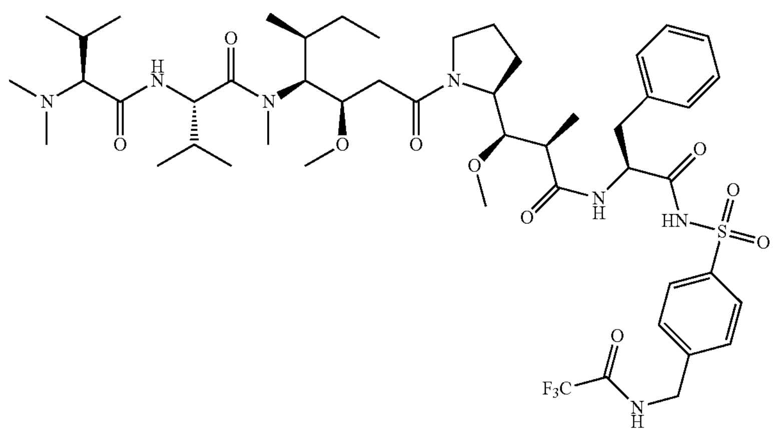 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(CNC(=O)C(F)(F)F)cc1)OC)N(C)C(=O)[C@@H](NC(=O)[C@H](C(C)C)N(C)C)C(C)C] | (S)-2-((S)-2-(dimethylamino)-3-methylbutanamido)-N-((3R,4S,5S)-3-methoxy-1-((S)-2-((1R,2R)-1-methoxy-2-methyl-3-oxo-(((S)-1-oxo-3-phenyl-1-((4-((2,2,2-trifluoroacetamido)methyl)phenyl)sulfonamido)propan-2-yl)amino)propyl)pyrrolidin-1-yl)-5-methyl-1-oxoheptan-4-yl)-N,3-dimethylbutanamide (Compound 23) |
| 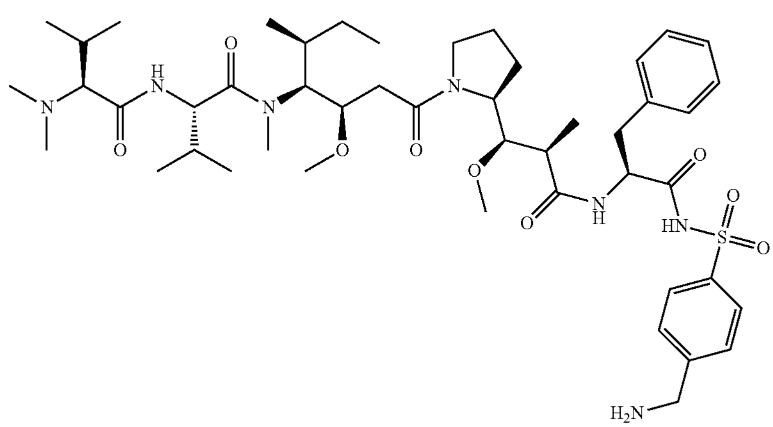 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(CN)cc1)OC)N(C)C(=O)[C@@H](NC(=O)[C@H](C(C)C)N(C)C)C(C)C] | (S)-N-((3R,4S,5S)-1-((S)-2-((1R,2R)-3-(((S)-1-((4-(aminomethyl)phenyl)sulfonamido)-1-oxo-3-phenyl-propan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 24) |
| 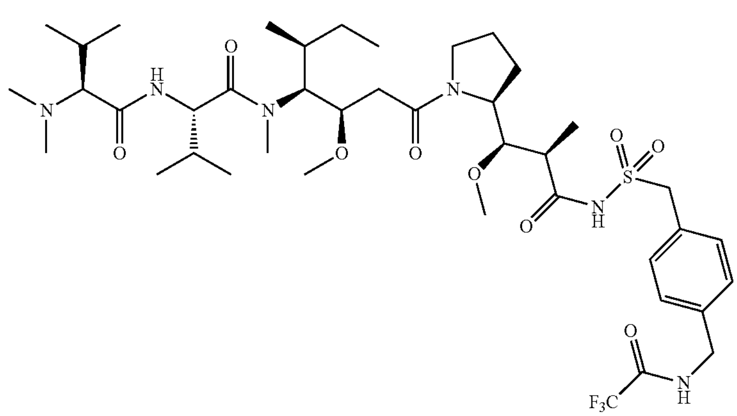 [SMILES: CC[C@H](C)[C@@H]([C@@H](CC(=O)N1CCC[C@H]1[C@H](OC)[C@@H](C)C(=O)NS(=O)(=O)Cc1ccc(CNC(=O)C(F)(F)F)cc1)OC)N(C)C(=O)[C@@H](NC(=O)[C@H](C(C)C)N(C)C)C(C)C] | (S)-2-((S)-2-(dimethylamino)-3-methylbutanamido)-N-((3R,4S,5S)-3-methoxy-1-((S)-2-((1R,2R)-1-methoxy-2-methyl-3-oxo-3-(((4-((2,2,2-trifluoroacetamido)methyl)phenyl)methyl)sulfonamido)propyl)pyrrolidin-1-yl)-5-methyl-1-oxoheptan-4-yl)-N,3-dimethylbutanamide (Compound 25) |

TABLE B-continued

| Chemical Structure | Chemical Name |
|---|---|
| 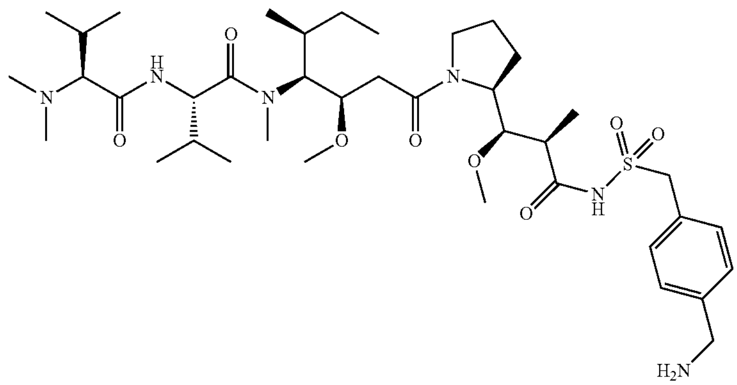 [SMILES: CC[C@H](C)[C@@H]([C@@H](CC(=O)N1CCC[C@H]1[C@H](OC)[C@@H](C)C(=O)NS(=O)(=O)Cc1ccc(CN)cc1)OC)N(C)C(=O)[C@@H](NC(=O)[C@H](C(C)C)N(C)C)C(C)C] | (S)-N-((3R,4S,5S)-1-((S)-2-((1R,2R)-3-(((4-(aminomethyl)phenyl)methyl)sulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methyl-butanamido)-N,3-dimethyl-butanamide (Compound 26) |
| 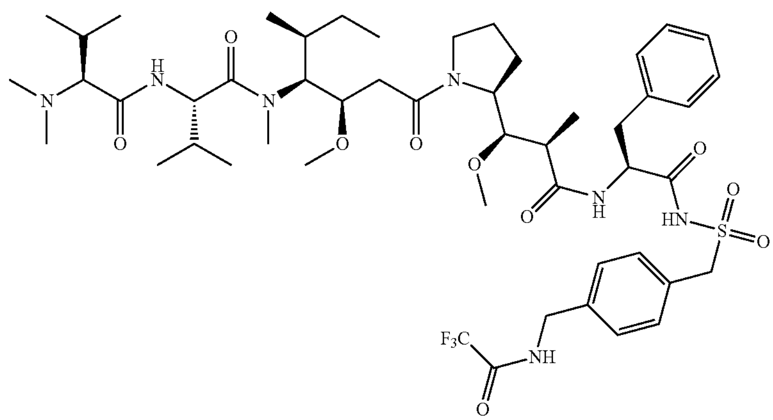 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)Cc1ccc(CNC(=O)C(F)(F)F)cc1)OC)N(C)C(=O)[C@@H](NC(=O)[C@H](C(C)C)N(C)C)C(C)C] | (S)-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-1-oxo-3-phenyl-1-(((4-((2,2,2-trifluoroacetamido)methyl)phenyl)methyl)sulfonamido)propan-2-yl)amino)propyl)pyrrolidin-1-yl)-5-methyl-1-oxoheptan-4-yl)-N,3-dimethylbutanamide (Compound 27) |
| 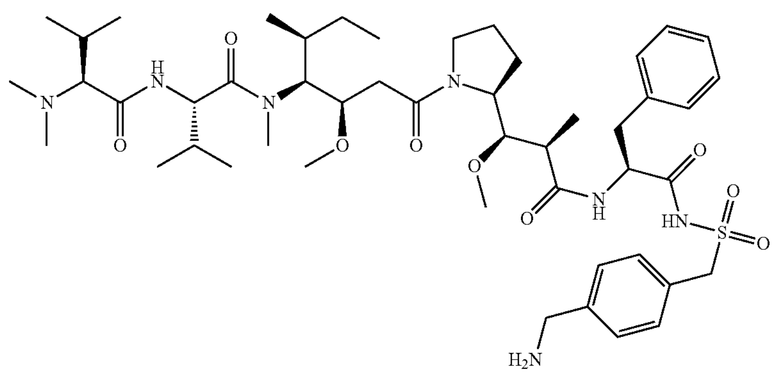 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)Cc1ccc(CN)cc1)OC)N(C)C(=O)[C@@H](NC(=O)[C@H](C(C)C)N(C)C)C(C)C] | (S)-N-((3R,4S,5S)-1-((S)-2-((1R,2R)-3-(((S)-1-(((4-(aminomethyl)phenyl)methyl)sulfonamido)-1-oxo-3-phenyl-propan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methyl-butanamido)-N,3-dimethyl-butanamide (Compound 28) |
| 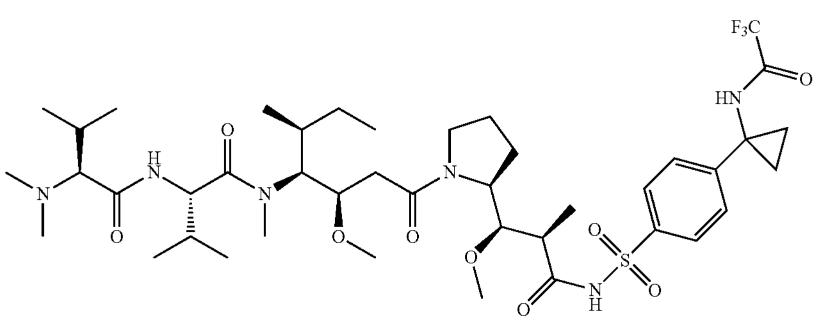 [SMILES: CC[C@H](C)[C@@H]([C@@H](CC(=O)N1CCC[C@H]1[C@H](OC)[C@@H](C)C(=O)NS(=O)(=O)c1ccc(C2(NC(=O)C(F)(F)F)CC2)cc1)OC)N(C)C(=O)[C@@H](NC(=O)[C@H](C(C)C)N(C)C)C(C)C] | (S)-2-((S)-2-(dimethylamino)-3-methylbutanamido)-N-((3R,4S,5S)-3-methoxy-1-((S)-2-((1R,2R)-1-methoxy-2-methyl-3-oxo-3-(4-(1-(2,2,2-trifluoroacetamido)cyclopropyl)phenylsulfonamido)propyl)pyrrolidin-1-yl)-5-methyl-1-oxoheptan-4-yl)-N,3-dimethylbutanamide (Compound 29) |

TABLE B-continued

| Chemical Structure | Chemical Name |
|---|---|
| 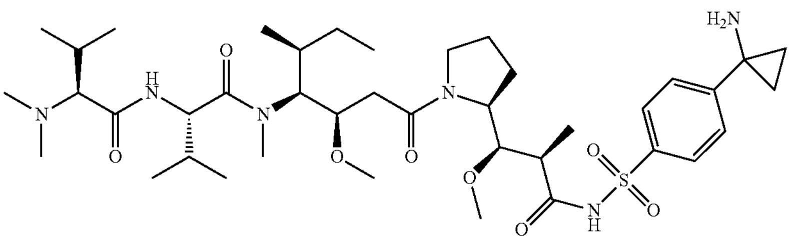 [SMILES: CC[C@H](C)[C@@H]([C@@H](CC(=O)N1CCC[C@H]1[C@H](OC)[C@@H](C)C(=O)NS(=O)(=O)c1ccc(C2(N)CC2)cc1)OC)N(C)C(=O)[C@@H](NC(=O)[C@H](C(C)C)N(C)C)C(C)C] | (S)-N-((3R,4S,5S)-1-((S)-2-((1R,2R)-3-(4-(1-amino-cyclopropyl)phenylsulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 30) |
| 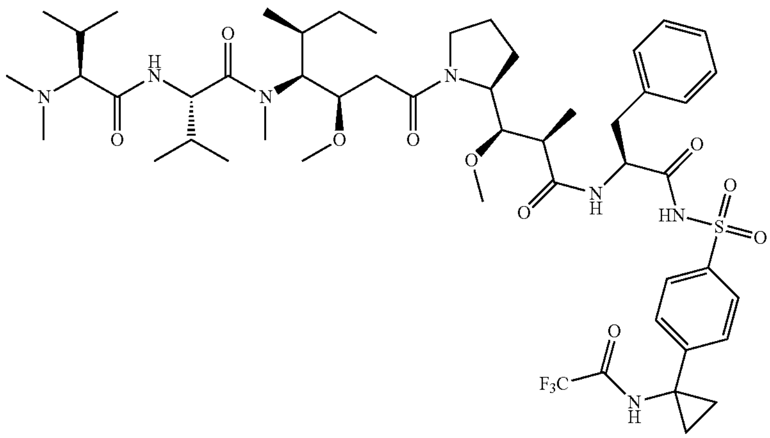 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(C2(NC(=O)C(F)(F)F)CC2)cc1)OC)N(C)C(=O)[C@@H](NC(=O)[C@H](C(C)C)N(C)C)C(C)C] | (S)-2-((S)-2-(dimethylamino)-3-methylbutanamido)-N-((3R,4S,5S)-3-methoxy-1-((S)-2-((1R,2R)-1-methoxy-2-methyl-3-oxo-3-((S)-1-oxo-3-phenyl-1-(4-(1-(2,2,2-trifluoroacetamido)cyclopropyl)phenylsulfonamido)propan-2-ylamino)propyl)pyrrolidin-1-yl)-5-methyl-1-oxoheptan-4-yl)-N,3-dimethylbutanamide (Compound 31) |
| 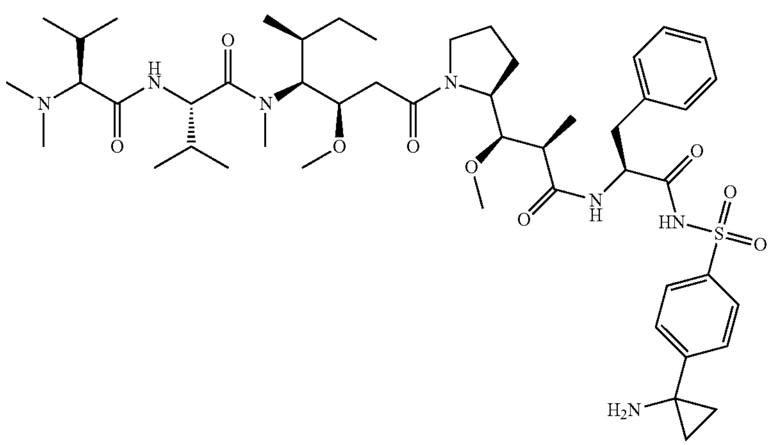 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(C2(N)CC2)cc1)OC)N(C)C(=O)[C@@H](NC(=O)[C@H](C(C)C)N(C)C)C(C)C] | (S)-N-((3R,4S,5S)-1-((S)-2-((1R,2R)-3-((S)-1-(4-(1-amino-cyclopropyl)phenylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 32) |
| 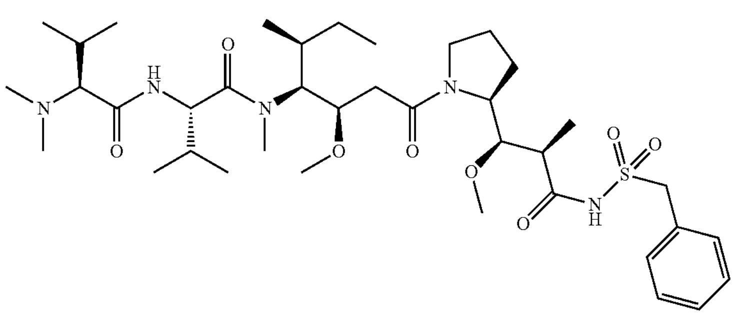 [SMILES: CC[C@H](C)[C@@H]([C@@H](CC(=O)N1CCC[C@H]1[C@H](OC)[C@@H](C)C(=O)NS(=O)(=O)Cc1ccccc1)OC)N(C)C(=O)[C@@H](NC(=O)[C@H](C(C)C)N(C)C)C(C)C] | (S)-N-((3R,4S,5S)-3-methoxy-1-((S)-2-((1R,2R)-1-methoxy-2-methyl-3-oxo-3-((phenylmethyl)sulfonamido)propyl)pyrrolidin-1-yl)-5-methyl-1-oxoheptan-4-yl)-N,3-dimethyl-2-((S)-3-methyl-2-(methylamino)butanamido)butanamide (Compound 33) |

TABLE B-continued

| Chemical Structure | Chemical Name |
|---|---|
|  | methyl 4-(N-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)benzoate (Compound 34). |

TABLE C

| Chemical Structure | Chemical Name |
|---|---|
| 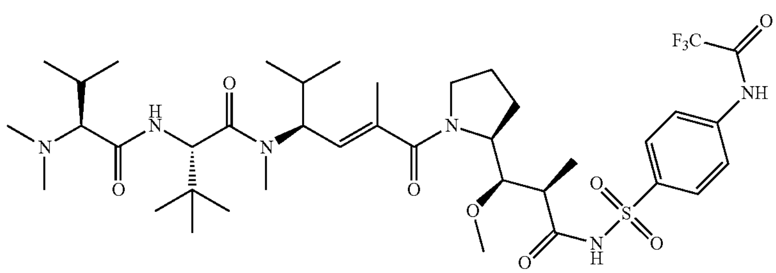 [SMILES: CO[C@H]([C@@H](C)C(=O)NS(=O)(=O)c1ccc(NC(=O)C(F)(F)F)cc1)[C@@H]1CCCN1C(=O)/C(C)=C/[C@H](C(C)C)N(C)C(=O)[C@@H](NC(=O)[C@H](C(C)C)N(C)C)C(C)(C)C] | (S)-2-((S)-2-(dimethylamino)-3-methylbutanamido)-N-((S,E)-6-((S)-2-((1R,2R)-1-methoxy-2-methyl-3-oxo-3-((4-(2,2,2-trifluoroacetamido)phenyl)sulfonamido)propyl)pyrrolidin-1-yl)-2,5-dimethyl-6-oxohex-4-en-3-yl)-N,3,3-trimethylbutanamide (Compound 35) |
| 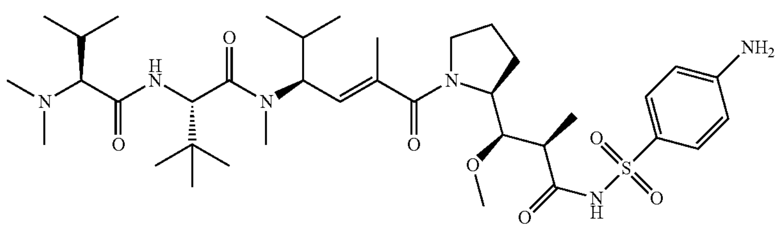 [SMILES: CO[C@H]([C@@H](C)C(=O)NS(=O)(=O)c1ccc(N)cc1)[C@@H]1CCCN1C(=O)/C(C)=C/[C@H](C(C)C)N(C)C(=O)[C@@H](NC(=O)[C@H](C(C)C)N(C)C)C(C)(C)C] | (S)-N-((S,E)-6-((S)-2-((1R,2R)-3-((4-aminophenyl)sulfonamido)-1-methoxy-2-methyl-3-oxopropyl)pyrrolidin-1-yl)-2,5-dimethyl-6-oxohex-4-en-3-yl)-2-((S)-2-(dimethylamino)-3-methylbutanamido)-N,3,3-trimethylbutanamide (Compound 36) |
| 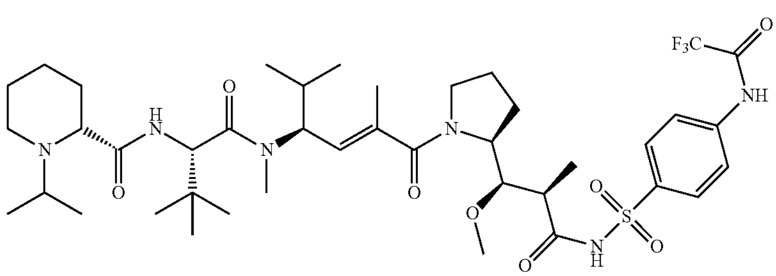 | (S)-1-isopropyl-N-((S)-1-(((S,E)-6-((S)-2-((1R,2R)-1-methoxy-2-methyl-3-oxo-3-((4-(2,2,2-trifluoroacetamido)phenyl)sulfonamido)propyl)pyrrolidin-1-yl)-2,5-dimethyl-6-oxohex-4-en-3-yl)(methyl)amino)-3,3-dimethyl-1-oxobutan-2-yl)piperidine-2-carboxamide (Compound 37) |
| 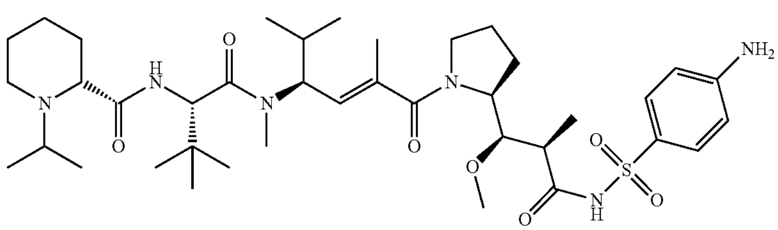 | (S)-N-((S)-1-(((S,E)-6-((S)-2-((1R,2R)-3-((4-aminophenyl)sulfonamido)-1-methoxy-2-methyl-3-oxopropyl)pyrrolidin-1-yl)-2,5-dimethyl-6-oxohex-4-en-3-yl)(methyl)amino)-3,3-dimethyl-1-oxobutan-2-yl)-1-isopropylpiperidine-2-carboxamide (Compound 38) |

TABLE C-continued

| Chemical Structure | Chemical Name |
|---|---|
| 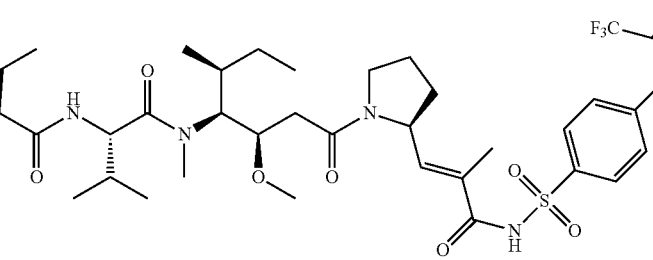 | (S)-2-((S)-2-(dimethylamino)-3-methylbutanamido)-N-((3R,4S,5S)-3-methoxy-5-methyl-1-((S)-2-((E)-2-methyl-3-oxo-3-((4-(2,2,2-trifluoroacetamido)phenyl)sulfonamido)prop-1-en-1-yl)pyrrolidin-1-yl)-1-oxoheptan-4-yl)-N,3-dimethylbutanamide (Compound 39) |

Additionally, individual compounds and chemical genera of the present invention, for example those compounds found in Table A, Table B, and Table C, including diastereoisomers and enantiomers thereof, encompass all pharmaceutically acceptable salts. The compounds of Formula I may be prepared according to relevant published literature procedures that are used by one skilled in the art. Exemplary reagents and procedures for these reactions appear hereinafter in the working Examples. In one embodiment, the invention provides a method of making a compound described herein.

Conjugates Comprising Novel Compounds

Compounds described herein may be used to form conjugates, for example antibody-drug conjugates (ADCs). Accordingly, in one embodiment of the present disclosure, conjugate compositions of Formula II are provided:

 (T)-(L)-(D)    II wherein (T) is a targeting moiety, (L) is an optional linker, and (D) is a compound of Formula I. In one embodiment, (T) is an antibody. Accordingly, in one embodiment, antibody-drug conjugates (ADCs) comprising compounds (D) of Formula I.

As will be appreciated by the artisan of reasonable skill, a wide variety of means are available to covalently link (T)-(L)-(D). Any known method may be used to link the conjugate components. Any known linker technology may be used to link (T) to (D). Further, (T), (L), and (D) may be modified in any suitable manner, as recognized by the artisan of reasonable skill, in order to facilitate conjugate formation.

Targeting Moiety (T)

The Targeting moiety (T) of the subject compositions includes within its scope any unit of a (T) that binds or reactively associates or complexes with a receptor, antigen or other receptive moiety associated with a given target-cell population. A (T) is a molecule that binds to, complexes with, or reacts with a moiety of a cell population sought to be targeted. In one aspect, the (T) acts to deliver the Drug (D) to the particular target cell population with which the (T) reacts. Such (T)s include, but are not limited to, large molecular weight proteins such as, for example, full-length antibodies, antibody fragments, smaller molecular weight proteins, polypeptide or peptides, lectins, glycoproteins, non-peptides, vitamins, nutrient-transport molecules (such as, but not limited to, transferrin), or any other cell binding molecule or substance.

A (T) can form a bond to a Linker unit (L) or a Drug (D). A (T) can form a bond to a (L) unit via a heteroatom of the (T). Heteroatoms that may be present on a (T) include sulfur (in one embodiment, from a sulfhydryl group of a (T)), oxygen (in one embodiment, from a carbonyl, carboxyl or hydroxyl group of a (T)) and nitrogen (in one embodiment, from a primary or secondary amino group of a (T)). These heteroatoms can be present on the (T) in the (T)'s natural state, for example a naturally-occurring antibody, or can be introduced into the (T) via chemical modification.

In one embodiment, a (T) has a sulfhydryl group and the (T) bonds to the (L) via the sulfhydryl group's sulfur atom. In another embodiment, the (T) has one or more lysine residues that can be chemically modified to introduce one or more sulfhydryl groups. The (T) bonds to the (L) unit via the sulfhydryl group. Reagents that can be used to modify lysines include, but are not limited to, N-succinimidyl S-acetylthioacetate (SATA) and 2-iminothiolane hydrochloride (Traut's Reagent).

In another embodiment, the (L) can have one or more carbohydrate groups that can be chemically modified to have one or more sulfhydryl groups. The (T) bonds to the (L) via the sulfhydryl group's sulfur atom. In yet another embodiment, the (T) can have one or more carbohydrate groups that can be oxidized to provide an aldehyde (—CHO) group (see, e.g., Laguzza et al., 1989, J. Med. Chem. 32(3):548-55). The corresponding aldehyde can form a bond with a reactive site on a portion of a (L). Reactive sites that can react with a carbonyl group on a (T) include, but are not limited to, hydrazine and hydroxylamine. Other protocols for the modification of proteins for the attachment or association of (D) are described in Coligan et al., Current Protocols in Protein Science, vol. 2, John Wiley & Sons (2002), incorporated herein by reference.

The (T) can include, for example a protein, polypeptide, or peptide include, but are not limited to, transferrin, epidermal growth factors ("EGF"), bombesin, gastrin, gastrin-releasing peptide, platelet-derived growth factor, IL-2, IL-6, transforming growth factor ("TGF"), such as TGF-α or TGF-β, vaccinia growth factor ("VGF"), insulin and insulin-like growth factors I and II, lectins and apoprotein from low density lipoprotein.

The (T) can also include an antibody, such as polyclonal antibodies or monoclonal antibodies. The antibody can be directed to a particular antigenic determinant, including for example, a cancer cell antigen, a viral antigen, a microbial antigen, a protein, a peptide, a carbohydrate, a chemical, nucleic acid, or fragments thereof. Methods of producing polyclonal antibodies are known in the art. A monoclonal antibody (mAb) to an antigen-of-interest can be prepared by using any technique known in the art. These include, but are not limited to, the hybridoma technique originally described by Kohler and Milstein (1975, Nature 256, 495-497), the human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp. 77-96). The Selected Lymphocyte Antibody Method (SLAM) (Babcook, J. S., et al., A novel strategy for generating monoclonal antibodies from single, isolated lymphocytes producing antibodies of defined specificities. Proc Natl Acad Sci USA, 1996. 93 (15): p. 7843-8.) and (McLean G R, Olsen O A, Watt I N, Rathanaswami P, Leslie K B, Babcook J S, Schrader J W. Recognition of human cytomegalovirus by human primary immunoglobulins identifies an innate foundation to an adaptive immune response. J Immunol. 2005 Apr. 15; 174(8): 4768-78. Such antibodies may be of any immunoglobulin class including IgG, IgM, IgE, IgA, and IgD and any subclass thereof. Hybridomas producing the mAbs of use in this invention may be cultivated in vitro or in vivo.

The monoclonal antibody can be, for example, a human monoclonal antibody, a humanized monoclonal antibody, an antibody fragment, or a chimeric antibody (e.g., a human-mouse antibody). Human monoclonal antibodies may be made by any of numerous techniques known in the art (e.g., Teng et al., 1983, Proc. Natl. Acad. Sci. USA 80:7308-7312; Kozbor et al., 1983, Immunology Today 4:72-79; and Olsson et al., 1982, Meth. Enzymol. 92:3-16). See also, Huse et al., 1989, Science 246:1275-1281 and McLean et al. J Immunol. 2005 Apr. 15; 174(8):4768-78.

The antibody can also be a bispecific antibody. Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, Nature 305:537-539; International Publication No. WO 93/08829, Traunecker et al., 1991, EMBO J. 10:3655-3659.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_{H2}$, and $C_{H3}$ regions. It is preferred to have the first heavy-chain constant region (CH1) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

For example, the bispecific antibodies can have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690) which is incorporated herein by reference in its entirety.

For further details for generating bispecific antibodies see, for example, Suresh et al., 1986, Methods in Enzymology 121:210; Rodrigues et al., 1993, J. Immunology 151:6954-6961; Carter et al., 1992, Bio/Technology 10:163-167; Carter et al., 1995, J. Hematotherapy 4:463-470; Merchant et al., 1998, Nature Biotechnology 16:677-681. Using such techniques, bispecific antibodies can be prepared for use in the treatment or prevention of disease as defined herein.

Bifunctional antibodies are also described in European Patent Publication No. EPA 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. EPA 0 217 577, both of which are incorporated herein by reference.

The antibody also can be a functionally active fragment, derivative or analog of an antibody that immunospecifically binds to a target antigen (e.g., a cancer antigen, a viral antigen, a microbial antigen, or other antibodies bound to cells or matrix). In this regard, "functionally active" means that the fragment, derivative or analog is able to recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (see, e.g., Kabat et al., 1991, Sequences of Proteins of Immunological Interest, Fifth Edition, National Institute of Health, Bethesda, Md.; Kabat et al., 1980, J. Immunology 125(3): 961-969).

Other useful antibodies include fragments of antibodies such as, but not limited to, F(ab')$_2$ fragments, Fab fragments, Fab', Fv fragments and heavy chain and light chain dimers of antibodies, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54).

Recombinant antibodies, such as chimeric and humanized monoclonal antibodies, comprising both human and non-human portions, which can be made using standard recombinant DNA techniques, also can be used. (See, e.g., U.S. Pat. Nos. 4,816,567; and 4,816,397.)

Humanized antibodies are antibody molecules from non-human species having one or more complementarity determining regions (CDRs) from the non-human species and a framework region from a human immunoglobulin molecule. (See, e.g., U.S. Pat. No. 5,585,089.) Chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; Shaw et al., 1988, J. Natl.

Cancer Inst. 80:1553-1559; Morrison, 1985, Science 229: 1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060.

Completely human antibodies can be used. Human antibodies can be prepared, for example, using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806.

Human antibodies that recognize a selected epitope also can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903.) Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan and Carter, 2002, "The rise of monoclonal antibodies as therapeutics," in Anti-IgE and Allergic Disease, Jardieu, P. M. and Fick Jr., R. B, eds., Marcel Dekker, New York, N.Y., Chapter 20, pp. 427-469).

In other embodiments, the antibody is a fusion protein of an antibody, or a functionally active fragment thereof. For example, an antibody can be fused via a covalent bond (e.g., a peptide bond) at either the N-terminus or the C-terminus to an amino acid sequence of another protein (or portion thereof, such as at least a 10, 20 or 50 amino acid portion of the protein) that is not the antibody.

Antibodies also include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including but not limited to specific chemical cleavage, acetylation, formylation, metabolic synthesis in the presence of tunicamycin, etc. Additionally, the analog or derivative can contain one or more unnatural amino acids.

The antibodies can have modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see, e.g., International Publication No. WO 97/34631, which is incorporated herein by reference in its entirety). Antibodies immunospecific for a target antigen can be obtained commercially or other source or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

Examples of antibodies available for the treatment of cancer include, but are not limited to, humanized anti HER2 monoclonal antibody, HERCEPTIN® (trastuzumab; Genentech); RITUXAN® (rituximab; Genentech) which is a chimeric anti CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine IgG2a antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; Campath I/H (Leukosite, MA) which is a humanized IgG1 antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens (exemplary cancers are indicated in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific membrane antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti transferrin receptor (carcinomas), p97 (melanoma), MUC1-KLH (breast cancer), CEA (colorectal), gp100 (melanoma), MART1 (melanoma), prostate specific antigen (PSA) (prostate), IL-2 receptor (T-cell leukemia and lymphomas), CD20 (non Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail et al., 1993, Science 261:212-215), BR64 (Trail et al., 1997, Cancer Research 57:100-105), mAbs against the CD40 antigen, such as S2C6 mAb (Francisco et al., 2000, Cancer Res. 60:3225-3231) and chimeric and humanized variants thereof, mAbs against the cD33 antigen; mAbs against the EphA2 antigen; mAbs against the CD70 antigen, such as 1F6 mAb and 2F2 mAb and chimeric and humanized variants thereof, and mAbs against the CD30 antigen, such as AC10 (Bowen et al., 1993, J. Immunol. 151:5896-5906; Wahl et al., 2002, Cancer Res. 62(13):3736-42) and chimeric and humanized variants thereof. Many other internalizing antibodies that bind to tumor associated antigens can be used and have been reviewed (see, e.g., Franke et al., 2000, Cancer Biother. Radiopharm. 15:459 76; Murray, 2000, Semin. Oncol. 27:64 70; Breitling et al., Recombinant Antibodies, John Wiley, and Sons, New York, 1998).

The antibody also can be an antibody that binds to an antigen that is present on a target cell or target cell population. For example, transmembrane polypeptides and other markers can be specifically expressed on the surface of one or more particular type(s) of target cells (e.g., a cancer cell) as compared to on one or more normal (e.g., a non-cancerous cell(S)). Often, such markers are more abundantly expressed on the surface of the target cells, or exhibit greater immunogenicity, as compared to those on the surface of the normal cells. The identification of such cell surface antigen polypeptides has given rise to the ability to specifically target cells for destruction via antibody-based therapies. Thus, in some embodiments, the antibodies include, but are not limited to, antibodies against tumor-associated antigens (TAA). Such tumor-associated antigens are known in the art, and can prepared for use in generating antibodies using methods and information which are well known in the art.

See also EP2552957, WO/2012/116453, WO/2012/032080. See also Zybody™, http://www.zyngenia.com/science-technology/technology-approach.asp. See also human heavy chain-only antibodies technology, http://www.crescendobiologics.com/. See also WO2010001251, yeast based human antibody yeast-based platform http://www.adimab.com/platform-overview, mAbLogix™ platform http://www.dna.com/OurApproach/ComplementaryTechnologies/AntibodyDiscovery, monoclonal discovery platform http://www.igenica.com/science.php, WO2009/157771, EP2560993, WO2013004842, WO2012166560.

In addition to antibodies, the targeting moiety (T) of the subject compositions includes within its scope any unit of a (T) that binds or reactively associates or complexes with a receptor, antigen or other receptive moiety associated with a given target-cell population. A (T) is a molecule that binds to, complexes with, or reacts with a moiety of a cell population sought to be targeted. For example, included within (T) are ligands for cell surface receptors derived from various sources, including those derived from human cells, ligands derived from bacteria, and pathogen derived ligands. A wide range of appropriate targeting moieties are known in the art. For example, see WO2013117705.

Linker Moiety (L)

The subject compositions optionally further include a Linker moiety (L). (L) is a bifunctional compound which can be used to link a (D) and a (T) to form a conjugate composition, T-L-D. Such conjugates allow the selective delivery of drugs to target cells (e.g., tumor cells). (L)s include a divalent substituent such as an alkyldiyl, an aryldiyl, a heteroaryldiyl, moieties such as: —$(CR2)_nO$ $(CR2)_n$—, repeating units of alkyloxy (e.g., polyethylenoxy, PEG, polymethyleneoxy) and alkylamino (e.g., polyethyl-eneamino, Jeffamine™); and diacid ester and amides including succinate, succinamide, diglycolate, malonate, and caproamide.

The subject compositions can be prepared using a (L) unit having a reactive site for binding to the (D) and (T). In some embodiments, (L) has a reactive site which has an electrophilic group that is reactive to a nucleophilic group present on (T). Useful nucleophilic groups on (T) include but are not limited to sulfhydryl, hydroxyl and amino groups. The heteroatom of the nucleophilic group of (T) is reactive to an electrophilic group on (L) and forms a covalent bond to (L). Useful electrophilic groups include, but are not limited to maleimide and haloacetamide groups. The nucleophilic group on (T) provides a convenient site for attachment to (L).

In another embodiment, (L) has a reactive site which has a nucleophilic group that is reactive to an electrophilic group present on (T). Useful electrophilic groups on (T) include, but are not limited to, aldehyde and ketone carbonyl groups. The heteroatom of a nucleophilic group of (L) can react with an electrophilic group on (T) and form a covalent bond to (T). Useful nucleophilic groups on (L) include, but are not limited to, hydrazide, oxime, amino, hydrazine, thiosemicarbazone, hydrazine carboxylate, and arylhydrazide. The electrophilic group on (T) provides a convenient site for attachment to (L).

Carboxylic acid functional groups and chloroformate functional groups are also useful reactive sites for (L) because they can react with amino groups of a (D) to form an amide linkage. Also useful as a reactive site is a carbonate functional group on (L), such as but not limited to p-nitrophenyl carbonate, which can react with an amino group of a (D) to form a carbamate linkage.

It will be appreciated that any linker moieties taught in the prior art, and particularly those taught for use in the context of drug delivery, may be used in the current invention. Without limiting the scope of the preceding statement, in one embodiment, (L) comprises a linker moiety disclosed in WO 2012/113847. In another embodiment, (L) comprises a linker moiety disclosed in U.S. Pat. No. 8,288,352. In another embodiment, (L) comprises a linker moiety disclosed in U.S. Pat. No. 5,028,697. In another embodiment, (L) comprises a linker moiety disclosed in U.S. Pat. No. 5,006,652. In another embodiment, (L) comprises a linker moiety disclosed in U.S. Pat. No. 5,094,849. In another embodiment, (L) comprises a linker moiety disclosed in U.S. Pat. No. 5,053,394. In another embodiment, (L) comprises a linker moiety disclosed in U.S. Pat. No. 5,122,368. In another embodiment, (L) comprises a linker moiety disclosed in U.S. Pat. No. 5,387,578. In another embodiment, (L) comprises a linker moiety disclosed in U.S. Pat. No. 5,547,667. In another embodiment, (L) comprises a linker moiety disclosed in U.S. Pat. No. 5,622,929. In another embodiment, (L) comprises a linker moiety disclosed in U.S. Pat. No. 5,708,146. In another embodiment, (L) comprises a linker moiety disclosed in U.S. Pat. No. 6,468,522. In another embodiment, (L) comprises a linker moiety disclosed in U.S. Pat. No. 6,103,236. In another embodiment, (L) comprises a linker moiety disclosed in U.S. Pat. No. 6,638,509. In another embodiment, (L) comprises a linker moiety disclosed in U.S. Pat. No. 6,214,345. In another embodiment, (L) comprises a linker moiety disclosed in U.S. Pat. No. 6,759,509. In another embodiment, (L) comprises a linker moiety disclosed in WO 2007/103288. In another embodiment, (L) comprises a linker moiety disclosed in WO 2008/083312. In another embodiment, (L) comprises a linker moiety disclosed in WO 2003/068144. In another embodiment, (L) comprises a linker moiety disclosed in WO 2004/016801. In another embodiment, (L) comprises a linker moiety disclosed in WO 2009/134976. In another embodiment, (L) comprises a linker moiety disclosed in WO 2009/134952. In another embodiment, (L) comprises a linker moiety disclosed in WO 2009/134977. In another embodiment, (L) comprises a linker moiety disclosed in WO 2002/08180. In another embodiment, (L) comprises a linker moiety disclosed in WO 2004/043493. In another embodiment, (L) comprises a linker moiety disclosed in WO 2007/018431. In another embodiment, (L) comprises a linker moiety disclosed in WO 2003/026577. In another embodiment, (L) comprises a linker moiety disclosed in WO 2005/077090. In another embodiment, (L) comprises a linker moiety disclosed in WO 2005/082023. In another embodiment, (L) comprises a linker moiety disclosed in WO 2007/011968. In another embodiment, (L) comprises a linker moiety disclosed in WO 2007/038658. In another embodiment, (L) comprises a linker moiety disclosed in WO 2007/059404. In another embodiment, (L) comprises a linker moiety disclosed in WO 2006/110476. In another embodiment, (L) comprises a linker moiety disclosed in WO 2005/112919. In another embodiment, (L) comprises a linker moiety disclosed in WO 2008/103693. In another embodiment, (L) comprises a linker moiety disclosed in U.S. Pat. No. 6,756,037. In another embodiment, (L) comprises a linker moiety disclosed in U.S. Pat. No. 7,087,229. In another embodiment, (L) comprises a linker moiety disclosed in U.S. Pat. No. 7,122,189. In another embodiment, (L) comprises a linker moiety disclosed in U.S. Pat. No. 7,332,164. In another embodiment, (L) comprises a linker moiety disclosed in U.S. Pat. No. 5,556,623. In another embodiment, (L) comprises a linker moiety disclosed in U.S. Pat. No. 5,643,573. In another embodiment, (L) comprises a linker moiety disclosed in U.S. Pat. No. 5,665,358.

In a preferred embodiment (L) comprises a linker moiety disclosed in U.S. Provisional Application 61/921,242, filed on Dec. 27, 2013. Accordingly, conjugate compositions of Formula III are provided:

$$(T)\text{-}(L^1)\text{-}(D^1) \quad \quad \text{III}$$

wherein (T) is a targeting moiety, wherein ($D^1$) has the following structure (IV):

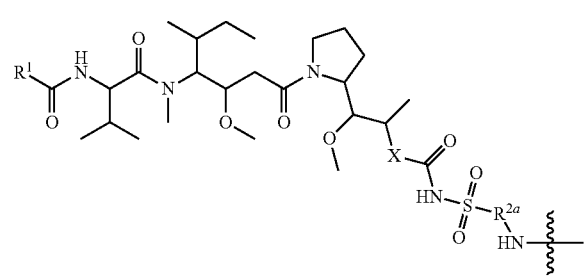
IV wherein $R^1$ and X are as described herein supra and infra; wherein $R^{2a}$ is selected from: $C_2$-$C_6$ alkyldiyl, aryldiyl, $C_4$-$C_7$ cycloalkyldiyl, heteroaryldiyl, and heterocyclyldiyl, each optionally substituted with one or more substituents selected from: $C_1$-$C_6$ alkoxy, $C_1$-$C_6$ alkoxycarbonyl, $C_1$-$C_6$ alkyl, $C_1$-$C_6$ alkylamino, amino, amino-$C_1$-$C_6$ alkyl, amino-aryl, amino-$C_3$-$C_7$ cycloalkyl, aryl, carboxamide, carboxyl, cyano, $C_1$-$C_6$ haloalkyl, $C_1$-$C_6$ haloalkoxy, halo, hydroxyl, nitro, thio, and thio-$C_1$-$C_6$ alkyl;

and wherein ($L^1$)-(T) has the following structure (V)

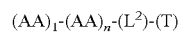
V wherein the —NH— group bonded to $R^{2a}$ in Formula IV forms a peptide bond (JPB) with $(AA)_1$ in Formula V, wherein the JPB is enzymatically cleavable, wherein each AA is independently an amino acid, wherein n is an integer from 0 to 25, wherein ($L^2$) is optionally the remaining portion of linker ($L^1$), wherein (T) is the targeting moiety, and wherein $(AA)_1$-$(AA)_n$, taken together comprises an amino acid sequence capable of facilitating enyzmatic cleavage of the JPB.

Linkers (L) comprising a self-immolative component may also be used. For example, see U.S. Pat. No. 6,214,345. An example of a self-immolative component is p-aminobenzyl-carbamoyl (PABC).

Commercially available linkers may be used in the invention. For example, the commercially available cleavable linker sulfosuccinimidyl 6-[3'(2-pyridyldithio)-propionamido]hexanoate (sulfo-LC-SPDP: Thermo Pierce Cat #21650) and Non-cleavable linker succinimidyl 4-[N-maleimidomethyl]cyclohexane-1-carboxylate (SMCC: Thermo Pierce Cat #22360) may be used, as demonstrated herein.

See also, WO2012171020, WO2010138719, the range of commercially available linkers, for example, from Concortis http://www.concortis.com/home. See also Kim et al., Bioconjugate Chemistry, 21 (8): 1513-1519 August 2010. See also EP2326349. See also copper free click chemistry linkers, Angew. Chem. Int. Ed., 2010, 49, p. 9422-9425, ChemBioChem, 2011, 12, p. 1309-1312, http://www.synaffix.com/technology/.

Drug Moiety (D)

(D) is a compound of Formula I as described herein. It will be recognized by the artisan of reasonable skill that compounds described herein may be appropriately modified to facilitate a conjugation reaction with (L), or if (L) is not present, with (T), and formation of a conjugate (T)-(L)-(D) or (T)-(D). Any point of attachment on (D) may be used. In one embodiment, the C-terminus of (D) forms the point of attachment in a (T)-(L)-(D) conjugate. In another embodiment, the N-terminus of (D) forms the point of attachment in a (T)-(L)-(D) conjugate. In another embodiment, a side chain of (D) forms the point of attachment in a (T)-(L)-(D) conjugate.

Administration

For the purposes of administration, the compounds of the present disclosure may be administered as a raw chemical or may be formulated as pharmaceutical compositions. Pharmaceutical compositions of the present disclosure comprise a compound described herein and a pharmaceutically acceptable carrier, diluent or excipient. The compound described herein is present in the composition in an amount which is effective to treat a particular disease or condition of interest, e.g., in an amount sufficient to treat cancer or tumor cell growth, and preferably with acceptable toxicity to the patient. The activity of compounds described herein can be determined by one skilled in the art, for example, as described in the Examples below. Appropriate concentrations and dosages can be readily determined by one skilled in the art.

Administration of the compounds described herein, or their pharmaceutically acceptable salts, in pure form or in an appropriate pharmaceutical composition, can be carried out via any of the accepted modes of administration of agents for serving similar utilities. The pharmaceutical compositions of the disclosure can be prepared by combining a compound described herein with an appropriate pharmaceutically acceptable carrier, diluent or excipient, and may be formulated into preparations in solid, semi solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the disclosure are formulated so as to allow the active ingredients contained therein to be bio available upon administration of the composition to a patient. Compositions that will be administered to a subject or patient take the form of one or more dosage units, where for example, a tablet may be a single dosage unit, and a container of a compound described herein in aerosol form may hold a plurality of dosage units. Actual methods of preparing such dosage forms are known, or will be apparent, to those skilled in this art; for example, see Remington: The Science and Practice of Pharmacy (22nd ed.) eds. Loyd V. Allen, Jr., et al., Pharmaceutical Press, 2012. The composition to be administered will, in any event, contain a therapeutically effective amount of a compound described herein, or a pharmaceutically acceptable salt thereof, for treatment of a disease or condition of interest in accordance with the teachings of this disclosure.

A pharmaceutical composition described herein may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, pharmaceutical compositions of the present disclosure typically are either solid or liquid form, where semi solid, semi liquid, suspension and gel forms are included within the forms considered herein as either solid or liquid.

As a solid composition for oral administration, the pharmaceutical compositions may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch, and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

Pharmaceutical compositions described herein may be in the form of a liquid, for example, an elixir, syrup, solution, emulsion or suspension. The liquid may be for oral administration or for delivery by injection, as two examples. When intended for oral administration, pharmaceutical compositions described herein typically contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Liquid pharmaceutical compositions described herein, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Parenteral hpreparations can be enclosed in ampoules, disposable syringes or multiple dose vials made of glass or plastic. Physiological saline is a preferred adjuvant. An injectable pharmaceutical composition is preferably sterile.

A liquid pharmaceutical composition described herein intended for either parenteral or oral administration should contain an amount of a compound described herein such that a suitable dosage will be obtained.

Pharmaceutical compositions described herein may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Pharmaceutical compositions described herein may be intended for rectal administration, in the form, for example, of a suppository, which will melt in the rectum and release the drug. Compositions for rectal administration may contain an oleaginous base as a suitable nonirritating excipient. Such bases include, without limitation, lanolin, cocoa butter and polyethylene glycol.

Pharmaceutical compositions described herein may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

Pharmaceutical compositions described herein may be prepared in dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds described herein may be delivered in single phase, bi phasic, or tri phasic systems in order to deliver the active ingredient (S). Delivery of the aerosol includes the necessary container, activators, valves, subcontainers, and the like, which together may form a kit. One skilled in the art, without undue experimentation may determine preferred aerosols.

The pharmaceutical compositions described herein may be prepared by methodology well known in the pharmaceutical art. For example, a pharmaceutical composition intended to be administered by injection can be prepared by combining a compound described herein with sterile, distilled water so as to form a solution. A surfactant may be added to facilitate the formation of a homogeneous solution or suspension. Surfactants are compounds that non covalently interact with the compound described herein so as to facilitate dissolution or homogeneous suspension of the compound in the aqueous delivery system.

The compounds described herein, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds described herein, or pharmaceutically acceptable derivatives thereof, may also be administered simultaneously with, prior to, or after administration of one or more other therapeutic agents. Such combination therapy includes administration of a single pharmaceutical dosage formulation which contains a compound described herein and one or more additional active agents, as well as administration of the compound described herein and each active agent in its own separate pharmaceutical dosage formulation. For example, a compound described herein and the other active agent can be administered to the patient together in a single oral dosage composition such as a tablet or capsule, or each agent administered in separate oral dosage formulations. Where separate dosage formulations are used, the compounds described herein and one or more additional active agents can be administered at essentially the same time, i.e., concurrently, or at separately staggered times, i.e., sequentially; combination therapy is understood to include all these regimens.

The following Examples illustrate various methods of making compounds described herein, i.e., compounds of Formula I and related formulae. It is understood that one skilled in the art may be able to make these compounds by similar methods or by combining other methods known to one skilled in the art. It is also understood that one skilled in the art would be able to make, in a similar manner as described below, other compounds of Formula I not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

The following examples are provided for purposes of illustration, not limitation.

EXAMPLES

Example 1: General Synthetic Procedures

Synthetic Scheme A
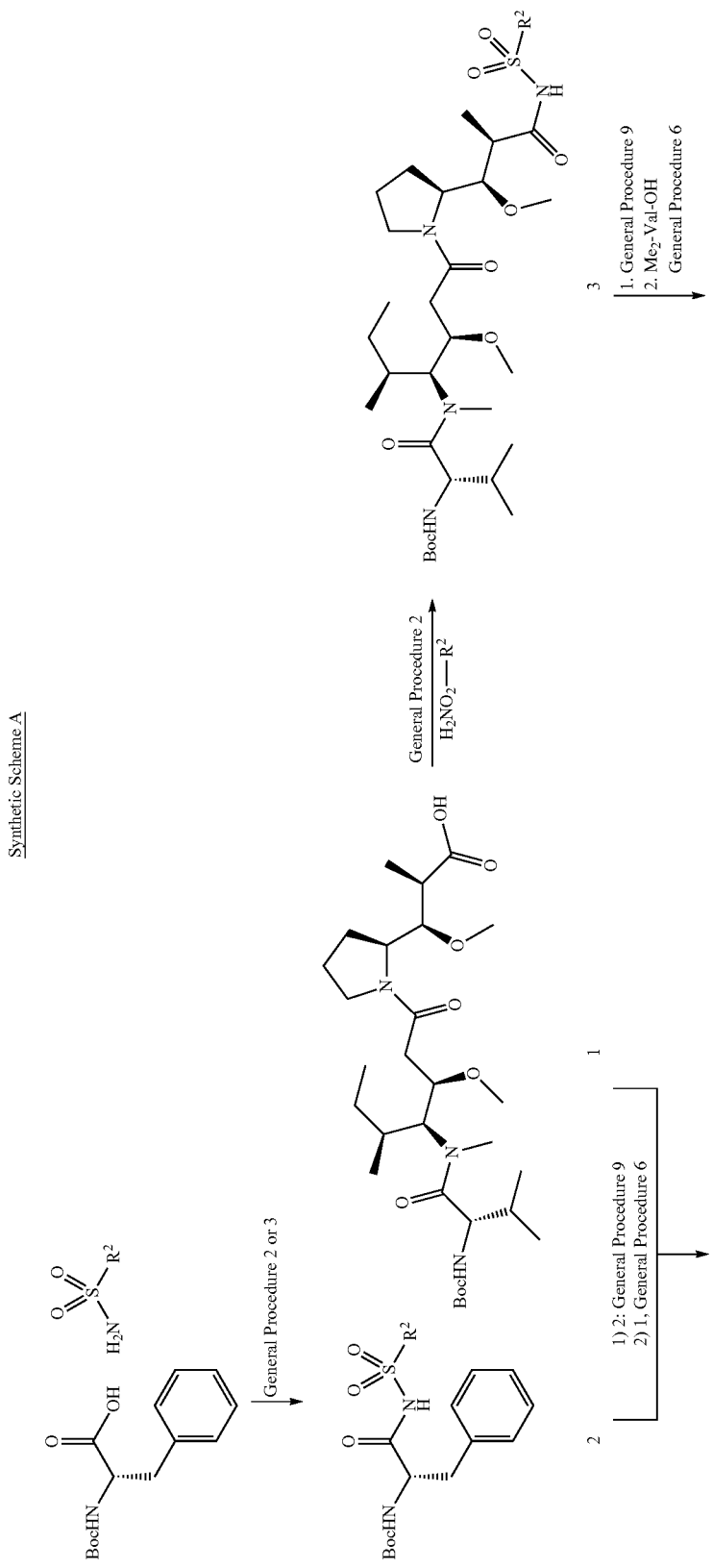

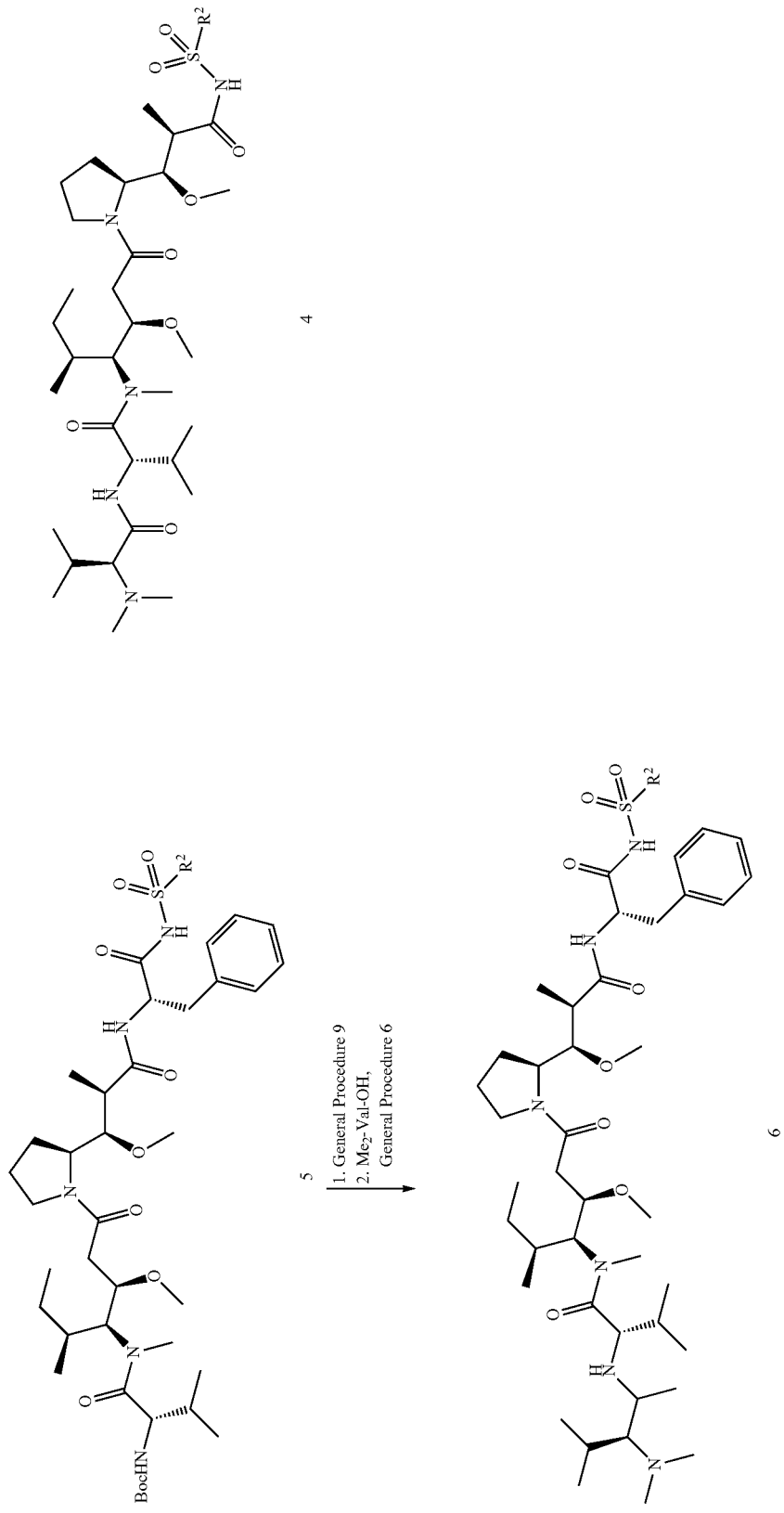

Synthetic Scheme B
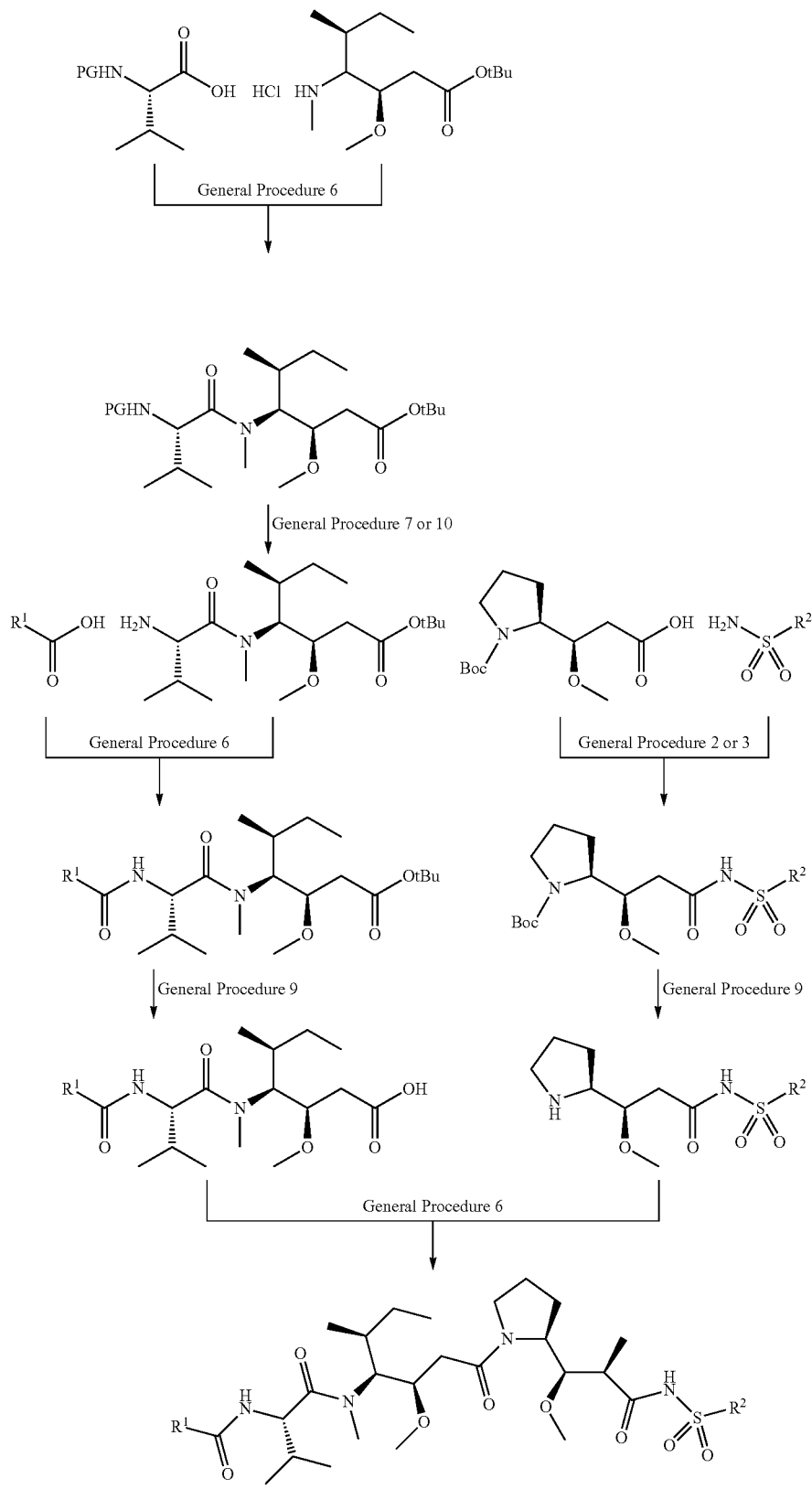
PG = Cbz, Fmoc

Scheme C
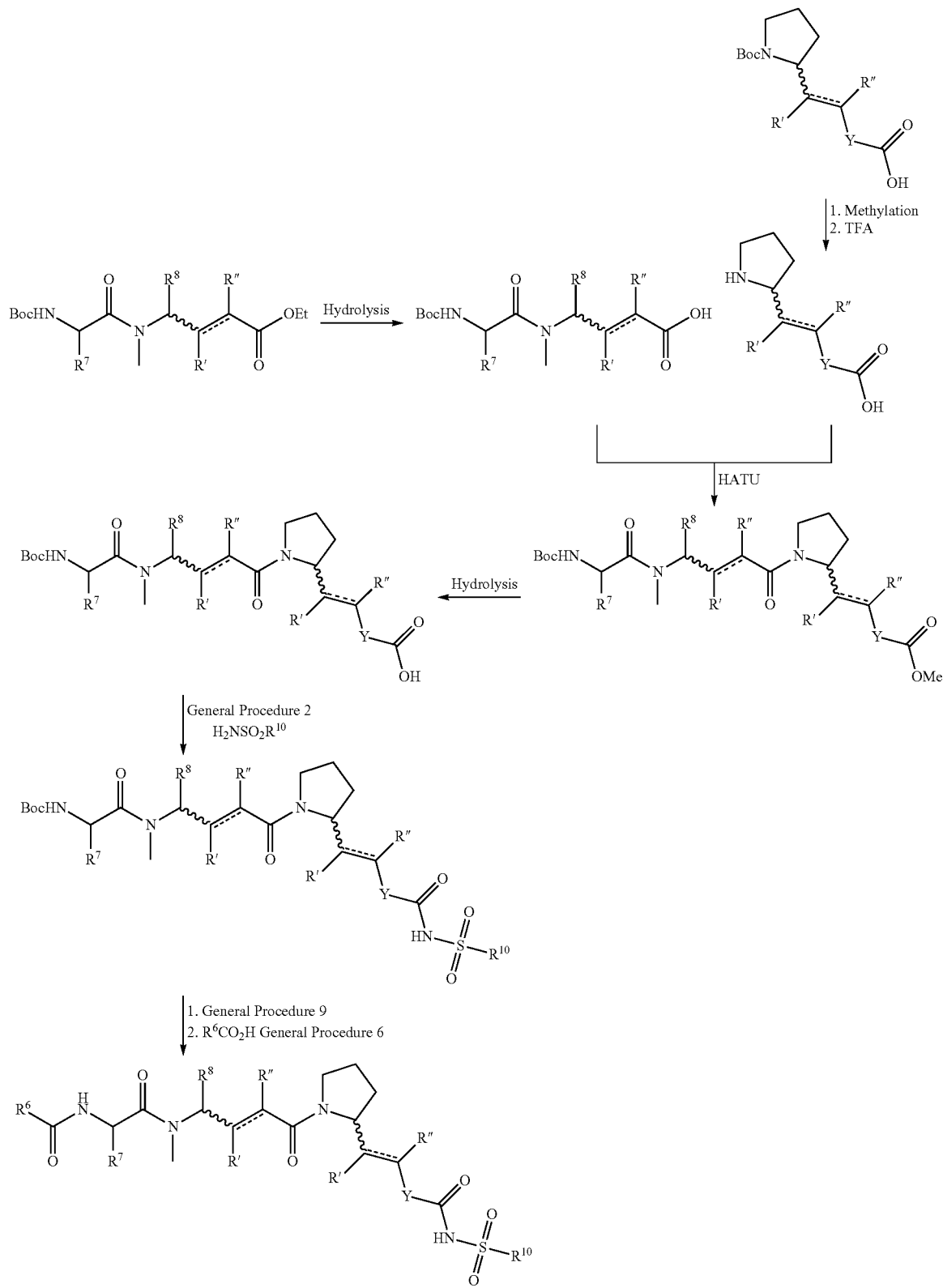
R' is H, or OMe
R" is H or C$_1$—C$_3$ alkyl
===== is a single bond or doubled bond

Example 1.1: General Procedure 1—Trifluoroacetamide Installation

To a stirred suspension of the amine in 1,4-dioxane was added trifluoroacetic anhydride (1.1 equivalents). The reaction mixture transitioned from a suspension to a solution and back to a suspension again. The progress of the reaction was monitored by TLC and/or HPLC-MS for completion. Once the starting material was fully consumed, the reaction was diluted with hexanes or diethyl ether, filtered on a Buchner funnel and the resulting solids were dried under reduced pressure to give the pure trifluoroacetamide.

Example 1.2: General Procedure 2

Method A: DCC/DMAP Mediated N-Acyl Sulfonamide Formation.

To a stirred solution of the acid in dichloromethane was added a solution of the sulfonamide (1.3 equivalents, in dichloromethane, N,N-dimethylformamide, or a mixture thereof, as necessary). Dicyclohexylcarbodiimide (1.2 equivalents) was added and subsequently N,N-dimethylaminopyridine (1.2 equivalents). Reaction course was monitored by HPLC-MS (typically 16 h) and excess by-products could be precipitated by the addition of diethyl ether. Solids were removed by filtration and washed with 1:1 diethyl ether/dichloromethane. The combined organic layers were concentrated, and the residue was purified by silica gel chromatography or optionally prep-HPLC to give the desired N-acyl sulfonamide.

Method B: DCC or EDCI/DMAP Mediated N-Acyl Sulfonamide Formation.

To a stirred solution of the acid in dichloromethane, ethyl acetate or a mixture thereof was added a solution of the sulfonamide (1.3 equivalents, in dichloromethane, ethyl acetate or N,N-dimethylformamide, or a mixture thereof, as necessary). Dicyclohexylcarbodiimide or EDCI (1.2 equivalents) was added and subsequently N,N-dimethylaminopyridine (1.2 equivalents). Reaction course was monitored by HPLC-MS (typically 16 h) and excess by-products could be precipitated by the addition of diethyl ether. Solids were removed by filtration and washed with 1:1 diethyl ether/dichloromethane. The combined organic layers were concentrated, and the residue was purified by silica gel chromatography or optionally prep-HPLC to give the desired N-acyl sulfonamide.

Example 1.3: General Procedure 3 Alternative—AcBt Mediated N-Acyl Sulfonamide Formation This procedure was adapted from the one described in ARKIVOC 2004 (xii), 14-22.

Example 1.4: General Procedure 4—Trifluoroacetamide Saponification

To a solution of the trifluoroacetamide containing construct in 1,4-dioxane or methanol was added lithium hydroxide (10 equivalents) and water (10% v/v). The reaction was allowed to stir at room temperature or optionally heated to 50° C. Reaction course was monitored by HPLC-MS. Upon completion, volatiles were removed under reduced pressure, the aqueous layer was pH adjusted if necessary and washed successively with dichloromethane or ethyl acetate. The organic phases were pooled, dried over $MgSO_4$, filtered and concentrated. The reaction product was either used "as is" or purified by silica gel chromatography as necessary.

Example 1.4.1: General Procedure 4.1—Amide/Ester Saponification

To a solution of the amide/ester containing construct in 1,4-dioxane or methanol was added lithium hydroxide (10 equivalents) and water (10% v/v). The reaction was allowed to stir at room temperature or optionally heated to 50° C. Reaction course was monitored by HPLC-MS. Upon completion, volatiles were removed under reduced pressure, the aqueous layer was pH adjusted if necessary and washed successively with dichloromethane or ethyl acetate. The organic phases were pooled, dried over $MgSO_4$, filtered and concentrated. The reaction product was either used "as is" or purified by silica gel chromatography as necessary.

Example 1.5: General Procedure 5—DIC/Cu(II) Mediated Peptide Bond Formation

To a stirred solution of the carboxylic acid in a minimal amount of 30% N,N-dimethylformamide in dichloromethane was added 1-ethyl-3-(3-dimethylaminopropyl)carbodiimide (0.95 equiv), 1-Hydroxy-7-azabenzotriazole (1.0 equiv), the amine (0.33 equiv) and anhydrous copper (II) chloride (1.0 equiv) in sequence with a brief pause between each additional reagent. Stirring was continued at room temperature and progress of the reaction was monitored by HPLC-MS. Upon completion, volatiles were removed under reduced pressure and the residual material was purified by silica gel chromatography or reverse phase HPLC to furnish the desired amide in adequate purity.

Example 1.6: General Procedure 6—HATU Mediated Peptide Bond Formation

To a stirred solution of the carboxylic acid in a minimal amount of dichloromethane or N,N-dimethylformamide or mixture thereof, at 0° C. was added HATU (1.05-1.2 equivalents) and either N,N-diisopropylamine (2-4 equivalents) or 2,4,6-collidine (2-4 equivalents). Stirring was continued for a brief induction period (5-20 minutes) at which time the reaction was charged with a solution of the amine in dichloromethane. The reaction was allowed to warm to room temperature and monitored for progress by HPLC-MS. Upon completion, volatiles were removed under reduced pressure and the residual material was purified by silica gel chromatography or reverse phase HPLC to furnish amide in adequate purity.

Example 1.7: General Procedure 7—Fmoc Group Removal

The Fmoc-protected peptide construct was dissolved in 20% piperidine in N,N-dimethylformamide. The reaction course was monitored by HPLC-MS. When complete, all volatiles were removed under reduced pressure to yield a residue that was either purified by silica gel chromatography or used directly in the next step.

Example 1.8: General Procedure 8—N-Acylation of Amines Using NHS-Activated Esters To a solution of the amine in a minimal amount of N,N-dimethylformamide was added the corresponding N-hydroxysuccinimide containing ester (1.5 equivalents)

and optionally di-isopropylamine (2-4 equivalents). The progress of the reaction was monitored by HPLC-MS (typically ~16h) at which point all volatiles were removed under reduced pressure. The residue was then purified by either silica gel chromatography or reverse phase HPLC to give the desired amide product.

Example 1.9: General Procedure 9—Boc Group Removal

To a solution of the Boc-protected construct in dichloromethane was added 10% v/v trifluoroacetic acid. Reaction course was monitored by HPLC-MS. Upon completion, all volatiles were removed under reduced pressure. The residual material was purified either by reverse phase HPLC, silica gel chromatography or precipitation from a mixture of cold methanol/dichloromethane/diethyl ether.

Example 1.9.1: General Procedure 9.1—Boc Group and t-Bu Ester Removal

To a solution of the Boc-protected amine or t-Bu ester in dichloromethane was added 10-20% v/v trifluoroacetic acid. Reaction course was monitored by HPLC-MS. Upon completion, all volatiles were removed under reduced pressure. The residual material was purified either by reverse phase HPLC, silica gel chromatography or precipitation from a mixture of cold methanol/dichloromethane/diethyl ether.

Example 1.10: Fmoc-Val-Cit-OH: (S)-2-((S)-2-((((9H-Fluoren-9-yl)methoxy)carbonyl)amino)-3-methylbutanamido)-5-ureidopentanoic Acid, Fmoc-Valine-Citrulline-OH, Fmoc-VC-OH

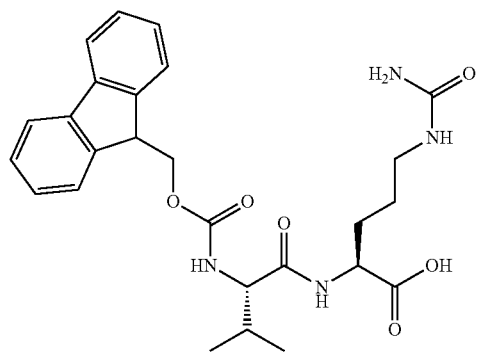 [SMILES: CC(C)[C@H](NC(=O)OCC1c2ccccc2-c2ccccc21)C(=O)N[C@@H](CCCNC(N)=O)C(=O)O]

The title compound was prepared according to Dubowchik et al., Bioconjugate Chem., 2002, 13, 855-869.

$^1$H NMR (400 MHz, DMSO-d6) δ 12.56 (s, 1H), 8.21 (d, J=7.3 Hz, 1H), 7.90 (d, J=7.5 Hz, 2H), 7.76 (t, J=7.0 Hz, 2H), 7.49-7.39 (m, 3H), 7.38-7.23 (m, 2H), 5.96 (t, J=5.9 Hz, 1H), 5.40 (s, 2H), 4.34-4.09 (m, 4H), 3.93 (dd, J=9.1, 7.1 Hz, 1H), 3.39 (q, J=7.0 Hz, 3H), 2.96 (q, J=6.5 Hz, 2H), 1.97 (d, J=6.9 Hz, 1H), 1.86-1.63 (m, 1H), 1.57 (dtd, J=13.9, 9.0, 5.4 Hz, 1H), 1.41 (dhept, J=13.2, 6.9 Hz, 2H), 0.88 (dd, J=13.3, 6.7 Hz, 6H).). C26H32N4O6 calcd. [M+H]+ 497.23. found [M+H]+ 497.19.

Example 1.11: (S)-2-((S)-2-((tert-Butoxycarbonyl)amino)-3-methylbutanamido)-5-ureidopentanoic acid, Boc-Valine-Citrulline-OH, Boc-VC-OH

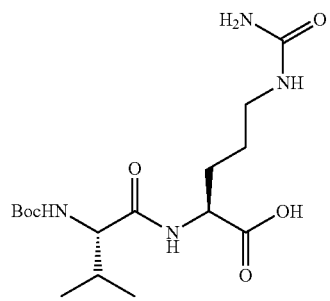 [SMILES: CC(C)[C@H](NC(=O)OC(C)(C)C)C(=O)N[C@@H](CCCNC(N)=O)C(=O)O]

The title compound was synthesized according to US2010/0233190 A1 with matching spectroscopic data.

Example 1.12: MC-NHS: 2,5-Dioxopyrrolidin-1-yl 6-(2,5-dioxo-2,5-dihydro-1H-pyrrol-1-yl)hexanoate

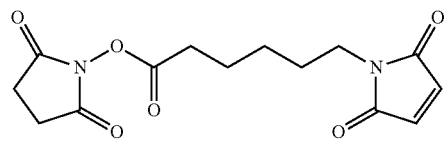 [SMILES: O=C(CCCCCN1C(=O)C=CC1=O)ON1C(=O)CCC1=O]

To a stirred solution of 6-aminocaproic acid (10.0 g, 76.2 mmol, 1.0 eq) in acetic acid (75 mL), maleic anhydride (7.85 g, 80.0 mmol, 1.05 eq) was added. The solids took a few minutes to dissolve, then after ca. 5 min, white solids began to crash out. After an hour, the suspension thickened to a white cake. This material was scooped onto a fritted funnel and washed with toluene and dried in vacuo with heating to remove all traces of acetic acid.

The intermediate powder was taken up in toluene (250 mL), triethylamine (21.3 mL, 152 mmol, 2.0 eq) was added, and the mixture heated to reflux with a Dean-Stark trap. After 5 h of reflux, the mixture was cooled and the clear toluene layer was decanted from the rest of the sticky residue in the flask. The toluene was removed in vacuo to yield the a triethylamine salt of 6-(2,5-dioxo-2,5-dihydro-1H-pyrrol-1-yl)hexanoate. The salt was redissolved in toluene, and a small amount of acetic acid was added, then concentrated. Next, the mixture was taken up in 50% saturated sodium bicarbonate, and 1 M HCl was added to adjust the pH to 3, forming a milky precipitate. This was extracted three times with EtOAc, combined organics dried over sodium sulfate, filtered, and concentrated in vacuo to yield pure 6-(2,5-dioxo-2,5-dihydro-1H-pyrrol-1-yl)hexanoate (3.08 g, 19%).

To a stirred solution of 6-(2,5-dioxo-2,5-dihydro-1H-pyrrol-1-yl)hexanoate (3.08 g, 14.6 mmol, 1.0 eq) and N-hydroxysuccinimide (1.76 g, 15.3 mmol, 1.05 eq) in EtOAc (30 mL) at 0° C., was added dicyclohexylcarbodiimide (3.16 g, 15.3 mmol, 1.05 eq). The reaction was then allowed to warm to rt. After 20 h, the reaction was filtered and washed with EtOAc and the filtrate concentrated. The residue was purified by flash chromatography to yield the title compound (2.16 g, 48%) as a clear oil that solidified slowly to a waxy white solid. $^1$H NMR (400 MHz, Chloroform-d) δ 6.71 (s, 2H), 3.56 (t, J=7.2 Hz, 2H), 2.86 (s, 4H), 2.63 (t, J=7.4 Hz, 2H), 1.80 (p, J=7.4 Hz, 2H), 1.73-1.57 (m, 2H), 1.50-1.35 (m, 2H). m/z calcd. for $C_{14}H_{16}N_2O_6$=308.10. Found [M+H]=309.13. $R_f$=0.28 (50% EtOAc/Hex).

Example 1.13: MT-OH: 3-(2-(2-(2-(2,5-Dioxo-2,5-dihydro-1H-pyrrol-1-yl)ethoxy)ethoxy)ethoxy)propanoic acid

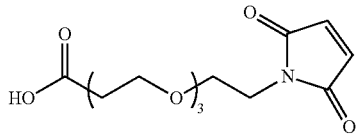

The title compound was prepared according to Warnecke, A., Kratz, F. Bioconjugate Chemistry 2003, 14, 377-387.
$^1$H NMR (400 MHz, Chloroform-d) δ 6.74 (s, 2H), 3.87-3.72 (m, 4H), 3.72-3.62 (m, 10H), 2.73-2.64 (m, 2H). m/z calcd. for C13H29NO7=301.12. Found [M+H]$^+$= 302.14.

Example 1.14: MT-NHS: 2,5-Dioxopyrrolidin-1-yl 3-(2-(2-(2-(2,5-dioxo-2,5-dihydro-1H-pyrrol-1-yl)ethoxy)ethoxy)ethoxy)propanoate

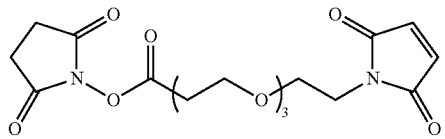

MT-OH (2.6 g, 8.6 mmol, 1.0 eq) was treated with dicyclohexylcarbodiimide (1.87 g, 9.06 mmol, 1.05 eq), and N-hydroxysuccinimide (1.04 g, 6.06 mmol, 1.05 eq) in 30 mL of 5:1 EtOAc/dioxane at rt. After 36 h, the mixture was filtered, washing with EtOAc, and the residue was purified by flash chromatography to yield the title compound (309 mg, 9.0%) as a clear oil along with starting material (1.31 g, 50% recovered).
$^1$H NMR (400 MHz, Chloroform-d) δ 6.72 (s, 2H), 3.87 (t, J=6.4 Hz, 2H), 3.74 (t, J=5.6 Hz, 2H), 3.70-3.58 (m, 10H), 2.93 (t, J=6.4 Hz, 2H), 2.86 (s, 4H), 1.32-1.19 (m, 2H). m/z calcd. for $C_{17}H_{22}N_2O_9$=398.13. Found [M+H]$^+$= 399.15, [M+Na]$^+$=421.14. $R_f$=0.59 (10% (5% AcOH/MeOH)/10% Hex/CH$_2$Cl$_2$).

Example 1.15: MT-VC-OH: (14R,17R)-1-(2,5-Dioxo-2,5-dihydro-1H-pyrrol-1-yl)-14-isopropyl-12,15-dioxo-17-(3-ureidopropyl)-3,6,9-trioxa-13,16-diazaoctadecan-18-oic Acid Method A To a solution of (R)-2-((R)-2-(tert-butoxycarbonylamino)-3-methylbutanamido)-5-ureidopentanoic acid (Boc-VC-OH, 0.600 g, 1.602 mmol) in dichloromethane (2.5 mL) was added trifluoroacetic acid (2.5 mL). The course of the reaction was monitored by HPLC for consumption of the starting material and then concentrated under reduced pressure, re-suspended in toluene, concentrated under reduced pressure and left under high vacuum for 4 hours. A portion of the product (H-VC-OH. TFA, 0.5 g, 1.287 mmol) was suspended in 1,4-dioxane (0.5 mL) and MT-NHS (0.512 g, 1.287 mmol) was added in a single portion, followed by di-isopropylethylamine (0.90 mL, 4 equiv) and the reaction was allowed to stir overnight. The reaction was concentrated to dryness and the resulting oil dissolved in methanol prior to being purified by preparative HPLC. Lyophilization of the desired fractions afforded the title compound as a white powder (0.351 g).

Method B The title compound was prepared according to the procedure set forth in WO 2015095953 A1.

Example 1.16: (S)-2-Amino-3-phenyl-N-(4-(2,2,2-trifluoroacetamido)phenylsulfonyl)propanamide (Compound 1)

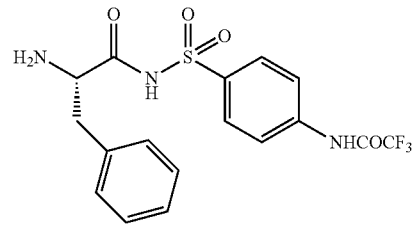

Prepared from Boc-phenylalanine and 2,2,2-trifluoro-N-(4-sulfamoylphenyl)acetamide according to General Procedures 2 and 9. $^1$H NMR (400 MHz, DMSO-d6) δ 11.42 (s, 1H), 7.84 (d, J=8.7 Hz, 2H), 7.73-7.64 (m, 1H), 7.69 (d, J=8.7 Hz, 2H), 7.24-7.14 (m, 3H), 7.13-7.06 (m, 2H), 3.65-3.60 (m, 1H), 3.06 (dd, J=14.2, 5.1 Hz, 1H), 2.91 (dd, J=14.1, 7.1 Hz, 1H). $C_{17}H_{16}F_3N_3O_4S$ calcd. m/z=415.08 found [M+H]$^+$=416.5.

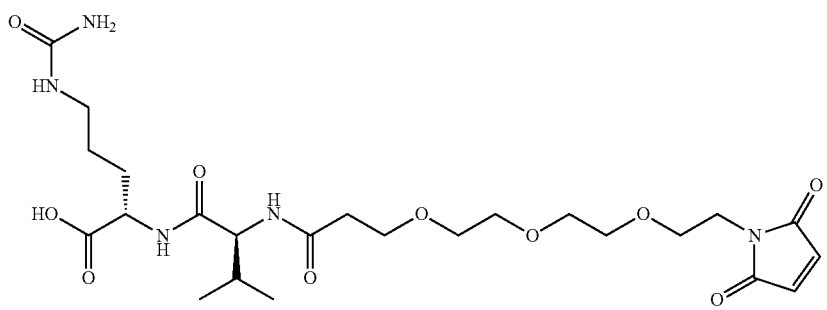 [SMILES: CC(C)[C@H](NC(=O)CCOCCOCCOCCN1C(=O)C=CC1=O)C(=O)N[C@@H](CCCNC(N)=O)C(=O)O]

Example 1.17: (S)-2-Amino-3-phenyl-N-((4-(2,2,2-trifluoroacetamido)benzyl)sulfonyl)propanamide (Compound 2)

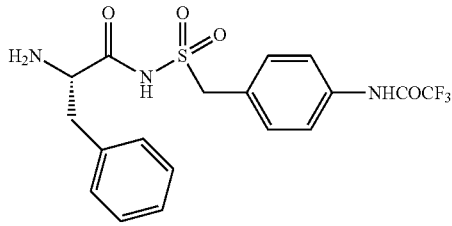

Prepared from Boc-phenylalanine and 2,2,2-trifluoro-N-(4-sulfamoylphenyl)acetamide (Example 1.39) according to General Procedures 3 and 9. $^1$H NMR (400 MHz, DMSO-d6) δ 7.76 7.71 (m, 2H), 7.58 (d, J=8.4 Hz, 2H), 7.36-7.21 (m, 8H), 4.34 (d, J=13.1 Hz, 1H), 4.30 (d, J=13.1 Hz, 1H), 3.62 (dd, J=8.2, 4.6 Hz, 1H), 3.21-3.09 (m, 1H), 2.89 (dd, J=14.3, 8.3 Hz, 1H). $C_{18}H_{18}F_3N_3O_4S$ calcd. m/z=429.10 found [M+H]$^+$=430.7.

Example 1.18: tert-Butyl (S)-1-(((3R,4S,5S)-3-Methoxy-1-((S)-2-((1R,2R)-1-methoxy-2-methyl-3-oxo-3-(4-(2,2,2-trifluoroacetamido)phenylsulfonamido)propyl)pyrrolidin-1-yl)-5-methyl-1-oxoheptan-4-yl)(methyl)amino)-3-methyl-1-oxobutan-2-ylcarbamate (Compound 3)

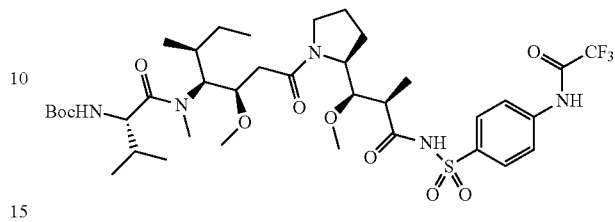

The title compound was synthesized from commercially available Boc-Val-Dip-Dap-OH (0.08 g) and 2,2,2-trifluoro-N-(4-sulfamoylphenyl)acetamide using General Procedure 2. $C_{37}H_{58}F_3N_5O_{10}S$ calcd. m/z=821.39 found [M+H]$^+$= 823.04.

Example 1.19: (S)-2-((S)-2-(Dimethylamino)-3-methylbutanamido)-N-((3R,4S,5S)-3-methoxy-1-((S)-2-((1R,2R)-1-methoxy-2-methyl-3-oxo-3-(4-(2,2,2-trifluoroacetamido)phenylsulfonamido)propyl)pyrrolidin-1-yl)-5-methyl-1-oxoheptan-4-yl)-N,3-dimethylbutanamide (Compound 4)

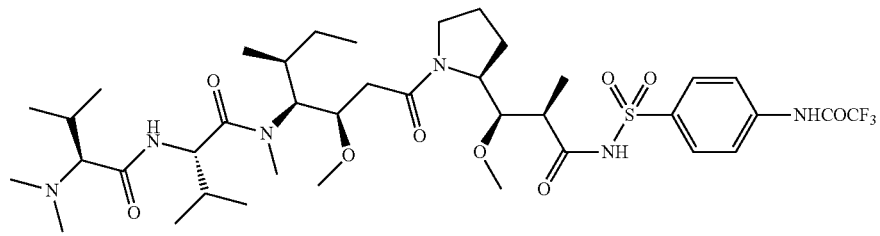

The title compound was prepared from Compound 3 and N,N-dimethyl valine using General Procedures 9 and 6. $C_{39}H_{63}F_3N_6O_9S$ calc'd m/z=848.43 found [M+H]$^+$ 850.11.

Example 1.20: (S)-N-((3R,4S,5S)-1-((S)-2-((1R,2R)-3-(4-Aminophenylsulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 5)

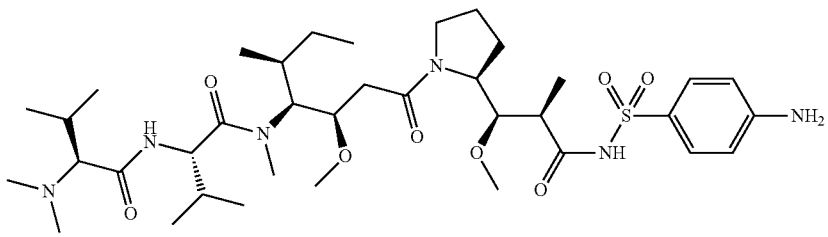 [SMILES: CC[C@H](C)[C@@H]([C@@H](CC(=O)N1CCC[C@H]1[C@H](OC)[C@@H](C)C(=O)NS(=O)(=O)c1ccc(N)cc1)OC)N(C)C(=O)[C@@H](NC(=O)[C@H](C(C)C)N(C)C)C(C)C]

The title compound was prepared from Compound 4 using General Procedure 4. C$_{37}$H$_{64}$N$_6$O$_8$S calc'd m/z=752.45 found [M+H]$^+$ 754.16.

Example 1.21: tert-Butyl (S)-1-(((3R,4S,5S)-3-Methoxy-1-((S)-2-((1R,2R)-1-methoxy-2-methyl-3-oxo-3-((4-(2,2,2-trifluoroacetamido)phenyl)methylsulfonamido)propyl)pyrrolidin-1-yl)-5-methyl-1-oxoheptan-4-yl)(methyl)amino)-3-methyl-1-oxobutan-2-ylcarbamate (Compound 6)

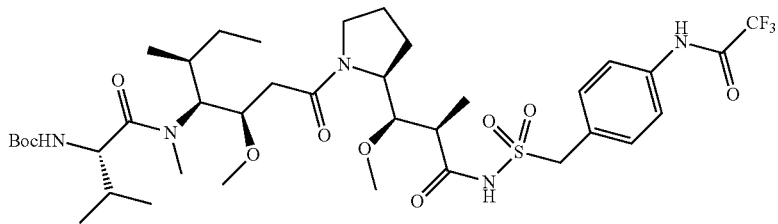 [SMILES: CC[C@H](C)[C@@H]([C@@H](CC(=O)N1CCC[C@H]1[C@H](OC)[C@@H](C)C(=O)NS(=O)(=O)Cc1ccc(NC(=O)C(F)(F)F)cc1)OC)N(C)C(=O)[C@@H](NC(=O)OC(C)(C)C)C(C)C]

The title compound was prepared from commercially available Boc-Val-Dil-Dap-OH through general procedure 2. C$_{38}$H$_{60}$F$_3$N$_5$O$_{10}$S calc'd m/z=835.40 found [M+H]$^+$=836.7.

Example 1.22: (S)-2-((S)-2-(Dimethylamino)-3-methylbutanamido)-N-((3R,4S,5S)-3-methoxy-1-((S)-2-((1R,2R)-1-methoxy-2-methyl-3-oxo-3-((4-(2,2,2-trifluoroacetamido)phenyl)methylsulfonamido)propyl)pyrrolidin-1-yl)-5-methyl-1-oxoheptan-4-yl)-N,3-dimethylbutanamide (Compound 7)

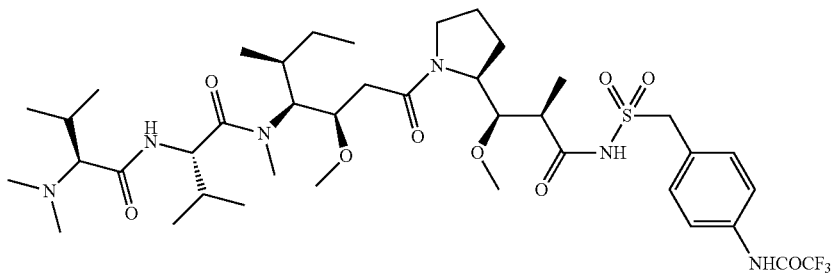

The title compound was prepared from Compound 6 by following General Procedure 6. C$_{40}$H$_{65}$F$_3$N$_6$O$_9$S calc'd m/z=862.45 found [M+H]$^+$=863.2.

Example 1.23: (S)-N-((3R,4S,5S)-1-((S)-2-((1R,2R)-3-((4-Aminophenyl)methylsulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 8)

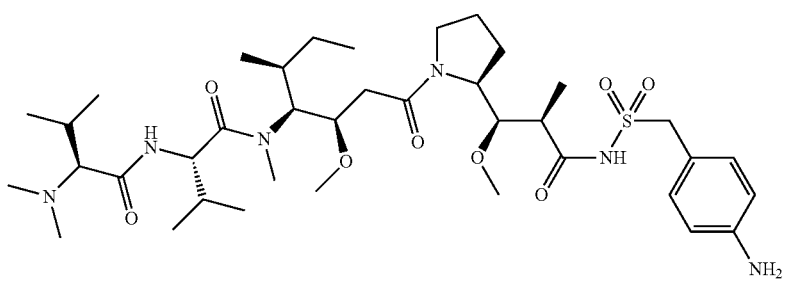 [SMILES: CC[C@H](C)[C@@H]([C@@H](CC(=O)N1CCC[C@H]1[C@H](OC)[C@@H](C)C(=O)NS(=O)(=O)Cc1ccc(N)cc1)OC)N(C)C(=O)[C@@H](NC(=O)[C@H](C(C)C)N(C)C)C(C)C]

The title compound was prepared from Compound 7 by following General Procedure 4. $C_{38}H_{66}N_6O_8S$ calc'd m/z=766.47 found $[M-C_7H_8O_2S+H]^+$=599.0 (Quinone methide fragmentation and loss of 4-aminobenzylsulfonate).

Example 1.24: tert-Butyl (S)-1-(((3R,4S,5S)-3-Methoxy-1-((S)-2-((1R,2R)-1-methoxy-2-methyl-3-oxo-3-((S)-1-oxo-3-phenyl-1-(4-(2,2,2-trifluoroacetamido)phenylsulfonamido)propan-2-ylamino)propyl)pyrrolidin-1-yl)-5-methyl-1-oxoheptan-4-yl)(methyl)amino)-3-methyl-1-oxobutan-2-ylcarbamate (Compound 9)

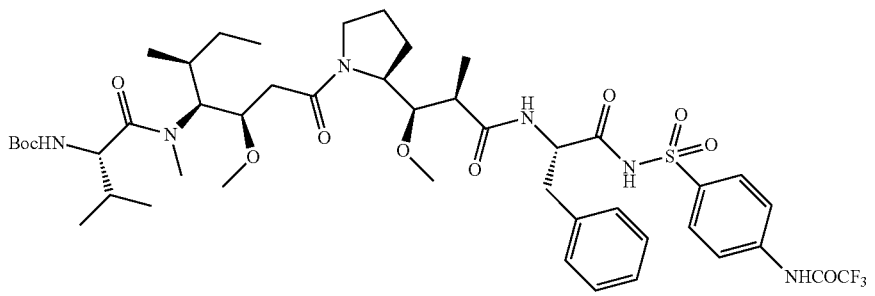

The title compound was synthesized from commercially available Boc-Val-Dip-Dap-OH (0.07 g) and Compound 1 using General Procedure 6. $C_{46}H_{67}F_3N_6O_{11}S$ calcd. m/z=968.45 found $[M+Na]^+$=992.1.

Example 1.25: (S)-2-((S)-2-(Dimethylamino)-3-methylbutanamido)-N-((3R,4S,5S)-3-methoxy-1-((S)-2-((1R,2R)-1-methoxy-2-methyl-3-oxo-3-((S)-1-oxo-3-phenyl-1-(4-(2,2,2-trifluoroacetamido)phenylsulfonamido)propan-2-ylamino)propyl)pyrrolidin-1-yl)-5-methyl-1-oxoheptan-4-yl)-N,3-dimethylbutanamide (Compound 10)

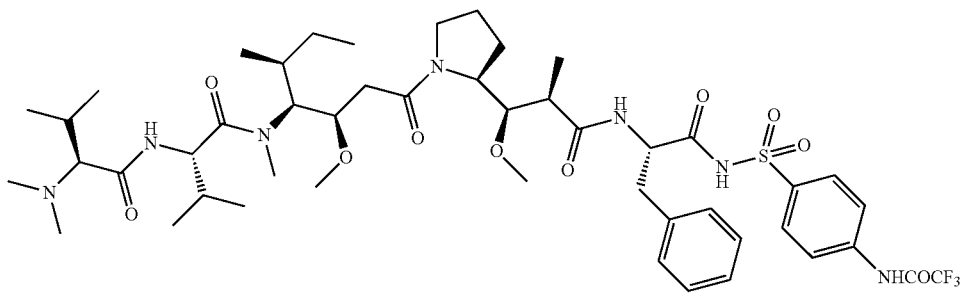

The title compound was prepared from Compound 9 (110 mg) and N,N-dimethyl valine using General Procedures 9 and 6. $C_{48}H_{72}F_3N_7O_{10}S$ calc'd m/z=995.50 found [M+H]$^+$ 997.3.

Example 1.26: (S)-N-((3R,4S,5S)-1-((S)-2-((1R,2R)-3-((S)-1-(4-Aminophenylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 11)

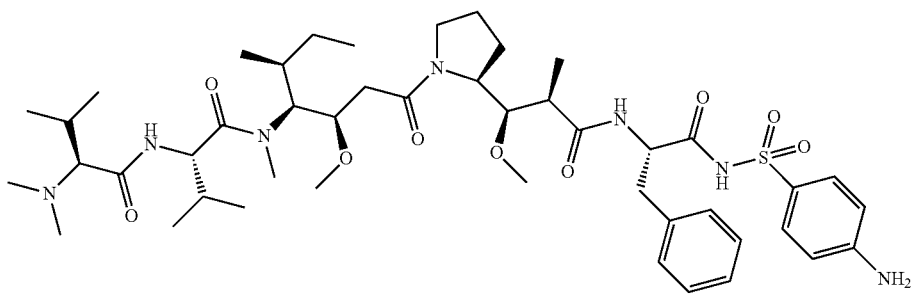 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(N)cc1)OC)N(C)C(=O)[C@@H](NC(=O)[C@H](C(C)C)N(C)C)C(C)C]

The title compound was prepared from Compound 10 (100 mg) using General Procedure 4. $C_{46}H_{73}N_7O_9S$ calc'd m/z=899.52 found [M+H]$^+$ 901.3.

Example 1.27: tert-Butyl (S)-1-(((3R,4S,5S)-3-Methoxy-1-((S)-2-((1R,2R)-1-methoxy-2-methyl-3-oxo-3-((S)-1-oxo-3-phenyl-1-(4-(2,2,2-trifluoroacetamido)phenylmethylsulfonamido)propan-2-ylamino)propyl)pyrrolidin-1-yl)-5-methyl-1-oxoheptan-4-yl)(methyl)amino)-3-methyl-1-oxobutan-2-ylcarbamate (Compound 12)

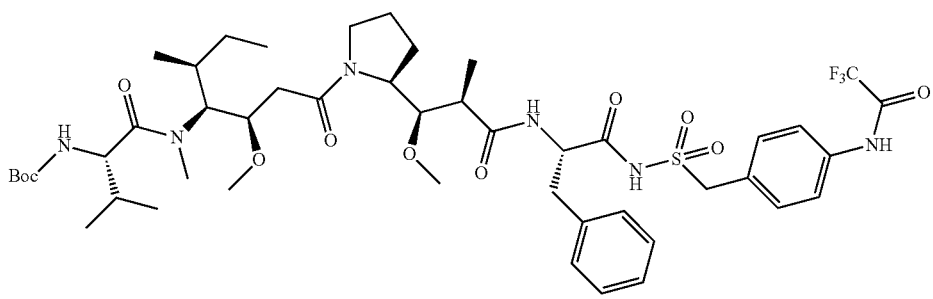 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)Cc1ccc(NC(=O)C(F)(F)F)cc1)OC)N(C)C(=O)[C@@H](NC(=O)OC(C)(C)C)C(C)C]

The title compound was prepared from commercially available Boc-Val-Dil-Dap-OH and Compound 2 by following general procedure 6. $C_{47}H_{69}F_3N_6O_{11}S$ calc'd m/z=982.47 found $[M+Na]^+$=1006.2.

Example 1.28: (S)-2-((S)-2-(Dimethylamino)-3-methylbutanamido)-N-((3R,4S,5S)-3-methoxy-1-((S)-2-((1R,2R)-1-methoxy-2-methyl-3-oxo-3-((S)-1-oxo-3-phenyl-1-(4-(2,2,2-trifluoroacetamido)phenylmethylsulfonamido)propan-2-ylamino)propyl)pyrrolidin-1-yl)-5-methyl-1-oxoheptan-4-yl)-N,3-dimethylbutanamide (Compound 13)

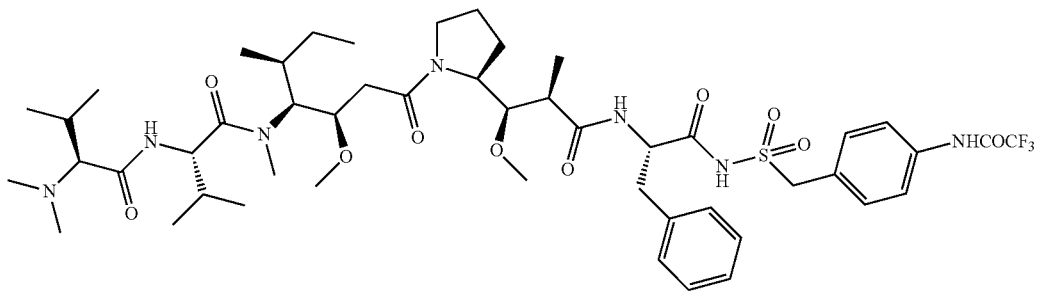

The title compound was prepared from Compound 12 and dimethylvaline by following general procedure 6. $C_{49}H_{74}F_3N_7O_{10}S$ calc'd m/z=1009.52 found $[M+H]^+$=1011.0.

Example 1.29: (S)-N-((3R,4S,5S)-1-((S)-2-((1R,2R)-3-((S)-1-(4-Aminophenylmethylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 14)

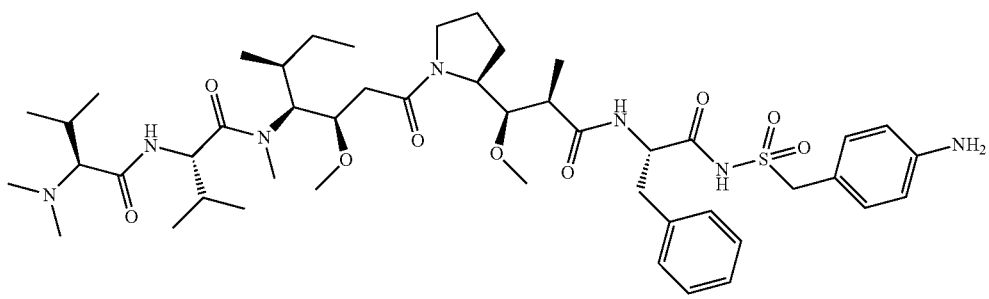 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)Cc1ccc(N)cc1)OC)N(C)C(=O)[C@@H](NC(=O)[C@H](C(C)C)N(C)C)C(C)C]

The compound was prepared from Compound 13 by following General Procedure 4. $C_{47}H_{75}N_7O_9S$ calc'd m/z=913.53 found $[M-C_7H_8O_2S+Na]^+$=768.1 (Quinone methide fragmentation and loss of 4-aminobenzylsulfonate).

Example 1.30: General Procedure 10—Hydrogenation

To a solution of the sample to be reduced in either methanol, ethanol, acetic acid, ethyl acetate, a mixture thereof or other suitable solvent was added a magnetic stirrer. The flask containing the stirred solution was fitted with a two-way gas line adapter and evacuated under reduced pressure and charged with nitrogen. This process was repeated 3 times. 10% Pd/C was added as either a solid or a slurry, typically at 10 mol % Palladium relative to the reactant. The vessel was again evacuated under reduced pressure and charged with a hydrogen containing balloon. The reaction was monitored for completion by HPLC-MS and upon completion, filtered through a pad of celite on a filter funnel.

The filtrate was concentrated under reduced pressure and used as-is or purified via silica gel or preparative HPLC chromatography.

Example 1.31: Perfluorophenyl 3-(2-(2-(2-(2,5-di-oxo-2,5-dihydro-1H-pyrrol-1-yl)ethoxy)ethoxy)ethoxy)propanoate To a stirred solution of 3-(2-(2-(2-(2,5-dioxo-2,5-dihydro-1H-pyrrol-1-yl)ethoxy)ethoxy)ethoxy)propanoic acid, (Example 1.13) (2.28 g, 7.57 mmol) in dichloromethane (100 mL) was added 1-ethyl-3-(3-dimethylaminopropyl)carbodiimide hydrochloride (1.59 g, 1.1 equiv) and pentafluorophenol (1.53 g, 1.1 equiv). The reaction was allowed to stir overnight at which time HPLC-MS indicated no remaining starting material (Rt=5.30 min, 490.4 m/z, full gradient). The crude reaction mixture was diluted with saturated sodium bicarbonate (~20 mL) and the mixture was transferred to a separatory funnel. The organic phase was washed with brine (~50 mL), dried over $MgSO_4$, filtered and concentrated to give a slightly yellow oil. The oil was dissolved in a minimal amount of dichloromethane and loaded on to a 100 g silica gel column for purification (Isolera, 10-100% EtOAc in hexanes over 12 column volumes). Fractions containing the desired material were pooled and concentrated under reduced pressure to give a colorless oil (3.32 g, 94%).

Example 1.32: (3R,4S,5S)-tert-butyl 4-((S)-2-(Benzyloxycarbonylamino)-N,3-dimethylbutanamido)-3-methoxy-5-methylheptanoate, Cbz-Val-Dil-OtBu

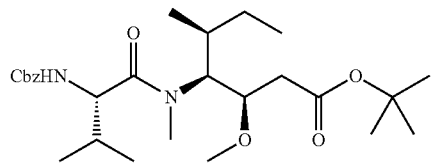 [SMILES: CC[C@H](C)[C@@H]([C@@H](CC(=O)OC(C)(C)C)OC)N(C)C(=O)[C@@H](NC(=O)OCc1ccccc1)C(C)C]

The title compound was prepared from commercially obtained Cbz-Val-OH and H-Dil-OtBu .HCl following general procedure 6.

$^1$H NMR (400 MHz, Chloroform-d) δ 7.40-7.30 (m, 5H), 5.54 (d, J=9.2 Hz, 1H), 5.12 (s, 2H), 4.73 (s, 1H), 4.54 (dd, J=9.2, 5.6 Hz, 1H), 3.91 (s, 1H), 3.37 (s, 3H), 2.98 (s, 3H), 2.47 (d, J=16.5 Hz, 1H), 2.33 (dd, J=15.6, 9.1 Hz, 1H), 2.07-1.96 (m, 1H), 1.84-1.60 (m, 1H), 1.48 (s, 9H), 1.45-1.32 (m, 2H), 1.04 (d, J=6.8 Hz, 3H), 0.98 (d, J=6.6 Hz, 3H), 0.94 (d, J=6.8 Hz, 3H), 0.86 (t, J=7.4 Hz, 3H). $C_{27}H_{44}N_2O_6$ calcd. m/z=492.32 found [M+H]$^+$=515.8 [M+Na]$^+$. R$_f$=0.78 (50% EtOAc/Hex).

Example 1.33: (3R,4S,5S)-4-((S)-2-(((Benzyloxy)carbonyl)amino)-N,3-dimethylbutanamido)-3-methoxy-5-methylheptanoic Acid, Cbz-Val-Dil-OH

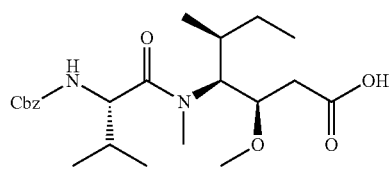 [SMILES: CC[C@H](C)[C@@H]([C@@H](CC(=O)O)OC)N(C)C(=O)[C@@H](NC(=O)OCc1ccccc1)C(C)C]

The title compound was prepared from Cbz-Val-Dil-OtBu (Example 1.32) using General Procedure 9. $C_{23}H_{36}N_2O_6$ calc'd m/z=436.26 found [M+Na]$^+$ 459.81. 1H NMR (400 MHz, Methanol-d$_4$) δ 7.47-7.22 (m, 5H), 5.21-4.99 (m, 2H), 4.83-4.54 (m, 1H), 4.39 (d, J=8.0 Hz, 1H), 3.96 (s, 1H), 3.43-3.33 (s, 3H), 3.07 (s, 3H), 2.63 (dd, J=15.9, 2.9 Hz, 1H), 2.38 (dd, J=15.8, 9.3 Hz, 1H), 2.15-1.95 (m, 1H), 1.83 (s, 1H), 1.52-1.30 (m, 1H), 1.07-0.91 (m, 9H), 0.85 (t, J=7.4 Hz, 3H).

Example 1.34: (3R,4S,5S)-tert-Butyl 4-((S)-2-Amino-N,3-dimethylbutanamido)-3-methoxy-5-methylheptanoate, H-Val-Dil-OtBu

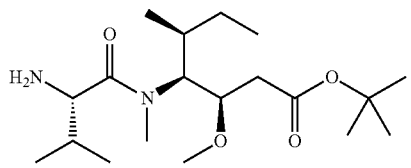 [SMILES: CC[C@H](C)[C@@H]([C@@H](CC(=O)OC(C)(C)C)OC)N(C)C(=O)[C@@H](N)C(C)C]

The title compound was generated from Cbz-Val-Dil-OtBu (438 mg, 0.889 mmol) according to General Procedure 10, to obtain the desired product (288 mg, 90%) as a clear film. $^1$H NMR (400 MHz, Chloroform-d) δ 4.76 (s, 1H), 3.92 (s, 1H), 3.50 (d, J=5.1 Hz, 1H), 3.38 (s, 3H), 2.92 (s, 3H), 2.48 (dd, J=15.7, 3.1 Hz, 1H), 2.35 (dd, J=15.6, 8.8 Hz, 1H), 1.93 (dq, J=10.9, 6.5 Hz, 1H), 1.82-1.60 (m, 1H), 1.51-1.46 (m, 11H), 1.05-0.85 (m, 12H). $C_{19}H_{38}N_2O_4$ calcd. m/z=358.28 found [M+Na]$^+$=381.8.

Example 1.35: (3R,4S,5S)-tert-Butyl 4-((S)-2-((S)-2-(Dimethylamino)-3-methylbutanamido)-N,3-dimethylbutanamido)-3-methoxy-5-methylheptanoate, Dov-Val-Dil-OtBu

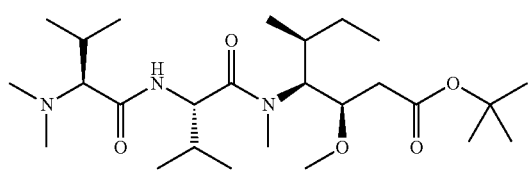 [SMILES: CC[C@H](C)[C@@H]([C@@H](CC(=O)OC(C)(C)C)OC)N(C)C(=O)[C@@H](NC(=O)[C@H](C(C)C)N(C)C)C(C)C]

The title compound was prepared from H-Val-Dil-OtBu and N,N-dimethylvaline following general procedure 6.

$^1$H NMR (400 MHz, Chloroform-d) δ 7.09 (d, J=8.8 Hz, 1H), 4.79 (t, J=7.6 Hz, 1H), 4.00-3.81 (m, 1H), 3.75 (s, 1H), 3.37 (s, 3H), 3.26 (s, 1H), 3.00 (s, 3H), 2.74 (s, 6H), 2.49 (d, J=15.9 Hz, 1H), 2.38-2.20 (m, 2H), 2.13-2.05 (m, 1H), 1.81-1.62 (m, 1H), 1.51-1.43 (m, 10H), 1.33 (s, 1H), 1.18-0.89 (m, 15H), 0.83 (t, J=7.2 Hz, 3H). $C_{26}H_{51}N_3O_5$ calcd. m/z=485.38 found [M+Na]$^+$=508.9. R$_f$=0.36 (5% MeOH/CH$_2$Cl$_2$).

Example 1.36: (3R,4S,5S)-tert-Butyl 4-((S)-2-((S)-2-(Dimethylamino)-3-methylbutanamido)-N,3-dimethylbutanamido)-3-methoxy-5-methylheptanoic Acid, Dov-Val-Dil-OH

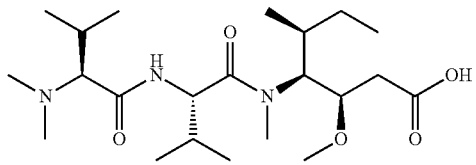 [SMILES: CC[C@H](C)[C@@H]([C@@H](CC(=O)O)OC)N(C)C(=O)[C@@H](NC(=O)[C@H](C(C)C)N(C)C)C(C)C]

The title compound was prepared from Dov-Val-Dil-OtBu following general procedure 9.

$^1$H NMR (400 MHz, Chloroform-d) δ 4.98 (t, J=10.0 Hz, 1H), 4.65 (dd, J=9.3, 3.1 Hz, 1H), 4.08 (d, J=10.6 Hz, 1H), 3.61-3.53 (m, 1H), 3.39 (s, 3H), 3.24 (s, 3H), 3.13 (s, 3H), 2.93 (s, 3H), 2.77 (dd, J=17.0, 9.8 Hz, 1H), 2.66 (dd, J=17.3, 1.9 Hz, 1H), 2.31-2.26 (m, 1H), 2.07 (dt, J=10.8, 5.5 Hz, 1H), 1.97-1.85 (m, 1H), 1.29-1.24 (m, 1H), 1.13 (d, J=6.7 Hz, 3H), 1.08-1.01 (m, 6H), 1.01-0.95 (m, 6H), 0.90-0.81 (m, 1H), 0.77 (t, J=6.9 Hz, 3H) $C_{22}H_{43}N_3O_5$ calcd. m/z=429.32. found [M+H]$^+$=430.8.

Example 1.37: tert-Butyl (5S,8S,11S,12R)-11-((S)-sec-Butyl)-1-(9H-fluoren-9-yl)-5,8-diisopropyl-12-methoxy-4,10-dimethyl-3,6,9-trioxo-2-oxa-4,7,10-triazatetradecan-14-oate, Fmoc-(Me)Val-Val-Dil-OtBu

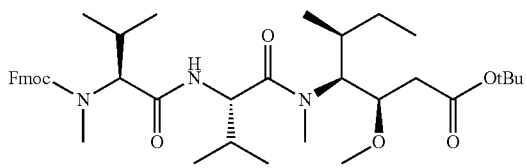

The title compound was prepared from Fmoc-(Me)-(L)-Valine-OH and H-Val-Dil-OtBu according to General Procedure 6. $C_{40}H_{59}N_3O_7$ calc'd $_{m/z}$=693.44 found [M+H]$^+$ 694.98.

Example 1.38: (5S,8S,11S,12R)-11-((S)-sec-Butyl)-1-(9H-fluoren-9-yl)-5,8-diisopropyl-12-methoxy-4,10-dimethyl-3,6,9-trioxo-2-oxa-4,7,10-triazatetradecan-14-oic Acid, Fmoc-(Me)Val-Val-Dil-OH

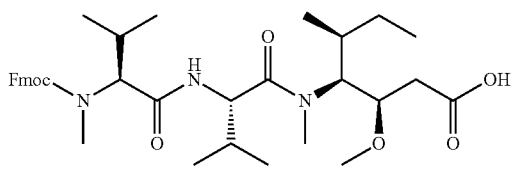

The title compound was prepared from Fmoc-(Me)Val-Val-Dil-OtBu using General Procedure 9. $C_{36}H_{51}N_3O_7$ calc'd m/z=637.37 found [M+H]$^+$ 638.91.

Example 1.39: 2,2,2-Trifluoro-N-(4-sulfamoylphenyl)acetamide

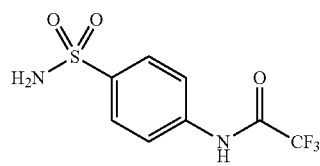 [SMILES: NS(=O)(=O)c1ccc(NC(=O)C(F)(F)F)cc1]

To a stirred suspension of sulfanilamide (1.72 g, 10 mmol) in dioxane (20 mL) was added trifluoroacetic anhydride (1.69 mL, 1.2 equiv). The solids slowly dissolved to create a uniform solution and after a brief period of time a new set of solids was formed. The reaction was diluted with diethyl ether (100 mL) and the resulting suspension filtered on a Buchner funnel. The solids were collected and dried under reduced pressure to afford the title compound in adequate purity for further use (2.60 g, 97%).

Example 1.40: (2R,3R)-3-Methoxy-2-methyl-3-((S)-pyrrolidin-2-yl)-N-(4-(2,2,2-trifluoroacetamido)phenylsulfonyl)propanamide

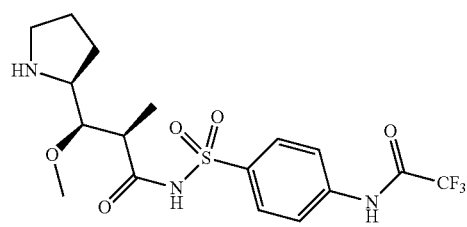 [SMILES: CO[C@@H]([C@@H]1CCCN1)[C@@H](C)C(=O)NS(=O)(=O)c1ccc(NC(=O)C(F)(F)F)cc1]

The title compound was prepared from commercially obtained Boc-Dap-OH and 2,2,2-trifluoro-N-(4-sulfamoylphenyl)acetamide following general procedures 2 and 9.

$^1$H NMR (400 MHz, Methanol-d$_4$) δ 8.06 (d, J=8.9 Hz, 2H), 7.92 (d, J=8.9 Hz, 2H), 3.69 (dd, J=6.6, 3.0 Hz, 1H), 3.48 (s, 3H), 3.51-3.39 (m, 1H), 3.33-3.14 (m, 2H), 2.64 (p, J=7.0 Hz, 1H), 2.06-1.68 (m, 4H), 1.19 (d, J=7.1 Hz, 3H). $C_{17}H_{22}F_3N_3O_5S$ calcd. m/z=437.12 found [M+H]$^+$=438.6.

Example 1.41: Benzyl ((S)-1-(((3R,4S,5S)-3-Methoxy-1-((S)-2-((1R,2R)-1-methoxy-2-methyl-3-oxo-3-((4-(2,2,2-trifluoroacetamido)phenyl)sulfonamido)propyl)pyrrolidin-1-yl)-5-methyl-1-oxoheptan-4-yl)(methyl)amino)-3-methyl-1-oxobutan-2-yl) carbamate

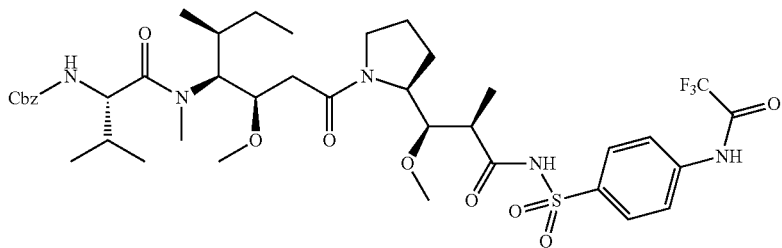 [SMILES: CC[C@H](C)[C@@H]([C@@H](CC(=O)N1CCC[C@H]1[C@H](OC)[C@@H](C)C(=O)NS(=O)(=O)c1ccc(NC(=O)C(F)(F)F)cc1)OC)N(C)C(=O)[C@@H](NC(=O)OCc1ccccc1)C(C)C]

The title compound was prepared from Cbz-Val-Dil-OH and the product of Example 1.40 according to General Procedure 2. $C_{40}H_{56}F_3N_5O_{10}S$ calc'd m/z=855.37 found [M+H]$^+$ 857.07.

Example 1.42: (S)-2-Amino-N-((3R,4S,5S)-3-methoxy-1-((S)-2-((1R,2R)-1-methoxy-2-methyl-3-oxo-3-((4-(2,2,2-trifluoroacetamido)phenyl)sulfonamido)propyl)pyrrolidin-1-yl)-5-methyl-1-oxoheptan-4-yl)-N,3-dimethylbutanamide

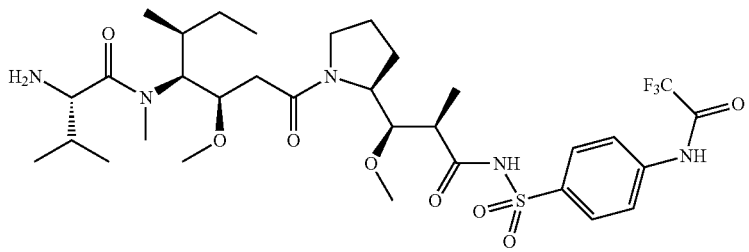 [SMILES: CC[C@H](C)[C@@H]([C@@H](CC(=O)N1CCC[C@H]1[C@H](OC)[C@@H](C)C(=O)NS(=O)(=O)c1ccc(NC(=O)C(F)(F)F)cc1)OC)N(C)C(=O)[C@@H](N)C(C)C]

The title compound was prepared from the product of Example 1.41 according to General Procedure 10. $C_{32}H_{50}F_3N_5O_8S$ calc'd m/z=721.33 found [M+H]$^+$ 722.70.

Example 1.43: tert-Butyl (3R,4S,5S)-4-((S)-2-((R)-1-Isopropylpiperidine-2-carboxamido)-N,3-dimethylbutanamido)-3-methoxy-5-methylheptanoate

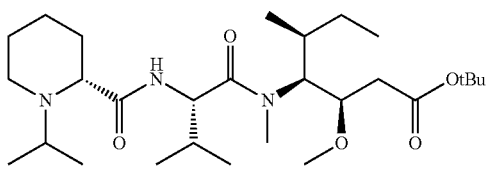 [SMILES: CC[C@H](C)[C@@H]([C@@H](CC(=O)OC(C)(C)C)OC)N(C)C(=O)[C@@H](NC(=O)[C@H]1CCCCN1C(C)C)C(C)C]

The title compound was prepared from (R)-1-isopropylpiperidine-2-carboxylic acid and H-Val-Dil-OtBu according to General Procedure 6. $C_{28}H_{53}N_3O_5$ calc'd m/z=511.40 found [M+H]$^+$ 512.77.

Example 1.44: (3R,4S,5S)-4-((S)-2-((R)-1-Isopropylpiperidine-2-carboxamido)-N,3-dimethylbutanamido)-3-methoxy-5-methylheptanoic Acid

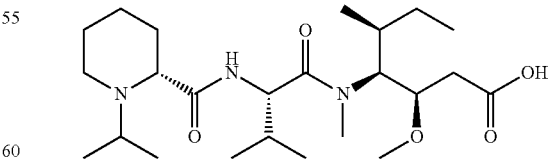

The title compound was prepared from tert-butyl the product of Example 1.43 according to General Procedure 9. $C_{24}H_{45}N_3O_5$ calc'd m/z=455.34 found [M+H]$^+$ 456.70.

Example 1.45: (R)-1-Isopropyl-N-((S)-1-(((3R,4S,5S)-3-methoxy-1-((S)-2-((1R,2R)-1-methoxy-2-methyl-3-oxo-3-((4-(2,2,2-trifluoroacetamido)phenyl)sulfonamido)propyl)pyrrolidin-1-yl)-5-methyl-1-oxoheptan-4-yl)(methyl)amino)-3-methyl-1-oxobutan-2-yl)piperidine-2-carboxamide (Compound 15)

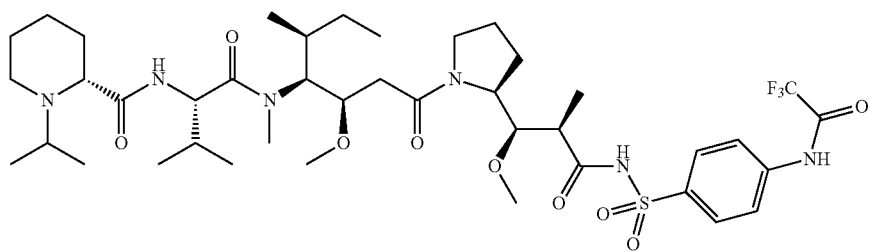 [SMILES: CC[C@H](C)[C@@H]([C@@H](CC(=O)N1CCC[C@H]1[C@H](OC)[C@@H](C)C(=O)NS(=O)(=O)c1ccc(NC(=O)C(F)(F)F)cc1)OC)N(C)C(=O)[C@@H](NC(=O)[C@H]1CCCCN1C(C)C)C(C)C]

The title compound was prepared from the product of Example 1.40 and the product of Example 1.44 according to General Procedure 6. $C_{41}H_{65}F_3N_6O_9S$ calc'd m/z=874.45 found [M+H]$^+$ 876.0.

Example 1.46: (R)-N-((S)-1-(((3R,4S,5S)-1-((S)-2-((1R,2R)-3-((4-Aminophenyl)sulfonamido)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-1-isopropylpiperidine-2-carboxamide (Compound 16)

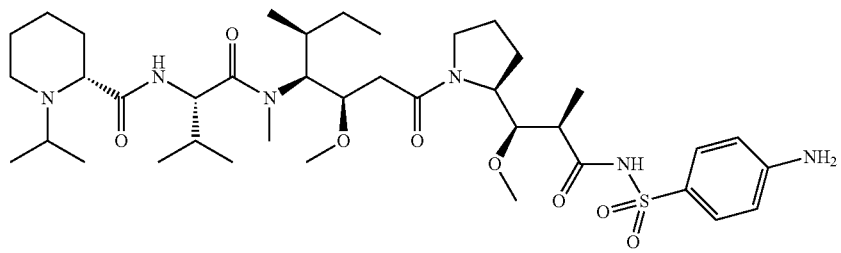 [SMILES: CC[C@H](C)[C@@H]([C@@H](CC(=O)N1CCC[C@H]1[C@H](OC)[C@@H](C)C(=O)NS(=O)(=O)c1ccc(N)cc1)OC)N(C)C(=O)[C@@H](NC(=O)[C@H]1CCCCN1C(C)C)C(C)C]

The title compound was prepared from Compound 15 according to General Procedure 4. $C_{39}H_{66}N_6O_8S$ calc'd m/z=778.47 found [M+H]$^+$ 780.06.

Example 1.47: tert-Butyl (1-(((S)-1-(((3R,4S,5S)-3-Methoxy-1-((S)-2-((1R,2R)-1-methoxy-2-methyl-3-oxo-3-((4-(2,2,2-trifluoroacetamido)phenyl)sulfonamido)propyl)pyrrolidin-1-yl)-5-methyl-1-oxoheptan-4-yl)(methyl)amino)-3-methyl-1-oxobutan-2-yl)amino)-2-methyl-1-oxopropan-2-yl)carbamate

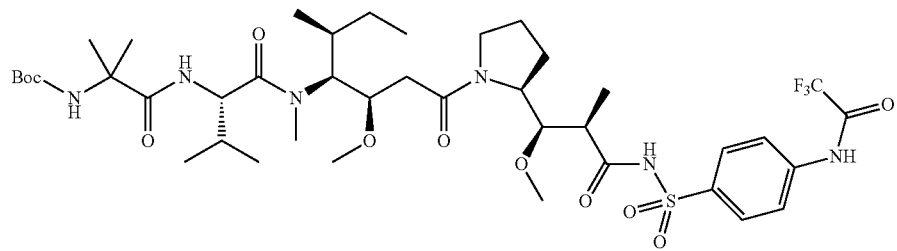 [SMILES: CC[C@H](C)[C@@H]([C@@H](CC(=O)N1CCC[C@H]1[C@H](OC)[C@@H](C)C(=O)NS(=O)(=O)c1ccc(NC(=O)C(F)(F)F)cc1)OC)N(C)C(=O)[C@@H](NC(=O)C(C)(C)NC(=O)OC(C)(C)C)C(C)C]

The title compound was prepared from the product of Example 1.42 and commercially obtained α-(Boc-amino) isobutyric acid according to General Procedure 6. $C_{41}H_{65}F_3N_6O_{11}S$ calc'd m/z=906.44 found [M+H]$^+$ 907.80.

Example 1.48: tert-Butyl (1-(((S)-1-(((3R,4S,5S)-1-((S)-2-((1R,2R)-3-((4-Aminophenyl)sulfonamido)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-2-methyl-1-oxopropan-2-yl)carbamate

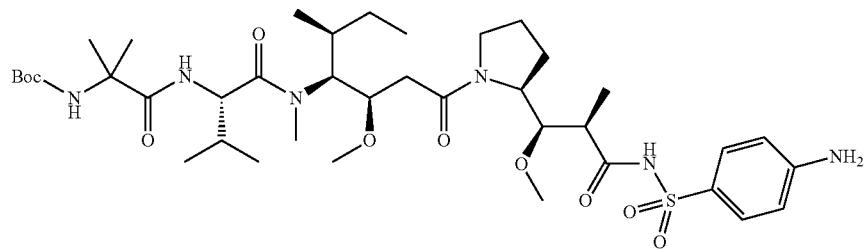 [SMILES: CC[C@H](C)[C@@H]([C@@H](CC(=O)N1CCC[C@H]1[C@H](OC)[C@@H](C)C(=O)NS(=O)(=O)c1ccc(N)cc1)OC)N(C)C(=O)[C@@H](NC(=O)C(C)(C)NC(=O)OC(C)(C)C)C(C)C]

The title compound was prepared from the product of Example 1.47 according to General Procedure 4. $C_{39}H_{66}N_6O_{10}S$ calc'd m/z=810.46 found [M+H]$^+$ 811.84.

Example 1.49: (S)-2-(2-Amino-2-methylpropanamido)-N-((3R,4S,5S)-1-((S)-2-((1R,2R)-3-((4-aminophenyl)sulfonamido)-1-methoxy-2-methyl-3-oxopropyl)pyrrolidin-1-yl)-3-methoxy-5-methyl-1-oxoheptan-4-yl)-N,3-dimethylbutanamide
(Compound 17)

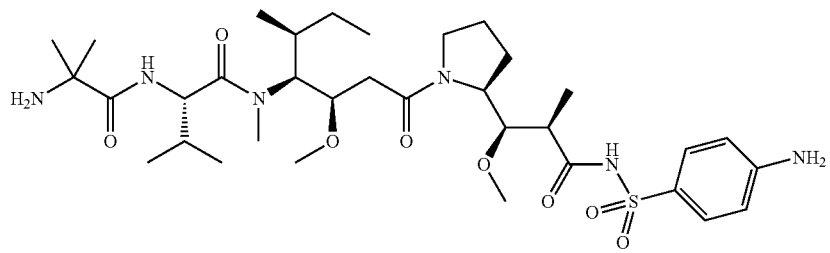 [SMILES: CC[C@H](C)[C@@H]([C@@H](CC(=O)N1CCC[C@H]1[C@H](OC)[C@@H](C)C(=O)NS(=O)(=O)c1ccc(N)cc1)OC)N(C)C(=O)[C@@H](NC(=O)C(C)(C)N)C(C)C]

The title compound was prepared from the product of Example 1.48 according to General Procedure 9. $C_{34}H_{58}N_6O_8S$ calc'd m/z=710.40 found [M+H]$^+$ 711.77.

Example 1.50 tert-Butyl (6S,9S,12S,13R)-12-((S)-sec-Butyl)-9-isopropyl-13-methoxy-2,2,5,11-tetramethyl-4,7,10-trioxo-6-(2-phenylpropan-2-yl)-3-oxa-5,8,11-triazapentadecan-15-oate

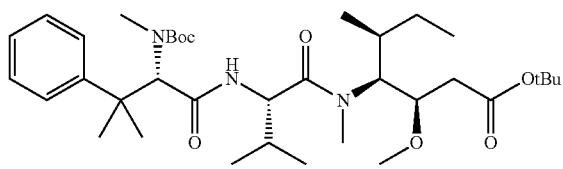 [SMILES: CC[C@H](C)[C@@H]([C@@H](CC(=O)OC(C)(C)C)OC)N(C)C(=O)[C@@H](NC(=O)[C@@H](N(C)C(=O)OC(C)(C)C)C(C)(C)c1ccccc1)C(C)C]

The title compound was prepared from (S)-2-((tert-butoxycarbonyl)(methyl)amino)-3-methyl-3-phenylbutanoic acid (prepared according to WO 2015095953 A1) and H-Val-Dil-OtBu using General Procedure 6. $C_{36}H_{61}N_3O_7$ calc'd m/z=647.45 found [M+H]$^+$ 649.12.

Example 1.51: (3R,4S,5S)-4-((S)-N,3-Dimethyl-2-((S)-3-methyl-2-(methylamino)-3-phenylbutanamido)butanamido)-3-methoxy-5-methylheptanoic acid

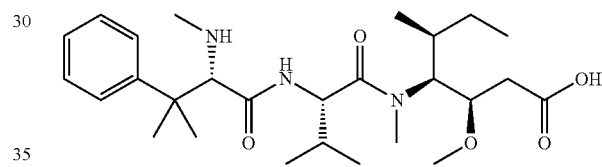

The title compound was prepared from the product of Example 1.50 according to General Procedure 9. $C_{27}H_{45}N_3O_5$ calc'd m/z=491.34 found [M+H]$^+$ 492.73.

Example 1.52: tert-Butyl (1-(((S)-1-(((3R,4S,5S)-3-Methoxy-1-((S)-2-((1R,2R)-1-methoxy-2-methyl-3-oxo-3-((4-(2,2,2-trifluoroacetamido)phenyl)sulfonamido)propyl)pyrrolidin-1-yl)-5-methyl-1-oxoheptan-4-yl)(methyl)amino)-3-methyl-1-oxobutan-2-yl)amino)-2-methyl-1-oxopropan-2-yl)carbamate
(Compound 18)

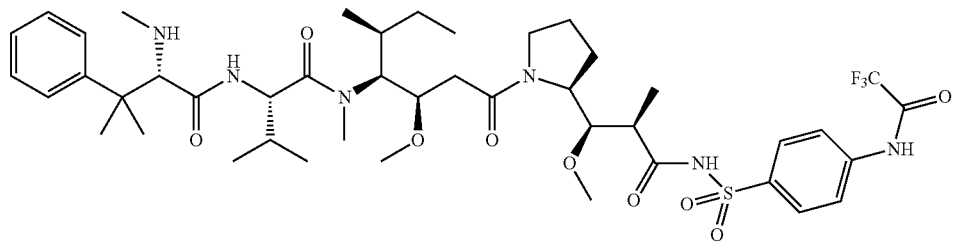 [SMILES: CC[C@H](C)[C@@H]([C@@H](CC(=O)N1CCC[C@H]1[C@H](OC)[C@@H](C)C(=O)NS(=O)(=O)c1ccc(NC(=O)C(F)(F)F)cc1)OC)N(C)C(=O)[C@@H](NC(=O)[C@@H](NC)C(C)(C)c1ccccc1)C(C)C]

The title compound was prepared from the product of Example 1.51 and the product of Example 1.42 according to General Procedure 6. $C_{44}H_{65}F_3N_6O_9S$ calc'd m/z=910.45 found [M+H]$^+$ 911.91.

Example 1.53 (S)-N-((3R,4S,5S)-1-((S)-2-((1R,2R)-3-((4-Aminophenyl)sulfonamido)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)-3-phenylbutanamido)butanamide (Compound 19)

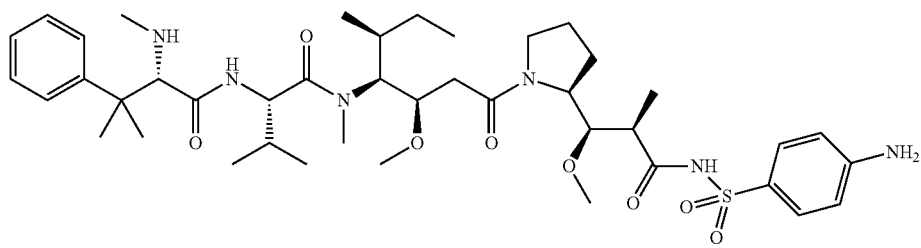 [SMILES: CC[C@H](C)[C@@H]([C@@H](CC(=O)N1CCC[C@H]1[C@H](OC)[C@@H](C)C(=O)NS(=O)(=O)c1ccc(N)cc1)OC)N(C)C(=O)[C@@H](NC(=O)[C@@H](NC)C(C)(C)c1ccccc1)C(C)C]

The title compound was prepared from the product of Example 1.52 using General Procedure 4. $C_{42}H_{66}N_6O_8S$ calc'd m/z=814.47 found $[M+H]^+$ 816.08.

Example 1.54: tert-Butyl ((S)-1-(((S)-1-(((3R,4S,5S)-3-Methoxy-1-((S)-2-((1R,2R)-1-methoxy-2-methyl-3-oxo-3-((4-(2,2,2-trifluoroacetamido)phenyl)sulfonamido)propylpyrrolidin-1-yl)-5-methyl-1-oxoheptan-4-yl)(methyl)amino)-3-methyl-1-oxobutan-2-yl)amino)-3-methyl-1-oxobutan-2-yl)(methyl)carbamate

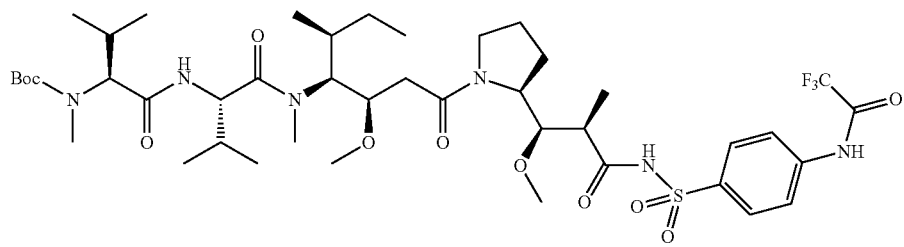 [SMILES: CC[C@H](C)[C@@H]([C@@H](CC(=O)N1CCC[C@H]1[C@H](OC)[C@@H](C)C(=O)NS(=O)(=O)c1ccc(NC(=O)C(F)(F)F)cc1)OC)N(C)C(=O)[C@@H](NC(=O)[C@H](C(C)C)N(C)C(=O)OC(C)(C)C)C(C)C]

The title compound was prepared from the product of Example 1.42 and commercially obtained Boc-(Me)-(L)-Valine-OH using General Procedure 6. $C_{43}H_{69}F_3N_6O_{11}S$ calc'd m/z=934.47 found [M+H]$^+$ 935.87.

Example 1.55: tert-Butyl ((S)-1-(((S)-1-(((3R,4S,5S)-1-((S)-2-((1R,2R)-3-((4-Aminophenyl)sulfonamido)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate

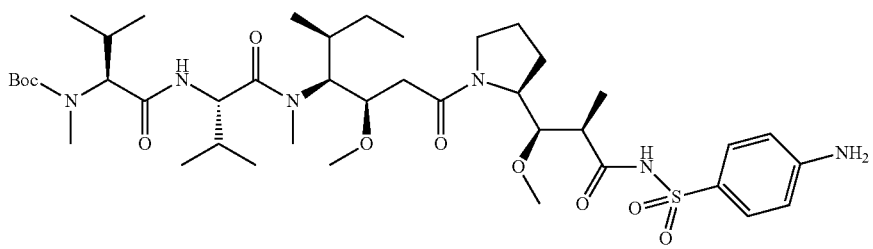 [SMILES: CC[C@H](C)[C@@H]([C@@H](CC(=O)N1CCC[C@H]1[C@H](OC)[C@@H](C)C(=O)NS(=O)(=O)c1ccc(N)cc1)OC)N(C)C(=O)[C@@H](NC(=O)[C@H](C(C)C)N(C)C(=O)OC(C)(C)C)C(C)C]

The title compound was prepared from the product of Example 1.54 using General Procedure 4. $C_{41}H_{70}N_6O_{10}S$ calc'd m/z=838.49 found [M+H]$^+$ 839.85.

Example 1.56: (S)-N-((3R,4S,5S)-1-((S)-2-((1R,2R)-3-((4-Aminophenyl)sulfonamido)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide (Compound 20)

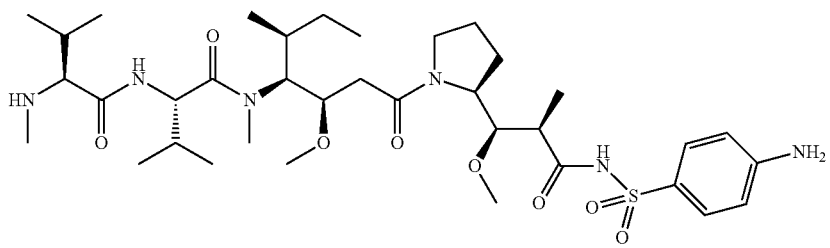 [SMILES: CC[C@H](C)[C@@H]([C@@H](CC(=O)N1CCC[C@H]1[C@H](OC)[C@@H](C)C(=O)NS(=O)(=O)c1ccc(N)cc1)OC)N(C)C(=O)[C@@H](NC(=O)[C@@H](NC)C(C)C)C(C)C]

The title compound was prepared from the product of Example 1.54 using General Procedure 9. $C_{36}H_{62}N_6O_8S$ calc'd m/z=738.43 found [M+H]$^+$ 739.84.

Example 1.57: 2,2,2-Trifluoro-N-(4-(sulfamoylmethyl)phenyl)acetamide

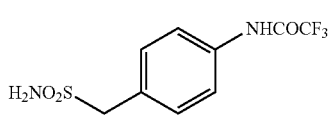

The title compound was prepared according to WO 2015095953 A1.

Example 1.58: 2,2,2-Trifluoro-N-(4-sulfamoylbenzyl)acetamide

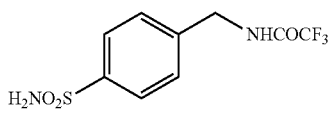

The title compound was prepared according to WO 2015095953 A1.

Example 1.59: tert-Butyl (S)-2-((1R,2R)-1-Methoxy-2-methyl-3-oxo-3-((4-((2,2,2-trifluoroacetamido)methyl)phenyl)sulfonamido)propyl)pyrrolidine-1-carboxylate

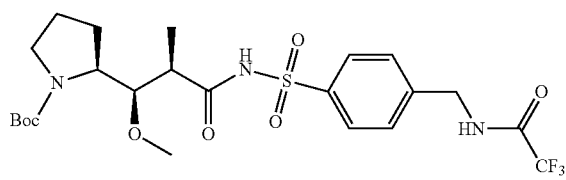 [SMILES: CO[C@H]([C@@H](C)C(=O)NS(=O)(=O)c1ccc(CNC(=O)C(F)(F)F)cc1)[C@@H]1CCCN1C(=O)OC(C)(C)C]

The title compound was prepared from commercially obtained Boc-dolaproline-OH and 2,2,2-trifluoro-N-(4-sulfamoylbenzyl)acetamide using General Procedure 2. $C_{23}H_{32}F_3N_3O_7S$ calc'd m/z=551.19 found [M+Na]$^+$ 574.92.

Example 1.60: (2R,3R)-3-Methoxy-2-methyl-3-((S)-pyrrolidin-2-yl)-N-((4-((2,2,2-trifluoroacetamido)methyl)phenyl)sulfonyl)propanamide

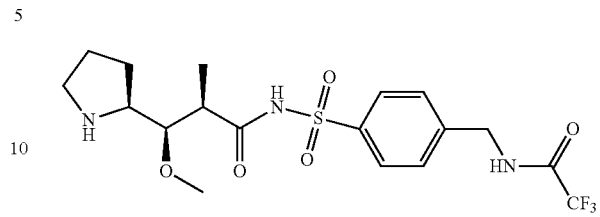

The title compound was prepared from the product of Example 1.59 using General Procedure 9. $C_{18}H_{24}F_3N_3O_5S$ calc'd m/z=451.14 found [M+H]$^+$ 452.71.

Example 1.61: (S)-2-((S)-2-(Dimethylamino)-3-methylbutanamido)-N-((3R,4S,5S)-3-methoxy-1-((S)-2-((1R,2R)-1-methoxy-2-methyl-3-oxo-3-((4-((2,2,2-trifluoroacetamido)methyl)phenyl)sulfonamido)propyl)pyrrolidin-1-yl)-5-methyl-1-oxoheptan-4-yl)-N,3-dimethylbutanamide (Compound 21)

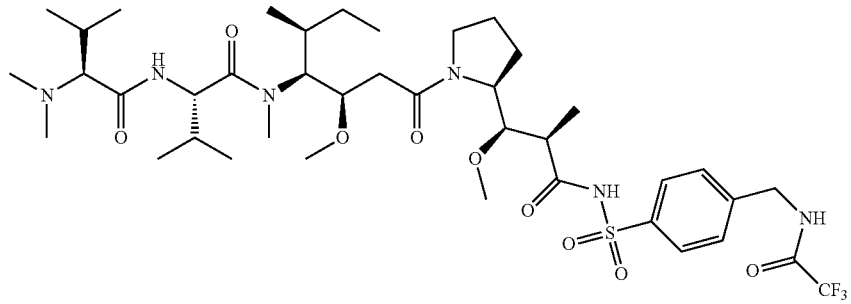 [SMILES: CC[C@H](C)[C@@H]([C@@H](CC(=O)N1CCC[C@H]1[C@H](OC)[C@@H](C)C(=O)NS(=O)(=O)c1ccc(CNC(=O)C(F)(F)F)cc1)OC)N(C)C(=O)[C@@H](NC(=O)[C@H](C(C)C)N(C)C)C(C)C]

The title compound was prepared from Dov-Val-Dil-OH (Example 1.36) and the product of Example 1.60 using General Procedure 6. $C_{40}H_{65}F_3N_6O_9S$ calc'd m/z=862.45 found [M+H]$^+$ 863.80.

Example 1.62: (S)-N-((3R,4S,5S)-1-((S)-2-((1R,2R)-3-((4-(Aminomethyl)phenyl)sulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 22)

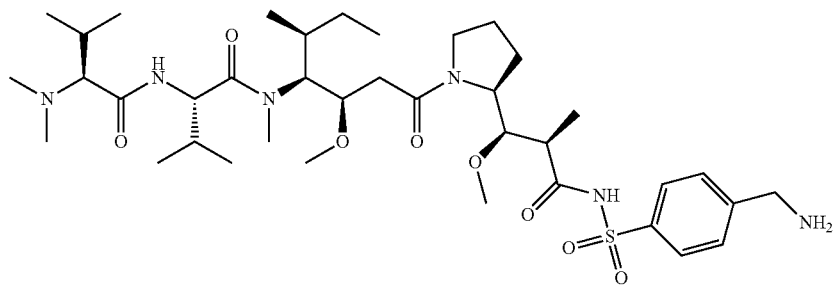 [SMILES: CC[C@H](C)[C@@H]([C@@H](CC(=O)N1CCC[C@H]1[C@H](OC)[C@@H](C)C(=O)NS(=O)(=O)c1ccc(CN)cc1)OC)N(C)C(=O)[C@@H](NC(=O)[C@H](C(C)C)N(C)C)C(C)C]

The title compound was prepared from Compound 51 according to General Procedure 4. $C_{38}H_{66}N_6O_8S$ calc'd m/z=766.47 found [M+H]$^+$ 767.85.

Example 1.63: tert-butyl (S)-(1-oxo-3-phenyl-1-((4-((2,2,2-trifluoroacetamido)methyl)phenyl)sulfonamido)propan-2-yl)carbamate (Compound 63)

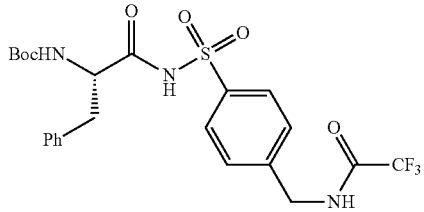 [SMILES: CC(C)(C)OC(=O)N[C@@H](Cc1ccccc1)C(=O)NS(=O)(=O)c1ccc(CNC(=O)C(F)(F)F)cc1]

The title compound was prepared from Boc-(L)-Phe-OH and 2,2,2-trifluoro-N-(4-sulfamoylbenzyl)acetamide (Example 1.58) using General Procedure 2. $C_{23}H_{26}F_3N_3O_6S$ calc'd m/z=529.15 found [M+Na]$^+$ 552.52.

Example 1.64: (S)-2-Amino-3-phenyl-N-((4-((2,2,2-trifluoroacetamido)methyl)phenyl)sulfonyl)propanamide

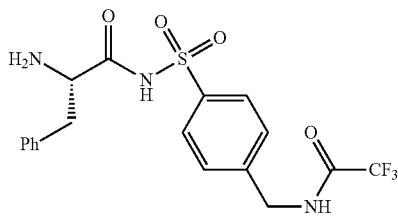 [SMILES: N[C@@H](Cc1ccccc1)C(=O)NS(=O)(=O)c1ccc(CNC(=O)C(F)(F)F)cc1]

The title compound was prepared from the product of Example 1.63 using General Procedure 9. $C_{18}H_{18}F_3N_3O_4S$ calc'd m/z=429.10 found [M+H]$^+$ 430.51. $^1$H NMR (400 MHz, Methanol-$d_4$) δ 8.05-7.98 (m, 2H), 7.56 (d, J=8.2 Hz, 2H), 7.33-7.22 (m, 3H), 7.09 (d, J=6.7 Hz, 2H), 4.59 (d, J=4.4 Hz, 2H), 4.06 (t, J=6.8 Hz, 1H), 3.15 (dd, J=14.1, 6.3 Hz, 1H), 3.03 (dd, J=14.2, 7.4 Hz, 1H).

Example 1.65: tert-butyl (S)-2-((1R,2R)-1-methoxy-2-methyl-3-oxo-3-(((S)-1-oxo-3-phenyl-1-((4-((2,2,2-trifluoroacetamido)methyl)phenyl)sulfonamido)propan-2-yl)amino)propyl)pyrrolidine-1-carboxylate

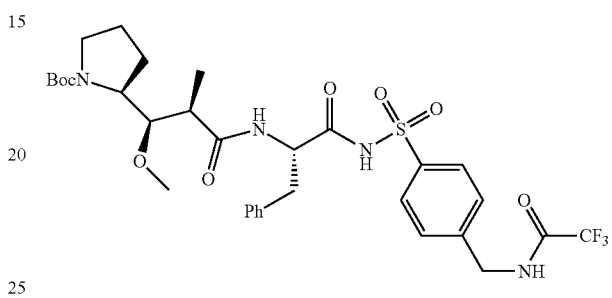

The title compound was prepared from commercially available Boc-dolaproline-OH and the product of Example 1.64 according to General Procedure 6. $C_{32}H_{41}F_3N_4O_8S$ calc'd m/z=698.26 found [M+Na]$^+$ 721.62.

Example 1.66: (2R,3R)-3-Methoxy-2-methyl-N-((S)-1-oxo-3-phenyl-1-((4-((2,2,2-trifluoroacetamido)methyl)phenyl)sulfonamido)propan-2-yl)-3-((S)-pyrrolidin-2-yl)propanamide

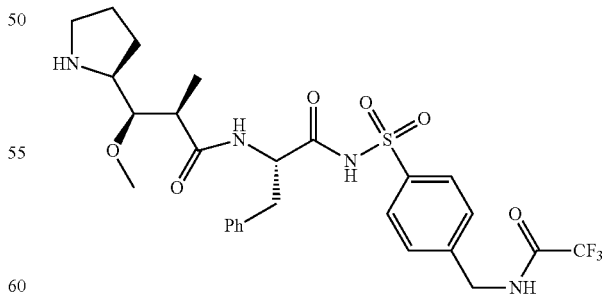

The title compound was prepared from the product of Example 1.65 using General Procedure 9. $C_{27}H_{33}F_3N_4O_6S$ calc'd m/z=598.21 found [M+H]$^+$ 599.62.

Example 1.67: (S)-2-((S)-2-(Dimethylamino)-3-methylbutanamido)-N-((3R,4S,5S)-3-methoxy-1-((S)-2-((1R,2R)-1-methoxy-2-methyl-3-oxo-3-(((S)-1-oxo-3-phenyl-1-((4-((2,2,2-trifluoroacetamido)methyl)phenyl)sulfonamido)propan-2-yl)amino)propyl)pyrrolidin-1-yl)-5-methyl-1-oxoheptan-4-yl)-N,3-dimethylbutanamide (Compound 23)

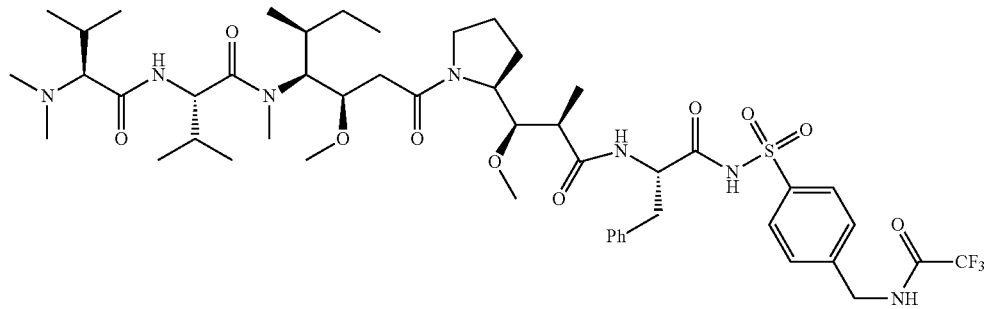 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(CNC(=O)C(F)(F)F)cc1)OC)N(C)C(=O)[C@@H](NC(=O)[C@H](C(C)C)N(C)C)C(C)C]

The title compound was prepared from Dov-Val-Dil-OH (Example 1.36) and the product of Example 1.66 according to General Procedure 6. $C_{49}H_{74}F_3N_7O_{10}S$ calc'd m/z=1009.52 found $[M+H]^+$ 1011.04.

Example 1.68: (S)-N-((3R,4S,5S)-1-((S)-2-((1R,2R)-3-(((S)-1-((4-(Aminomethyl)phenyl)sulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 24)

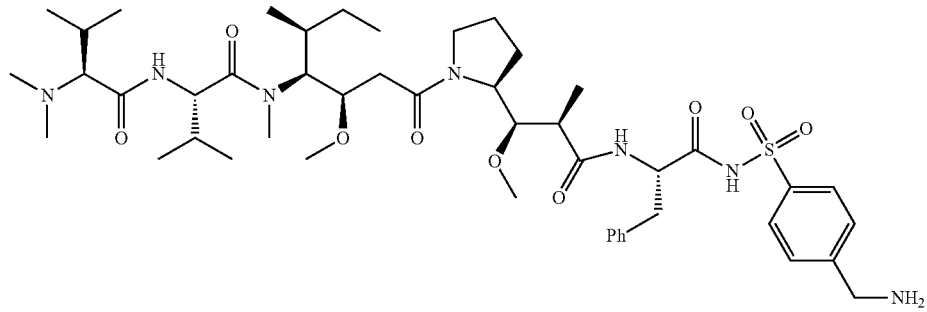 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(CN)cc1)OC)N(C)C(=O)[C@@H](NC(=O)[C@H](C(C)C)N(C)C)C(C)C]

The title compound was prepared from the product of Example 1.67 according to General Procedure 4. $C_{47}H_{75}N_7O_9S$ calc'd m/z=913.53 found $[M+H]^+$ 915.09.

Example 1.69: 2,2,2-Trifluoro-N-(4-(sulfamoylmethyl)benzyl)acetamide

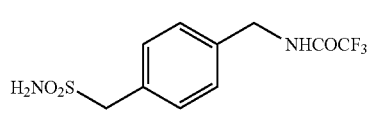

The title compound was prepared according to WO 2015095953 A1.

Example 1.70: tert-Butyl (S)-2-((1R,2R)-1-Methoxy-2-methyl-3-oxo-3-(((4-((2,2,2-trifluoroacetamido)methyl)phenyl)methyl)sulfonamido)propyl)pyrrolidine-1-carboxylate

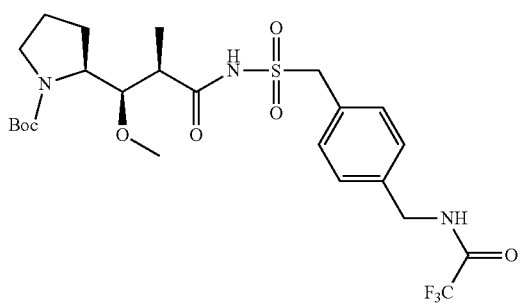 [SMILES: CO[C@H]([C@@H](C)C(=O)NS(=O)(=O)Cc1ccc(CNC(=O)C(F)(F)F)cc1)[C@@H]1CCCN1C(=O)OC(C)(C)C]

The title compound was prepared from commercially obtained Boc-dolaproline-OH and 2,2,2-trifluoro-N-(4-(sulfamoylmethyl)benzyl)acetamide (Example 1.69) using General Procedure 2. $C_{24}H_{34}F_3N_3O_7S$ calc'd m/z=565.21 found [M+Na]$^+$ 588.75.

Example 1.71: (2R,3R)-3-Methoxy-2-methyl-3-((S)-pyrrolidin-2-yl)-N-((4-((2,2,2-trifluoroacetamido)methyl)benzyl)sulfonyl)propanamide

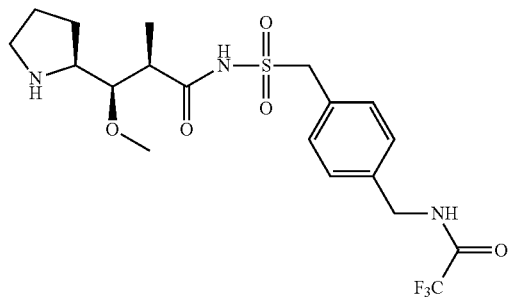 [SMILES: CO[C@@H]([C@@H]1CCCN1)[C@@H](C)C(=O)NS(=O)(=O)Cc1ccc(CNC(=O)C(F)(F)F)cc1]

The title compound was prepared from the product of Example 1.69 according to General Procedure 9. $C_{19}H_{26}F_3N_3O_5S$ calc'd m/z=465.15 found [M+H]$^+$ 466.77.

Example 1.72: (S)-2-((S)-2-(Dimethylamino)-3-methylbutanamido)-N-((3R,4S,5S)-3-methoxy-1-((S)-2-((1R,2R)-1-methoxy-2-methyl-3-oxo-3-(((4-((2,2,2-trifluoroacetamido)methyl)phenyl)methyl)sulfonamido)propyl)pyrrolidin-1-yl)-5-methyl-1-oxoheptan-4-yl)-N,3-dimethylbutanamide (Compound 25)

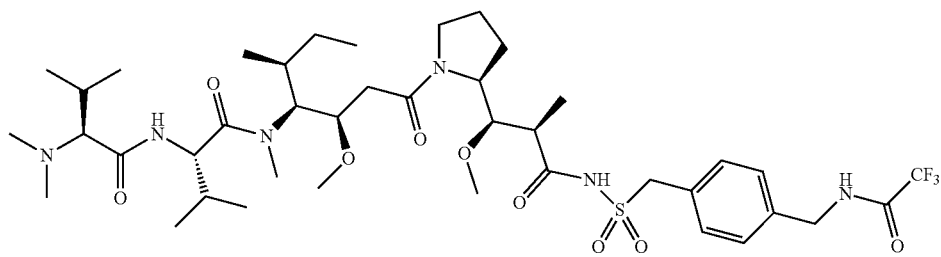 [SMILES: CC[C@H](C)[C@@H]([C@@H](CC(=O)N1CCC[C@H]1[C@H](OC)[C@@H](C)C(=O)NS(=O)(=O)Cc1ccc(CNC(=O)C(F)(F)F)cc1)OC)N(C)C(=O)[C@@H](NC(=O)[C@H](C(C)C)N(C)C)C(C)C]

The title compound was prepared from the product of Example 1.36 and the product of Example 1.71 according to General Procedure 6. $C_{41}H_{67}F_3N_6O_9S$ calc'd m/z=876.46 found [M+H]$^+$ 878.22.

Example 1.73: (S)-N-((3R,4S,5S)-1-((S)-2-((1R,2R)-3-(((4-(Aminomethyl)phenyl)methyl)sulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 26)

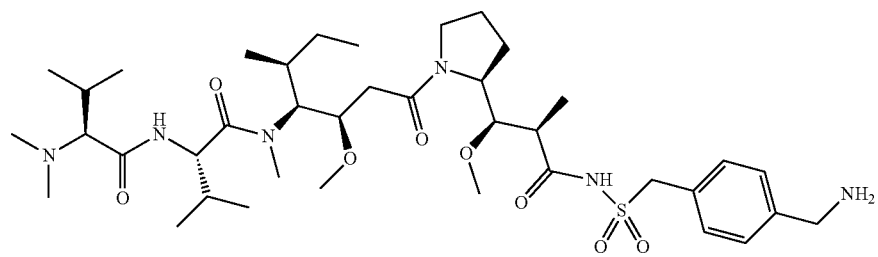 [SMILES: CC[C@H](C)[C@@H]([C@@H](CC(=O)N1CCC[C@H]1[C@H](OC)[C@@H](C)C(=O)NS(=O)(=O)Cc1ccc(CN)cc1)OC)N(C)C(=O)[C@@H](NC(=O)[C@H](C(C)C)N(C)C)C(C)C]

The title compound was prepared from the product of Example 1.72 according to General Procedure 4. $C_{39}H_{68}N_6O_8S$ calc'd m/z=780.48 found [M+H]$^+$ 782.20.

Example 1.74: tert-Butyl (S)-(1-Oxo-3-phenyl-1-(((4-((2,2,2-trifluoroacetamido)methyl)phenyl)methyl)sulfonamido)propan-2-yl)carbamate

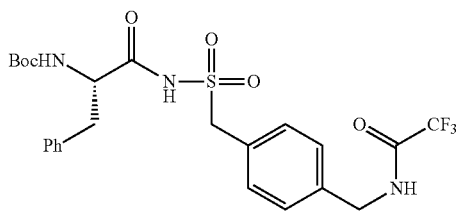 [SMILES: CC(C)(C)OC(=O)N[C@@H](Cc1ccccc1)C(=O)NS(=O)(=O)Cc1ccc(CNC(=O)C(F)(F)F)cc1]

The title compound was prepared from Boc-(L)-Phe-OH and 2,2,2-trifluoro-N-(4-(sulfamoylmethyl)benzyl)acetamide (Example 1.69) according to General Procedure 2. $C_{24}H_{28}F_3N_3O_6S$ calc'd m/z=543.17 found [M+Na]$^+$ 566.78.

Example 1.75: (S)-2-Amino-3-phenyl-N-((4-((2,2,2 trifluoroacetamido)methyl)benzyl)sulfonyl)propanamide

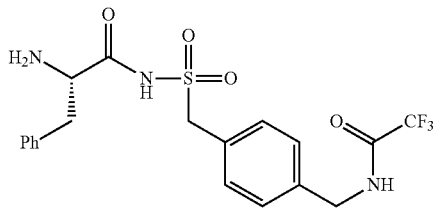 [SMILES: N[C@@H](Cc1ccccc1)C(=O)NS(=O)(=O)Cc1ccc(CNC(=O)C(F)(F)F)cc1]

The title compound was prepared from the product of Example 1.74 using General Procedure 9. $C_{19}H_{20}F_3N_3O_4S$ calc'd m/z=443.11 found [M+H]$^+$ 444.55. $^1$H NMR (400 MHz, Methanol-d$_4$) δ 7.46-7.27 (m, 9H), 4.51 (s, 2H), 4.46 (s, 2H), 3.84 (dd, J=9.3, 4.3 Hz, 1H), 3.29 (dd, 1H), 2.95 (dd, J=14.5, 9.4 Hz, 1H).

Example 1.76: (S)-2-((1R,2R)-1-Methoxy-2-methyl-3-oxo-3-(((S)-1-oxo-3-phenyl-1-(((4-((2,2,2-trifluoroacetamido)methyl)phenyl)methyl)sulfonamido)propan-2-yl)amino)propyl)pyrrolidine-1-carboxylate

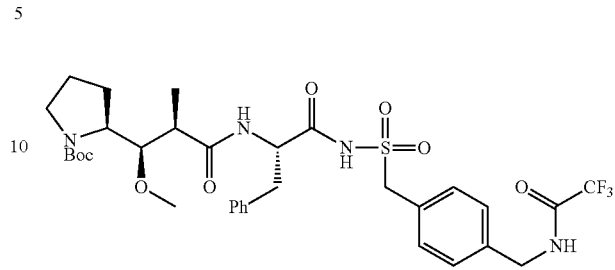

The title compound was prepared from commercially available Boc-dolaproline-OH and the product of Example 1.75 according to General Procedure 6. $C_{33}H_{43}F_3N_4O_8S$ calc'd m/z=712.28 found [M+Na]$^+$ 735.65.

Example 1.77: (2R,3R)-3-Methoxy-2-methyl-N-((S)-1-oxo-3-phenyl-1-(((4-((2,2,2-trifluoroacetamido)methyl)phenyl)methyl)sulfonamido)propan-2-yl)-3-((S)-pyrrolidin-2-yl)propanamide

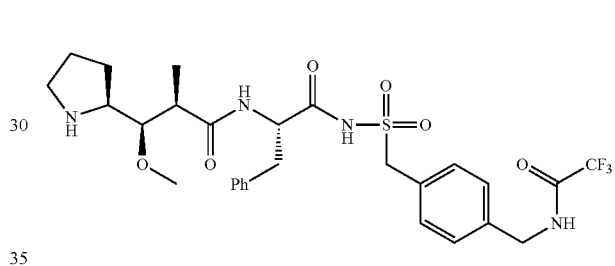

The title compound was prepared from the product of Example 1.76 using General Procedure 9. $C_{28}H_{35}F_3N_4O_6S$ calc'd m/z=612.22 found [M+H]$^+$ 613.58.

Example 1.78: (S)-2-((S)-2-(Dimethylamino)-3-methylbutanamido)-N-((3R,4S,5S)-3-methoxy-1-((S)-2-((1R,2R)-1-methoxy-2-methyl-3-oxo-3-(((S)-1-oxo-3-phenyl-1-(((4-((2,2,2-trifluoroacetamido)methyl)phenyl)methyl)sulfonamido)propan-2-yl)amino)propyl)pyrrolidin-1-yl)-5-methyl-1-oxoheptan-4-yl)-N,3-dimethylbutanamide
(Compound 27)

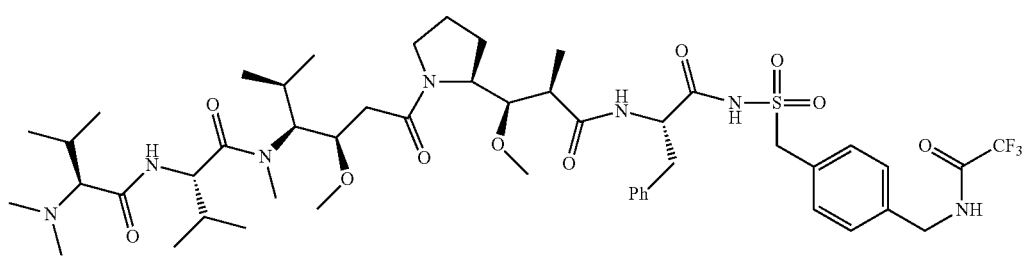

The title compound was prepared from Dov-Val-Dil-OH (Example 1.36) and the product of Example 1.77 using General Procedures 9 and 6. $C_{50}H_{76}F_3N_7O_{10}S$ calc'd m/z=1023.53 found [M+H]$^+$ 1024.94.

Example 1.79: (S)-N-((3R,4S,5S)-1-((S)-2-((1R,2R)-3-(((S)-1-(((4-(Aminomethyl)phenyl)methyl)sulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 28)

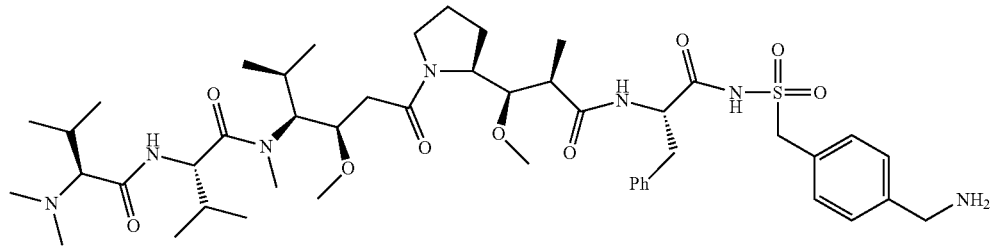

The title compound was prepared from the product of Example 1.78 using General Procedure 4. $C_{48}H_{77}N_7O_9S$ calc'd m/z=927.55 found [M+H]$^+$ 928.92.

Example 1.80: 2,2,2-Trifluoro-N-(1-(4-sulfamoylphenyl)cyclopropyl)acetamide

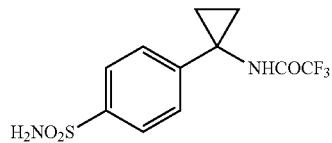

The title compound was prepared according to WO 2015095953 A1.

Example 1.81: (2R,3R)-3-Methoxy-2-methyl-3-((S)-pyrrolidin-2-yl)-N-(4-(1-(2,2,2-trifluoroacetamido)cyclopropyl)phenylsulfonyl)propanamide

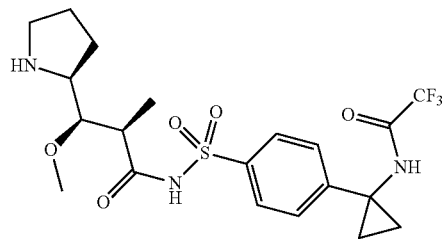 [SMILES: CO[C@@H]([C@@H]1CCCN1)[C@@H](C)C(=O)NS(=O)(=O)c1ccc(C2(NC(=O)C(F)(F)F)CC2)cc1]

The title compound was prepared from commercially obtained Boc-Dap-OH and 2,2,2-trifluoro-N-(1-(4-sulfamoylphenyl)cyclopropyl)acetamide (Example 1.80) following general procedures 2 and 9. $^1$H NMR (400 MHz, DMSO-d$^6$) δ 12.19 (s, 1H), 10.32 (s, 1H), 7.86 (d, J=8.6 Hz, 2H), 7.35 (d, J=8.6 Hz, 2H), 7.31 (s, 1H), 3.58 (dd, J=5.7, 3.7 Hz, 1H), 3.28 (s, 3H), 3.11 (t, J=6.8 Hz, 2H), 2.59 (dq, J=13.0, 6.5 Hz, 1H), 1.90-1.68 (m, 3H), 1.63-1.56 (m, 1H), 1.44-1.35 (m, 4H), 1.04 (d, J=7.0 Hz, 3H). $C_{20}H_{26}F_3N_3O_5S$ calcd. m/z=477.15 found [M+H]$^+$=478.6.

Example 1.82: (S)-2-((S)-2-(Dimethylamino)-3-methylbutanamido)-N-((3R,4S,5S)-3-methoxy-1-((S)-2-((1R,2R)-1-methoxy-2-methyl-3-oxo-3-(4-(1-(2,2,2-trifluoroacetamido)cyclopropyl)phenylsulfonamido)propyl)pyrrolidin-1-yl)-5-methyl-1-oxoheptan-4-yl)-N,3-dimethylbutanamide (Compound 29)

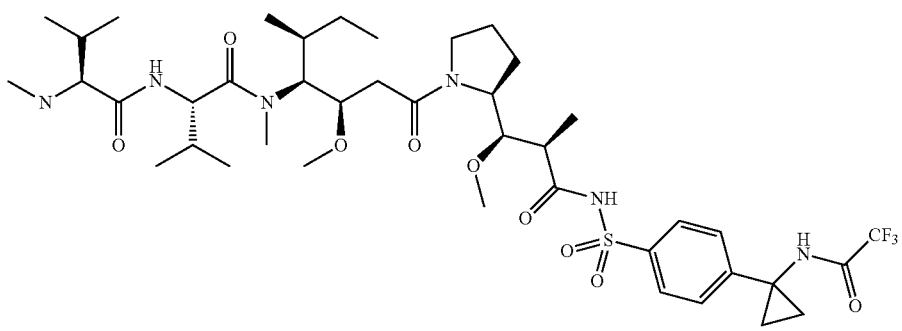 [SMILES: CC[C@H](C)[C@@H]([C@@H](CC(=O)N1CCC[C@H]1[C@H](OC)[C@@H](C)C(=O)NS(=O)(=O)c1ccc(C2(NC(=O)C(F)(F)F)CC2)cc1)OC)N(C)C(=O)[C@@H](NC(=O)[C@@H](NC)C(C)C)C(C)C]

The title compound was prepared from Dov-Val-Dil-OH (Example 1.36) and the product of Example 1.81 according to General Procedure 6. $C_{42}H_{67}F_3N_6O_9S$ calcd. m/z=888.46 found $[M+H]^+$=889.3.

Example 1.83: (S)-N-((3R,4S,5S)-1-((S)-2-((1R,2R)-3-(4-(1-Aminocyclopropyl)phenylsulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 30)

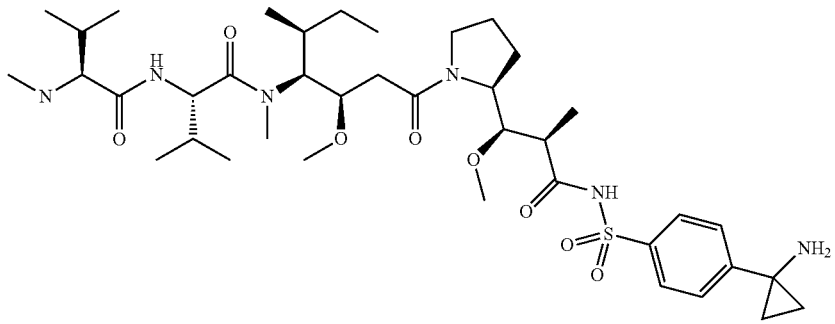 [SMILES: CC[C@H](C)[C@@H]([C@@H](CC(=O)N1CCC[C@H]1[C@H](OC)[C@@H](C)C(=O)NS(=O)(=O)c1ccc(C2(N)CC2)cc1)OC)N(C)C(=O)[C@@H](NC(=O)[C@@H](NC)C(C)C)C(C)C]

The title compound was prepared from the product of Example 1.82 according to general procedure 4. $C_{40}H_{68}N_6O_8S$ calcd. m/z=792.48 found $[M+Na]^+$=815.9.

Example 1.84: (S)-2-Amino-3-phenyl-N-(4-(1-(2,2,2-trifluoroacetamido)cyclopropyl)phenylsulfonyl)propanamide

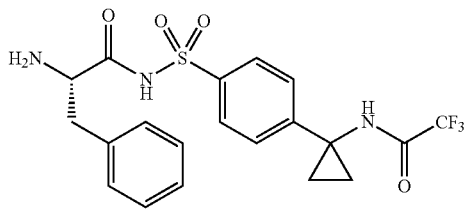 [SMILES: N[C@@H](Cc1ccccc1)C(=O)NS(=O)(=O)c1ccc(C2(NC(=O)C(F)(F)F)CC2)cc1]

The title compound was prepared from Boc-Phe-OH and 2,2,2-trifluoro-N-(1-(4-sulfamoylphenyl)cyclopropyl)acetamide (Example 1.80) following general procedures 2 and 9. $^1$H NMR (400 MHz, DMSO-d$^6$) δ 10.30 (s, 1H), 7.87 (b, 3H), 7.79 (d, J=8.3 Hz, 2H), 7.25 (d, J=8.2 Hz, 2H), 7.23-7.16 (m, 3H), 7.08 (dd, J=6.6, 2.9 Hz, 2H), 3.78 (s, 1H), 3.06 (dd, J=14.2, 5.3 Hz, 1H), 2.93 (dd, J=14.1, 7.2 Hz, 1H), 1.36 (dd, J=6.6, 3.0 Hz, 4H). $C_{20}H_{20}F_3N_3O_4S$ calcd. m/z=455.11 found $[M+H]^+$=456.6.

Example 1.85: tert-Butyl (S)-1-(((3R,4S,5S)-3-Methoxy-1-((S)-2-((1R,2R)-1-methoxy-2-methyl-3-oxo-3-((S)-1-oxo-3-phenyl-1-(4-(1-(2,2,2-trifluoroacetamido)cyclopropyl)phenylsulfonamido)propan-2-ylamino)propyl)pyrrolidin-1-yl)-5-methyl-1-oxoheptan-4-yl)(methyl)amino)-3-methyl-1-oxobutan-2-ylcarbamate

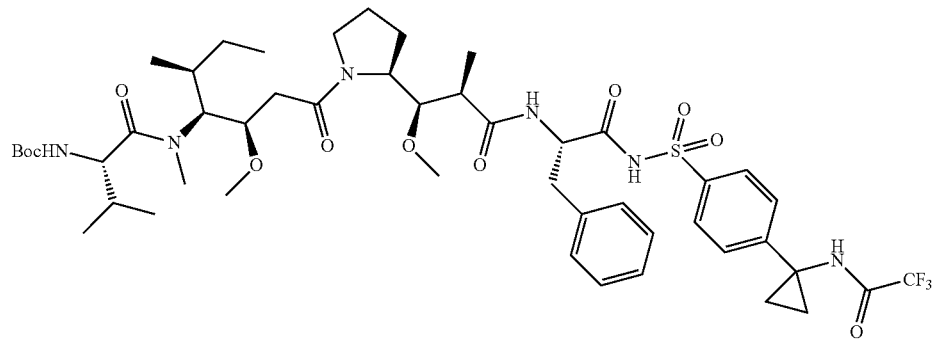 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(C2(NC(=O)C(F)(F)F)CC2)cc1)OC)N(C)C(=O)[C@@H](NC(=O)OC(C)(C)C)C(C)C]

The title compound was prepared from commercially obtained Boc-Val-Dil-Dap-OH and the product of Example 1.84 following general procedure 2. $C_{49}H_{71}F_3N_6O_{11}S$ calcd. m/z=1008.49 found $[M+Na]^+$=1031.9.

Example 1.86: (S)-2-((S)-2-(Dimethylamino)-3-methylbutanamido)-N-((3R,4S,5S)-3-methoxy-1-((S)-2-((1R,2R)-1-methoxy-2-methyl-3-oxo-3-((S)-1-oxo-3-phenyl-1-(4-(1-(2,2,2-trifluoroacetamido)cyclopropyl)phenylsulfonamido)propan-2-ylamino)propyl)pyrrolidin-1-yl)-5-methyl-1-oxoheptan-4-yl)-N,3-dimethylbutanamide (Compound 31)

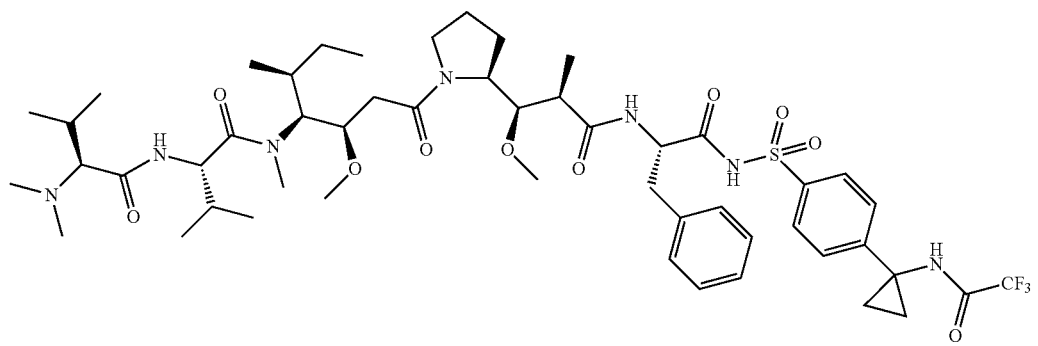 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(C2(NC(=O)C(F)(F)F)CC2)cc1)OC)N(C)C(=O)[C@@H](NC(=O)[C@H](C(C)C)N(C)C)C(C)C]

The title compound was prepared from the product of Example 1.85 and N,N-dimethylvaline following general procedures 9 and 6. $C_{51}H_{76}F_3N_7O_{10}S$ calcd. m/z=1035.53 found $[M+H]^+$=1036.5.

Example 1.87: (S)-N-((3R,4S,5S)-1-((S)-2-((1R,2R)-3-((S)-1-(4-(1-Aminocyclopropyl)phenylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 32)

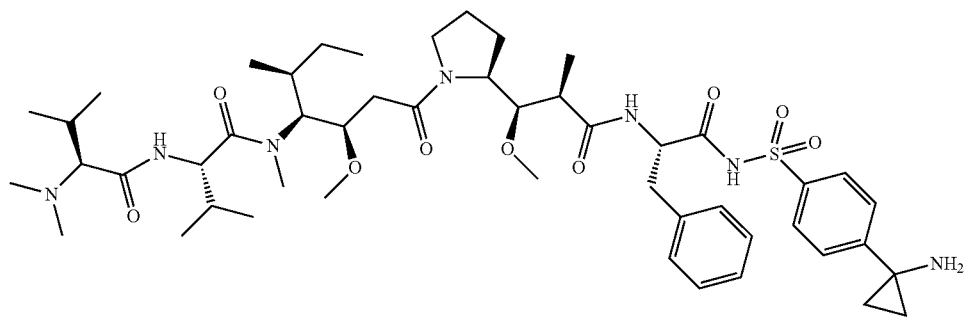 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(C2(N)CC2)cc1)OC)N(C)C(=O)[C@@H](NC(=O)[C@H](C(C)C)N(C)C)C(C)C]

The title compound was prepared from the product of Example 1.86 according to general procedure 4. $C_{49}H_{77}N_7O_9S$ calcd. m/z=939.55 found [M+H]$^+$=940.5.

Example 1.88: tert-Butyl (S)-2-((1R,2R)-1-methoxy-2-methyl-3-oxo-3-((phenylmethyl)sulfonamido)propyl)pyrrolidine-1-carboxylate

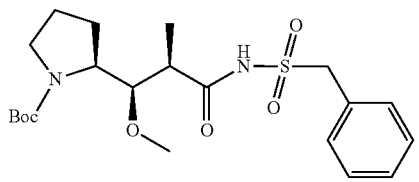 [SMILES: CO[C@H]([C@@H](C)C(=O)NS(=O)(=O)Cc1ccccc1)[C@@H]1CCCN1C(=O)OC(C)(C)C]

The title compound was prepared from commercially obtained Boc-dolaproline-OH and benzylsulfonamide using General Procedure 2. $C_{21}H_{32}N_2O_6S$ calc'd m/z=440.20 found [M+H]$^+$ 463.71.

Example 1.89: (2R,3R)-N-(Benzylsulfonyl)-3-methoxy-2-methyl-3-((S)-pyrrolidin-2-yl)propanamide

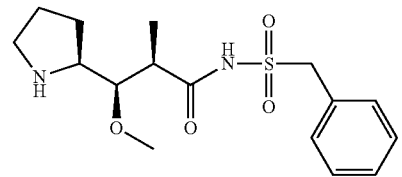 [SMILES: CO[C@@H]([C@@H]1CCCN1)[C@@H](C)C(=O)NS(=O)(=O)Cc1ccccc1]

The title compound was prepared from the product of Example 1.88 using General Procedure 9. $C_{16}H_{24}N_2O_4S$ calc'd m/z=340.15 found [M+H]$^+$ 341.75.

Example 1.90: (9H-Fluoren-9-yl)methyl ((S)-1-(((S)-1-(((3R,4S,5S)-3-Methoxy-1-((S)-2-((1R,2R)-1-methoxy-2-methyl-3-oxo-3-((phenylmethyl)sulfonamido)propyl)pyrrolidin-1-yl)-5-methyl-1-oxoheptan-4-yl)(methyl)amino)-3-methyl-1-oxobutan-2-yl)amino)-3-methyl-1-oxobutan-2-yl)(methyl)carbamate

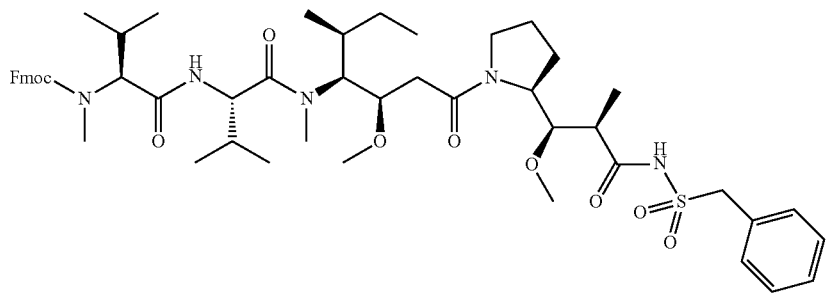

The title compound was prepared from the product of Example 1.89 and the product of Example 1.38 according to General Procedure 6. $C_{52}H_{73}N_5O_{10}S$ calc'd m/z=959.51 found [M+H]$^+$ 961.15.

Example 1.91: (S)-N-((3R,4S,5S)-3-Methoxy-1-((S)-2-((1R,2R)-1-methoxy-2-methyl-3-oxo-3-((phenylmethyl)sulfonamido)propyl)pyrrolidin-1-yl)-5-methyl-1-oxoheptan-4-yl)-N,3-dimethyl-2-((S)-3-methyl-2-(methylamino)butanamido)butanamide (Compound 33)

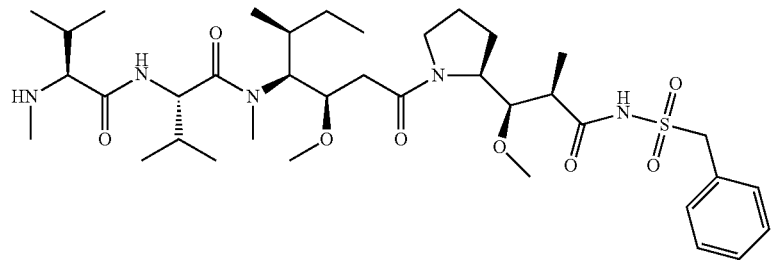 [SMILES: CC[C@H](C)[C@@H]([C@@H](CC(=O)N1CCC[C@H]1[C@H](OC)[C@@H](C)C(=O)NS(=O)(=O)Cc1ccccc1)OC)N(C)C(=O)[C@@H](NC(=O)[C@@H](NC)C(C)C)C(C)C]

The title compound was prepared from the product of Example 1.90 according to General Procedure 7. $C_{37}H_{63}N_5O_8S$ calc'd m/z=737.44 found [M+H]⁺ 739.07.

Example 1.92: tert-Butyl (S)-2-((1R,2R)-1-Methoxy-3-((4-(methoxycarbonyl)phenyl)sulfonamido)-2-methyl-3-oxopropyl)pyrrolidine-1-carboxylate

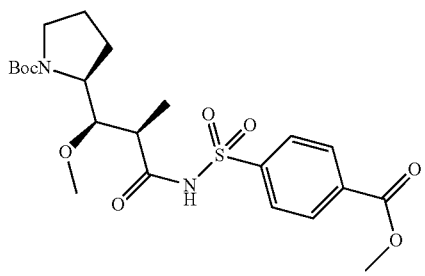 [SMILES: COC(=O)c1ccc(S(=O)(=O)NC(=O)[C@H](C)[C@@H](OC)[C@@H]2CCCN2C(=O)OC(C)(C)C)cc1]

The title compound was prepared from methyl 4-sulfamoylbenzoate and Boc-Dap-OH according to General Procedure 2. $C_{22}H_{32}N_2O_8S$ calcd. m/z=484.19 found [M+Na]⁺= 507.6.

Example 1.93: Methyl 4-(N-((2R,3R)-3-((S)-1-((3R,4S,5S)-4-((S)-2-((S)-2-(Dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)benzoate (Compound 34)

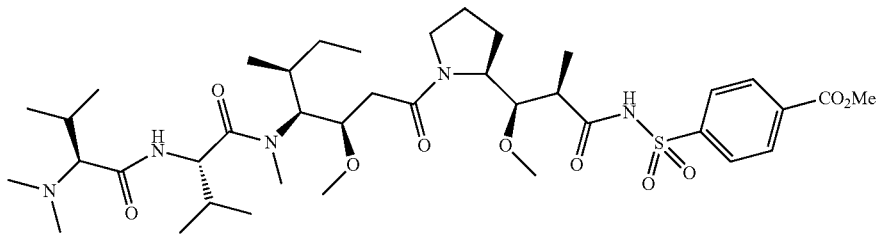 [SMILES: CC[C@H](C)[C@@H]([C@@H](CC(=O)N1CCC[C@H]1[C@H](OC)[C@@H](C)C(=O)NS(=O)(=O)c1ccc(C(=O)OC)cc1)OC)N(C)C(=O)[C@@H](NC(=O)[C@H](C(C)C)N(C)C)C(C)C]

The title compound was prepared from the product of Example 1.92 and Dov-Val-Dil-OH (Example 1.36) according to General Procedures 9 and 6. $C_{22}H_{32}N_2O_8S$ calcd. m/z=795.45 found [M+Na]⁺=818.8.

Example 1.94: (S,E)-4-((S)-2-((tert-butoxycarbonyl)amino)-N,3,3-trimethylbutanamido)-2,5-dimethylhex-2-enoic Acid (Compound 83)

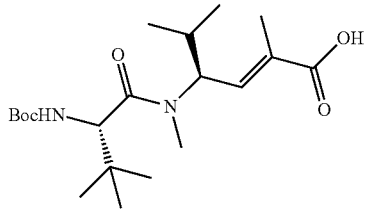 [SMILES: C/C(=C\[C@H](C(C)C)N(C)C(=O)[C@@H](NC(=O)OC(C)(C)C)C(C)(C)C)C(=O)O]

The title compound was prepared from ethyl (S,E)-4-((S)-2-((tert-butoxycarbonyl)amino)-N,3,3-trimethylbutanamido)-2,5-dimethylhex-2-enoate according to General Procedure 4. $C_{20}H_{36}N_2O_5$ calcd. m/z=384.26 found [M+H]⁺= 407.71. ¹H NMR (400 MHz, Chloroform-d) δ 6.80 (dd, J=9.6, 1.8 Hz, 1H), 5.29 (d, J=10.1 Hz, 1H), 5.16 (t, J=10.0 Hz, 1H), 4.46 (d, J=10.1 Hz, 1H), 3.03 (s, 3H), 1.95 (d, J=1.5 Hz, 3H), 1.44 (s, 9H), 0.99 (s, 9H), 0.92 (d, J=6.5 Hz, 3H), 0.88 (d, J=6.5 Hz, 3H).

Example 1.95: Methyl (2R,3R)-3-Methoxy-2-methyl-3-((S)-pyrrolidin-2-yl)propanoate

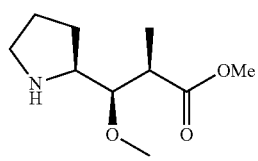

To a stirred solution of Boc-Dap-OH (0.635 g, 2.21 mmol) in dichloromethane/methanol (95:5, v/v, 10 mL) was added TMS-diazomethane (2 M in hexanes, 1.35 mL, 1.2 equiv). The reaction was monitored and at such a time that effervescence had ceased, HPLC-MS analysis indicated complete conversion to the ester. Remaining TMS-diazomethane was quenched by the addition of acetic acid and upon disappearance of all yellow color, the reaction was concentrated under reduced pressure. The residue was dissolved in dichloromethane and the Boc-protecting group removed according to General Procedure 9.1. The material was used "as is" with no further purification. $C_{10}H_{19}NO_3$ calcd. m/z=201.14 found [M+H]⁺=202.56. ¹H NMR (400 MHz, Methanol-d₄) δ 3.88 (dd, J=6.0, 3.6 Hz, 1H), 3.74 (s, 3H), 3.73-3.62 (m, 1H), 3.52 (s, 3H), 3.32-3.26 (m, 2H), 2.88-2.74 (m, 1H), 2.15-1.87 (m, 4H), 1.29 (d, J=7.2 Hz, 3H).

Example 1.96: Methyl (2R,3R)-3-((S)-1-((S,E)-4-((S)-2-((tert-Butoxycarbonyl)amino)-N,3,3-trimethylbutanamido)-2,5-dimethylhex-2-enoyl)pyrrolidin-2-yl)-3-methoxy-2-methylpropanoate

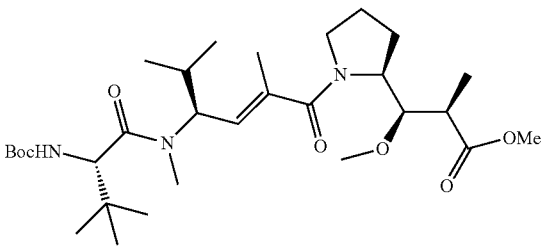 [SMILES: COC(=O)[C@H](C)[C@@H](OC)[C@@H]1CCCN1C(=O)/C(C)=C/[C@H](C(C)C)N(C)C(=O)[C@@H](NC(=O)OC(C)(C)C)C(C)(C)C]

The title compound was prepared from the product of Example 1.94 and the product of Example 1.95 according to General Procedure 6. C₃₀H₅₃N₃O₇ calcd. m/z=567.39 found [M+Na]⁺=590.85. ¹H NMR (400 MHz, Chloroform-d) δ 5.53 (dd, J=9.0, 1.8 Hz, 1H), 5.18 (d, J=10.1 Hz, 1H), 5.02 (dd, J=10.6, 8.8 Hz, 1H), 4.37 (d, J=10.1 Hz, 1H), 4.11-4.01 (m, 1H), 3.92 (dd, J=8.2, 2.8 Hz, 1H), 3.66 (s, 3H), 3.51-3.42 (m, 1H), 3.39 (s, 3H), 3.34-3.23 (m, 1H), 2.89 (s, 3H), 2.54-2.43 (m, 1H), 1.86 (s, 3H), 1.95-1.77 (m, 3H), 1.70-1.52 (m, 1H), 1.36 (s, 9H), 1.21 (d, J=6.9 Hz, 3H), 0.92 (s, 9H), 0.88 (d, J=6.6 Hz, 3H), 0.78 (d, J=6.6 Hz, 3H).

Example 1.97: (2R,3R)-3-((S)-1-((S,E)-4-((S)-2-((tert-Butoxycarbonyl)amino)-N,3,3-trimethylbutanamido)-2,5-dimethylhex-2-enoyl)pyrrolidin-2-yl)-3-methoxy-2-methylpropanoic Acid

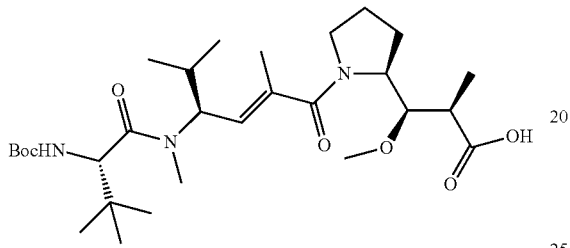

The title compound was prepared from the product of Example 1.96 according to General Procedure 4.1. C₂₉H₅₁N₃O₇ calcd. m/z=553.37 found [M+Na]⁺=576.81. ¹H NMR (400 MHz, Chloroform-d) δ 5.64 (d, J=8.8 Hz, 1H), 5.37 (d, J=10.1 Hz, 1H), 5.05 (s, 1H), 4.42 (d, J=10.1 Hz, 1H), 4.23-4.17 (m, 1H), 4.02 (dd, J=8.8, 2.5 Hz, 1H), 3.53-3.46 (m, 1H), 3.45 (s, 3H), 3.39-3.27 (m, 1H), 2.93 (s, 3H), 2.51-2.36 (m, 1H), 2.08-1.77 (m, 4H), 1.90 (s, 3H), 1.73-1.60 (m, 1H), 1.40 (s, 9H), 1.25 (d, J=7.1 Hz, 3H), 0.95 (s, 9H), 0.91 (d, J=6.5 Hz, 3H), 0.82 (d, J=6.5 Hz, 3H).

Example 1.98: tert-Butyl ((S)-1-(((S,E)-6-((S)-2-((1R,2R)-1-Methoxy-2-methyl-3-oxo-3-((4-(2,2,2-trifluoroacetamido)phenyl)sulfonamido)propyl)pyrrolidin-1-yl)-2,5-dimethyl-6-oxohex-4-en-3-yl)(methyl)amino)-3,3-dimethyl-1-oxobutan-2-yl)carbamate

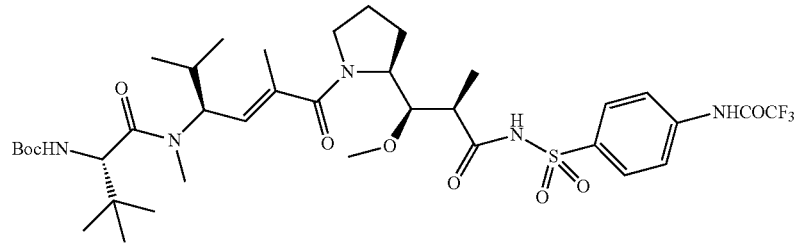

The title compound was prepared from the product of Example 1.97 and the product of Example 1.39 according to General Procedure 2. C₃₇H₅₆F₃N₅O₉S calcd. m/z=803.38 found [M+Na]⁺=826.69. ¹H NMR (400 MHz, Chloroform-d) δ 9.66 (s, 1H), 8.03 (d, J=8.8 Hz, 2H), 7.82 (d, J=8.8 Hz, 2H), 5.62 (d, J=8.6 Hz, 1H), 5.54 (d, J=10.0 Hz, 1H), 5.10-4.98 (m, 1H), 4.45 (d, J=10.1 Hz, 1H), 4.01 (dd, J=7.2, 2.4 Hz, 1H), 3.94-3.83 (m, 1H), 3.48-3.43 (m, 1H), 3.41 (s, 3H), 3.35-3.22 (m, 1H), 2.95 (s, 3H), 2.66-2.55 (m, 1H), 1.87 (s, 3H), 1.91-1.75 (m, 2H), 1.67-1.53 (m, 2H), 1.41 (s, 9H), 1.14 (d, J=6.9 Hz, 3H), 0.96 (s, 9H), 0.89 (d, J=6.4 Hz, 3H), 0.82 (d, J=6.5 Hz, 3H).

Example 1.99: (S)-2-Amino-N-((S,E)-6-((S)-2-((1R,2R)-1-methoxy-2-methyl-3-oxo-3-((4-(2,2,2-trifluoroacetamido)phenyl)sulfonamido)propyl)pyrrolidin-1-yl)-2,5-dimethyl-6-oxohex-4-en-3-yl)-N,3,3-trimethylbutanamide

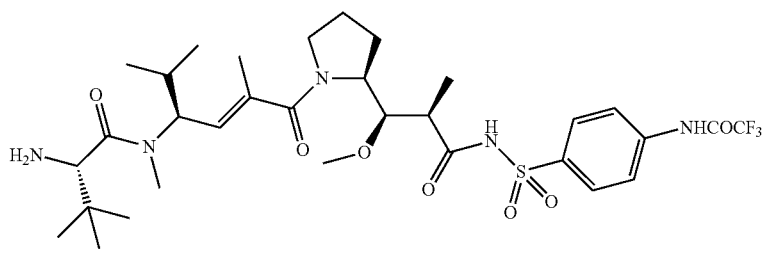

The title compound was prepared from the product of Example 1.98 according to General Procedure 9.1. $C_{32}H_{48}F_3N_5O_7S$ calcd. m/z=703.32 found $[M+H]^+$=704.68. $^1$H NMR (400 MHz, Methanol-$d_4$) δ 8.06 (d, J=8.5 Hz, 2H), 7.90 (d, J=8.5 Hz, 2H), 5.71 (dd, J=9.5, 1.9 Hz, 1H), 5.10-5.00 (m, 2H), 4.30 (s, 1H), 3.85 (dd, J=8.1, 2.7 Hz, 1H), 3.79-3.71 (m, 1H), 3.55-3.48 (m, 1H), 3.36 (s, 3H), 3.40-3.28 (m, 1H), 3.00 (s, 3H), 2.52-2.39 (m, 1H), 2.09-1.96 (m, 1H), 1.91 (s, 3H), 1.95-1.83 (m, 1H), 1.79-1.69 (m, 1H), 1.69-1.51 (m, 1H), 1.14 (d, J=6.9 Hz, 3H), 1.10 (s, 9H), 0.97 (d, J=6.5 Hz, 3H), 0.93 (d, J=6.5 Hz, 3H).

Example 1.100: (S)-2-((S)-2-(Dimethylamino)-3-methylbutanamido)-N-((S,E)-6-((S)-2-((1R,2R)-1-methoxy-2-methyl-3-oxo-3-((4-(2,2,2-trifluoroacetamido)phenyl)sulfonamido)propyl)pyrrolidin-1-yl)-2,5-dimethyl-6-oxohex-4-en-3-yl)-N,3,3-trimethylbutanamide (Compound 35)

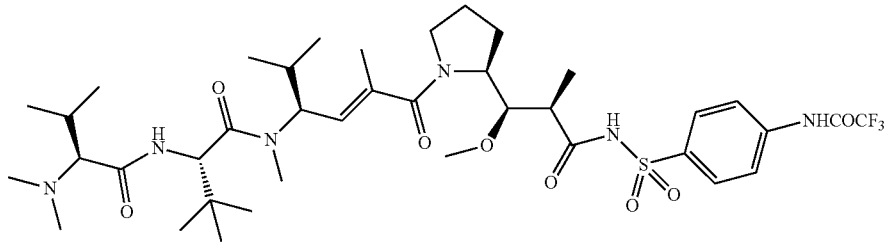

The title compound was prepared from the product of Example 1.99 and N,N-dimethylvaline according to General Procedure 6. $C_{39}H_{61}F_3N_6O_8S$ calcd. m/z=830.42 found $[M+H]^+$=831.75.

Example 1.101: (S)-N-((S,E)-6-((S)-2-((1R,2R)-3-((4-Aminophenyl)sulfonamido)-1-methoxy-2-methyl-3-oxopropyl)pyrrolidin-1-yl)-2,5-dimethyl-6-oxohex-4-en-3-yl)-2-((S)-2-(dimethylamino)-3-methylbutanamido)-N,3,3-trimethylbutanamide (Compound 36)

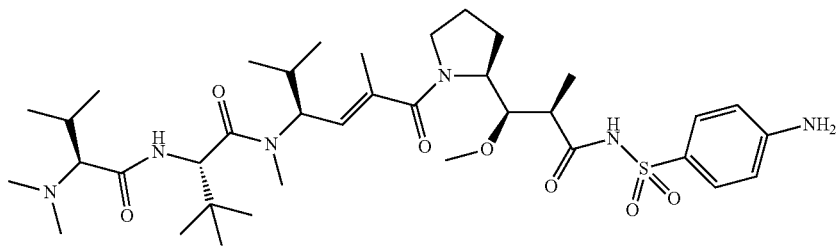 [SMILES: CO[C@H]([C@@H](C)C(=O)NS(=O)(=O)c1ccc(N)cc1)[C@@H]1CCCN1C(=O)/C(C)=C/[C@H](C(C)C)N(C)C(=O)[C@@H](NC(=O)[C@H](C(C)C)N(C)C)C(C)(C)C]

The title compound was prepared from the product of Example 1.100 according to General Procedure 4.1. $C_{37}H_{62}N_6O_7S$ calcd. m/z=734.44 found $[M+H]^+$=735.72.

Example 1.102: (S)-1-Isopropyl-N-((S)-1-(((S,E)-6-((S)-2-((1R,2R)-1-methoxy-2-methyl-3-oxo-3-((4-(2,2,2-trifluoroacetamido)phenyl)sulfonamido)propyl)pyrrolidin-1-yl)-2,5-dimethyl-6-oxohex-4-en-3-yl)(methyl)amino)-3,3-dimethyl-1-oxobutan-2-yl)piperidine-2-carboxamide (Compound 37)

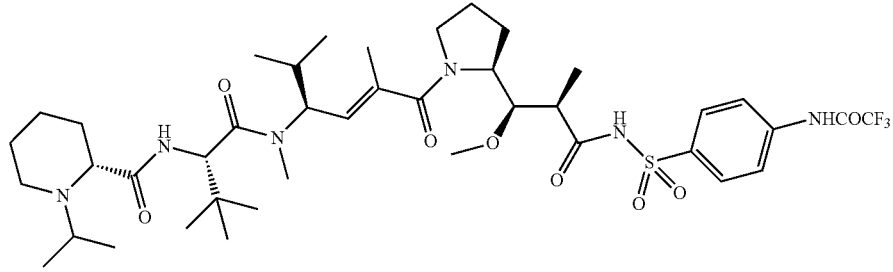

The title compound was prepared from the product of Example 1.99 and (R)-1-isopropylpiperidine-2-carboxylic acid according to General Procedure 6. $C_{41}H_{63}F_3N_6O_8S$ calcd. m/z=856.44 found [M+H]$^+$=857.80.

Example 1.103 (S)-N-((S)-1-(((S,E)-6-((S)-2-((1R,2R)-3-((4-Aminophenyl)sulfonamido)-1-methoxy-2-methyl-3-oxopropyl)pyrrolidin-1-yl)-2,5-dimethyl-6-oxohex-4-en-3-yl)(methyl)amino)-3,3-dimethyl-1-oxobutan-2-yl)-1-isopropylpiperidine-2-carboxamide (Compound 38)

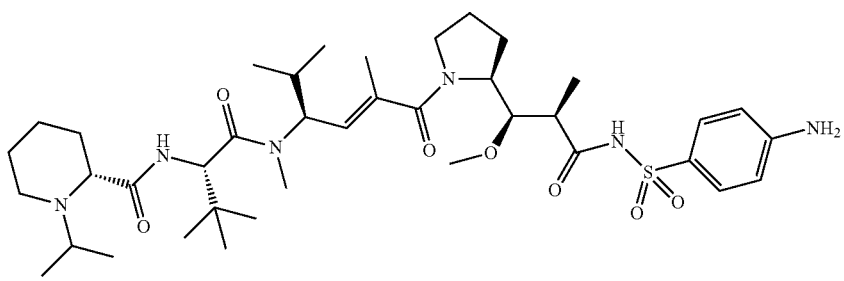 [SMILES: CO[C@H]([C@@H](C)C(=O)NS(=O)(=O)c1ccc(N)cc1)[C@@H]1CCCN1C(=O)/C(C)=C/[C@H](C(C)C)N(C)C(=O)[C@@H](NC(=O)[C@H]1CCCCN1C(C)C)C(C)(C)C]

The title compound was prepared from the product of Example 1.102 according to General Procedure 4.1. $C_{39}H_{64}N_6O_7S$ calcd. m/z=760.46 found [M+H]$^+$=761.77.

Example 1.104: (S,E)-3-(1-(tert-Butoxycarbonyl)pyrrolidin-2-yl)-2-methylacrylic Acid

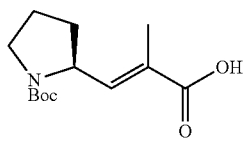 [SMILES: C/C(=C\[C@@H]1CCCN1C(=O)OC(C)(C)C)C(=O)O]

The title compound was synthesized from tert-butyl (S,E)-2-(3-ethoxy-2-methyl-3-oxoprop-1-en-1-yl)pyrrolidine-1-carboxylate (prepared according to J. Org. Chem., 2003, 68 (16), pp 6459-6462) according to General Procedure 4.1. $C_{13}H_{21}NO_4$ calcd. m/z=255.15 found [M-Boc+H]$^+$= 156.5, [M-Boc+MeCN]$^+$=197.5.

Example 1.105: tert-Butyl (S,E)-2-(2-Methyl-3-oxo-3-((4-(2,2,2-trifluoroacetamido)phenyl)sulfonamido)prop-1-en-1-yl)pyrrolidine-1-carboxylate

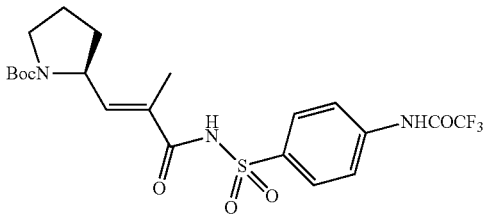

The title compound was prepared from the product of Example 1.104 and the product of Example 1.39 according to General Procedure 2. $C_{21}H_{26}F_3N_3O_6S$ calcd. m/z=505.15 found [M-Boc+H]$^+$=406.5, [M+Na]$^+$=528.5.

Example 1.106: (S,E)-2-Methyl-3-(pyrrolidin-2-yl)-N-((4-(2,2,2-trifluoroacetamido)phenyl)sulfonyl)acrylamide

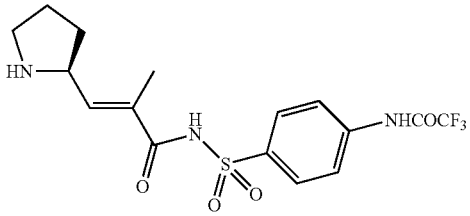

The title compound was prepared from the product of Example 1.105 according to General Procedure 9.1. $C_{16}H_{18}F_3N_3O_4S$ calcd. m/z=405.10, found $[M+H]^+$=406.5.

Example 1.107: (S)-2-((S)-2-(Dimethylamino)-3-methylbutanamido)-N-((3R,4S,5S)-3-methoxy-5-methyl-1-((S)-2-((E)-2-methyl-3-oxo-3-((4-(2,2,2-trifluoroacetamido)phenyl)sulfonamido)prop-1-en-1-yl)pyrrolidin-1-yl)-1-oxoheptan-4-yl)-N,3-dimethylbutanamide (Compound 39)

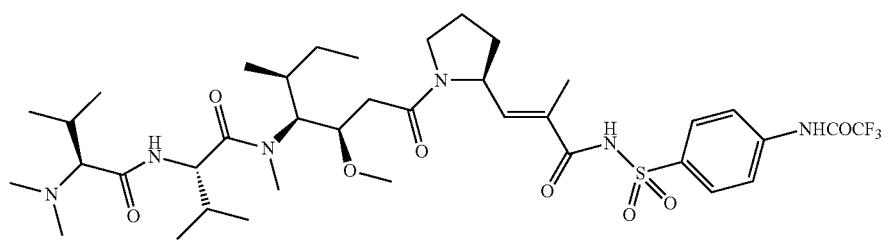

The title compound was prepared from the product of Example 1.106 and the product of Example 1.36 according to General Procedure 6. $C_{38}H_{59}F_3N_6O_8S$ calcd. m/z=816.41, found $[M+H]^+$=817.7.

Example 2: Syntheses of Drug-Linker Conjugates of the Present Invention

Scheme 1

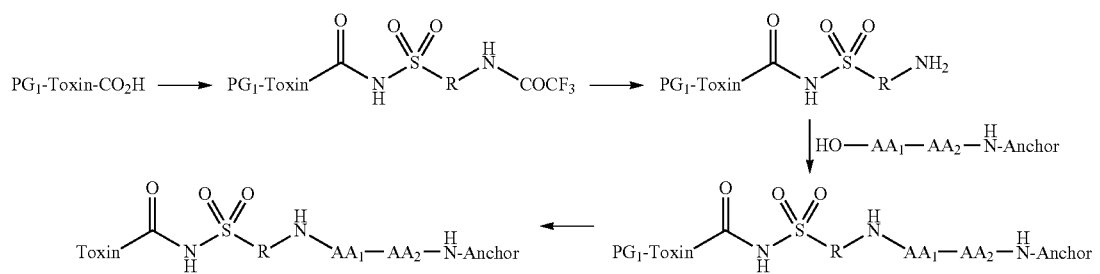

Scheme 1 illustrates a particular embodiment of a general scheme for the synthesis of a D-L complex. In further embodiments of the invention, the protecting group ($PG_1$) is removed from the Toxin (or drug) before amino acid (e.g., $AA_1$-$AA_2$) addition. In certain embodiments of the invention, the Anchor includes a functional group that can form a covalent bond with the Target. In other embodiments of the invention the Anchor comprises a Stretcher.

Example 2.1: (S)-N-(4-(N-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)phenyl)-2-((S)-1-(2,5-dioxo-2,5-dihydro-1H-pyrrol-1-yl)-14-isopropyl-12-oxo-3,6,9-trioxa-13-azapentadecan-15-amido)-5-ureidopentanamide

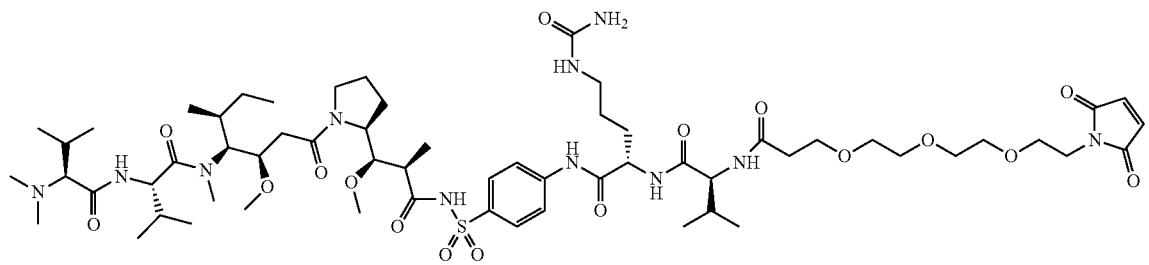 [SMILES: CC[C@H](C)[C@@H]([C@@H](CC(=O)N1CCC[C@H]1[C@H](OC)[C@@H](C)C(=O)NS(=O)(=O)c1ccc(NC(=O)[C@H](CCCNC(N)=O)NC(=O)[C@@H](NC(=O)CCOCCOCCOCCN2C(=O)C=CC2=O)C(C)C)cc1)OC)N(C)C(=O)[C@@H](NC(=O)[C@H](C(C)C)N(C)C)C(C)C]

The title compound was synthesized using General Procedure 5 from MT-VC-OH and Compound 5 and purified by preparative HPLC chromatography. $C_{61}H_{101}N_{11}O_{17}S$ calc'd m/z=1291.71 found [M+H]$^+$ 1292.89.

Example 2.2: (S)-N-(4-((N-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)methyl)phenyl)-2-((S)-1-(2,5-dioxo-2,5-dihydro-1H-pyrrol-1-yl)-14-isopropyl-12-oxo-3,6,9-trioxa-13-azapentadecan-15-amido)-5-ureidopentanamide

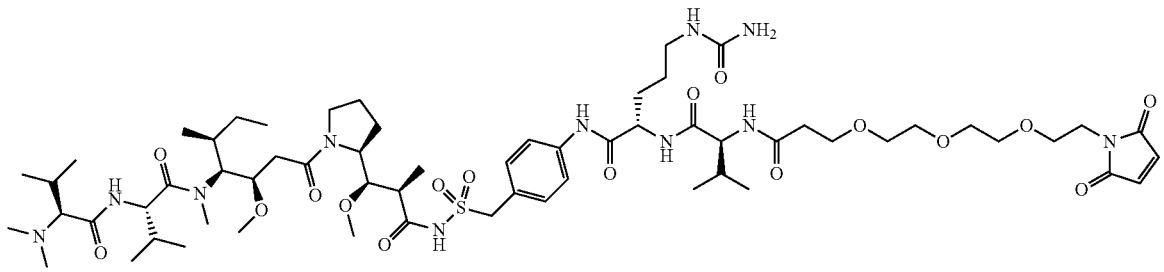 [SMILES: CC[C@H](C)[C@@H]([C@@H](CC(=O)N1CCC[C@H]1[C@H](OC)[C@@H](C)C(=O)NS(=O)(=O)Cc1ccc(NC(=O)[C@H](CCCNC(N)=O)NC(=O)[C@@H](NC(=O)CCOCCOCCOCCN2C(=O)C=CC2=O)C(C)C)cc1)OC)N(C)C(=O)[C@@H](NC(=O)[C@H](C(C)C)N(C)C)C(C)C]

The title compound was synthesized using General Procedure 5 from MT-VC-OH and Compound 8 and purified by preparative HPLC chromatography. $C_{61}H_{101}N_{11}O_{17}S$ calc'd m/z=1305.73 found [M+H]$^+$=1306.9.

Example 2.3: (S)-N-(4-(N-(((2R,3R)-3-((S)-1-((3R,4S,5S)-4-((S)-2-((S)-2-(Dimethylamino)-3-methylbutanamido)-N,3-dimethylbutanamido)-3-methoxy-5-methylheptanoyl)pyrrolidin-2-yl)-3-methoxy-2-methylpropanoyl)-L-phenylalanyl)sulfamoyl)phenyl)-2-((S)-1-(2,5-dioxo-2,5-dihydro-1H-pyrrol-1-yl)-14-isopropyl-12-oxo-3,6,9-trioxa-13-azapentadecan-15-amido)-5-ureidopentanamide

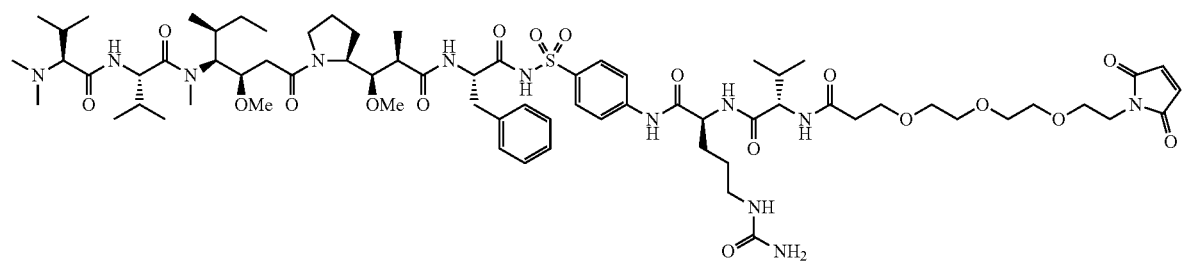 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(NC(=O)[C@H](CCCNC(N)=O)NC(=O)[C@@H](NC(=O)CCOCCOCCOCCN2C(=O)C=CC2=O)C(C)C)cc1)OC)N(C)C(=O)[C@@H](NC(=O)[C@H](C(C)C)N(C)C)C(C)C]

The title compound was prepared from MT-VC-OH and Compound 11 according to General Procedure 5. $C_{70}H_{110}N_{12}O_{18}S$ calcd m/z=1438.8 amu; found $[M+H]^+$=1440.2, $[(M+2H)/2]^{2+}$=720.5.

Example 2.4: (S)-N-(4-((N-(((2R,3R)-3-((S)-1-((3R,4S,5S)-4-((S)-2-((S)-2-(Dimethylamino)-3-methylbutanamido)-N,3-dimethylbutanamido)-3-methoxy-5-methylheptanoyl)pyrrolidin-2-yl)-3-methoxy-2-methylpropanoyl)-L-phenylalanyl)sulfamoyl)methyl)phenyl)-2-((S)-1-(2,5-dioxo-2,5-dihydro-1H-pyrrol-1-yl)-14-isopropyl-12-oxo-3,6,9-trioxa-13-azapentadecan-15-amido)-5-ureidopentanamide

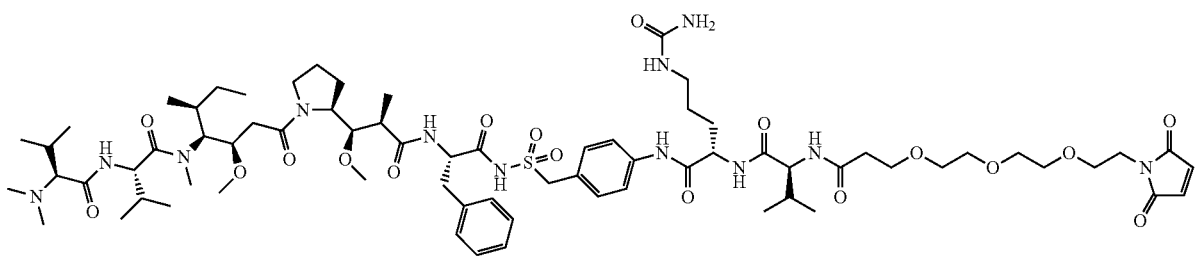 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)Cc1ccc(NC(=O)[C@H](CCCNC(N)=O)NC(=O)[C@@H](NC(=O)CCOCCOCCOCCN2C(=O)C=CC2=O)C(C)C)cc1)OC)N(C)C(=O)[C@@H](NC(=O)[C@H](C(C)C)N(C)C)C(C)C]

Prepared from Compound 14 and MT-VC-OH according to General Procedure 5 and purified by preparative HPLC. $C_{71}H_{112}N_{12}O_{18}S$ calcd m/z=1452.80 amu; found $[M+H]^+$=1453.7.

Example 2.5: (S)-2-((S)-2-(Dimethylamino)-3-methylbutanamido)-N-((3R,4S,5S)-1-((S)-2-((1R,2R)-3-((4-(3-(2-(2-(2-(2,5-dioxo-2,5-dihydro-1H-pyrrol-1-yl)ethoxy)ethoxy)ethoxy)propanamido)phenyl)sulfonamido)-1-methoxy-2-methyl-3-oxopropyl)pyrrolidin-1-yl)-3-methoxy-5-methyl-1-oxoheptan-4-yl)-N,3-dimethylbutanamide

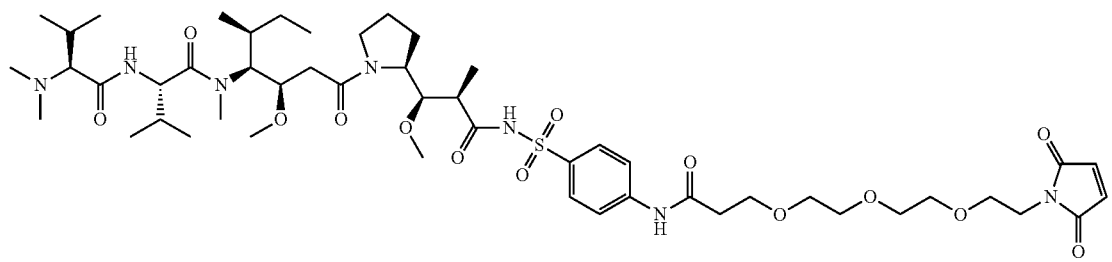 [SMILES: CC[C@H](C)[C@@H]([C@@H](CC(=O)N1CCC[C@H]1[C@H](OC)[C@@H](C)C(=O)NS(=O)(=O)c1ccc(NC(=O)CCOCCOCCOCCN2C(=O)C=CC2=O)cc1)OC)N(C)C(=O)[C@@H](NC(=O)[C@H](C(C)C)N(C)C)C(C)C]

The title compound was prepared from Compound 5 and MT-OH using General Procedure 6. $C_{50}H_{81}N_7O_{14}S$ calc'd m/z 1035.56=found [M+H]$^+$ 1037.97.

Example 2.6: (S)-N-(1-(4-(N-((2R,3R)-3-((S)-1-((3R,4S,5S)-4-((S)-2-((S)-2-(Dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)phenyl)cyclopropyl)-2-((S)-1-(2,5-dioxo-2,5-dihydro-1H-pyrrol-1-yl)-14-isopropyl-12-oxo-3,6,9-trioxa-13-azapentadecan-15-amido)-5-ureidopentanamide

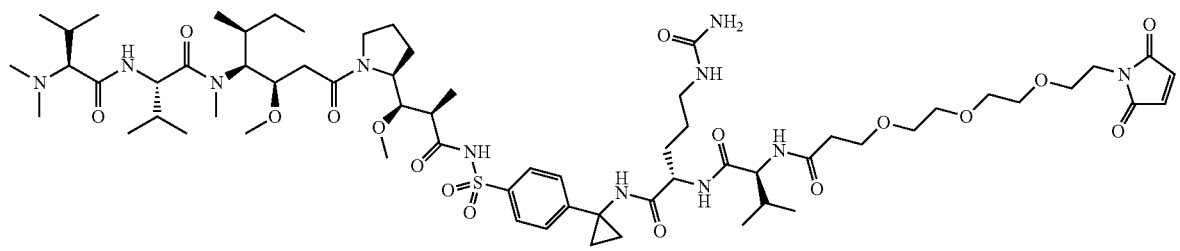 [SMILES: CC[C@H](C)[C@@H]([C@@H](CC(=O)N1CCC[C@H]1[C@H](OC)[C@@H](C)C(=O)NS(=O)(=O)c1ccc(C2(NC(=O)[C@H](CCCNC(N)=O)NC(=O)[C@@H](NC(=O)CCOCCOCCOCCN3C(=O)C=CC3=O)C(C)C)CC2)cc1)OC)N(C)C(=O)[C@@H](NC(=O)[C@H](C(C)C)N(C)C)C(C)C]

The title compound was prepared from Compound 30, Boc-VC-OH, and MT-NHS following General Procedure 8. $C_{64}H_{105}N_{11}O_{17}S$ calcd. m/z=1331.74 found [M+H]$^+$= 1332.8.

Example 2.7: tert-Butyl ((S)-1-(((S)-1-((1-(4-(N-(((2R,3R)-3-((S)-1-((3R,4S,5S)-4-((S)-2-((S)-2-(Dimethylamino)-3-methylbutanamido)-N,3-dimethylbutanamido)-3-methoxy-5-methylheptanoyl)pyrrolidin-2-yl)-3-methoxy-2-methylpropanoyl)-L-phenylalanyl)sulfamoyl)phenyl)cyclopropyl)amino)-1-oxo-5-ureidopentan-2-yl)amino)-3-methyl-1-oxobutan-2-yl)carbamate

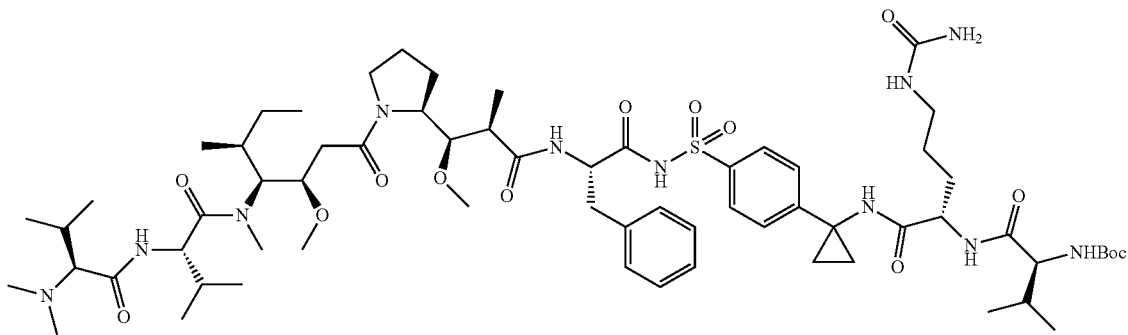 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(C2(NC(=O)[C@H](CCCNC(N)=O)NC(=O)[C@@H](NC(=O)OC(C)(C)C)C(C)C)CC2)cc1)OC)N(C)C(=O)[C@@H](NC(=O)[C@H](C(C)C)N(C)C)C(C)C]

The title compound was prepared from Compound 32 and Boc-VC-OH following General Procedure 5. $C_{65}H_{105}N_{11}O_{14}S$ calcd. m/z=1295.76 found $[M+H]^+$= 1297.2.

Example 2.8: (S)-N-(1-(4-(N-(((2R,3R)-3-((S)-1-((3R,4S,5S)-4-((S)-2-((S)-2-(Dimethylamino)-3-methylbutanamido)-N,3-dimethylbutanamido)-3-methoxy-5-methylheptanoyl)pyrrolidin-2-yl)-3-methoxy-2-methylpropanoyl)-L-phenylalanyl)sulfamoyl)phenyl)cyclopropyl)-2-((S)-1-(2,5-dioxo-2,5-dihydro-1H-pyrrol-1-yl)-14-isopropyl-12-oxo-3,6,9-trioxa-13-azapentadecan-15-amido)-5-ureidopentanamide

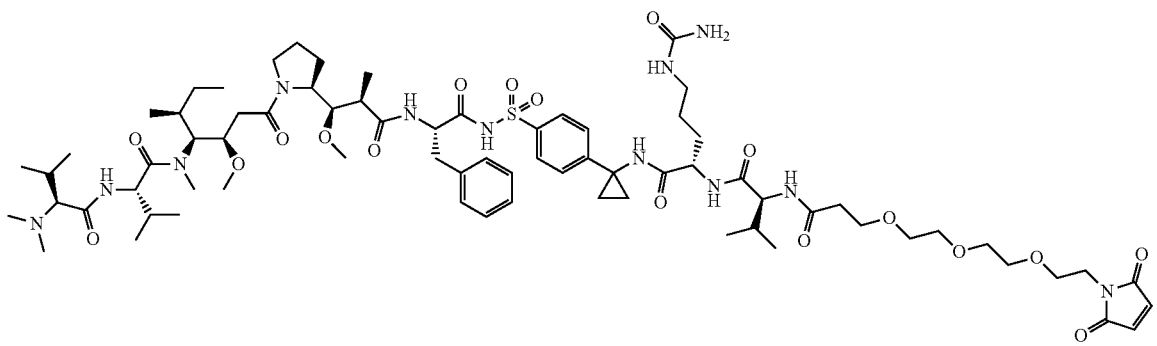 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(C2(NC(=O)[C@H](CCCNC(N)=O)NC(=O)[C@@H](NC(=O)CCOCCOCCOCCN3C(=O)C=CC3=O)C(C)C)CC2)cc1)OC)N(C)C(=O)[C@@H](NC(=O)[C@H](C(C)C)N(C)C)C(C)C]

The title compound was prepared from the product of Example 2.7 and MT-NHS following General Procedures 9 and 8. $C_{73}H_{114}N_{12}O_{18}S$ calcd. m/z=1478.81 found $[M+H]^+$= 1479.7.

Example 2.9: 4-(((S)-2-(((S)-2-(6-(2,5-Dioxo-2,5-dihydro-1H-pyrrol-1-yl)hexanamido)-3-methylbutanamido)-5-ureidopentanamido)benzyl ((S)-1-(((S)-1-(((3R,4S,5R)-3-methoxy-1-((S)-2-((1R,2R)-1-methoxy-2-methyl-3-oxo-3-((phenylmethyl)sulfonamido)propyl)pyrrolidin-1-yl)-5-methyl-1-oxoheptan-4-yl)(methyl)amino)-3-methyl-1-oxobutan-2-yl)amino)-3-methyl-1-oxobutan-2-yl)(methyl)carbamate

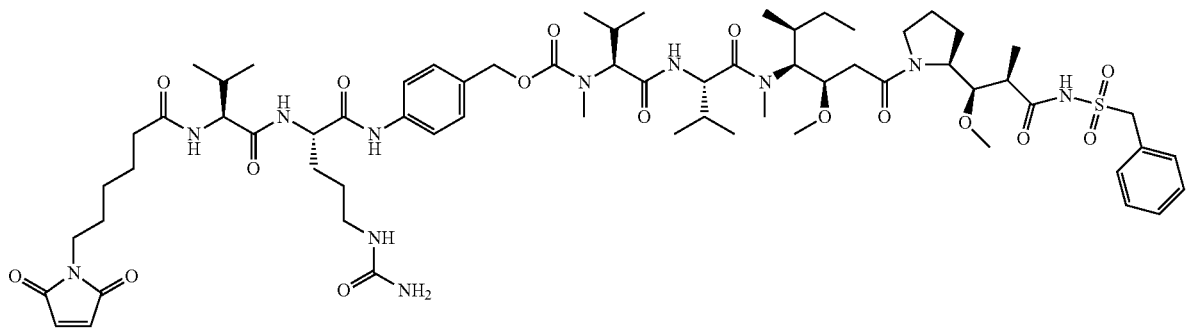 [SMILES: CC[C@H](C)[C@@H]([C@@H](CC(=O)N1CCC[C@H]1[C@H](OC)[C@@H](C)C(=O)NS(=O)(=O)Cc1ccccc1)OC)N(C)C(=O)[C@@H](NC(=O)[C@H](C(C)C)N(C)C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

The title compound was prepared from Compound 33 and commercially obtained MC-VC-PABC-OPnp. $C_{66}H_{101}N_{11}O_{16}S$ calc'd m/z=1335.71 found $[M+H]^+$ 1337.28.

It is understood to those skilled in the art that it may be possible to carry out the chemical conversions shown in the schemes above with modifications of one or more parameters. As examples, alternate non-nucleophilic solvents may be suitable for the chemistry, such as THF, DMF, Toluene etc. Reaction temperatures may be varied. Alternate reagents may be suitable to act as dehydrating or acid-activating agents which are normally used in amide formation reactions, such as pentafluorophenyl esters, NHS esters, EDAC, HBTU, HOBT etc.

Example 3: Cytotoxicity of Compounds of Formula I in Jurkat and HCC1954 Cells Lines Compounds were tested on Jurkat and HCC1954 cell lines to assess their cytotoxicity. Compounds were titrated 1:3 starting at various concentrations (30 nM to 1000 nM). Control cytotoxin HTI-286 (see, e.g., U.S. Pat. No. 7,579,323) was also titrated 1:3 across starting with a 30 nM concentration. Plates were incubated for 3 days. Cell viability was quantified using 30 µL/well of 1× CellTiter-Glo reagent. Control cytotoxin successfully killed Jurkats at an expected concentration.

Figure 2:
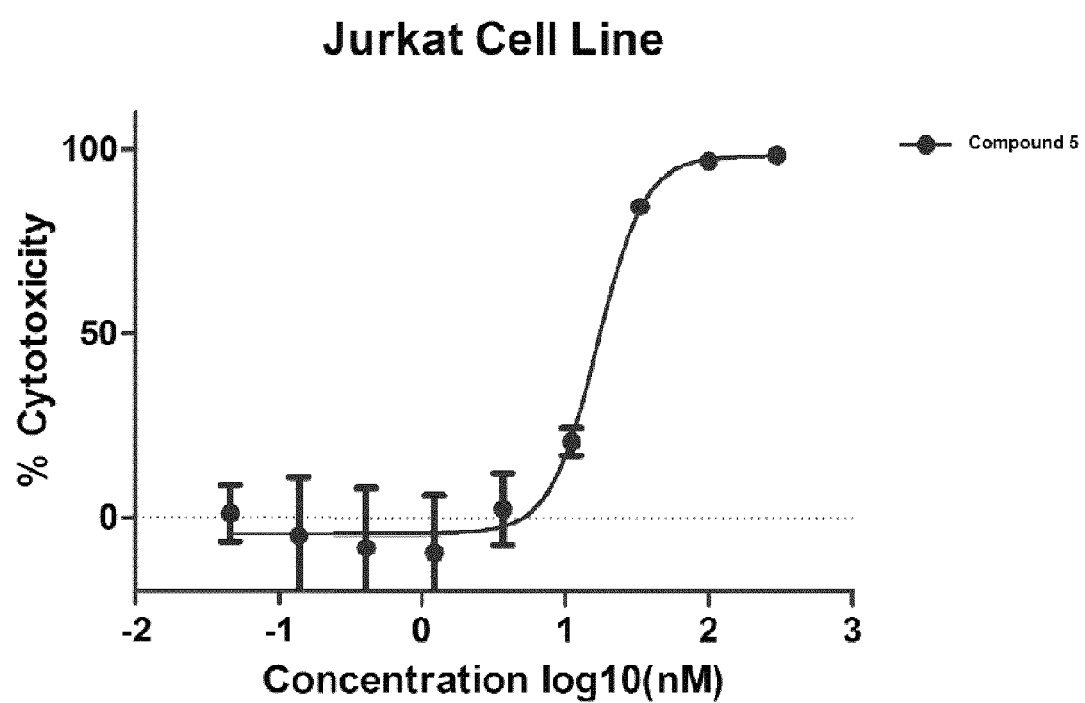
FIG. 2 shows the cytotoxicity of Compound 5 on the Her2-Negative Jurkat cell line.

Each cell line was grown in its respective growth medium until seeding day. Cells were removed from their culture vessels and the resulting cell suspension was counted using the ViCell. Cells were then diluted in their growth medium to 25000/mL such that 100 µL/well=2500 cells/well. Each cell line was seeded in the inner 60 wells of 96-well black walled TC plates, outer wells filled with water. HCC1954 were seeded a day prior to assay set up. Cytotoxins were diluted as described below a 5× dose-response of each compound was prepared using RPMI+10% FBS in a deep-well 96-well plate. This "master" dilution plate was used for each cell line. 25 µL of the 5× dose responses was spiked into each cell line in triplicate. The plates were returned to the incubator and were incubated for 3 nights. After the 3 nights, cell viability was quantified using 30 µL/well of 1× CellTiter-glo reagent. After at least 10 minutes of incubation, the luminescence was measured using the SpectraMax (500 ms integration). The results are shown in Table 2 and FIGS. 1 and 2.

TABLE 2

| Cell Line | Compound | $EC_{50}$ (nM) |
|---|---|---|
| Jurkat | 4 | 18.1 |
|  | 5 | 16.8 |
|  | 7 | 29.9 |
|  | 10 | 45.3 |
|  | 11 | 52 |
|  | 13 | 20.9 |
| HCC1954 | 5 | 8.9 |

Example 3.1: Assessment of the Cellular Cytotoxicity of Compounds of Formula I in Jurkat, HCC1954, NCI-N87, BxPC-3, SK-OV-3, and JIMT-1 Cell Lines Compounds were tested on one or more of Human T-cell leukemia cell line Jurkat (ATCC: TIB-152); Human breast cancer cell lines HCC1954 (ATCC: CRL-2338) and JIMT-1 (DSMZ: ACC 589); Human Pancreatic cell line BxPC-3 (ATCC: CRL.1687), Human ovarian adenocarcinoma cell line SK-OV-3 (ATCC: HTB-77) and Human gastric carcinoma cell line NCI-N87 (ATCC: CRL. 5822); to assess their cytotoxicity.

Briefly, cells were obtained from commercial sources and cultured as described in the product sheet provided. Cells were removed from their culture vessels and the resulting cell suspension was counted using a ViCell (Beckman Coulter), then seeded at 25,000 cells/mL (2,500 cells/well) in Costar 3904 black walled, flat bottomed 96-well plates (cells were seeded in the inner 60 wells of 96-well TC plates, and outer edge wells filled with water). Adherent cell lines were incubated for one night at 37° C./5% $CO_2$ atmosphere to allow the cells to attach to the microtiter plate surface, while suspension (Jurkat) cells were plated immediately before use. Cytotoxins were dissolved and serially diluted in dimethyl sulfoxide and then the solutions were added to complete growth medium at five-times the desired maximum final concentration. The cytotoxins were then titrated in growth medium, normally 1:3, over eight steps. A control with no test article present (growth medium alone) was included on each microtiter plate in sextuplicate. The prepared toxin titrations were added (25 µL/well) in triplicate to each cell line assayed. The cells and titrations were incubated at 37° C./5% $CO_2$ for three nights (Jurkat) and five nights (all other cell lines). After the incubation, cell viability was measured using CellTiter-Glo® by adding 30 µL of prepared CellTiter-Glo® reagent to each assay well. The mixtures were incubated for at least twenty minutes in the dark prior to measuring emitted luminescence using a microplate luminometer (500 ms integration time). The collected relative luminescence units (RLU) were converted to % cytotoxicity using the growth medium alone control mentioned above (% Cytotoxicity=1-[well RLU/average medium alone control RLU]×100%). Data (% Cytotoxicity vs. Concentration of ADC (log 10(nM)) were plotted and were fitted to curves using non-linear regression methods (four parameter-variable slope) using GraphPad Prism software v. 5.02 to obtain $EC_{50}$ estimates. Control cytotoxin, normally HTI-286 (see, e.g., U.S. Pat. No. 7,579,323) successfully killed all cell lines at an expected concentration.

The results are shown in Table 2.1.

TABLE 2.1

| Compound | $EC_{50}$ (nM) | | | | |
|---|---|---|---|---|---|
| | NCI-N87 | Jurkat | BxPC-3 | HCC-1954 | SKOV-3 | JIMT-1 |
| 4 | | 18.1 | | | | |
| 5 | 12.0 | 13.6 | 18.2 | 8.9 | 23.7 | 9.3 |
| 10 | | 45.3 | | | | |
| 11 | | 52 | | | | |
| 15 | 11.7 | 10.1 | 14.5 | | | |
| 16 | 14.4 | 11.5 | 17.0 | | | |
| 17 | >100 | 30.5 | >100 | | | |
| 18 | 0.9 | 1.5 | 2.3 | | | |
| 19 | 12.8 | 2.2 | 10.2 | | | |
| 20 | * | >100 | * | | | |
| 7 | | 29.9 | | | | |
| 13 | | 20.9 | | | | |
| 21 | * | ~100 | >100 | | | |
| 23 | 11.3 | 11.8 | 17.2 | | | |
| 24 | >100 | ~100 | >100 | | | |
| 25 | >100 | 34.3 | >100 | | | |
| 27 | 17.4 | 24.2 | 19.0 | | | |
| 28 | >100 | ~100 | >100 | | | |
| 29 | | 22.1 | | | | |
| 30 | | >100 | | | | |
| 31 | | 31.1 | | | | |
| 32 | | >100 | | | | |
| 34 | * | >100 | * | | | |

* Not cytotoxic at 300 nM

Example 4: Biological Assays

Cell lines: Human T-cell leukemia cell line Jurkat (ATCC: TIB-152); HCC1954 (ATCC: CRL. 2338); Human Pancreatic cells lines: AsPC-1 (ATCC: CRL-1682), BxPC-3 (ATCC: CRL.1687), HPAF-II (ATCC: CRL.1997), MiaPaCa2 (ATCC: CRL.1420), PANC-1 (ATCC: CRL.1469), Capan-1 (ATCC: HTB-79), Capan-2 (ATCC: HTB-80) and the Human gastric carcinoma cell line NCI-N87 (ATCC: CRL. 5822); AML-193 (ATCC: CRL.9589), CCRF-CEM (ATCC: CCL-119), DU145 (ATCC: HTB-81), PC-3 (ATCC: CRL.1435), A-431 (ATCC: CRL.1555), HT-29 (ATCC: HTB-38), A-172 (ATCC: CRL.1620), NCI-H358 (ATCC: CRL.5807), A549 (ATCC: CCL-185), Colo-205 (ATCC: CCL-222), MDA-MB-231 (ATCC: HTB-26), OVCAR-3 (ATCC: HTB-161), OV-90 (ATCC: CRL.11732), OE19 (Sigma: 96071721), RT112/84 (Sigma: 85061106).

On the day prior to adding compounds, HCC1954 AsPC-1, BxPC-3, HPAF-II, MiaPaCa2, PANC-1, Capan-1, Capan-2 and NCI-N87 cells are added to opaque-walled 96-well tissue culture-treated microtiter plates using complete growth medium at a density of 2500 cells/100 microliter (µL) of medium. These adherent cell lines cells are incubated for one night at 37° C./5% $CO_2$ to allow the cells to attach to the microtiter plate surface. On the day that compounds are added, Jurkat cells are added to separate 96-well microtiter plates at 2500 cells/100 µL, using the same growth medium as HCC1954. Compounds are first serially diluted using dimethyl sulfoxide, and then the prepared dilutions are added to complete growth medium at five-times the final concentration. Compounds are then titrated 1:3, eight steps. A control with no compound (growth medium alone) is included on each microtiter plate in sextuplicate. The prepared compounds titrations are added (25 µL/well) in triplicate. The cells and compound titrations are incubated at 37° C./5% $CO_2$ for three nights. After the incubation, cell viability is measured using Cell-Titer-Glo® reagent by adding 30 µL, of prepared CellTiter-Glo® to each assay well. The assay is incubated for at least twenty minutes in the dark prior to measuring emitted luminescence using a microplate luminometer (500 ms integration time). The collected relative luminescence units (RLU) are converted to % cytotoxicity using the growth medium alone control mentioned above (% Cytotoxicity=1-[Well RLU/average medium alone control RLU]).

GraphPad Prism® is used for generation of $EC_{50}$ values using three parameter non-linear regression curve fitting.

Example 5: Exemplary Antibody-Drug Conjugates

1. Exemplary Linkers

As recognized by the artisan of reasonable skill, the particular linker used for conjugate formation will depend upon the reactive group of the reactant compound being used for bond formation. As an example, and within the scope of the present invention, compounds having a thiol moiety may be used for conjugate formation. In some of the present examples, the commercially available cleavable linker sulfosuccinimidyl 6-[3'(2-pyridyldithio)-propionamido]hexanoate (sulfo-LC-SPDP: Thermo Pierce Cat #21650) and non-cleavable linker succinimidyl 4-[N-maleimidomethyl]cyclohexane-1-carboxylate (SMCC: Thermo Pierce Cat #22360) are utilized for antibody-drug conjugation reactions. The coupling procedure is performed in two major steps: 1) incorporation of the linkers onto the antibody via reaction with antibody primary amine groups (lysine residues) and the N-hydroxysuccinimide (NHS) ester moiety of the linkers; and 2) reaction of the incorporated maleimide group (SMCC) or 2-pyridyldithio group (LC-SPDP) with thiol-containing compounds.

2. Activation of Antibody with Cleavable (LC-SPDP) or Non-Cleavable (SMCC) Linkers Antibody (Herceptin®) is diluted into either potassium phosphate pH 8 (sulfo-LC-SPDP) or D-PBS (Invitrogen) pH 7.4 (SMCC) to 5 mg/mL. To the diluted antibody, freshly dissolved linker is added, using ultra-pure water for sulfo-LC-SPDP or anhydrous N,N-Dimethylacetamide (DMA) for SMCC. 10-14 fold molar-excesses of SMCC:antibody or sulfo-LC-SPDP:antibody result in incorporation of 5-7 linkers/antibody. The linker-antibody "activation" reaction is incubated at 28° C. for 2 hours. Following the incubation, the unreacted linker is removed from each antibody sample using 40 kda Zeba™ size-exclusion chromatography/desalting columns (Thermo Pierce Cat #87771, or 87772 depending on the scale). During the same chromatography step the buffer is exchanged in preparation for the next reaction: either phosphate buffer/EDTA pH 6.5 (LC-SPDP), or citrate buffer/EDTA pH 5 (SMCC). The purified preparations are then assayed for total protein content versus an antibody standard curve using the microplate adapted BCA assay (Thermo Pierce Cat #23225). To estimate the extent of linker incorporation a small scale reaction with excess (~10-fold compared to protein concentration) cysteine is performed. Following a 10 min incubation the unreacted cysteine is detected using 5,5-dithio-bis-(2-nitrobenzoic acid) (Ellman's reagent, Thermo Pierce Cat #22582). By interpolating the concentration from a cysteine standard curve the linker concentration is determined by subtracting the determined value from the known concentration of cysteine used.

3. Reaction of Thiol-Containing Compounds to Linker-Activated Antibody

In the second step of the coupling reaction, the activated-antibody is utilized by first diluting the preparation to 2 mg/mL using either phosphate buffer/EDTA pH 6.5 (LC-SPDP), or citrate buffer/EDTA pH 5 (SMCC). Prior to use, the thiol containing N-acyl sulfonamide compounds are reduced using TCEP-agarose beads to ensure the thiol group is available to react to the incorporated linkers. In brief, compounds are diluted to 5 mM using phosphate buffer/EDTA pH 6.5. In instances where aqueous solubility is an issue, a small volume of 37% HCl (1:300) is added and this is sufficient to solubilize the compounds at 5 mM. TCEP-agarose beads (Thermo Pierce Cat #77712), are equilibrated with phosphate buffer/EDTA/10% DMA prior to use. The compound dilutions are rotated with TCEP-agarose beads for at least 0.5 hours, or up to 3 hours. The reduced compounds are collected by centrifugation over a filter which excludes the TCEP-agarose. The extent of reduction and thiol concentration is measured using Ellman's reagent (compared to a cysteine standard curve). The reduced thiol-containing compounds are then added to the activated antibody samples at a molar excess of ~2-fold compared to the previously determined linker concentrations. In order to monitor the coupling reaction effectiveness an "overnight" conjugation control is prepared by diluting each compound into phosphate buffer/EDTA pH 6.5 or citrate buffer/EDTA pH 5 at the same dilution factor that is used in the conjugation reaction. The remaining compound stocks are frozen at −80° C. The reactions and overnight controls are incubated at ambient temperature overnight. The next morning the frozen compound stocks are thawed and another control is prepared for each compound exactly like the "overnight" control—this is the "fresh" control. A small volume of each conjugation reaction is compared to the overnight and fresh compound controls using Ellman's reagent. Non-reacted compound is purified away from the ADCs using 40 kda Zeba™ Size-exclusion/desalting columns; during the same step the buffer is exchanged to D-PBS pH 7.4 (Invitrogen). The purified ADCs are then analyzed for: total protein content (BCA assay, Pierce microBCA protocol), relative affinity for antigen binding (equilibrium native binding), and selective cytotoxic killing of HER2-positive cells (HCC1954) compared HER2-negative cells (Jurkat).

4. Cytotoxicity Assay

On the day prior to adding test articles, HCC1954 cells are added to opaque-walled 96-well tissue culture-treated microtiter plates using complete growth medium at a density of 2,500 cells/100 µL, of medium. The HCC1954 cells are incubated for one night at 37° C./5% $CO_2$ to allow the cells to attach to the microtiter plate surface. On the day that test articles are added, Jurkat cells are added to separate 96-well microtiter plates at 2,500 cells/100 µL, using the same growth medium as HCC1954. To compare the ADC killing to that obtained from the free compounds, the N-acyl sulfonamide compounds are first serially diluted using dimethyl sulfoxide or DMA, and then the prepared dilutions are added to complete growth medium at five-times the final concentration. Compounds are then titrated 1:3, eight steps. To test the ADCs, they are diluted directly in growth medium at five-times the final concentration. ADCs are then titrated 1:3, eight steps. A control with no test article present (growth medium alone) is included on each microtiter plate in sextuplicate. The prepared compound/ADC titrations are added (25 µL/well) in triplicate to both the HCC1954 cells and Jurkat cells. The cells and titrations are incubated at 37° C./5% $CO_2$ for three nights. After the incubation, cell viability is measured using CellTiter-Glo® reagent by adding 30 µL of prepared CellTiter-Glo® to each assay well. The assay is incubated for at least twenty min in the dark prior to measuring emitted luminescence using a microplate luminometer (500 ms integration time). The collected relative luminescence units (RLU) are converted to % cytotoxicity using the growth medium alone control mentioned above (% Cytotoxicity=1−[Well RLU/average medium alone control RLU]).

5. Analysis of Antibody-Drug Conjugate (ADC) by EsiToF Mass Spectrometry

An electrospary ionization time of flight (EsiToF) mass spectrometer (MS) instrument (QStar XL Hybrid quadrupole-TOF LC/MSMS; AB Sciex) is used to determine the molecular weight of the ADCs and to evaluate the drug-to-antibody ratio (DAR). The EsiToF MS instrument is equipped with an electrospray ionization turbo spray source. Data acquisition is performed in the positive ion mode, and the sample's total ion current is acquired over the mass range 2,000 m/z to 4,000 m/z using Analyst QS 1.1 software. The ion source is operated with an ion spray needle voltage of 5.2 KV, a nebulization (gas 1) at 25 (arbitrary units), a curtain gas of 30 (arbitrary units), a declustering potential of 150 V and at a temperature of 150° C. The ADC test sample solutions is introduced at 5 µL/min into the ion source by direct infusion via a fused silica capillary with the help of syringe and syringe pump. Typically the DAR ranges from 0 to 4.

6. Preparation of the ADC Sample for ESI-ToF MS Analysis

All ADC samples are deglycosylated using EndoS(IgG-ZERO)™ endoglycosidase and buffer exchanged with water prior to EsiToF-MS analysis. Briefly, the original ADC sample is run through a 100 K MWCO Amicon concentrator for buffer exchange in sodium phosphate buffer. The buffer exchanged sample is then treated with IgGZERO™ (1 unit/1 µg of antibody) in sodium phosphate cleavage buffer, containing 150 mM NaCl, and incubated for 30 min at 37° C. The resulting deglycosylated ADC is again buffer-exchanged with water using a 100 K MWCO Amicon concentrator, and diluted with 0.1% formic acid in acetonitrile/water (50/50 v/v %) to a concentration of 3.0 µg/µL prior to analysis.

Example 6: Exemplary Antibody-Drug Conjugates

1. Preparation of Antibody-Drug Conjugates from MCvc-PABC-Toxins, General Methods To a solution of antibody (1-10 mg/mL) in 25 mM sodium borate, 25 mM sodium chloride, 1 mM DTPA (pH 8.0) is added TCEP from a freshly prepared stock (1-10 mM) in the same buffer (2.0-3.0 molar equivalents). The solution is mixed thoroughly and incubated at 37° C. for 2 h before cooling on ice. In some instances the reduced antibody solution is further diluted with either ice-cold phosphate buffered saline containing 1 mM DTPA (final protein concentration 2.0 mg/mL) or ice-cold 25 mM sodium borate, 25 mM sodium chloride, 1 mM DTPA (pH 8.0), to obtain a solution with a final protein concentration of between 1 and 4 mg/mL. To the reduced protein solution stored on ice is added the maleimide functionalized toxin (10-12 molar equivalents) from a 10 mM DMSO stock solution. The conjugation reaction is immediately mixed thoroughly by inversion and conjugation is allowed to proceed on ice for a period of approximately 1 hour before purification by passage over Zeba™ Spin Desalting Columns (40 KDa MWCO; Peirce) pre-equilibrated with phosphate buffered saline or 10 mM sodium citrate, 150 mM sodium chloride, pH 5.5. The eluate is pooled, filter sterilized (Steriflip®, Millipore), and stored at 4° C. The purified ADCs are analyzed for total protein content (bicinchonic acid assay, Pierce microBCA protocol, catalogue #23225). The ADC product is characterized by reducing and non-reducing PAGE, HPLC-HIC, SEC, and RP-UPLC-MS. The average DAR and drug distribution are derived from interpretation of HIC and LC-MS data with reference to non-reducing PAGE. Average DAR estimates are normally in the range of 3.5-4.5. Relative affinity of ADCs for antigen binding (equilibrium native binding) is performed as described (above/below). The selective cytotoxicity of the antibody drug conjugates is assessed by testing for killing of both antigen positive and antigen negative cell lines.

2. Assay of Selective In Vitro Cytotoxicity of Antigen-positive Cells by Antibody Drug Conjugates Selective killing of an antigen positive cell line (including HCC1954, NCI-N87, HPAF-II and BxPC-3 cell lines) over antigen-negative Jurkat cells is demonstrated for each conjugate prepared. Briefly, cells are obtained from the ATCC and cultured as described in the product sheet provided. Cells are seeded at 25,000 cells/mL (2,500 cells/well) in Costar 3904 black walled, flat bottomed 96-well plates. Adherent cell lines cells are incubated for one night at 37° C./5% $CO_2$ atmosphere to allow the cells to attach to the microtiter plate surface, while suspension (Jurkat) cells are plated immediately before use. ADCs are diluted directly in the appropriate cell growth medium at five-times the desired final concentration. These ADCs are then titrated, normally 1:3, over eight steps. A control with no test article present (growth medium alone) is included on each microtiter plate in sextuplicate. The prepared ADC titrations are added (25 µL/well) in triplicate to each cell line assayed. The cells and titrations are incubated at 37° C./5% $CO_2$ for three nights (Jurkat) and five nights (all other cell lines). After the incubation, cell viability is measured using CellTiter-Glo® reagent by adding 30 µL, of prepared CellTiter-Glo® to each assay well. The mixtures are incubated for at least twenty minutes in the dark prior to measuring emitted luminescence using a microplate luminometer (500 ms integration time). The collected relative luminescence units (RLU) are converted to % cytotoxicity using the growth medium alone control mentioned above (% Cytotoxicity=1−[Well RLU/average medium alone control RLU]). Data (% Cytotoxicity vs. Concentration of ADC (log 10(nM)) are plotted and are analyzed by non-linear regression methods using GraphPad Prism software v. 5.02 to obtain $EC_{50}$ estimates.

3. Estimation of Drug to Antibody Ratio (DAR)

The average degree of conjugation of toxin-linker to antibody is assessed by hydrophobic interaction chromatography and high performance liquid chromatography-mass spectrometry. These techniques are described in Antibody Drug Conjugates, Methods in Molecular Biology vol. 1045, 2013. pp 275-284. L. Ducry, Ed., and Asish B. Chakraborty, Scott J. Berger and John C. Gebler, Characterization of an IgG1 Monoclonal Antibody and related Sub-structures by LC/ESI-TOF/MS: Application note, Waters Corporation. March 2007. 720002107EN. Typically, the DAR ranges from 0 to 4.

Method 1. Hydrophobic Interaction Chromatography

Antibody drug conjugates are subjected to hydrophobic interaction chromatography (HIC) on a TSKgel® Butyl-NPR column (Tosoh Bioscience; 4.6 mm×35 mm i.d.; 2.5 µm particle size) connected to an Agilent 1100 series HPLC. Samples are injected (5 µL) at or above 4 mg/mL. Where necessary, ADCs are concentrated prior to injection using PALL Nanosep Omega centrifugal concentration devices (part #OD010C34). A linear gradient elution is employed starting at 95% mobile phase A/5% mobile phase B, transitioning to 5% mobile phase A/95% mobile phase B over a period of 12 min (mobile phase A: 1.5 M ammonium sulfate+25 mM sodium phosphate at pH 6.95 and mobile phase B: 25% isopropanol, 75% 25 mM sodium phosphate at pH 6.95). Injection of unmodified antibody provided a means of identifying the peak with DAR=0. Antibodies are detected on the basis of absorbance at 280 nm.

Method 2. Ultra Performance Liquid Chromatography-Mass Spectrometry for DAR Estimation Reversed phase ultra performance liquid-chromatography tandem ESI-QToF-mass spectrometry (UPLC-ESI-QToF-MS) is used to characterize antibody drug conjugates for extent of drug conjugation following reduction with dithiothreitol. The characterization is performed using Acquity-UPLC® (H-class) Bio coupled to a Quattro-Premier™ QToF mass spectrometer with an electrospray ion source (WATERS Corporation). UPLC analysis of the reduced ADC sample is performed at 70° C. with a PolymerX™ 5 u PR-1 100 A, 50×2.0 mm column (Phenomenex, Inc.) and with a mobile phase composed of solvent A: acetonitrile/water/trifluoroacetic acid/formic acid (10/90/0.1/0.1, v/v %), and solvent B: acetonitrile/formic acid (100/0.1, v/v). Components of the reduced ADC sample are eluted with a linear gradient starting at solvent A/solvent B (80/20 v/v and a flow rate of 0.3 mL/min to solvent A/solvent B (40/60, v/v) over 25 min, and then to solvent A/solvent B(10/90, v/v %) over 2 min before equilibrating back to initial conditions. The total run time is 30 min. The ESI-ToF MS total ion current (TIC) data is acquired over 500-4,500 m/z range using MassLynx™ data acquisition software (Waters Corporation). Sample component mass data is acquired in the positive ion V-mode, and the ESI source is operated at source temperature: 150° C., desolvation temperature: 350° C., desolvation gas: 800 L/h, sample cone voltage: 60 V, capillary voltage: 3.0 kV, desolvation gas: nitrogen, and collision gas: argon. The summed TIC mass spectra for each peak is deconvoluted by the Maximum Entropy™ 1 (MaxEnt1) algorithm to generate the neutral mass data of the peak component.

4. Preparation of Reduced ADC Samples for UPLC/ESI-ToF MS Analysis

Reduction of the disulfide bonds in the antibody of the ADC (~1 µg/µL solution) to generate the light and heavy chains is performed using 20 mM DTT at 60° C. for 20 min. An injection volume of 5-10 µL of the reduced ADC sample is employed for UPLC/ESI-ToF-MS analysis.

Example 6.1 Exemplary Antibody-Drug Conjugates

1. Preparation of Antibody-Drug Conjugates from Maleimide Functionalized Drug-Linkers, General Methods To a solution of antibody (1-10 mg/mL) in phosphate buffered saline (pH 7.4) was added TCEP from a freshly prepared stock (1-10 mM) in the same buffer (2.0-3.0 molar equivalents). The solution was mixed thoroughly and incubated at 37° C. for 2 h before cooling on ice. In some instances the reduced antibody solution was further diluted with ice-cold phosphate buffered saline containing 1 mM DTPA to obtain a solution with a final protein concentration of between 1 and 5 mg/mL. To the reduced protein solution stored on ice was added the maleimide functionalized drug-linker (8-10 molar equivalents) from a 10-20 mM DMSO stock solution. The conjugation reaction was immediately mixed thoroughly by inversion and conjugation was allowed to proceed on ice for a period of approximately 1 hour before purification by passage over Zeba™ Spin Desalting Columns (40 KDa MWCO; Peirce) pre-equilibrated with phosphate buffered saline. The eluate was pooled, filter sterilized (Steriflip®, Millipore), and stored at 4° C. The purified ADCs were analyzed for total protein content (bicinchonic acid assay, Pierce microBCA protocol, catalogue #23225). The ADC product was characterized by reducing and non-reducing PAGE, HPLC-HIC, SEC, and RP-UPLC-MS. The average DAR and drug distribution were derived from interpretation of HIC and LC-MS data with reference to non-reducing PAGE. Average DAR estimates were normally in the range of 3.5-4.2. Relative affinity of ADCs for antigen binding (equilibrium native binding) was performed as described (below). The selective cytotoxicity of the antibody drug conjugates was assessed by testing for killing of both antigen positive and antigen negative cell lines in a cellular cytotoxicity assay.

2. Assay of Selective In Vitro Cytotoxicity of Antibody Drug Conjugates on Antigen-Positive Cells Antibody drug conjugates were tested for cytotoxicity on cultured cell lines including Human T-cell leukemia cell line Jurkat (ATCC: TIB-152); Human breast cancer cell lines HCC1954 (ATCC: CRL-2338) and JIMT-1 (DSMZ: ACC 589), Human ovarian adenocarcinoma cell line SK-OV-3 (ATCC: HTB-77); Human gastric carcinoma cell line NCI-N87 (ATCC: CRL-5822); Human non-Hodgkin's lymphoma cell line Karpas299 (Health Protection Agency Culture Collections: 06072604); and Human Burkitt's lymphoma cell line Ramos (ATCC: CRL-1596). Selective killing of an antigen positive cell line (including HCC1954, NCI-N87, SK-OV-3, and JIMT-1 cell lines for Trastuzumab-based conjugates; Ramos cell line for Rituximab-based conjugates; Karpas 299 for brentuximab (cAC-10)-based conjugates) over one or more antigen-negative cell lines (Jurkat, Karpas299 and Ramos for Trastuzumab-based conjugates; NCI-N87 for brentuximab (cAC-10) and Rituximab-based conjugates) was demonstrated for each conjugate prepared. Briefly, cells were obtained from commercial sources and cultured as described in the product sheet provided. Cells were seeded at 25,000 cells/mL (2,500 cells/well) in Costar 3904 black walled, flat bottomed 96-well plates. Adherent cell lines were incubated for one night at 37° C./5% $CO_2$ atmosphere to allow the cells to attach to the microtiter plate surface, while suspension (Jurkat) cells were plated immediately before use. ADCs were diluted directly in the appropriate cell growth medium at five-times the desired final maximum concentration. These ADCs were then titrated, normally 1:3, over eight steps. A control with no test article present (growth medium alone) was included on each microtiter plate in sextuplicate. The prepared ADC titrations were each added (25 µL/well) in triplicate to each cell line assayed. The cells and titrations were incubated at 37° C./5% $CO_2$ for three nights (Jurkat) and five nights (all other cell lines). After the incubation, cell viability was measured using CellTiter-Glo® by adding 30 µL, of prepared CellTiter-Glo® reagent to each assay well. The mixtures were incubated for at least twenty minutes in the dark prior to measuring emitted luminescence using a microplate luminometer (500 ms integration time). The collected relative luminescence units (RLU) were converted to % cytotoxicity using the growth medium alone control mentioned above (% Cytotoxicity=1−[Well RLU/average medium alone control RLU]). Data (% Cytotoxicity vs. Concentration of ADC (log 10(nM)) were plotted and were fitted to curves using non-linear regression methods (four parameter-variable slope) using GraphPad Prism software v. 5.02 to obtain $EC_{50}$ estimates.

3. Estimation of Drug to Antibody Ratio (DAR)

The average degree of conjugation of toxin-linker to antibody was assessed by hydrophobic interaction chromatography and high performance liquid chromatography-mass spectrometry. These techniques are described in Antibody Drug Conjugates, Methods in Molecular Biology vol. 1045, 2013. pp 275-284. L. Ducry, Ed., and Asish B. Chakraborty, Scott J. Berger and John C. Gebler, Characterization of an IgG1 Monoclonal Antibody and related Sub-structures by LC/ESI-TOF/MS: Application note, Waters Corporation. March 2007. 720002107EN.

Method 1. Hydrophobic Interaction Chromatography

Antibody drug conjugates were subjected to hydrophobic interaction chromatography (HIC) on a TSKgel® Butyl-NPR column (Tosoh Bioscience; 4.6 mm×35 mm i.d.; 2.5 µm particle size) connected to an Agilent 1100 series HPLC. Samples were injected (5 µL) at or above 4 mg/mL. A linear gradient elution was employed starting at 95% mobile phase A/5% mobile phase B, transitioning to 5% mobile phase A/95% mobile phase B over a period of 12 min (mobile phase A: 1.5 M ammonium sulfate+25 mM sodium phosphate at pH 6.95 and mobile phase B: 25% isopropanol, 75% 25 mM sodium phosphate at pH 6.95). Alternative gradients using the same mobile phase components offered improved resolution of some conjugates. Injection of unmodified antibody provided a means of identifying the peak with DAR=0. Antibodies were detected on the basis of absorbance at 280 nm.

Method 2. Ultra Performance Liquid Chromatography-Mass Spectrometry for DAR Estimation Reversed phase ultra performance liquid-chromatography tandem ESI-QToF-mass spectrometry (UPLC-ESI-QToF-MS) was used to characterize antibody drug conjugates for extent of drug conjugation following reduction with dithiothreitol. The characterization was performed using Acquity-UPLC® (H-class) Bio coupled to a Quattro-Premier™ QToF mass spectrometer with an electrospray ion source (WATERS Corporation). UPLC analysis of the reduced ADC sample is performed at 70° C. with a PolymerX™ 5 u PR-1 100 A, 50×2.0 mm column (Phenomenex, Inc.) and with a mobile phase composed of solvent A: acetonitrile/water/trifluoroacetic acid/formic acid (10/90/0.1/0.1, v/v %), and solvent B: acetonitrile/formic acid (100/0.1, v/v). Components of the reduced ADC sample were eluted with a linear gradient starting at solvent A/solvent B (80/20 v/v and a flow rate of 0.3 mL/min to solvent A/solvent B (40/60, v/v) over 25 min, and then to solvent A/solvent B(10/90, v/v %) over 2 min before equilibrating back to initial conditions. The total run time was 30 min. The ESI-ToF MS total ion current (TIC) data was acquired over 500-4,500 m/z range using MassLynx™ data acquisition software (Waters Corporation). Sample component mass data was acquired in the positive ion V-mode, and the ESI source was operated at source temperature: 150° C., desolvation temperature: 350° C., desolvation gas: 800 L/h, sample cone voltage: 60 V, capillary voltage: 3.0 kV, desolvation gas: nitrogen, and collision gas: argon. The summed TIC mass spectra for each peak was deconvoluted by the Maximum Entropy™ 1 (Max-Ent1) algorithm to generate the neutral mass data of the peak component.

4. Preparation of Reduced ADC Samples for UPLC/ESI-ToF MS Analysis

Reduction of the disulfide bonds in the antibody of the ADC (~1 μg/μL solution) to generate the light and heavy chains was performed using 20 mM DTT at 60° C. for 20 min. An injection volume of 5-10 μL of the reduced ADC sample was employed for UPLC/ESI-ToF-MS analysis.

Figure 6:
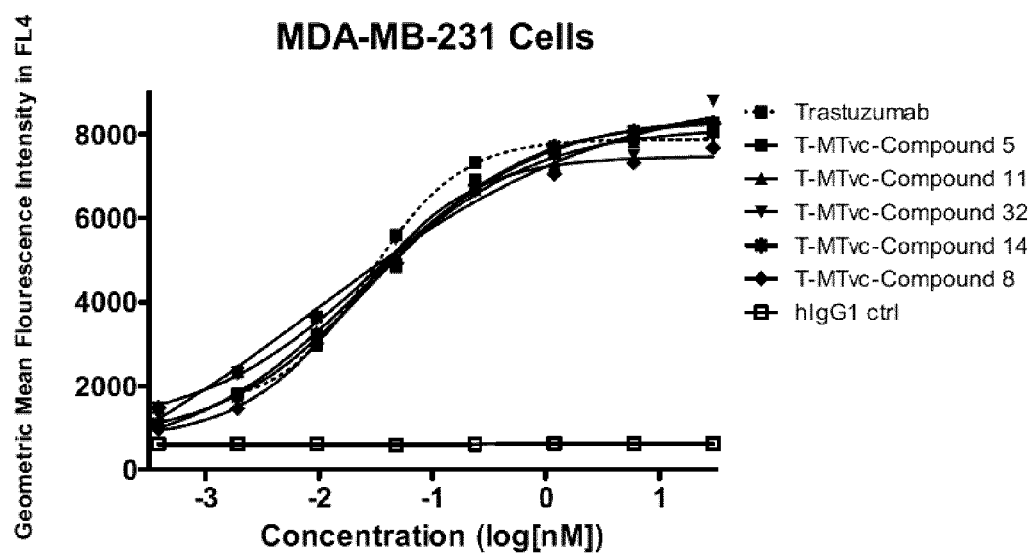
FIG. 6 shows the results of an equilibrium native binding assay used to compare binding of certain ADCs to the MDA-MB-231 cell line.

5. Determination of Relative Affinity of ADCs for Antigen Using Equilibrium Native Binding Assay Binding of antibodies and conjugates thereof was ranked using an equilibrium native binding assay. The experiment was performed to compare binding of Trastuzumab and Trastuzumab-based antibody drug conjugates to MDA-MB-231 cell line (ATCC: HTB-26). MDA-MB-231 cells were cultured as described on the product sheet provided by the supplier. Cells (~60% confluent) were washed once with PBS and removed from the culture flask using cell dissociation buffer (Sigma 5914), then resuspended in cell culture medium and transferred to a 96-well V-bottomed plate (Sartstedt 82.1583.001; 50000 cells per well) before pelleting cells (400×g, 3 min) and discarding supernatant. Antibody and antibody drug conjugates were titrated in ice cold cell culture medium, 1:3 from 60 μg/mL starting concentration. These titrations (20 μL) were used to resuspend cell pellets and then incubated with cells overnight to reach equilibrium. Unbound antibody was washed away by twice pelleting and re-suspending cells in FACS buffer (200 μL; PBS pH 7.4 containing 1% FBS), then pelleting and re-suspending in the same buffer (200 μL) containing 2 μg/mL Gt anti-Human IgG-Fc-Alexa647 (Jackson Immuno Cat #109-605-098) and 2.5 μg/mL 7-actinomycin D (Sigma Cat #A9400) and incubating on ice for 30 min. Cells were washed as above, resuspended in 50 μL FACS buffer and analyzed by flow cytometry (BD Accuri) and excluding 7-AAD positive events. GraphPad Prism was used to fit curves to data using non-linear regression analysis with 4 parameters and variable slope. Data from a representative relative affinity ranking experiment is shown in FIG. 6.

Example 7: Anti-body Drug Conjugates of Compounds of Formula I

Using methods similar to those described in Examples 5 and 6, the following trastuzumab ADC was prepared, wherein n=0, 1, 2, 3, 4, 5, 6, 7, or 8. The average n was ~4.

T-MTvc-Compound 5

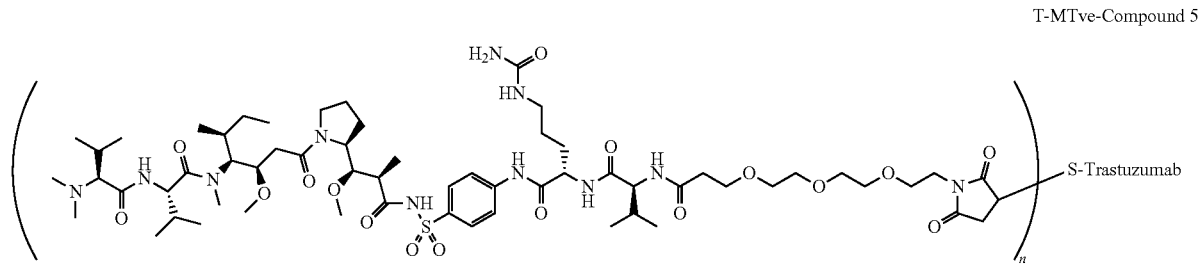

Figure 3:
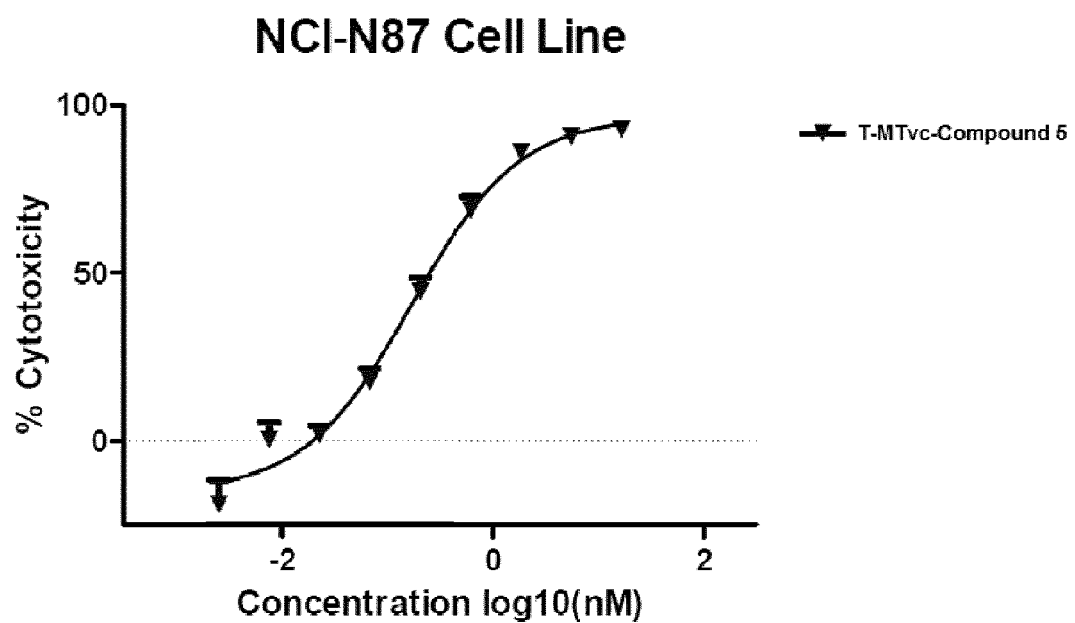
FIG. 3 shows the cytotoxicity of a trastuzumab ADC of Compound 5 on the Her2-Positive NCI-N87 cell line.
Figure 4:
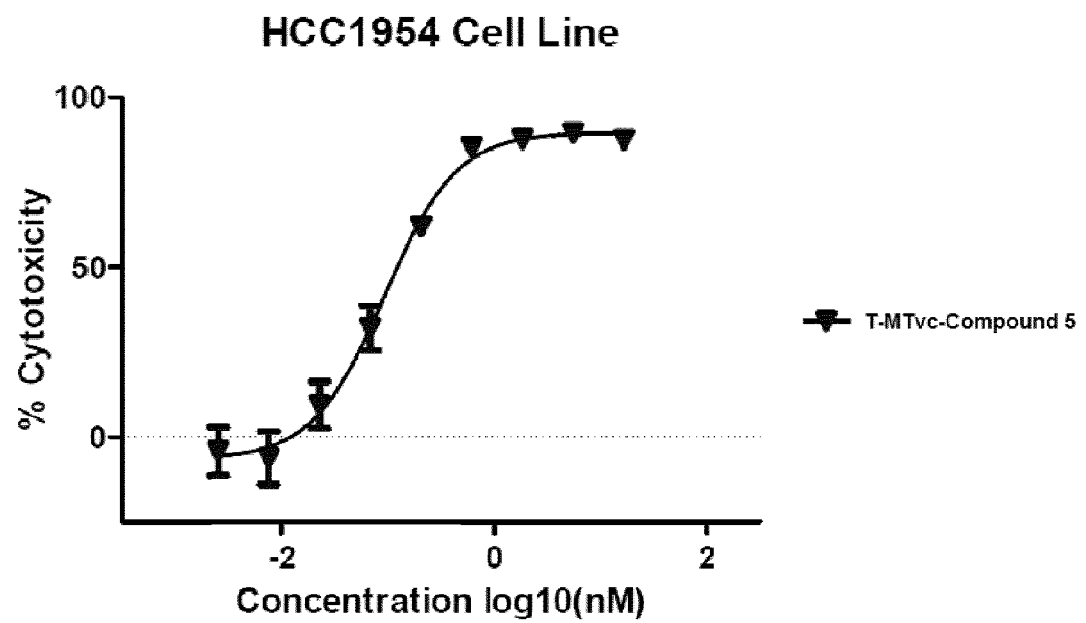
FIG. 4 shows the cytotoxicity of a trastuzumab ADC of Compound 5 on the Her2-Positive HCC1954 cell line.
Figure 5:
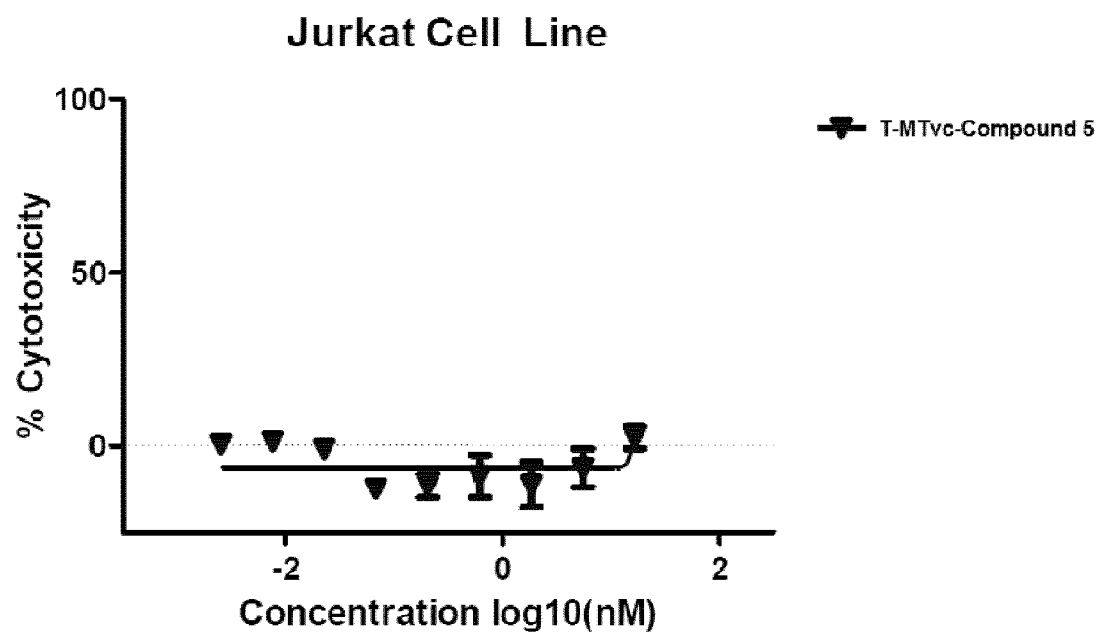
FIG. 5 shows the cytotoxicity of a trastuzumab ADC of Compound 5 on the Her2-Negative Jurkat cell line.

The cytotoxicity of T-MTvc-Compound 5 on Her2-Positive NCI-N87 and HCC1954 cell lines and on Her2-Negative Jurkat cell line is shown in Table 3 and FIGS. 3-5.

TABLE 3

| Cell Line | Compound | $EC_{50}$ (nM) |
| --- | --- | --- |
| NCI-N87 | T-MTvc-Compound 5 | 0.17 |
| HCC1954 | T-MTvc-Compound 5 | 0.09 |

Example 7.1: Antibody Drug Conjugates of Compounds of Formula I

Using methods similar to those described in Example 6.1, the following antibody drug conjugates were prepared from Trastuzumab (Herceptin, Roche), Rituximab (Rituxan, Roche) and brentuximab (cAC-10) wherein on average n is approximately 4.

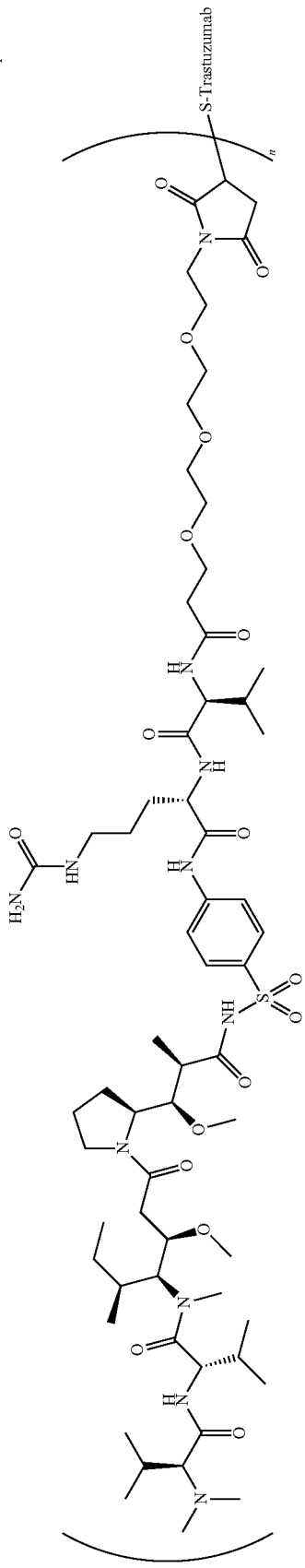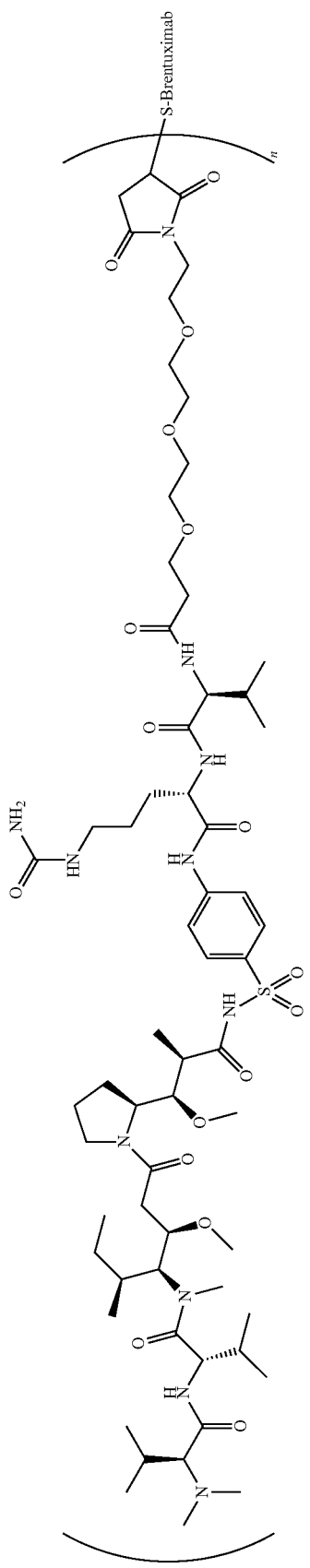

-continued
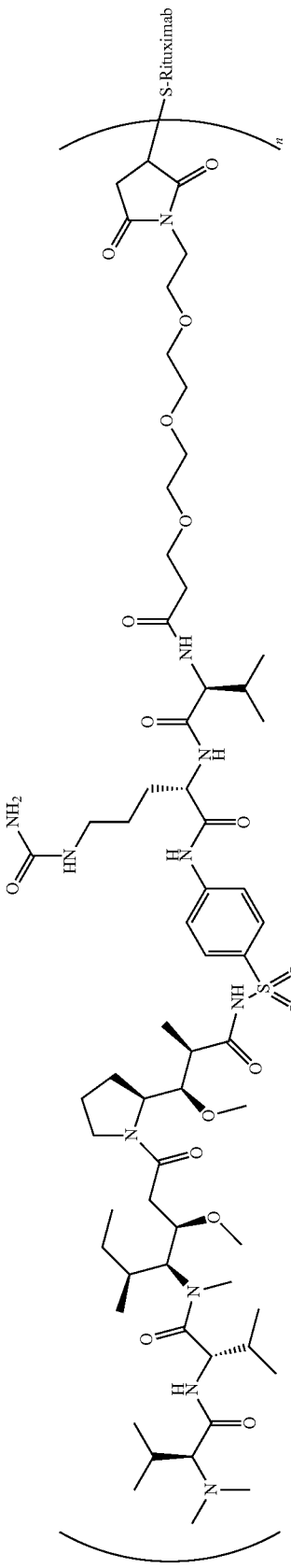
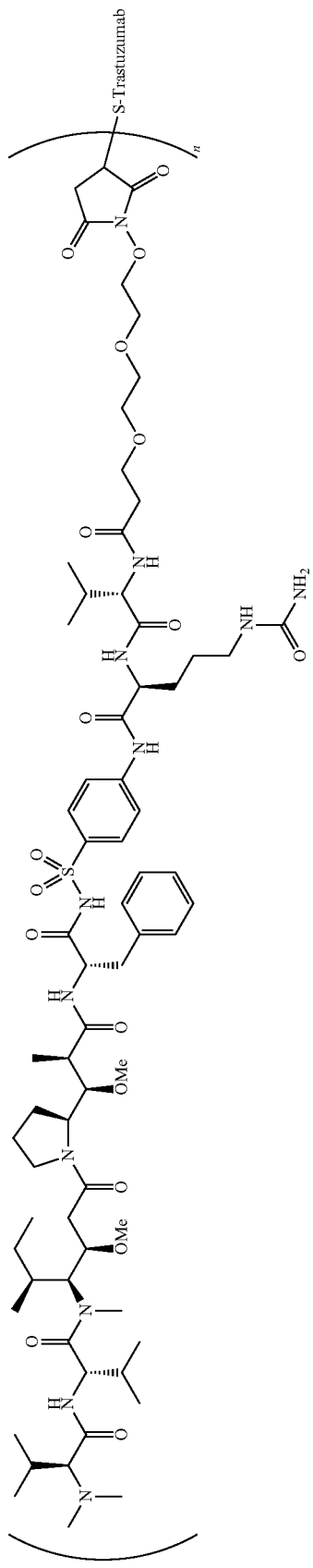

-continued
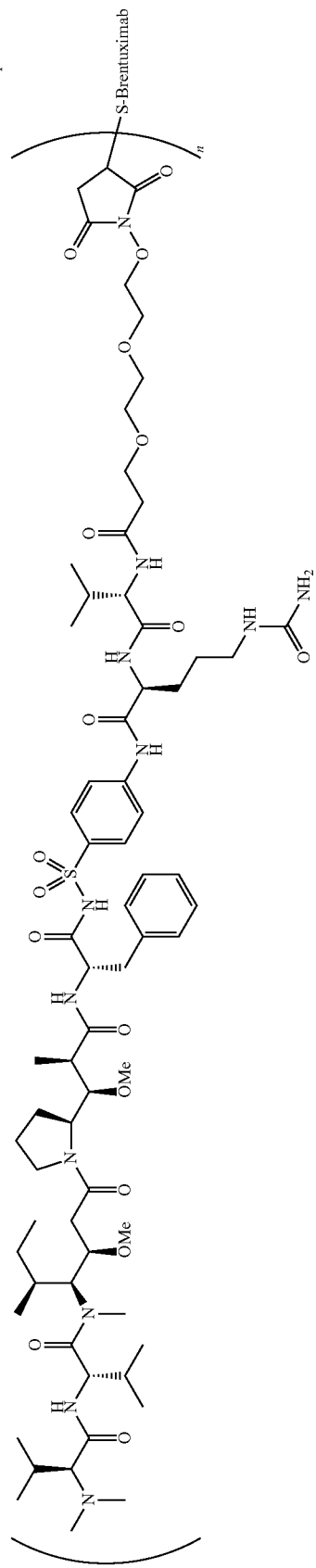
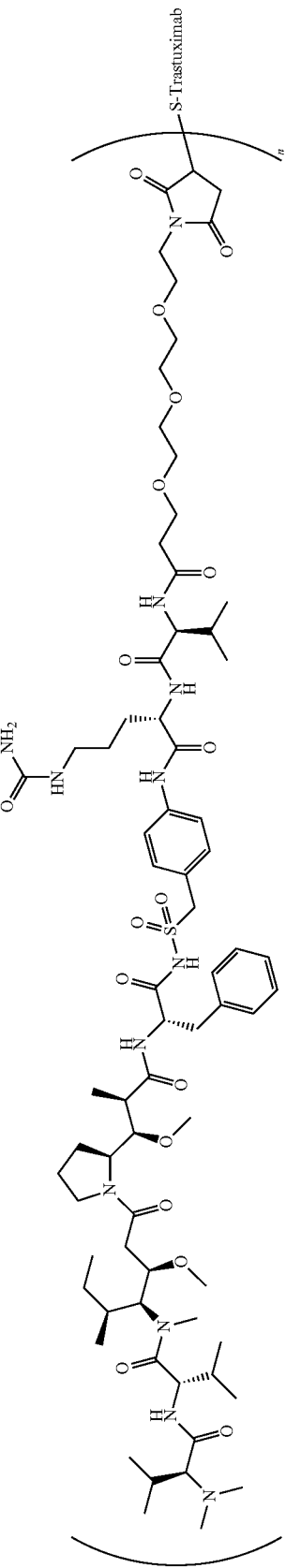

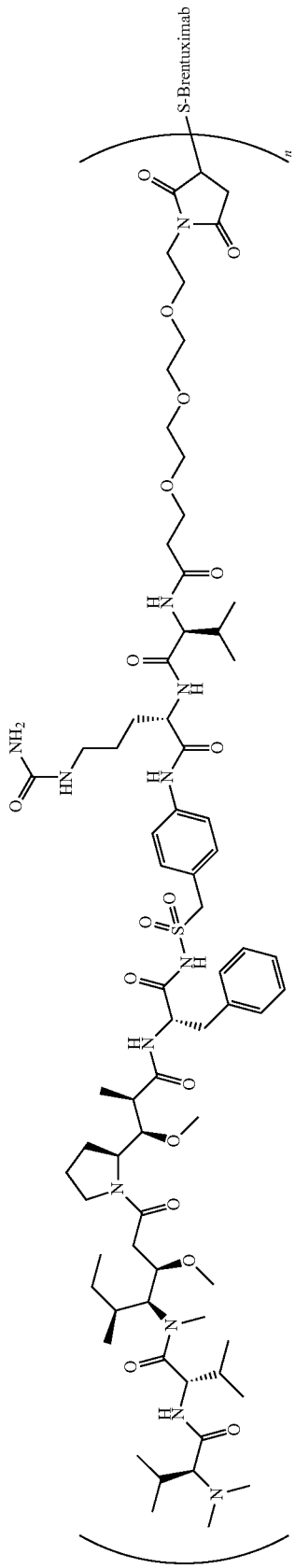
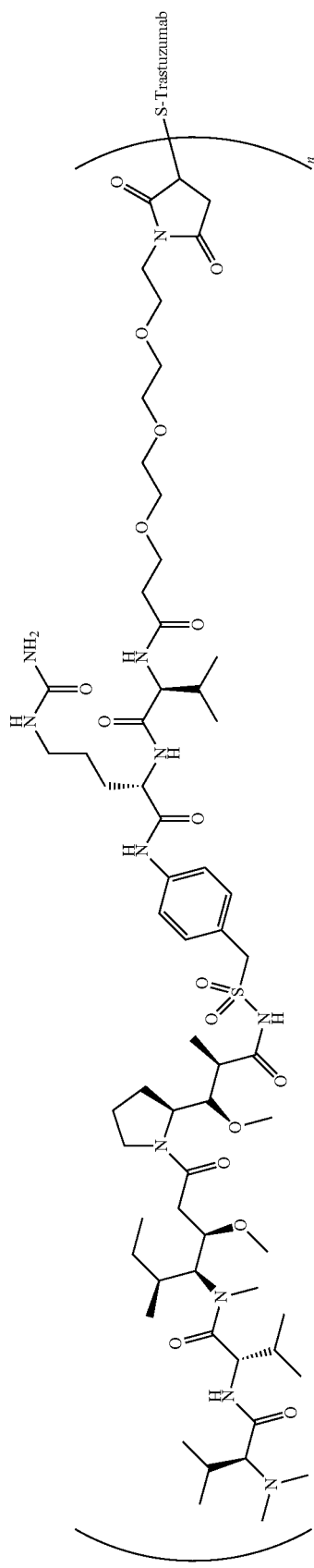

-continued
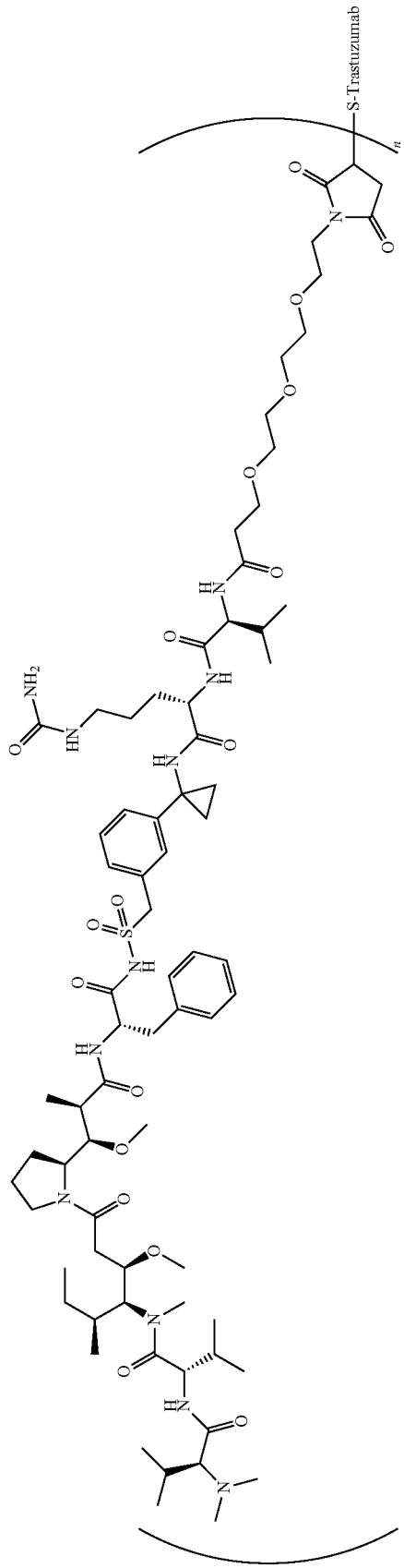
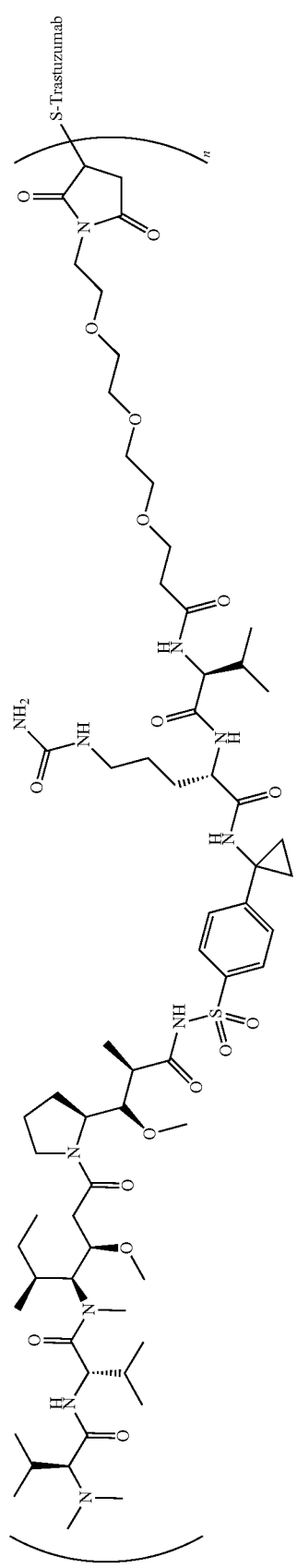

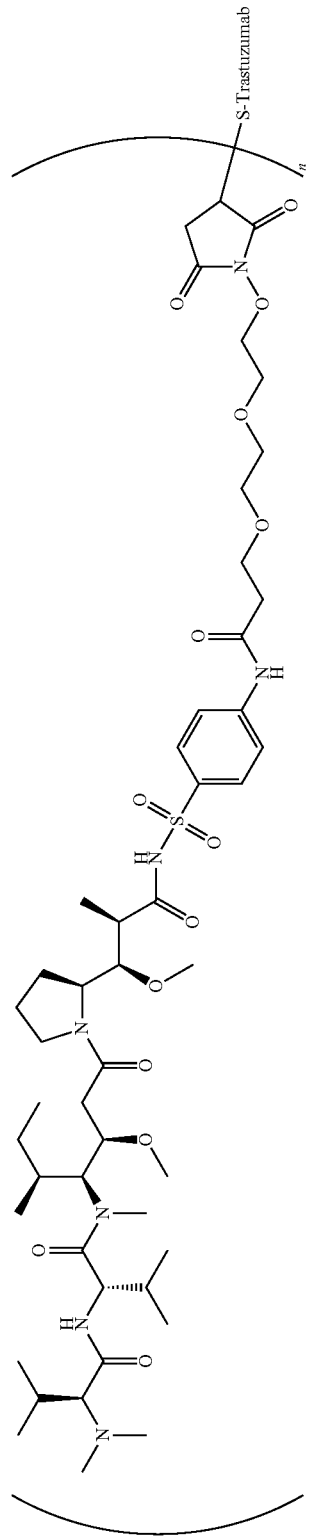
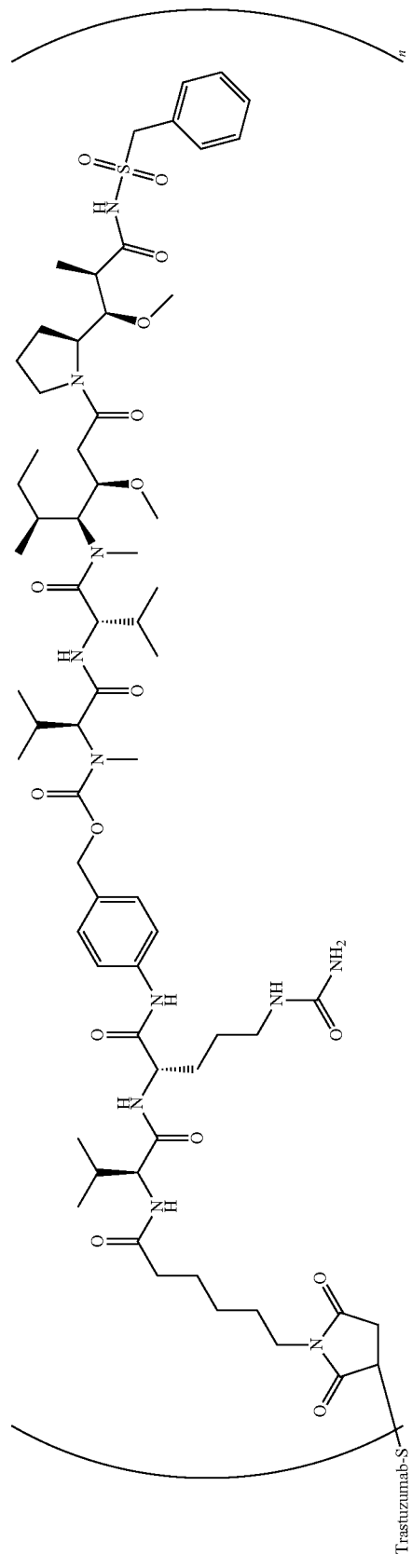

The cytotoxicities of the antibody drug conjugates from Example 7 were tested on both antigen positive and antigen negative cell line. The results are shown in Table 3.1.

TABLE 3.1

| Compound | $EC_{50}$ (nM) | | | | | | |
|---|---|---|---|---|---|---|---|
| | NCI-N87 | HCC-1954 | SKOV-3 | Karpas299 | Ramos | Jurkat | JIMT-1 |
| T-MTvc-Compound 5 | 0.016 | 0.093 | 0.012 | NC | NC | NC | ~0.01 |
| T-MTvc-Compound 11 | 0.008 | | | | | NC | |
| T-MTvc-Compound 32 | 0.011 | | | | | NC | |
| T-MTvc-Compound 14 | 0.011 | | 0.004 | | | NC | ~0.01 |
| T-MTvc-Compound 8 | 0.090 | | | | | NC | |
| T-MTvc-Compound 30 | 0.270 | | | | | NC | |
| T-MT-Compound 5 | 0.111 | | | | | NC | |
| T-MCvcPABC-Compound 33 | 0.157 | | | | | NC | |
| B-MTvc-Compound 5 | NC | | | 0.001 | | | |
| B-MTvc-Compound 11 | | | | 0.004 | | | |
| B-MTvc-Compound 14 | | | | 0.001 | | | |
| R-MTvc-Compound 5 | NC | | | | 0.688 | | |

NC = Not Cytotoxic.

Example 8: Efficacy Study of Toxins in PC-3 Tumor-bearing Mice

Test articles are administered IV. Dosage is near the maximum tolerated dosage. One injection of test article is delivered every seven days for four repeats/injections or one injection every seven days for three repeats/injections. Vehicle: 6.3% trehalose, 0.05% Tween® 20, 20 mM citrate buffer, pH 5.0, 4° C.

1. Procedure Overview

Female athymic nude mice, purchased from Harlan Laboratories at 7-8 weeks of age, are inoculated subcutaneously in the back with $5 \times 10^6$ PC-3 tumor cells on experimental day 0. Tumors are measured every Monday, Wednesday, and Friday. Once tumors reach 150-200 mm³ in size, animals are assigned to one of 4 treatment groups by counterbalancing the average tumor size across groups. Animals are treated with their respective compound, and tumor measures continue every Monday, Wednesday, and Friday.

2. PC-3 Cells: Cell Preparation—Tissue Culture

The PC-3 human prostate adenocarcinoma cell line is obtained from ATCC (Cat #CRL-1435). Cells are started from a frozen vial of lab stock which are frozen down from the original ATCC vial, tested for mycoplasma negative and kept in lab liquid nitrogen tanks. Cell cultures with passage #3 to #10 and a confluence of 80-90% are harvested for in vivo studies. Cells are grown in Ham's F12 medium supplemented with 2 mM L-glutamine and 10% FBS at 37° C./5% $CO_2$ environment. Cells are sub-cultured once a week with split ratio 1:3 to 1:6 and expanded. The medium is renewed once a week.

3. Cell Preparation—Harvesting for Implantation

Cells are rinsed briefly one time with 2 mL of fresh trypsin/EDTA solution (0.25% trypsin with EDTA 4Na), then the extra trypsin/EDTA is aspirated. Then 1.5 mL of trypsin/EDTA is added, and the flask is laid horizontally to ensure the cells are covered by trypsin/EDTA. The cells are then incubated at 37° C. for a few minutes. The cells are observed under an inverted microscope to ensure the cell layer is dispersed, then fresh medium is added, and 50 μL of cell suspension is sampled and mixed with trypan blue (1:1) and the cells are counted and cell viability assessed using the Cellometer® Auto T4. The cells are centrifuged at 1,000 rpm for 7 min and the supernatant aspirated. The cells are then re-suspended in growth medium to the appropriate concentration for inoculation. Injection volume is 100 μL per animal.

4. Tumor Cell Implantation—SC Back

On Day 0, $5.0 \times 10^6$ tumor cells are implanted subcutaneously into the back of mice in a volume of 100 μL using a 27/28-gauge needle under isoflurane anesthesia.

5. Animal Housing

Animals are housed in ventilated cages, 2 to 5 animals per cage, in a 12-hour light/dark cycle. Animals receive sterile food and water ad libitum and housing and use of animals is performed in accordance with Canadian Council on Animal Care guidelines. Animals are handled aseptically, and cages changed once every 10-14 days.

6. Data Collection (Tumor Size)

Mice are monitored every Monday, Wednesday and Friday for tumor development.

Dimensions of established tumors are measured with calipers. Tumor volumes are calculated according to the equation $[L \times W^2] \div 2$ with the length (L) being the longer axis of the tumor. Animals are also weighed at the time of tumor measurement. Tumors are allowed to grow to a maximum of 800 mm³.

7. Analysis Methods: Tumor Volume X Experimental Day Growth Curves

Tumor volumes of each group across the treatment days are plotted. Growth curves are cutoff for each group at the time point when the first animal reaches the tumor-size experimental endpoint (800 mm³), or at the last day of the study. Any animal that is withdrawn from the study prior to the group growth curve cutoff is removed entirely from the study.

8. Animal Exclusions

Any animal with ulcerating tumors, necessitating euthanasia of the animal, with tumor volume of 700 mm³ or smaller are removed from the study and do not contribute to the data analysis (except for Days to Recurrence if the final tumor volume is >2.0 fold higher than on the treatment day).

Example 9: Efficacy Dose Range Finding of Antibody Drug Conjugates in the NCI-N87 Tumor Model Using NOD SCID Gamma Mice Test articles are administered IV, one treatment only. Dosages tested are 3, 7, and 12 mg/kg. Vehicle: 20 mM sodium citrate, 6.3% trehalose, 0.02% Tween® 20, pH 5, 4° C.

1. Procedure Overview

Seventy-six (76) female NOD/SCID Gamma mice (NSG), purchased from The Jackson Laboratory (JAX® Mice) at 7-8 weeks of age, are inoculated subcutaneously in the lower back with 5×10⁶ NCI-N87 tumor cells in matrigel on experimental day 0. Tumors are measured every Monday, Wednesday, and Friday. Once tumors reach 150-200 mm³ in size, animals are assigned to one of 10 treatment groups by counterbalancing the average tumor size across groups. Animals are treated with their respective compound, and tumor measures continue every Monday, Wednesday, and Friday.

2. Cell Preparation—Tissue Culture: NCI-N87 Cells

NCI-N87 human gastric carcinoma cells are derived from a liver metastasis of a well differentiated carcinoma of the stomach taken prior to cytotoxic therapy. The tumor is passaged as a xenograft in athymic nude mice for three passages before the cell line is established. NCI-N87 cells are obtained from the ATCC (Cat #CRL-5822) and are tested negative at RADIL for Mycoplasma and mouse pathogens.

Cells are started from a frozen vial of lab stock which is frozen down from the original ATCC vial and kept in lab liquid nitrogen tanks. Cell cultures with passage #3 to #10 and a confluence of 80-90% are harvested for in vivo studies. NCI-N87 cells are grown in RPMI 1640 medium with 1.0 mM L-glutamine and 10% FBS at 37° C./5% $CO_2$ environment. Cells are subcultured once or twice a week with the split ratio 1:3 or 1:4 and expanded. The medium is renewed once a week. Cell are frozen with 5% DMSO.

3. Cell Preparation—Harvesting for Implantation

Cells are rinsed briefly one time with Hank's Balanced Salt Solution without Ca, Mg. Fresh trypsin/EDTA solution (0.25% trypsin with EDTA 4Na) is added, and the flask is laid horizontally to ensure the cells are covered by trypsin/EDA, and then the extra trypsin/EDTA is aspirated. The cells are incubated at 37° C. for a few minutes. Cells are observed under an inverted microscope until the cell layer is dispersed, and fresh medium is then added. Then, 50 μL of cell suspension is collected and mixed with trypan blue (1:1), and the cells are counted and assessed for viability on a haemocytometer. Viability should be ≥90%. The cells are centrifuged at 125 RCF (1,000 rpm) for 7 min and the supernatant is aspirated off. The cells are resuspended in cold growth medium to 2 times the desired final concentration (100×10⁶/mL). The suspension is mixed (on ice) with matrigel (1:1). The resulting cell suspensions (50×10⁶ cells/mL) is used to deliver 5×10⁶ cells in an injection volume of 100 μL per animal. All equipment coming into contact with matrigel (needles, syringes, pipette tips) is chilled prior to injection.

4. Tumor Cell Implantation—SC (NCI-N87)

Prior to inoculation, an area, approximately 2×2 cm, is shaved in the lower back region of each mouse and cleaned with alcohol. On Day 0, 5.0×10⁶ tumor cells are implanted subcutaneously into the back of mice in a volume of 100 μL, using a 27/28-gauge needle under isoflurane anesthesia.

5. Animal Housing

Animals are housed in ventilated cages, 2 to 5 animals per cage, in a 12-hour light/dark cycle. Animals received sterile food and water ad libitum and housing and use of animals is performed in accordance with Canadian Council on Animal Care guidelines. Animals are handled aseptically, and cages changed once every 10-14 days.

6. Data Collection (Tumor size)

Mice are monitored every Monday, Wednesday and Friday for tumor development. Dimensions of established tumors is measured with calipers. Tumor volumes are calculated according to the equation $[L \times W^2] \div 2$ with the length (L) being the longer axis of the tumor. Animals are also weighed at the time of tumor measurement. Tumors are allowed to grow to a maximum of 800 mm³.

7. Analysis Methods: Tumor Volume X Experimental Day Growth Curves

Tumor volumes of each group across the treatment days are plotted. Growth curves are cutoff for each group at the time point when the first animal reaches the tumor-size experimental endpoint (800 mm³), or at the last day of the study. Any animal that is withdrawn from the study prior to the group growth curve cutoff is removed entirely from the study.

8. Animal Exclusions

Any animal with ulcerating tumors, necessitating euthanasia of the animal, with tumor volume of 700 mm³ or smaller are removed from the study and do not contribute to the data analysis (except for Days to Recurrence if the final tumor volume is >2.0 fold higher than on the treatment day).

Example 10: Efficacy Comparison of Antibody Drug Conjugates in the NCI-N87 Tumor Model Using NOD SCID Gamma Mice Test articles are administered IV, with one administration of 3 mg/kg. Vehicle: 20 mM sodium citrate, 6.3% trehalose, 0.02% Tween® 20, pH 5.

1. Procedure Overview

Twenty-four (24) female NOD/SCID Gamma mice (NSG), purchased from The Jackson Laboratory (JAX® Mice) at 7-8 weeks of age, are inoculated subcutaneously in the lower back with 5×10⁶ NCI-N87 tumor cells in matrigel on experimental day 0. Tumors are measured every Monday, Wednesday, and Friday. Once tumors reach 150-200 mm³ in size, animals are assigned to one of 3 treatment groups by counterbalancing the average tumor size across groups. Animals are treated with their respective compound, and tumor measures continued every Monday, Wednesday, and Friday.

2. Cell Preparation—Tissue Culture: NCI-N87 Cells

NCI-N87 human gastric carcinoma cells are derived from a liver metastasis of a well differentiated carcinoma of the stomach taken prior to cytotoxic therapy. The tumor is passaged as a xenograft in athymic nude mice for three passages before the cell line is established. NCI-N87 cells are obtained from the ATCC (Cat #CRL-5822 and are tested negative at RADIL for Mycoplasma and mouse pathogens.

Cells are started from a frozen vial of lab stock which is frozen down from the original ATCC vial and kept in lab liquid nitrogen tanks. Cell cultures with passage #3 to #10 and a confluence of 80-90% are harvested for in vivo studies. NCI-N87 cells are grown in RPMI 1640 medium with 1.0 mM L-glutamine and 10% FBS at 37° C./5% $CO_2$ environment. Cells are subcultured once or twice a week with the split ratio 1:3 or 1:4 and expanded. The medium is renewed once a week. Cell are frozen with 5% DMSO.

3. Cell Preparation—Harvesting for Implantation

Cells are rinsed briefly one time with Hank's Balanced Salt Solution without Ca, Mg. Fresh trypsin/EDTA solution (0.25% trypsin with EDTA 4Na) is added, and the flask laid horizontally to ensure the cells are covered by trypsin/EDA, and then the extra trypsin/EDTA is aspirated. The cells are incubated at 37° C. for a few minutes. Cells are observed under an inverted microscope until cell layer is dispersed, fresh medium is then added. Then, 50 μL of cell suspension is collected and mixed with trypan blue (1:1), and the cells counted and assessed for viability on a haemocytometer. Viability should be ≥90%. The cells are centrifuged at 125 RCF (1,000 rpm) for 7 min and the supernatant is aspirated off. The cells are resuspended in cold growth medium to 2 times the desired final concentration ($100 \times 10^6$/mL). The suspension is mixed (on ice) with matrigel (1:1). The resulting cell suspensions ($50 \times 10^6$ cells/mL) is used to deliver $5 \times 10^6$ cells in an injection volume of 100 μL per animal. All equipment coming into contact with matrigel (needles, syringes, pipette tips) is chilled prior to injection.

4. Tumor Cell Implantation—Subcutaneous (NCI-N87)

Prior to inoculation, an area, approximately 2×2 cm, is shaved in the lower back region of each mouse and cleaned with alcohol. On Day 0, $5.0 \times 10^6$ tumor cells are implanted subcutaneously into the back of mice in a volume of 100 μL, using a 27/28-gauge needle under Isoflurane anesthesia.

5. Animal Housing

Animals are housed in ventilated cages, 2 to 5 animals per cage, in a 12-hour light/dark cycle. Animals received sterile food and water ad libitum and housing and use of animals is performed in accordance with Canadian Council on Animal Care guidelines. Animals are handled aseptically, and cages changed once every 10-14 days.

6. Data Collection (Tumor Size)

Mice are monitored every Monday, Wednesday and Friday for tumor development. Dimensions of established tumors is measured with calipers. Tumor volumes are calculated according to the equation $[L \times W^2] \div 2$ with the length (L) being the longer axis of the tumor. Animals are also weighed at the time of tumor measurement. Tumors are allowed to grow to a maximum of 800 $mm^3$.

7. Analysis Methods: Tumor Volume X Experimental Day Growth Curves

Tumor volumes of each group across the treatment days are plotted. Growth curves are cutoff for each group at the time point when the first animal reaches the tumor-size experimental endpoint (800 $mm^3$), or at the last day of the study. Any animal that is withdrawn from the study prior to the group growth curve cutoff is removed entirely from the study.

8. Animal Exclusions

Any animal with ulcerating tumors, necessitating euthanasia of the animal, with tumor volume of 700 $mm^3$ or smaller are removed from the study and do not contribute to the data analysis (except for Days to Recurrence if the final tumor volume is >2.0 fold higher than on the treatment day).

Example 10.1: Efficacy Comparison of Antibody Drug Conjugates in the NCI-N87 Tumor Model Using NOD SCID Gamma Mice Test articles were administered IV, one treatment only, 5 mg/kg. Vehicle: Phosphate Buffered Saline without Calcium or Magnesium, pH 7.4.

1. Procedure Overview

Female NOD/SCID Gamma mice (NSG), purchased from The Jackson Laboratory (JAX® Mice) at 7-8 weeks of age, were inoculated subcutaneously in the lower back with $5 \times 10^6$ NCI-N87 tumor cells in matrigel on experimental day 0. Tumors were measured every Monday, Wednesday, and Friday. Once tumors reached 150-200 $mm^3$ in size, animals were assigned to one of 10 treatment groups by counterbalancing the average tumor size across groups. Animals were treated with their respective compound, and tumor measures continued every Monday, Wednesday, and Friday.

2. Cell Preparation—Tissue Culture: NCI-N87 Cells

NCI-N87 human gastric carcinoma cells were derived from a liver metastasis of a well differentiated carcinoma of the stomach taken prior to cytotoxic therapy. The tumor was passaged as a xenograft in athymic nude mice for three passages before the cell line was established. NCI-N87 cells were obtained from the ATCC (Cat #CRL-5822) and were tested negative at RADIL for Mycoplasma and mouse pathogens.

Cells were started from a frozen vial of lab stock which was frozen down from the original ATCC vial and kept in lab liquid nitrogen tanks. Cell cultures with passage #3 to #10 and a confluence of 80-90% were harvested for in vivo studies. NCI-N87 cells were grown in RPMI 1640 medium with 1.0 mM L-glutamine and 10% FBS at 37° C./5% $CO_2$ environment. Cells were subcultured once or twice a week with the split ratio 1:3 or 1:4 and expanded. The medium was renewed once a week. Cell are frozen with 5% DMSO.

3. Cell Preparation—Harvesting for Implantation

Cells were rinsed briefly one time with Hank's Balanced Salt Solution without Ca, Mg. Fresh trypsin/EDTA solution (0.25% trypsin with EDTA 4Na) was added, and the flask was laid horizontally to ensure the cells were covered by trypsin/EDA, and then the extra trypsin/EDTA was aspirated. The cells were incubated at 37° C. for a few minutes. Cells were observed under an inverted microscope until the cell layer was dispersed, and fresh medium was then added. Then, 50 μL of cell suspension was collected and mixed with trypan blue (1:1), and the cells were counted and assessed for viability on a haemocytometer. Viability was ≥90%. The cells were centrifuged at 125 RCF (1,000 rpm) for 7 min and the supernatant was aspirated off. The cells were resuspended in cold growth medium to 2 times the desired final concentration ($100 \times 10^6$/mL). The suspension was mixed (on ice) with matrigel (1:1). The resulting cell suspensions ($50 \times 10^6$ cells/mL) was used to deliver $5 \times 10^6$ cells in an injection volume of 100 μL per animal. All equipment coming into contact with matrigel (needles, syringes, pipette tips) was chilled prior to injection.

4. Tumor Cell Implantation—SC (NCI-N87)

Prior to inoculation, an area, approximately 2×2 cm, was shaved in the lower back region of each mouse and cleaned with alcohol. On Day 0, $5.0 \times 10^6$ tumor cells were implanted subcutaneously into the back of mice in a volume of 100 μL, using a 27/28-gauge needle under isoflurane anesthesia.

5. Animal Housing

Animals are housed in ventilated cages, 2 to 5 animals per cage, in a 12-hour light/dark cycle. Animals received sterile food and water ad libitum and housing and use of animals was performed in accordance with Canadian Council on Animal Care guidelines. Animals were handled aseptically, and cages changed once every 10-14 days.

6. Data Collection (Tumor Size)

Mice were monitored every Monday, Wednesday and Friday for tumor development. Dimensions of established tumors was measured with calipers. Tumor volumes were calculated according to the equation $[L \times W^2] \div 2$ with the length (L) being the longer axis of the tumor. Animals were also weighed at the time of tumor measurement. Tumors were allowed to grow to a maximum of 800 mm$^3$.

7. Analysis Methods: Tumor Volume X Experimental Day Growth Curves

Figure 7:
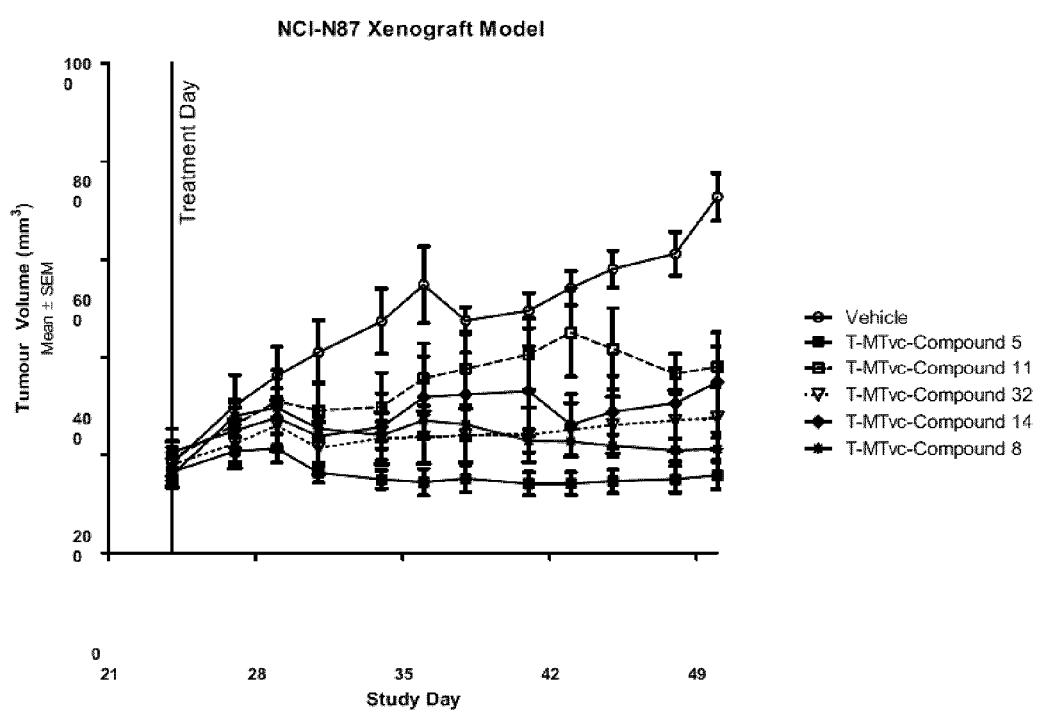
FIG. 7 shows the efficacy of certain ADCs in the NCI-N87 tumor model using NOD SCID Gamma Mice.

Tumor volumes of certain treatment groups across the treatment days are plotted in FIG. 7. Growth curves are cutoff for each group at the time point when the first animal reached the tumor-size experimental endpoint (800 mm$^3$), or at the last day of the study. Any animal that was withdrawn from the study prior to the group growth curve cutoff was removed entirely from the study.

8. Animal Exclusions

Any animal with ulcerating tumors, necessitating euthanasia of the animal, with tumor volume of 700 mm$^3$ or smaller was removed from the study and did not contribute to the data analysis (except for Days to Recurrence if the final tumor volume was >2.0 fold higher than on the treatment day).

Example 11: Efficacy Comparison of Antibody Drug Conjugates in the Karpas 299 Tumor Model Using C.B-17/IcrHsd-Prkdc$^{scid}$ Mice Test articles were administered IV, with four administrations of 1 mg/kg on day 21, day 25, day 29, and day 33. Vehicle: Phosphate Buffered Saline without Calcium or Magnesium, pH 7.4.

1. Procedure Overview

Female C.B-17/IcrHsd-Prkdcscid (CB.17-SCID) mice purchased from Harlan were inoculated with 1 million Karpas 299 CD30-expressing tumor cell line subcutaneously in the lower back. Mice were monitored every Monday, Wednesday and Friday for tumor development. Dimensions of established tumors were measured with calipers. Tumor volumes were calculated according to the equation $[L \times W^2] \div 2$ with the length being the longer axis of the tumor. Animals were also weighed at the time of tumor measurement. Mice were randomized on Day 21 on the basis of tumor volume when the mean tumor volume was 141.32 mm$^3$. The mice per group was reduced to 6 at the time of randomization. Mice were scheduled to receive four separate intravenous bolus administrations on Day 21, Day 25, Day 29 and Day 33 of their respective compound, and tumors were measured every Monday, Wednesday, and Friday.

1. Cell Preparation—Tissue Culture: Karpas 299

Karpas 299 human T cell lymphoma cell line established from the peripheral blood of a 25-year-old man with T cell non-Hodgkin's lymphoma in 1986; now classed as CD30+ anaplastic large cell lymphoma (ALCL); cells carry the NPM-ALK fusion gene. Karpas 299 cells were obtained from Health Protection Agency Culture Collections (Cat #06072604 and were tested negative for Mycoplasma).

Cells were started from a frozen vial of lab stock. Cell cultures with passage 3 to 10 and a density maintained between $5 \times 10^5$ and $2 \times 10^6$ cells/mL were harvested for in vivo studies. Cells were grown as suspension in RPMI 1640+2 mM Glutamine+20% Fetal Bovine Serum at 37° C. in 5% $CO_2$ environment. Cells were sub-cultured twice a week with split ratio of 1:3 and expanded.

2. Cell Preparation—Harvesting for Implantation

Cells were centrifuged and washed one time with Hanks Balanced Salt Solution without Ca, Mg. Then, 50 µL of cell suspension is collected and mixed with trypan blue (1:1) and the cells counted and assessed for viability on a Cellometer Auto4. Viability was ≥90%. The cells were centrifuged at 200 g for 7 min and the supernatant was aspirated off. The cells were resuspended in growth medium for sc inoculation. The resulting cell suspension was used to deliver $1 \times 10^6$ cells subcutaneously in 50 µL volume.

3. Tumor Cell Implantation—Subcutaneous (Karpas 299)

Prior to inoculation, an area, approximately 2×2 cm, was shaved in the lower back region of each mouse and cleaned with alcohol. On Day 0, $1 \times 10^6$ cells were implanted subcutaneously into the back of mice in a volume of 50 µL using a 27/28-gauge needle under isoflurane anesthesia.

4. Animal Housing

Animals were housed in ventilated cages, 3 to 4 animals per cage, in a 12-hour light/dark cycle. Animals received sterile food and water ad libitum and housing and use of animals was performed in accordance with Canadian Council on Animal Care guidelines. Animals were handled aseptically, and cages changed once every 10-14 days.

5. Data Collection (Tumor Size)

Mice were monitored for tumor development every weekday commencing 11 days post-inoculation. Dimensions of established tumors were be measured with calipers. Tumor volumes were calculated according to the equation $[L \times W^2] \div 2$ with the length (mm) being the longer axis of the tumor. Animals were also weighed at the time of tumor measurement (Mon, Wed, and Friday only). Once treatments were administered, tumors were measured thrice weekly on Monday, Wednesday and Friday. Tumors were allowed to grow to a maximum of 800 mm$^3$.

6. Analysis Methods: Tumor Volume X Experimental Day Growth Curves

Figure 8:
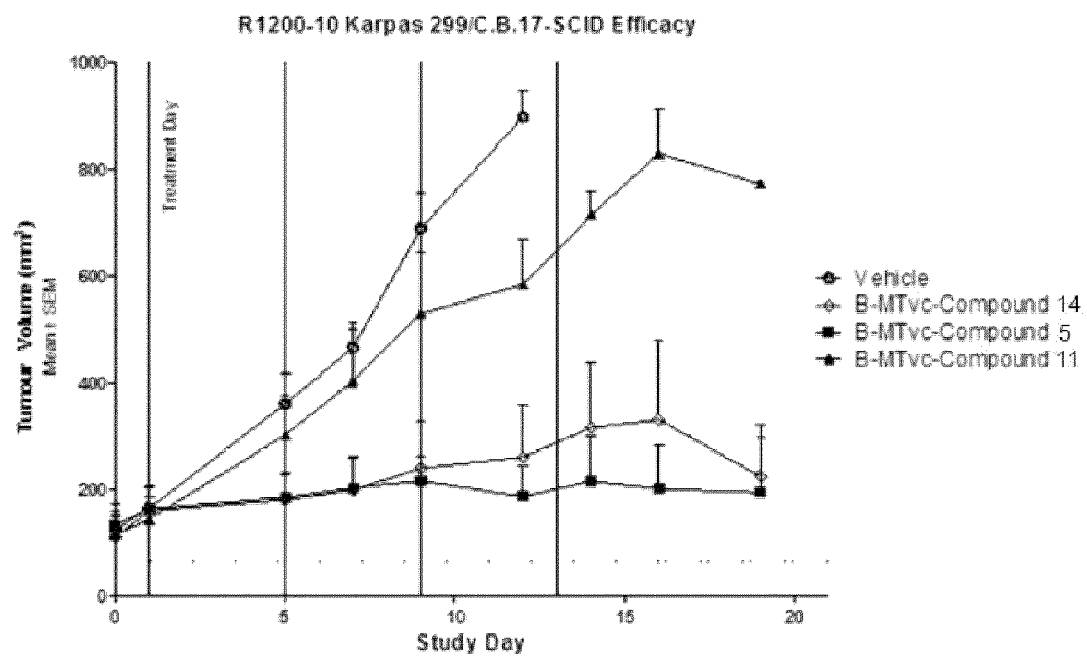
FIG. 8 shows the efficacy of certain ADCs in the Karpas 299 tumor model using C.B-17/IcrHsd-Prkdc$^{scid}$ mice.

Tumor volumes of each group across the treatment days are plotted in FIG. 8. Growth curves are cutoff for each group at the time point when the first animal reached the tumor-size experimental endpoint (800 mm$^3$), or at the last day of the study. Any animal that was withdrawn from the study prior to the group growth curve cutoff was removed entirely from the study.

7. Animal Exclusions

Any animal with ulcerating tumors, necessitating euthanasia of the animal, with tumor volume of 700 mm$^3$ or smaller was removed from the study and did not contribute to the data analysis (except for Days to Recurrence if the final tumor volume was >2.0 fold higher than on the treatment day).

Example 12: Tolerability of Antibody Drug Conjugates in Female Sprague Dawley Rats Test articles were administered IV, with a single administration on day 0. Test article formulation: Phosphate Buffered Saline without Calcium or Magnesium, pH 7.4.

1. Procedure Overview

Forty-three female Sprague Dawley (strain 001) rats were purchased from Charles River Labs and were allowed a 5 day acclimation period before study commencement. Test articles were administered IV on day 0. Animal body weights and clinical observations were taken pre-injection on the injection day, daily for at least three days after the administration, three times per week thereafter until the study endpoint (preferably every Monday, Wednesday, and Friday), and just prior to euthanasia. On day 22, animals were euthanized by $CO_2$ and a necropsy performed. Any unusual observations were photographed.

2. Animal Housing

Animals were housed in ventilated cages, 2-3 per cage, in a 12-hour light/dark cycle. Animals received food and water ad libitum and housing and use of animals was performed in accordance with Canadian Council on Animal Care guidelines. Cages were changed once a week. An acclimation period of at least 5 days was mandatory before the initiation of the treatment. A detailed physical examination and body weight determination was done during the acclimation period. Only healthy animals were used for the study. All animals were identified by a tattoo on the tail. The cages were marked with individual cards with information about the protocol number, room number, study director, phone of the study director, species and strain, sex, weight, date of reception and supplier.

3. Test Article Administration

Animals were individually weighed and administered with the required volumes of test article to administer the prescribed dose.

4. Intravenous Administration

Rats were administered solutions by bolus intravenous (IV) injection. The dosing solutions were administered by intravenous bolus using a <23G needle via the lateral tail vein. The dosing volume of 7 mL/kg was adjusted to individual body weight taken one day prior the day of injection. Treated rats were returned to their home cages and observed until hemostasis is observed.

5. Observations of Animals and Data Collection

Monitoring for acute toxicity effects was facilitated using a "Post Injection Clinical Observation Record" to assess morbidity and help determine humane endpoints up to 24 hours after administration. At the end of the working day on an administration day (~6 hours post-dosing), if animals showed clinical symptoms at a level where they cannot be left overnight without observation, they were either euthanized and considered to have reached a toxicity endpoint, or monitored regularly until they were deemed safe to be left overnight.

Past 24 hours post-administration, animals were monitored for chronic toxicity using a "Tolerability Monitoring Clinical Observation Record." Animals were monitored on with the following frequency/schedule: Pre-injection on the injection day, daily for at least three days after the administration, three times per week thereafter until the study endpoint (preferably every Monday, Wednesday, and Friday), and just prior to euthanasia. Animals were monitored more frequently if they were presenting significant signs of morbidity. Any animals reaching the humane endpoint were euthanized and necropsies performed to identify any gross abnormalities in the liver, spleen, kidney, lung, heart, gastrointestinal tract and bladder.

Figure 9:
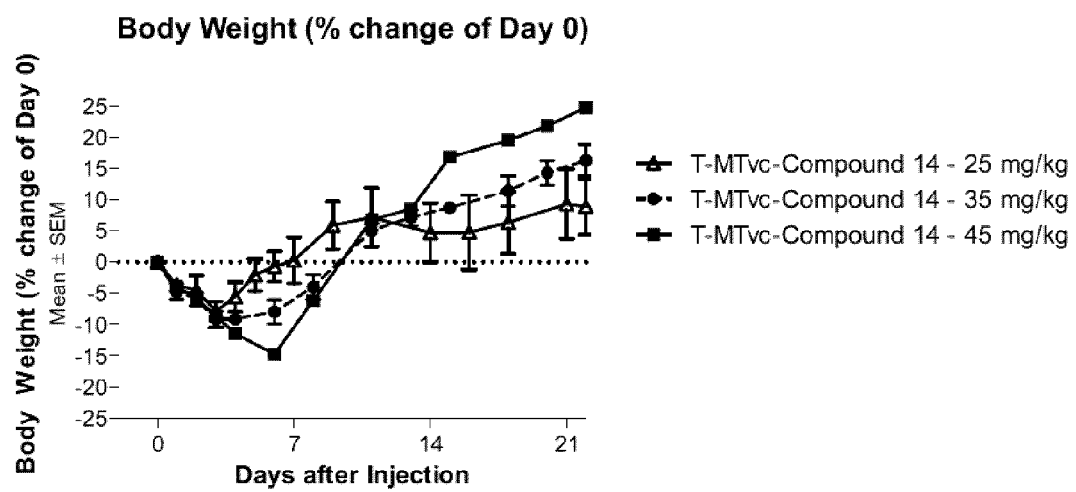
FIG. 9 shows the results of a tolerability study of a trastuzumab ADC of Compound 14 in female Sprague Dawley rats.
Figure 10:
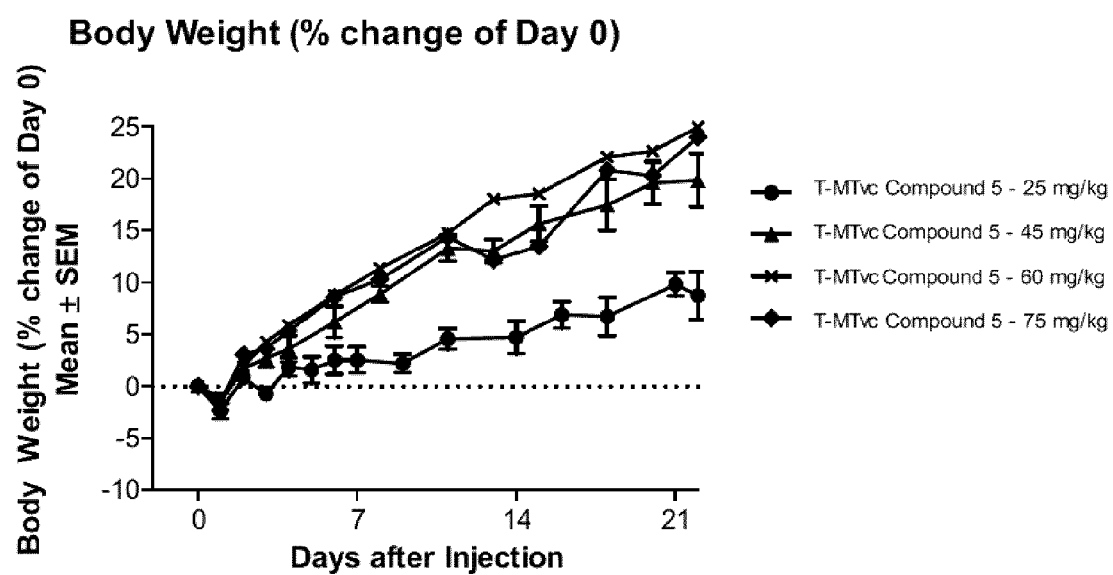
FIG. 10 shows the results of a tolerability study of a trastuzumab ADC of Compound 5 in female Sprague Dawley rats.

The results from the tolerability study are shown in FIGS. 9 and 10.

These data demonstrate that truncated compounds of Formula I, wherein X is absent, are better tolerated than their full-length counterparts, wherein X is —C(O)NHCH($CH_2R^3$)—.

Example 13. Cell Cycle Arrest Assay

Jurkat cells (ATCC), cultured in RMPI-1640 media supplemented with 10% FBS, were obtained in logarithmic growth. 1 million cells/ml were seeded into a 12-well tissue-culture treated plate in a 950 μL, volume. Cells were treated with Compound 5 in 50 μL of growth media such that the final concentration of Compound 5 was 50 nM, control cells were given 50 μL of growth media alone. Cells were incubated for 24 h at 37° C., 5% $CO_2$ in a humidified incubator. Following incubation, cells were thoroughly resuspended and transferred to 5 mL FACS tubes, and stored on ice. Two washes were performed by spinning cells down in a swinging-bucket centrifuge at 450×g for 4 min, resuspending in 1 mL ice-cold PBS. Cells were fixed through the addition of 3 mL ice-cold 100% ethanol in a dropwise fashion under vortex, and immediately stored at 4° C. for 1 h. During the 1 h incubation, the following staining solution was prepared in ice-cold PBS: 10 μg/ml propidium iodide, 10 U/ml RNAse 1f, and 0.05% Triton X-100. Following the 1 h fixation incubation, ethanol was removed by spinning cells as described above, and washing twice in 1 mL ice-cold PBS. Cells were resuspended in 500 μL of the above-mentioned staining solution, and incubated at room temperature for 1 h. Events were acquired on a BD C6 HTFC cytometer, removing debris and doublets by gating. Histograms were generated using FCS Express, plotting # of events against fluorescence in FL-3.

Figure 11:
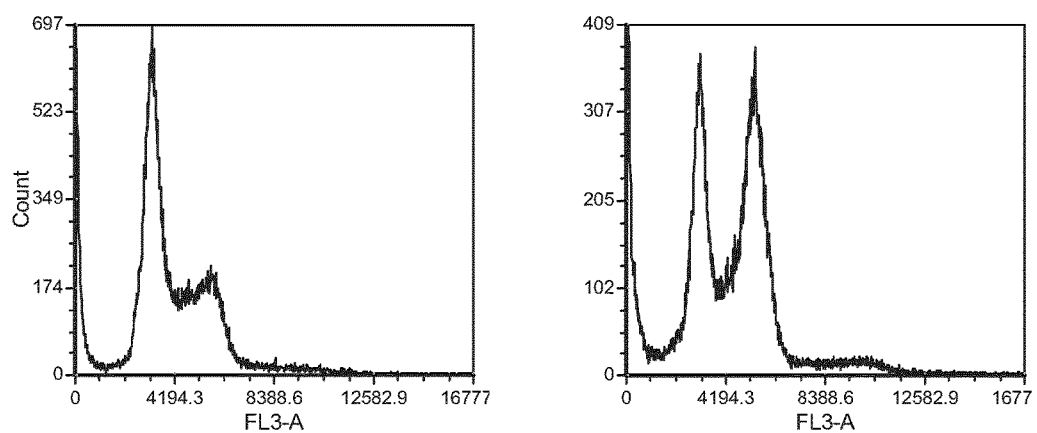
FIG. 11 shows the results of a cell cycle arrest assay in Jurkat cells treated with Compound 5.

Representative data from this assay is shown in FIG. 11. DNA Content histograms show the majority of untreated cells in the G0/G1 phase with a pronounced shift towards G2/M phase of the cell cycle after treatment with Compound 5.

All of the U.S. patents, U.S. patent application publications, U.S. patent applications, foreign patents, foreign patent applications and non-patent publications referred to in this specification are incorporated herein by reference, in their entirety to the extent not inconsistent with the present description. From the foregoing it will be appreciated that, although specific embodiments described herein have been described herein for purposes of illustration, various modifications may be made without deviating from the spirit and scope described herein. Accordingly, the disclosure is not limited except as by the appended claims.

What is claimed is:

1. A compound of Formula I:

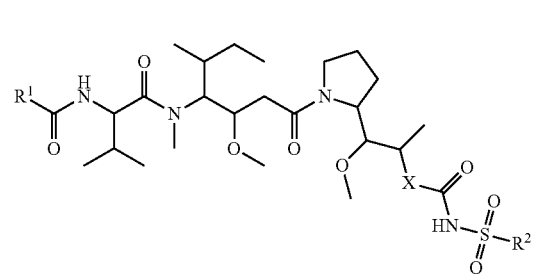

or a pharmaceutically acceptable salt thereof,
wherein:
$R^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from aryl, aryl-$C_1$-$C_6$ alkyl, $C_1$-$C_6$ alkyl, $C_1$-$C_6$ alkylthio, carboxyl, carboxamide, $C_3$-$C_7$ cycloalkyl, $C_3$-$C_7$ cycloalkyl-$C_1$-$C_6$ alkyl, guanidino, halo, $C_1$-$C_6$ haloalkyl, heterocyclyl, heterocyclyl-$C_1$-$C_6$ alkyl, hydroxyl, and thio; or
$R^1$ is $R^aR^bNCH(R^c)$—;
$R^a$ is selected from: H and $C_1$-$C_6$ alkyl;
$R^b$ is $C_1$-$C_6$ alkyl; and
$R^c$ is $R^d$—$C(CH_3)_2$—; and
$R^d$ is selected from: H, aryl, $C_3$-$C_7$ cycloalkyl, and heteroaryl, each of which is optionally substituted with one or more substituents selected from: $C_1$-$C_4$ acylthio, $C_2$-$C_4$ alkenyl, $C_1$-$C_4$ alkyl, $C_1$-$C_4$ alkylamino, $C_1$-$C_4$ alkyloxy, amino, amino-$C_1$-$C_4$ alkyl, halo, $C_1$-$C_4$ haloalkyl, hydroxyl, hydroxy-$C_1$-$C_4$ alkyl, and thio, wherein $C_2$-$C_4$ alkenyl, $C_1$-$C_4$ alkylamino and $C_1$-$C_4$ alkyloxy are further optionally substituted with one substituent selected from $C_1$-$C_4$ alkylaryl, hydroxyl, and thio; or $R^b$ and $R^c$ taken together with the atoms to which they are each bonded form a heterocyclyldiyl;

$R^2$ is aryl or aryl-$C_1$-$C_6$ alkyl each substituted with one or more substituents selected from: amino, amino-$C_1$-$C_6$ alkyl and amino-$C_3$-$C_7$ cycloalkyl; and X is —C(O)NHCH($CH_2R^3$)—; and $R^3$ is selected from: aryl, heteroaryl, and $C_3$-$C_7$ cycloalkyl, each optionally substituted with one substituent selected from amino and hydroxyl.

2. The compound according to claim 1, wherein $R^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from $C_1$-$C_6$ alkyl and halo.

3. The compound according to claim 1, wherein $R^1$ is $R^aR^bNCH(R^c)$—.

4. The compound according to claim 1 having Formula Ie:

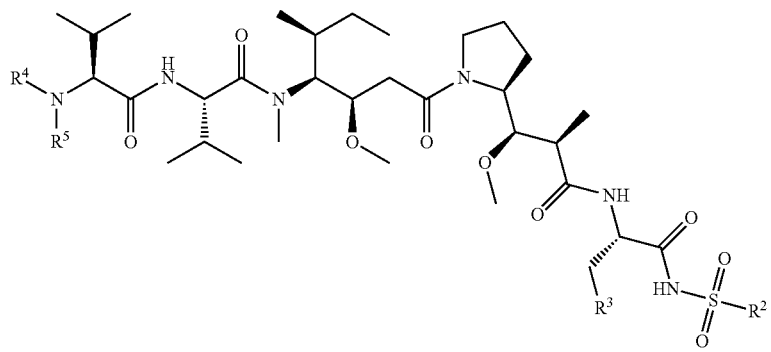

or a pharmaceutically acceptable salt thereof,
wherein:
$R^2$ is aryl or aryl-$C_1$-$C_6$ alkyl, each substituted with one or more substituents selected from: amino, amino-$C_1$-$C_6$ alkyl and amino-$C_3$-$C_7$ cycloalkyl;

$R^3$ is selected from: aryl, heteroaryl, and $C_3$-$C_7$ cycloalkyl, each optionally substituted with one substituent selected from amino and hydroxyl; and $R^4$ and $R^5$ are each independently selected from: H and $C_1$-$C_6$ alkyl.

5. The compound according to claim 4, wherein $R^4$ and $R^5$ are each $C_1$-$C_6$ alkyl.

6. The compound according to claim 4, wherein $R^4$ is H, and $R^5$ is $C_1$-$C_6$ alkyl.

7. The compound according to claim 1 having Formula Ih:

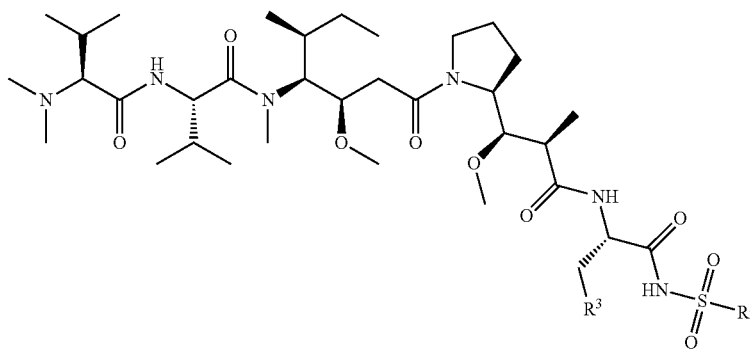

or Formula Ik:

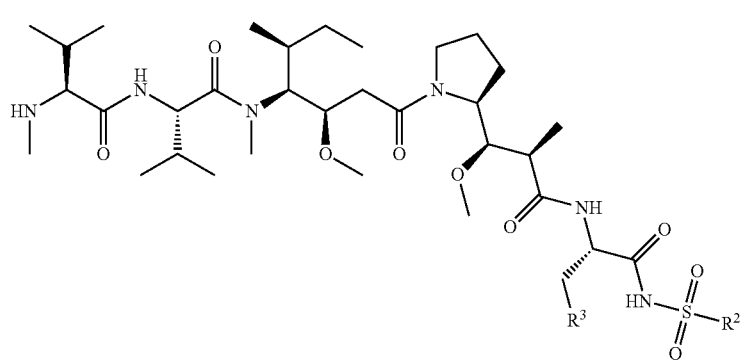

or a pharmaceutically acceptable salt thereof, wherein:
R² is aryl or aryl-$C_1$-$C_6$ alkyl, each substituted with one or more substituents selected from: amino, amino-$C_1$-$C_6$ alkyl and amino-$C_3$-$C_7$ cycloalkyl; and
R³ is selected from: aryl, heteroaryl, and $C_3$-$C_7$ cycloalkyl, each optionally substituted with one substituent selected from amino and hydroxyl.

8. The compound according to claim 7, wherein R³ is aryl optionally substituted with one substituent selected from amino and hydroxyl.

9. The compound according to claim 1 selected from the following, or a pharmaceutically acceptable salt thereof:

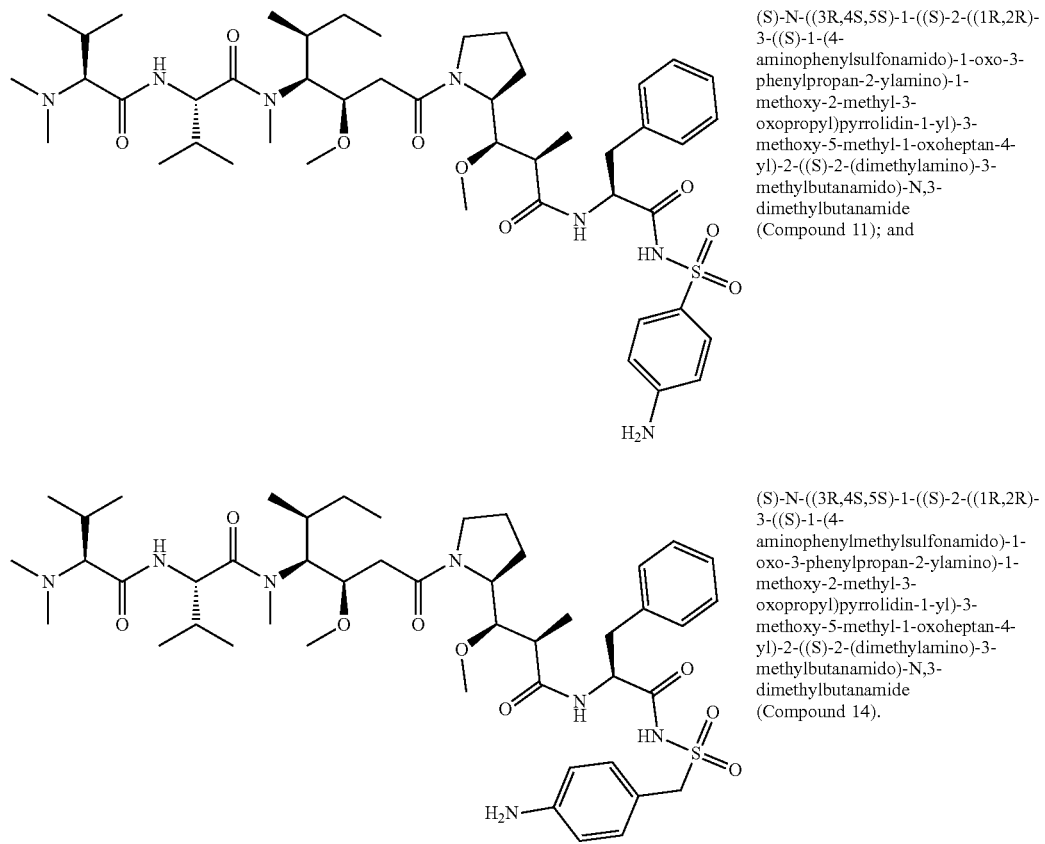

(S)-N-((3R,4S,5S)-1-((S)-2-((1R,2R)-3-((S)-1-(4-aminophenylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 11); and (S)-N-((3R,4S,5S)-1-((S)-2-((1R,2R)-3-((S)-1-(4-aminophenylmethylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 14).

10. A pharmaceutical composition comprising the compound according to claim 1, or a pharmaceutically acceptable salt thereof, and a pharmaceutically acceptable carrier, diluent or excipient.

11. A method of inhibiting cancer in a mammal, relieving cancer in a mammal, or relieving the symptoms of cancer in a mammal comprising administering to a mammal in need thereof an effective amount of the compound according to claim 1.

12. A method of inhibiting tumor growth in a mammal comprising administering to a mammal in need thereof an effective amount of the compound according to claim 1.

13. A composition of Formula II:

$$(T)\text{-}(L)\text{-}(D) \qquad\qquad II$$

wherein (T) is a targeting moiety, (L) is a linker, and (D) is the compound according to claim 1.

14. The composition according to claim 13, wherein $R^1$ is selected from: amino-$C_1$-$C_6$ alkyl, amino-aryl, amino-$C_3$-$C_7$ cycloalkyl, amino-heterocyclyl, and heterocyclyl, each optionally substituted with one or more substituents selected from $C_1$-$C_6$ alkyl and halo.

15. The composition according to claim 13, wherein $R^1$ is $R^aR^bNCH(R^c)$—.

16. The composition according to claim 13, wherein (D) is a compound having Formula Ie:

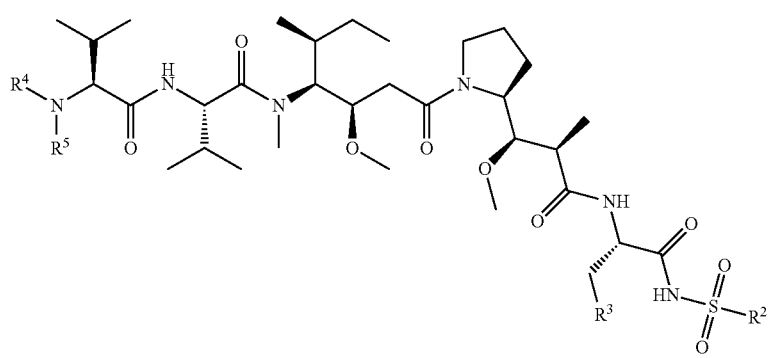

Ie wherein:
$R^2$ is aryl or aryl-$C_1$-$C_6$ alkyl, each substituted with one or more substituents selected from: amino, amino-$C_1$-$C_6$ alkyl and amino-$C_3$-$C_7$ cycloalkyl;

$R^3$ is selected from: aryl, heteroaryl, and $C_3$-$C_7$ cycloalkyl, each optionally substituted with one substituent selected from amino and hydroxyl; and $R^4$ and $R^5$ are each independently selected from: H and $C_1$-$C_6$ alkyl.

17. The composition according to claim 16, wherein $R^4$ and $R^5$ are each $C_1$-$C_6$ alkyl.

18. The composition according to claim 16, wherein $R^4$ is H, and $R^5$ is $C_1$-$C_6$ alkyl.

19. The composition according to claim 13, wherein (D) is a compound having Formula Ih:

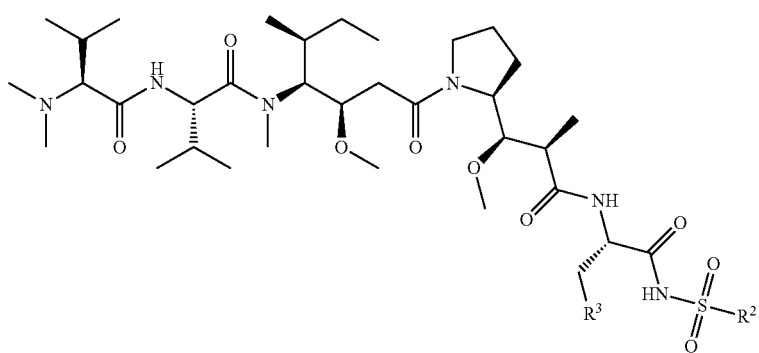

Ih or Formula Ik:

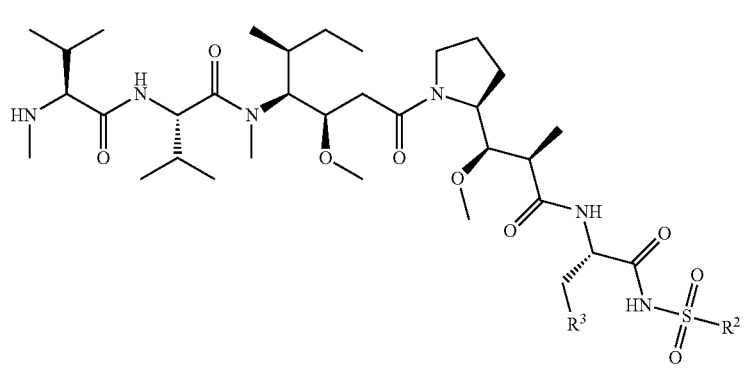

wherein:
R² is aryl or aryl-$C_1$-$C_6$ alkyl, each substituted with one or more substituents selected from: amino, amino-$C_1$-$C_6$ alkyl and amino-$C_3$-$C_7$ cycloalkyl; and
R³ is selected from: aryl, heteroaryl, and $C_3$-$C_7$ cycloalkyl, each optionally substituted with one substituent selected from amino and hydroxyl.

20. The composition according to claim 19, wherein R³ is aryl optionally substituted with one substituent selected from amino and hydroxyl.

21. The composition according to claim 13, wherein (D) is a compound selected from the following:

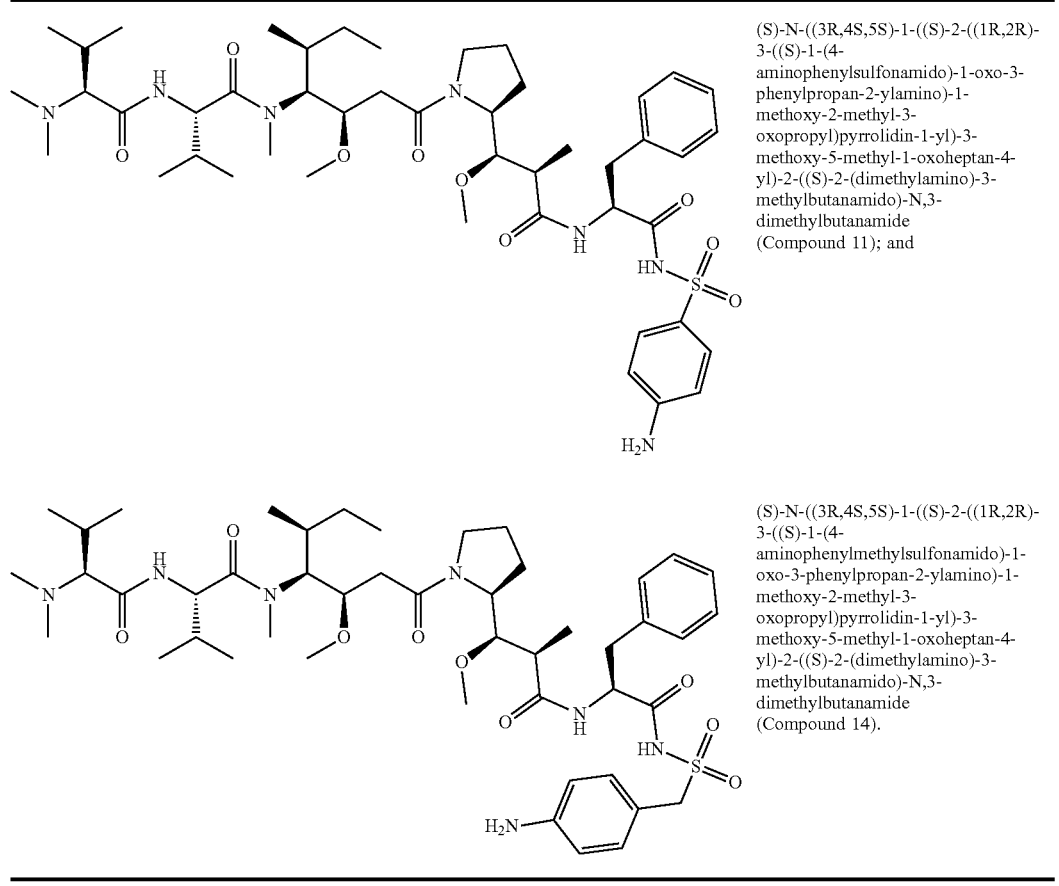

(S)-N-((3R,4S,5S)-1-((S)-2-((1R,2R)-3-((S)-1-(4-aminophenylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 11); and (S)-N-((3R,4S,5S)-1-((S)-2-((1R,2R)-3-((S)-1-(4-aminophenylmethylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 14).

22. The composition according to claim 13, wherein (L)-(D) has the following structure:

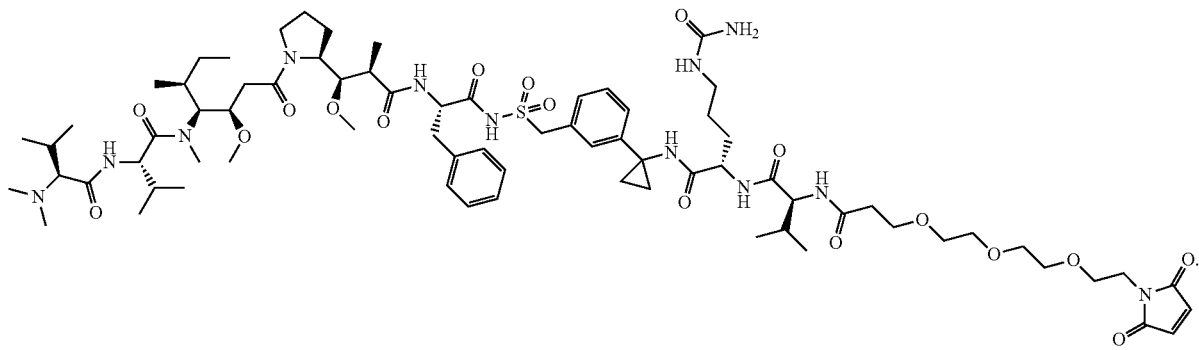 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)Cc1cccc(C2(NC(=O)[C@H](CCCNC(N)=O)NC(=O)[C@@H](NC(=O)CCOCCOCCOCCN3C(=O)C=CC3=O)C(C)C)CC2)c1)OC)N(C)C(=O)[C@@H](NC(=O)[C@H](C(C)C)N(C)C)C(C)C]

23. The composition according to claim 13, wherein (T) is a monoclonal antibody or antibody fragment.

24. The composition according to claim 23, wherein the monoclonal antibody or antibody fragment is a bispecific antibody or antibody fragment.

25. The composition according to claim 23, wherein the monoclonal antibody or antibody fragment specifically binds to a cancer cell antigen.

26. A pharmaceutical composition comprising the composition according to claim 13 and a pharmaceutically acceptable carrier, diluent or excipient.

27. A method of inhibiting cancer in a mammal, relieving cancer in a mammal, or relieving the symptoms of cancer in a mammal comprising administering to a mammal in need thereof an effective amount of the composition according to claim 13.

28. A method of inhibiting tumor growth in a mammal comprising administering to a mammal in need thereof an effective amount of the composition according to claim 13.

29. A compound selected from the following, or a pharmaceutically acceptable salt thereof:

(S)-2-((S)-2-(dimethylamino)-3-methylbutanamido)-N-((3R,4S,5S)-3-methoxy-1-((S)-2-((1R,2R)-1-mcthoxy-2-methyl-3-oxo-3-((S)-1-oxo-3-phenyl-1-(4-(2,2,2-trifluoroacetamido)phenyl-sulfonamido)propan-2-ylamino)propyl)pyrrolidin-1-yl)-5-methyl-1-oxoheptan-4-yl)-N,3-dimethylbutanamide (Compound 10); and

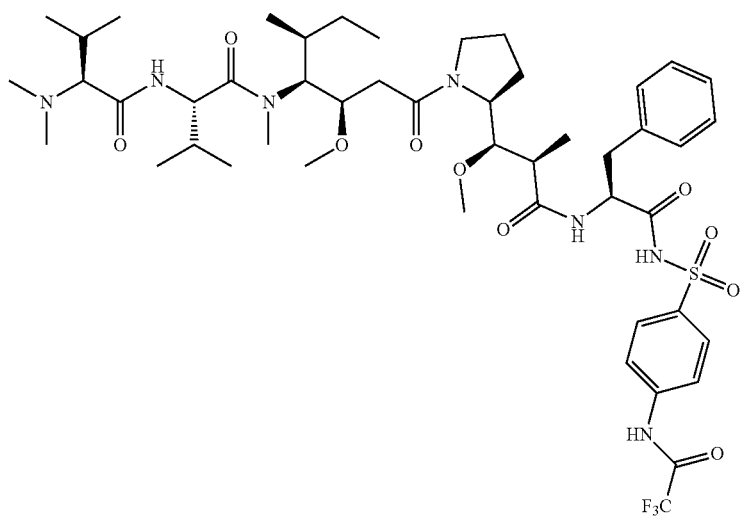 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)c1ccc(NC(=O)C(F)(F)F)cc1)OC)N(C)C(=O)[C@@H](NC(=O)[C@H](C(C)C)N(C)C)C(C)C]

-continued

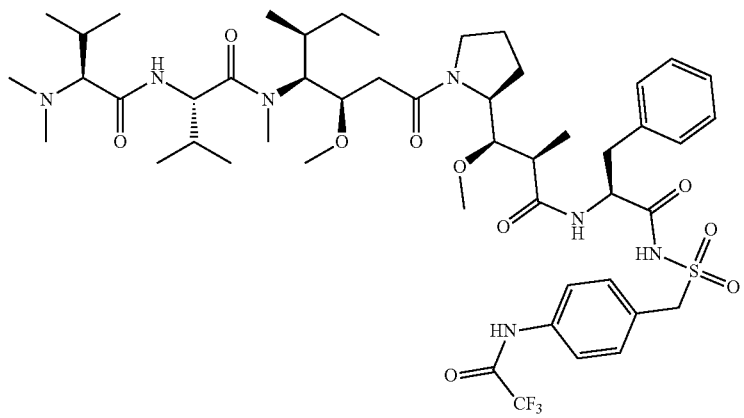 [SMILES: CC[C@H](C)[C@@H]([C@@H](CC(=O)N1CCC[C@H]1[C@H](OC)[C@@H](C)C(=O)N[C@@H](Cc1ccccc1)C(=O)NS(=O)(=O)Cc1ccc(NC(=O)C(F)(F)F)cc1)OC)N(C)C(=O)[C@@H](NC(=O)[C@H](C(C)C)N(C)C)C(C)C]

(S)-2-((S)-2-(dimethylamino)-3-methylbutanamido)-N-((3R,4S,5S)-3-methoxy-1-((S)-2-((1R,2R)-1-methoxy-2-methyl-3-oxo-3-((S)-1-oxo-3-phenyl-1-(4-(2,2,2-trifluoroacetamido)phenylmethylsulfonamido)propan-2-ylamino)propyl)pyrrolidin-1-yl)-5-methyl-1-oxoheptan-4-yl)-N,3-dimethylbutanamide (Compound 13).

30. The composition according to claim 13, wherein (L)-(D) is formed by reacting (D) with a compound:

HO-AA$_1$-AA$_2$-NH-Anchor wherein AA$_1$ and AA$_2$ are each independently an amino acid, and Anchor comprises a functional group that forms a covalent bond with (T).

31. The composition according to claim 30, wherein Anchor further comprises a stretcher.

32. The composition according to claim 13, wherein (L) does not include a self-immolative group.

33. The composition according to claim 21, wherein (L)-(D) is formed by reacting (D) with a compound:

HO-AA$_1$-AA$_2$-NH-Anchor wherein AA$_1$ and AA$_2$ are each independently an amino acid, and Anchor comprises a functional group that forms a covalent bond with (T).

34. The composition according to claim 33, wherein Anchor further comprises a stretcher.

35. The composition according to claim 21, wherein (L) does not include a self-immolative group.

36. The composition according to claim 21, wherein (T) is a monoclonal antibody or antibody fragment.

37. The composition according to claim 36, wherein the monoclonal antibody or antibody fragment is a bispecific antibody or antibody fragment.

38. The composition according to claim 36, wherein the monoclonal antibody or antibody fragment specifically binds to a cancer cell antigen.

39. A pharmaceutical composition comprising the composition according to claim 21 and a pharmaceutically acceptable carrier, diluent or excipient.

40. A method of inhibiting cancer in a mammal, relieving cancer in a mammal, or relieving the symptoms of cancer in a mammal comprising administering to a mammal in need thereof an effective amount of the composition according to claim 21.

41. A method of inhibiting tumor growth in a mammal comprising administering to a mammal in need thereof an effective amount of the composition according to claim 21.

42. The composition according to claim 22, wherein (T) is a monoclonal antibody or antibody fragment.

43. The composition according to claim 42, wherein the monoclonal antibody or antibody fragment is a bispecific antibody or antibody fragment.

44. The composition according to claim 42, wherein the monoclonal antibody or antibody fragment specifically binds to a cancer cell antigen.

45. A pharmaceutical composition comprising the composition according to claim 22 and a pharmaceutically acceptable carrier, diluent or excipient.

46. A method of inhibiting cancer in a mammal, relieving cancer in a mammal, or relieving the symptoms of cancer in a mammal comprising administering to a mammal in need thereof an effective amount of the composition according to claim 22.

47. A method of inhibiting tumor growth in a mammal comprising administering to a mammal in need thereof an effective amount of the composition according to claim 22.

48. The compound according to claim 1 having Formula Ib:

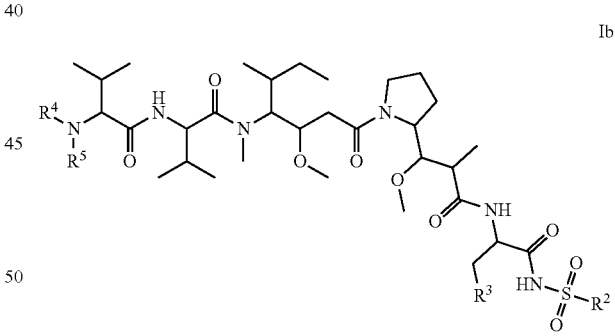

Ib or a pharmaceutically acceptable salt thereof, wherein:

$R^2$ is aryl or aryl-$C_1$-$C_6$ alkyl, each substituted with one or more substituents selected from: amino, amino-$C_1$-$C_6$ alkyl and amino-$C_3$-$C_7$ cycloalkyl;

$R^3$ is selected from: aryl, heteroaryl, and $C_3$-$C_7$ cycloalkyl, each optionally substituted with one substituent selected from amino and hydroxyl; and $R^4$ and $R^5$ are each independently selected from: H and $C_1$-$C_6$ alkyl.

49. The composition according to claim 13, wherein (D) is a compound having Formula Ib:

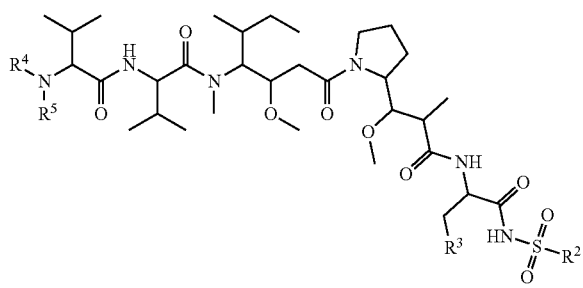

Ib or a pharmaceutically acceptable salt thereof, wherein:

$R^2$ is aryl or aryl-$C_1$-$C_6$ alkyl, each substituted with one or more substituents selected from: amino, amino-$C_1$-$C_6$ alkyl and amino-$C_3$-$C_7$ cycloalkyl;

$R^3$ is selected from: aryl, heteroaryl, and $C_3$-$C_7$ cycloalkyl, each optionally substituted with one substituent selected from amino and hydroxyl; and $R^4$ and $R^5$ are each independently selected from: H and $C_1$-$C_6$ alkyl.

50. The compound according to claim 1 selected from the following, or a pharmaceutically acceptable salt thereof:

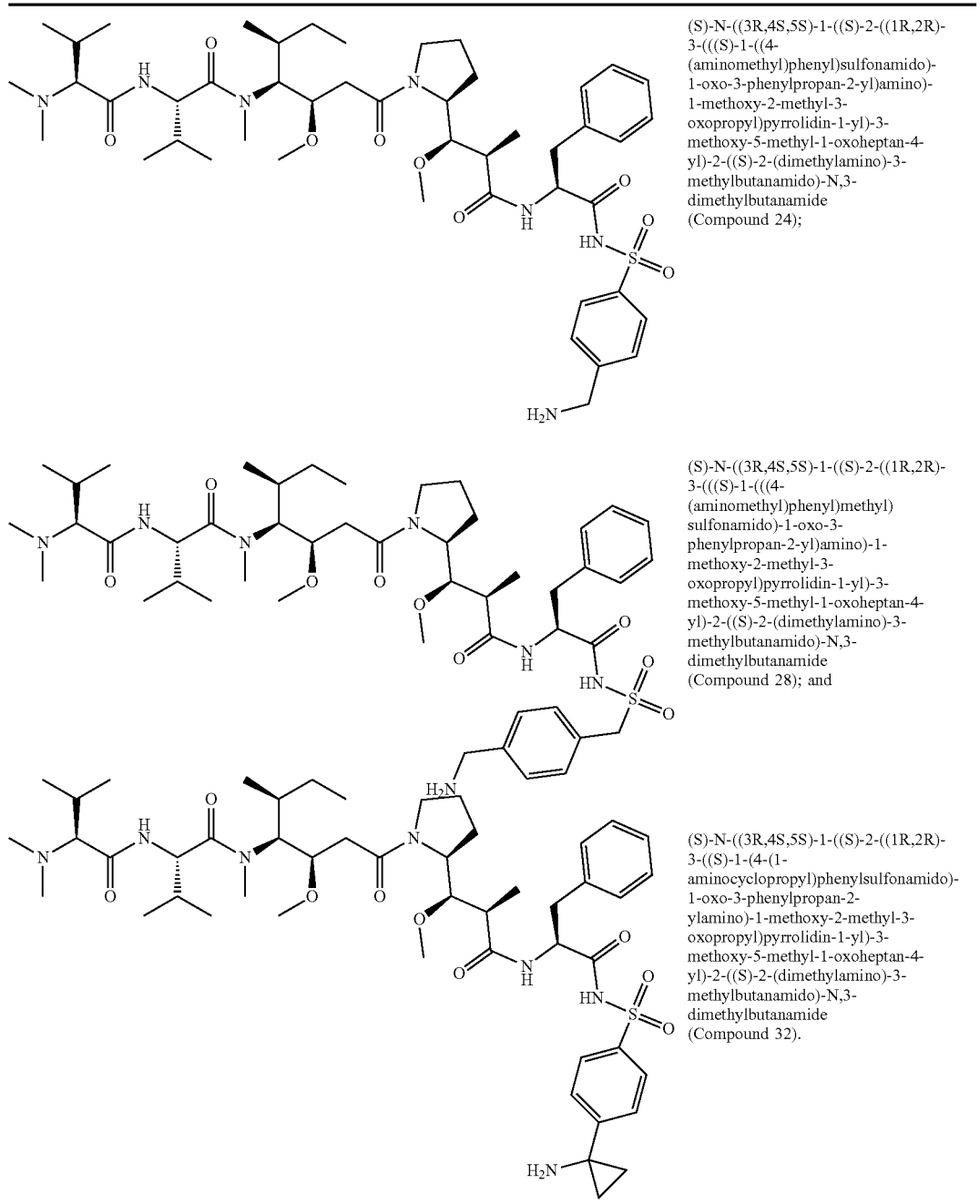

(S)-N-((3R,4S,5S)-1-((S)-2-((1R,2R)-3-(((S)-1-((4-(aminomethyl)phenyl)sulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 24);

(S)-N-((3R,4S,5S)-1-((S)-2-((1R,2R)-3-(((S)-1-(((4-(aminomethyl)phenyl)methyl)sulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 28); and (S)-N-((3R,4S,5S)-1-((S)-2-((1R,2R)-3-((S)-1-(4-(1-aminocyclopropyl)phenylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 32).

51. The composition according to claim 13, wherein (D) is a compound selected from the following:

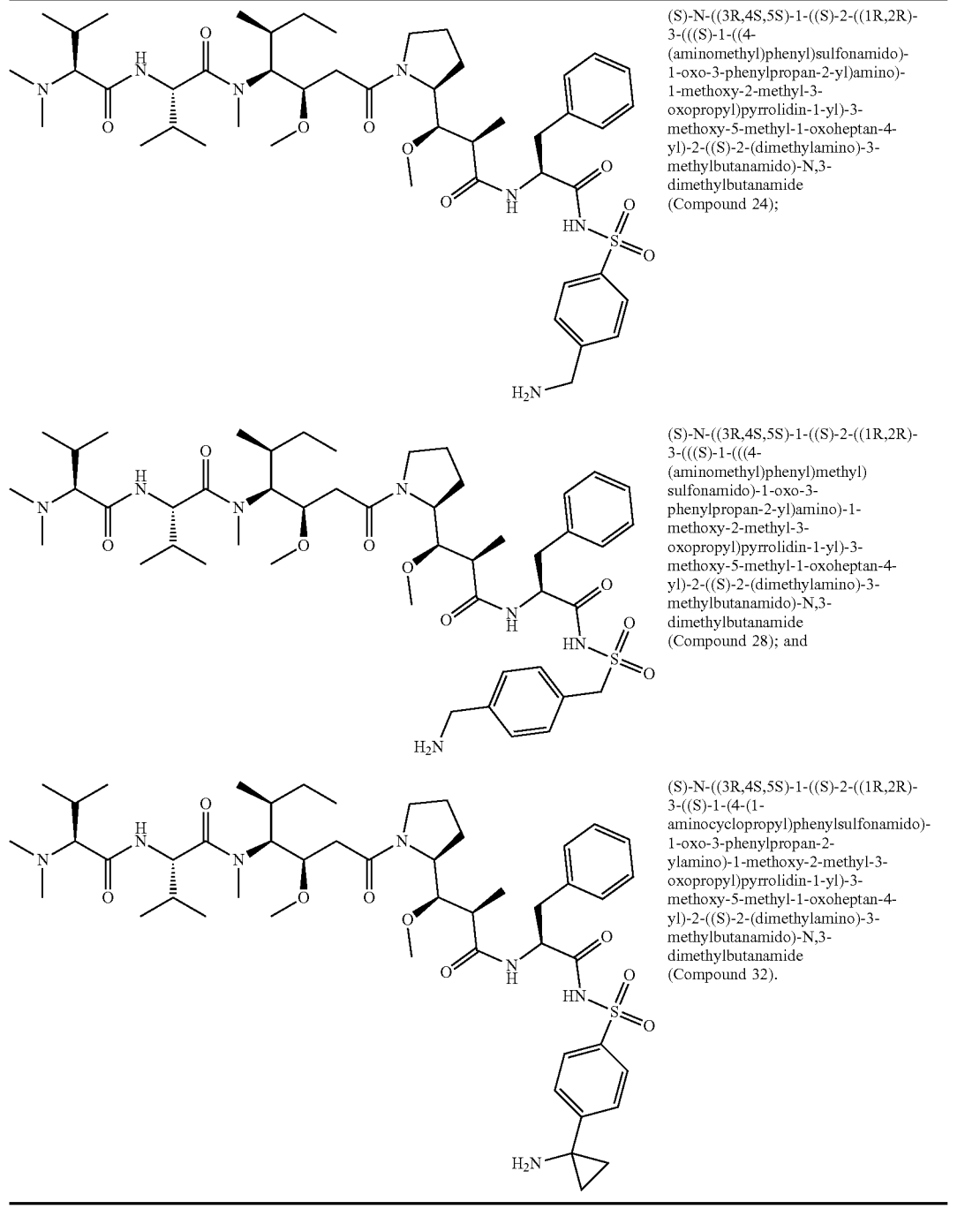

(S)-N-((3R,4S,5S)-1-((S)-2-((1R,2R)-3-(((S)-1-((4-(aminomethyl)phenyl)sulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 24);

(S)-N-((3R,4S,5S)-1-((S)-2-((1R,2R)-3-(((S)-1-(((4-(aminomethyl)phenyl)methyl)sulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 28); and (S)-N-((3R,4S,5S)-1-((S)-2-((1R,2R)-3-((S)-1-(4-(1-aminocyclopropyl)phenylsulfonamido)-1-oxo-3-phenylpropan-2-ylamino)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 32).

52. The composition according to claim 51, wherein (L)-(D) is formed by reacting (D) with a compound:

HO-AA$_1$-AA$_2$-NH-Anchor wherein AA$_1$ and AA$_2$ are each independently an amino acid, and Anchor comprises a functional group that forms a covalent bond with (T).

53. The composition according to claim 52, wherein Anchor further comprises a stretcher.

54. The composition according to claim 51, wherein (L) does not include a self-immolative group.

55. The composition according to claim 51, wherein (T) is a monoclonal antibody or antibody fragment.

56. The composition according to claim 55, wherein the monoclonal antibody or antibody fragment is a bispecific antibody or antibody fragment.

57. The composition according to claim 55, wherein the monoclonal antibody or antibody fragment specifically binds to a cancer cell antigen.

58. A pharmaceutical composition comprising the composition according to claim 51 and a pharmaceutically acceptable carrier, diluent or excipient.

59. A method of inhibiting cancer in a mammal, relieving cancer in a mammal, or relieving the symptoms of cancer in a mammal comprising administering to a mammal in need thereof an effective amount of the composition according to claim 51.

60. A method of inhibiting tumor growth in a mammal comprising administering to a mammal in need thereof an effective amount of the composition according to claim 51.

61. A compound selected from the following, or a pharmaceutically acceptable salt thereof:

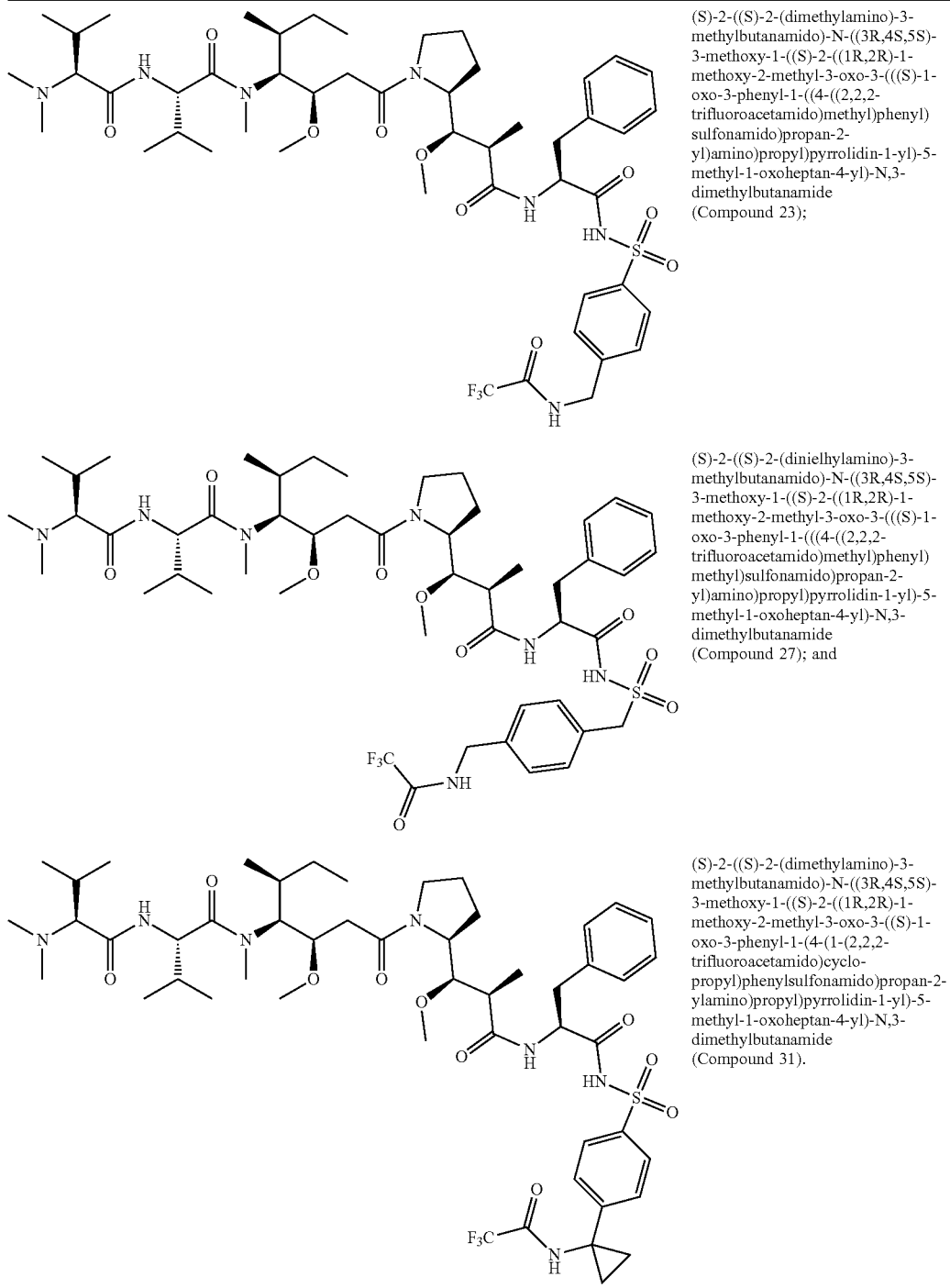

(S)-2-((S)-2-(dimethylamino)-3-methylbutanamido)-N-((3R,4S,5S)-3-methoxy-1-((S)-2-((1R,2R)-1-methoxy-2-methyl-3-oxo-3-(((S)-1-oxo-3-phenyl-1-((4-((2,2,2-trifluoroacetamido)methyl)phenyl)sulfonamido)propan-2-yl)amino)propyl)pyrrolidin-1-yl)-5-methyl-1-oxoheptan-4-yl)-N,3-dimethylbutanamide (Compound 23);

(S)-2-((S)-2-(dinielhylamino)-3-methylbutanamido)-N-((3R,4S,5S)-3-methoxy-1-((S)-2-((1R,2R)-1-methoxy-2-methyl-3-oxo-3-(((S)-1-oxo-3-phenyl-1-(((4-((2,2,2-trifluoroacetamido)methyl)phenyl)methyl)sulfonamido)propan-2-yl)amino)propyl)pyrrolidin-1-yl)-5-methyl-1-oxoheptan-4-yl)-N,3-dimethylbutanamide (Compound 27); and (S)-2-((S)-2-(dimethylamino)-3-methylbutanamido)-N-((3R,4S,5S)-3-methoxy-1-((S)-2-((1R,2R)-1-methoxy-2-methyl-3-oxo-3-((S)-1-oxo-3-phenyl-1-(4-(1-(2,2,2-trifluoroacetamido)cyclopropyl)phenylsulfonamido)propan-2-ylamino)propyl)pyrrolidin-1-yl)-5-methyl-1-oxoheptan-4-yl)-N,3-dimethylbutanamide (Compound 31).

* * * * *